US012173335B2

(12) United States Patent
Nie et al.

(10) Patent No.: US 12,173,335 B2
(45) Date of Patent: Dec. 24, 2024

(54) RECRUITMENT OF DNA POLYMERASE FOR TEMPLATED EDITING

(71) Applicant: Pairwise Plants Services, Inc., Durham, NC (US)

(72) Inventors: Jingyi Nie, Durham, NC (US); Aaron Hummel, Hillsborough, NC (US); Shai Joshua Lawit, Durham, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 99 days.

(21) Appl. No.: 17/142,570

(22) Filed: Jan. 6, 2021

(65) Prior Publication Data
US 2021/0207113 A1 Jul. 8, 2021

Related U.S. Application Data

(60) Provisional application No. 62/957,542, filed on Jan. 6, 2020.

(51) Int. Cl.
| | |
|---|---|
| *C12N 9/12* | (2006.01) |
| *C12N 9/16* | (2006.01) |
| *C12N 9/22* | (2006.01) |
| *C12N 15/113* | (2010.01) |

(52) U.S. Cl.
CPC .............. *C12N 9/16* (2013.01); *C12N 15/113* (2013.01); *C12N 2310/20* (2017.05); *C12N 2310/3513* (2013.01); *C12N 2310/3517* (2013.01); *C12N 2310/3519* (2013.01); *C12Y 301/00* (2013.01)

(58) Field of Classification Search
None
See application file for complete search history.

(56) References Cited

U.S. PATENT DOCUMENTS

| | | |
|---|---|---|
| 9,790,490 B2 | 10/2017 | Zhang et al. |
| 2014/0377767 A1 | 12/2014 | Gong et al. |
| 2015/0067922 A1 | 3/2015 | Yang et al. |
| 2017/0138937 A1 | 5/2017 | Sheehan et al. |
| 2019/0062734 A1 | 2/2019 | Cotta-Ramusino et al. |

FOREIGN PATENT DOCUMENTS

| | | | | |
|---|---|---|---|---|
| WO | WO-2019051097 A1 | * | 3/2019 | ......... C12N 15/1024 |

OTHER PUBLICATIONS

Carlson-Stevermer et al., Nat. Commun. vol. 8, 1711, 2017.*
El-Andaloussi et al. , Faseb J. vol. 21, pp. 26-34 Jan. 2007.*
Aird, Eric J., et al., "Increasing Cas9-mediated homology-directed repair efficiency through covalent tethering of DNA repair template", Communications Biology 1:54, pp. 1-6 (2018).
International Search Report and Written Opinion corresponding to PCT/US2021/012283; mailed Mar. 29, 2021 (15 pages).
Anzalone, Andrew V., et al., "Search-and-replace genome editing without double-strand breaks or donor DNA", Nature 576, 2019, 149-157.
Halperin, Shakked O., et al., "CRISPR-guided DNA polymerases enable diversification of all nucleotides in a tunable window", Nature 560, 2018, 248-252.
Hogg, Matthew , et al., "Structural basis for processive DNA synthesis by yeast DNA polymerase ε", Nature Structural & Molecular Biology 21(1), 2014, 49-55.
Pursell, Zachary F., et al., "DNA Polymerase ε: A Polymerase of Unusual Size (and Complexity)", Progress in Nucleic Acid Research and Molecular Biology 82, 2008, 101-145.
Slaymaker, Ian M., et al., "Rationally engineered Cas9 nucleases with improved specificity", Science 351(6268), 2016, 84-88.
Wang, Yan , et al., "A novel strategy to engineer DNA polymerases for enhanced processivity and improved performance in vitro", Nucleic Acids Research 32(3), 2004, 1197-1207.
Chen, Cheng-Yao, "DNA polymerases drive DNA sequencing-by-synthesis technologies: both past and present", Frontiers in Microbiology. vol. 5, Article 305, 2014, 1-11.
Cong, Le, et al., "Multiplex Genome Engineering Using CRISPR/Cas Systems", Science. 339(6121), 2013, 819-823.
Lee, Seung Hwan, et al., "CRISPR and Target-Specific DNA Endonucleases for Efficient DNA Knock-in in Eukaryotic Genomes", Mol. Cells. 41(11), 2018, 943-952.
Extended European Search Report corresponding to EP 21738783.6 mailed Dec. 22, 2023 (6 pages).
Anonymous, "High-Fidelity PCR Enzymes: Properties and Error Rate Determinations", Agilent. Retrieved from https://www.agilent.com/genomics/lifestyle, 2019.
Coulther, Timothy A., et al., "Engineering Polymerases for New Functions", Trends in Biotechnology. 37(10): 1091-1103, 2019.
Jasin, Maria, et al., "The democratization of gene editing: Insights from site-specific cleavage and double-strand break repair", DNA Repair. 44: 6-16, 2016.

* cited by examiner

*Primary Examiner* — Richard G Hutson
(74) *Attorney, Agent, or Firm* — Myers Bigel, P.A.

(57) ABSTRACT

This invention relates to recombinant nucleic constructs comprising a sequence-specific DNA binding protein, DNA-dependent DNA polymerase and a DNA encoded repair template, optionally a DNA endonuclease or wherein the sequence-specific DNA binding protein comprises DNA endonuclease activity, and methods of use thereof for modifying nucleic acids in cells and organisms.

16 Claims, No Drawings

Specification includes a Sequence Listing.

SEQUENCE LISTING

```
<160> NUMBER OF SEQ ID NOS: 94

<210> SEQ ID NO 1
<211> LENGTH: 1228
<212> TYPE: PRT
<213> ORGANISM: Unknown
<220> FEATURE:
<223> OTHER INFORMATION: Lachnospiraceae bacterium

<400> SEQUENCE: 1

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
                20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
```

```
                    85                  90                  95
Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
                180                 185                 190

Val Asp Ala Ile Phe Asp Lys His Glu Val Gln Glu Ile Lys Glu Lys
            195                 200                 205

Ile Leu Asn Ser Asp Tyr Asp Val Glu Asp Phe Phe Glu Gly Glu Phe
            210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
                260                 265                 270

Phe Lys Pro Leu Tyr Lys Gln Val Leu Ser Asp Arg Glu Ser Leu Ser
            275                 280                 285

Phe Tyr Gly Glu Gly Tyr Thr Ser Asp Glu Glu Val Leu Glu Val Phe
            290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
                340                 345                 350

Gly Glu Trp Asn Val Ile Arg Asp Lys Trp Asn Ala Glu Tyr Asp Asp
            355                 360                 365

Ile His Leu Lys Lys Lys Ala Val Val Thr Glu Lys Tyr Glu Asp Asp
            370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
            450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510
```

-continued

```
Gln Lys Pro Tyr Ser Lys Asp Lys Phe Lys Leu Tyr Phe Gln Asn Pro
            515                 520                 525
Gln Phe Met Gly Gly Trp Asp Lys Asp Lys Glu Thr Asp Tyr Arg Ala
530                 535                 540
Thr Ile Leu Arg Tyr Gly Ser Lys Tyr Tyr Leu Ala Ile Met Asp Lys
545                 550                 555                 560
Lys Tyr Ala Lys Cys Leu Gln Lys Ile Asp Lys Asp Val Asn Gly
                565                 570                 575
Asn Tyr Glu Lys Ile Asn Tyr Lys Leu Leu Pro Gly Pro Asn Lys Met
            580                 585                 590
Leu Pro Lys Val Phe Phe Ser Lys Lys Trp Met Ala Tyr Tyr Asn Pro
            595                 600                 605
Ser Glu Asp Ile Gln Lys Ile Tyr Lys Asn Gly Thr Phe Lys Lys Gly
            610                 615                 620
Asp Met Phe Asn Leu Asn Asp Cys His Lys Leu Ile Asp Phe Phe Lys
625                 630                 635                 640
Asp Ser Ile Ser Arg Tyr Pro Lys Trp Ser Asn Ala Tyr Asp Phe Asn
                645                 650                 655
Phe Ser Glu Thr Glu Lys Tyr Lys Asp Ile Ala Gly Phe Tyr Arg Glu
            660                 665                 670
Val Glu Glu Gln Gly Tyr Lys Val Ser Phe Glu Ser Ala Ser Lys Lys
            675                 680                 685
Glu Val Asp Lys Leu Val Glu Glu Gly Lys Leu Tyr Met Phe Gln Ile
690                 695                 700
Tyr Asn Lys Asp Phe Asp Lys Ser His Gly Thr Pro Asn Leu His
705                 710                 715                 720
Thr Met Tyr Phe Lys Leu Leu Phe Asp Glu Asn Asn His Gly Gln Ile
                725                 730                 735
Arg Leu Ser Gly Gly Ala Glu Leu Phe Met Arg Arg Ala Ser Leu Lys
            740                 745                 750
Lys Glu Glu Leu Val Val His Pro Ala Asn Ser Pro Ile Ala Asn Lys
            755                 760                 765
Asn Pro Asp Asn Pro Lys Lys Thr Thr Thr Leu Ser Tyr Asp Val Tyr
770                 775                 780
Lys Asp Lys Arg Phe Ser Glu Asp Gln Tyr Glu Leu His Ile Pro Ile
785                 790                 795                 800
Ala Ile Asn Lys Cys Pro Lys Asn Ile Phe Lys Ile Asn Thr Glu Val
                805                 810                 815
Arg Val Leu Leu Lys His Asp Asp Pro Tyr Val Ile Gly Ile Asp
            820                 825                 830
Arg Gly Glu Arg Asn Leu Leu Tyr Ile Val Val Asp Gly Lys Gly
            835                 840                 845
Asn Ile Val Glu Gln Tyr Ser Leu Asn Glu Ile Ile Asn Asn Phe Asn
850                 855                 860
Gly Ile Arg Ile Lys Thr Asp Tyr His Ser Leu Leu Asp Lys Lys Glu
865                 870                 875                 880
Lys Glu Arg Phe Glu Ala Arg Gln Asn Trp Thr Ser Ile Glu Asn Ile
                885                 890                 895
Lys Glu Leu Lys Ala Gly Tyr Ile Ser Gln Val Val His Lys Ile Cys
            900                 905                 910
Glu Leu Val Glu Lys Tyr Asp Ala Val Ile Ala Leu Glu Asp Leu Asn
            915                 920                 925
```

```
Ser Gly Phe Lys Asn Ser Arg Val Lys Val Glu Lys Gln Val Tyr Gln
        930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
            965                 970                 975

Thr Asn Lys Phe Glu Ser Phe Lys Ser Met Ser Thr Gln Asn Gly Phe
        980                 985                 990

Ile Phe Tyr Ile Pro Ala Trp Leu Thr Ser Lys Ile Asp Pro Ser Thr
    995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 2
<211> LENGTH: 1307
<212> TYPE: PRT
<213> ORGANISM: Acidaminococcus sp.

<400> SEQUENCE: 2

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60
```

```
Cys Leu Gln Leu Val Gln Leu Asp Trp Glu Asn Leu Ser Ala Ala Ile
 65                  70                  75                  80

Asp Ser Tyr Arg Lys Glu Lys Thr Glu Thr Arg Asn Ala Leu Ile
                 85                  90                  95

Glu Glu Gln Ala Thr Tyr Arg Asn Ala Ile His Asp Tyr Phe Ile Gly
                100                 105                 110

Arg Thr Asp Asn Leu Thr Asp Ala Ile Asn Lys Arg His Ala Glu Ile
                115                 120                 125

Tyr Lys Gly Leu Phe Lys Ala Glu Leu Phe Asn Gly Lys Val Leu Lys
130                 135                 140

Gln Leu Gly Thr Val Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
                195                 200                 205

Thr Arg Leu Ile Thr Ala Val Pro Ser Leu Arg Glu His Phe Glu Asn
210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
                290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
                370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
                450                 455                 460

Glu Ile Leu Lys Ser Gln Leu Asp Ser Leu Leu Gly Leu Tyr His Leu
465                 470                 475                 480
```

-continued

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
        530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg

```
                900             905              910
Asn Leu Ile Tyr Ile Thr Val Ile Asp Ser Thr Gly Lys Ile Leu Glu
            915             920              925

Gln Arg Ser Leu Asn Thr Ile Gln Gln Phe Asp Tyr Gln Lys Lys Leu
            930             935              940

Asp Asn Arg Glu Lys Glu Arg Val Ala Ala Arg Gln Ala Trp Ser Val
945             950             955              960

Val Gly Thr Ile Lys Asp Leu Lys Gln Gly Tyr Leu Ser Gln Val Ile
            965             970              975

His Glu Ile Val Asp Leu Met Ile His Tyr Gln Ala Val Val Leu
            980             985              990

Glu Asn Leu Asn Phe Gly Phe Lys  Ser Lys Arg Thr Gly  Ile Ala Glu
            995             1000             1005

Lys Ala  Val Tyr Gln Gln Phe  Glu Lys Met Leu Ile  Asp Lys Leu
    1010             1015             1020

Asn Cys  Leu Val Leu Lys Asp  Tyr Pro Ala Glu Lys  Val Gly Gly
    1025             1030             1035

Val Leu  Asn Pro Tyr Gln Leu  Thr Asp Gln Phe Thr  Ser Phe Ala
    1040             1045             1050

Lys Met  Gly Thr Gln Ser Gly  Phe Leu Phe Tyr Val  Pro Ala Pro
    1055             1060             1065

Tyr Thr  Ser Lys Ile Asp Pro  Leu Thr Gly Phe Val  Asp Pro Phe
    1070             1075             1080

Val Trp  Lys Thr Ile Lys Asn  His Glu Ser Arg Lys  His Phe Leu
    1085             1090             1095

Glu Gly  Phe Asp Phe Leu His  Tyr Asp Val Lys Thr  Gly Asp Phe
    1100             1105             1110

Ile Leu  His Phe Lys Met Asn  Arg Asn Leu Ser Phe  Gln Arg Gly
    1115             1120             1125

Leu Pro  Gly Phe Met Pro Ala  Trp Asp Ile Val Phe  Glu Lys Asn
    1130             1135             1140

Glu Thr  Gln Phe Asp Ala Lys  Gly Thr Pro Phe Ile  Ala Gly Lys
    1145             1150             1155

Arg Ile  Val Pro Val Ile Glu  Asn His Arg Phe Thr  Gly Arg Tyr
    1160             1165             1170

Arg Asp  Leu Tyr Pro Ala Asn  Glu Leu Ile Ala Leu  Leu Glu Glu
    1175             1180             1185

Lys Gly  Ile Val Phe Arg Asp  Gly Ser Asn Ile Leu  Pro Lys Leu
    1190             1195             1200

Leu Glu  Asn Asp Asp Ser His  Ala Ile Asp Thr Met  Val Ala Leu
    1205             1210             1215

Ile Arg  Ser Val Leu Gln Met  Arg Asn Ser Asn Ala  Ala Thr Gly
    1220             1225             1230

Glu Asp  Tyr Ile Asn Ser Pro  Val Arg Asp Leu Asn  Gly Val Cys
    1235             1240             1245

Phe Asp  Ser Arg Phe Gln Asn  Pro Glu Trp Pro Met  Asp Ala Asp
    1250             1255             1260

Ala Asn  Gly Ala Tyr His Ile  Ala Leu Lys Gly Gln  Leu Leu Leu
    1265             1270             1275

Asn His  Leu Lys Glu Ser Lys  Asp Leu Lys Leu Gln  Asn Gly Ile
    1280             1285             1290

Ser Asn  Gln Asp Trp Leu Ala  Tyr Ile Gln Glu Leu  Arg Asn
    1295             1300             1305
```

<210> SEQ ID NO 3
<211> LENGTH: 1241
<212> TYPE: PRT
<213> ORGANISM: Utyrivibrio proteoclasticus

<400> SEQUENCE: 3

Met Leu Leu Tyr Glu Asn Tyr Thr Lys Arg Asn Gln Ile Thr Lys Ser
1               5                   10                  15

Leu Arg Leu Glu Leu Arg Pro Gln Gly Lys Thr Leu Arg Asn Ile Lys
            20                  25                  30

Glu Leu Asn Leu Leu Glu Gln Asp Lys Ala Ile Tyr Ala Leu Leu Glu
        35                  40                  45

Arg Leu Lys Pro Val Ile Asp Glu Gly Ile Lys Asp Ile Ala Arg Asp
    50                  55                  60

Thr Leu Lys Asn Cys Glu Leu Ser Phe Glu Lys Leu Tyr Glu His Phe
65                  70                  75                  80

Leu Ser Gly Asp Lys Lys Ala Tyr Ala Lys Glu Ser Glu Arg Leu Lys
                85                  90                  95

Lys Glu Ile Val Lys Thr Leu Ile Lys Asn Leu Pro Glu Gly Ile Gly
            100                 105                 110

Lys Ile Ser Glu Ile Asn Ser Ala Lys Tyr Leu Asn Gly Val Leu Tyr
        115                 120                 125

Asp Phe Ile Asp Lys Thr His Lys Asp Ser Glu Glu Lys Gln Asn Ile
    130                 135                 140

Leu Ser Asp Ile Leu Glu Thr Lys Gly Tyr Leu Ala Leu Phe Ser Lys
145                 150                 155                 160

Phe Leu Thr Ser Arg Ile Thr Thr Leu Glu Gln Ser Met Pro Lys Arg
                165                 170                 175

Val Ile Glu Asn Phe Glu Ile Tyr Ala Ala Asn Ile Pro Lys Met Gln
            180                 185                 190

Asp Ala Leu Glu Arg Gly Ala Val Ser Phe Ala Ile Glu Tyr Glu Ser
        195                 200                 205

Ile Cys Ser Val Asp Tyr Tyr Asn Gln Ile Leu Ser Gln Glu Asp Ile
    210                 215                 220

Asp Ser Tyr Asn Arg Leu Ile Ser Gly Ile Met Asp Glu Asp Gly Ala
225                 230                 235                 240

Lys Glu Lys Gly Ile Asn Gln Thr Ile Ser Glu Lys Asn Ile Lys Ile
                245                 250                 255

Lys Ser Glu His Leu Glu Glu Lys Pro Phe Arg Ile Leu Lys Gln Leu
            260                 265                 270

His Lys Gln Ile Leu Glu Glu Arg Glu Lys Ala Phe Thr Ile Asp His
        275                 280                 285

Ile Asp Ser Asp Glu Glu Val Val Gln Val Thr Lys Glu Ala Phe Glu
    290                 295                 300

Gln Thr Lys Glu Gln Trp Glu Asn Ile Lys Lys Ile Asn Gly Phe Tyr
305                 310                 315                 320

Ala Lys Asp Pro Gly Asp Ile Thr Leu Phe Ile Val Val Gly Pro Asn
                325                 330                 335

Gln Thr His Val Leu Ser Gln Leu Ile Tyr Gly Glu His Asp Arg Ile
            340                 345                 350

Arg Leu Leu Leu Glu Glu Tyr Glu Lys Asn Thr Leu Glu Val Leu Pro
        355                 360                 365

Arg Arg Thr Lys Ser Glu Asp Ala Arg Tyr Asp Lys Phe Val Asn Ala

```
                  370                 375                 380
Val Pro Lys Lys Val Ala Lys Glu Ser His Thr Phe Asp Gly Leu Gln
385                 390                 395                 400

Lys Met Thr Gly Asp Asp Arg Leu Phe Ile Leu Tyr Arg Asp Glu Leu
                405                 410                 415

Ala Arg Asn Tyr Met Arg Ile Lys Glu Ala Tyr Gly Thr Phe Glu Arg
                420                 425                 430

Asp Ile Leu Lys Ser Arg Arg Gly Ile Lys Gly Asn Arg Asp Val Gln
                435                 440                 445

Glu Ser Leu Val Ser Phe Tyr Asp Glu Leu Thr Lys Phe Arg Ser Ala
                450                 455                 460

Leu Arg Ile Ile Asn Ser Gly Asn Asp Glu Lys Ala Asp Pro Ile Phe
465                 470                 475                 480

Tyr Asn Thr Phe Asp Gly Ile Phe Glu Lys Ala Asn Arg Thr Tyr Lys
                485                 490                 495

Ala Glu Asn Leu Cys Arg Asn Tyr Val Thr Lys Ser Pro Ala Asp Asp
                500                 505                 510

Ala Arg Ile Met Ala Ser Cys Leu Gly Thr Pro Ala Arg Leu Arg Thr
                515                 520                 525

His Trp Trp Asn Gly Glu Glu Asn Phe Ala Ile Asn Asp Val Ala Met
                530                 535                 540

Ile Arg Arg Gly Asp Glu Tyr Tyr Tyr Phe Val Leu Thr Pro Asp Val
545                 550                 555                 560

Lys Pro Val Asp Leu Lys Thr Lys Asp Glu Thr Asp Ala Gln Ile Phe
                565                 570                 575

Val Gln Arg Lys Gly Ala Lys Ser Phe Leu Gly Leu Pro Lys Ala Leu
                580                 585                 590

Phe Lys Cys Ile Leu Glu Pro Tyr Phe Glu Ser Pro Glu His Lys Asn
                595                 600                 605

Asp Lys Asn Cys Val Ile Glu Glu Tyr Val Ser Lys Pro Leu Thr Ile
                610                 615                 620

Asp Arg Arg Ala Tyr Asp Ile Phe Lys Asn Gly Thr Phe Lys Lys Thr
625                 630                 635                 640

Asn Ile Gly Ile Asp Gly Leu Thr Glu Glu Lys Phe Lys Asp Asp Cys
                645                 650                 655

Arg Tyr Leu Ile Asp Val Tyr Lys Glu Phe Ile Ala Val Tyr Thr Arg
                660                 665                 670

Tyr Ser Cys Phe Asn Met Ser Gly Leu Lys Arg Ala Asp Glu Tyr Asn
                675                 680                 685

Asp Ile Gly Glu Phe Phe Ser Asp Val Asp Thr Arg Leu Cys Thr Met
                690                 695                 700

Glu Trp Ile Pro Val Ser Phe Glu Arg Ile Asn Asp Met Val Asp Lys
705                 710                 715                 720

Lys Glu Gly Leu Leu Phe Leu Val Arg Ser Met Phe Leu Tyr Asn Arg
                725                 730                 735

Pro Arg Lys Pro Tyr Glu Arg Thr Phe Ile Gln Leu Phe Ser Asp Ser
                740                 745                 750

Asn Met Glu His Thr Ser Met Leu Leu Asn Ser Arg Ala Met Ile Gln
                755                 760                 765

Tyr Arg Ala Ala Ser Leu Pro Arg Arg Val Thr His Lys Lys Gly Ser
                770                 775                 780

Ile Leu Val Ala Leu Arg Asp Ser Asn Gly Glu His Ile Pro Met His
785                 790                 795                 800
```

Ile Arg Glu Ala Ile Tyr Lys Met Lys Asn Asn Phe Asp Ile Ser Ser
                805                 810                 815

Glu Asp Phe Ile Met Ala Lys Ala Tyr Leu Ala Glu His Asp Val Ala
            820                 825                 830

Ile Lys Lys Ala Asn Glu Asp Ile Ile Arg Asn Arg Arg Tyr Thr Glu
            835                 840                 845

Asp Lys Phe Phe Leu Ser Leu Ser Tyr Thr Lys Asn Ala Asp Ile Ser
850                 855                 860

Ala Arg Thr Leu Asp Tyr Ile Asn Asp Lys Val Glu Glu Asp Thr Gln
865                 870                 875                 880

Asp Ser Arg Met Ala Val Ile Val Thr Arg Asn Leu Lys Asp Leu Thr
            885                 890                 895

Tyr Val Ala Val Val Asp Glu Lys Asn Asn Val Leu Glu Glu Lys Ser
            900                 905                 910

Leu Asn Glu Ile Asp Gly Val Asn Tyr Arg Glu Leu Leu Lys Glu Arg
            915                 920                 925

Thr Lys Ile Lys Tyr His Asp Lys Thr Arg Leu Trp Gln Tyr Asp Val
930                 935                 940

Ser Ser Lys Gly Leu Lys Glu Ala Tyr Val Glu Leu Ala Val Thr Gln
945                 950                 955                 960

Ile Ser Lys Leu Ala Thr Lys Tyr Asn Ala Val Val Val Glu Ser
            965                 970                 975

Met Ser Ser Thr Phe Lys Asp Lys Phe Ser Phe Leu Asp Glu Gln Ile
            980                 985                 990

Phe Lys Ala Phe Glu Ala Arg Leu Cys Ala Arg Met Ser Asp Leu Ser
            995                 1000                1005

Phe Asn Thr Ile Lys Glu Gly Glu Ala Gly Ser Ile Ser Asn Pro
    1010                1015                1020

Ile Gln Val Ser Asn Asn Asn Gly Asn Ser Tyr Gln Asp Gly Val
    1025                1030                1035

Ile Tyr Phe Leu Asn Asn Ala Tyr Thr Arg Thr Leu Cys Pro Asp
    1040                1045                1050

Thr Gly Phe Val Asp Val Phe Asp Lys Thr Arg Leu Ile Thr Met
    1055                1060                1065

Gln Ser Lys Arg Gln Phe Ala Lys Met Lys Asp Ile Arg Ile
    1070                1075                1080

Asp Asp Gly Glu Met Leu Phe Thr Phe Asn Leu Glu Glu Tyr Pro
    1085                1090                1095

Thr Lys Arg Leu Leu Asp Arg Lys Glu Trp Thr Val Lys Ile Ala
    1100                1105                1110

Gly Asp Gly Ser Tyr Phe Asp Lys Asp Lys Gly Glu Tyr Val Tyr
    1115                1120                1125

Val Asn Asp Ile Val Arg Glu Gln Ile Ile Pro Ala Leu Leu Glu
    1130                1135                1140

Asp Lys Ala Val Phe Asp Gly Asn Met Ala Glu Lys Phe Leu Asp
    1145                1150                1155

Lys Thr Ala Ile Ser Gly Lys Ser Val Glu Leu Ile Tyr Lys Trp
    1160                1165                1170

Phe Ala Asn Ala Leu Tyr Gly Ile Ile Thr Lys Lys Asp Gly Glu
    1175                1180                1185

Lys Ile Tyr Arg Ser Pro Ile Thr Gly Thr Glu Ile Asp Val Ser
    1190                1195                1200

```
Lys Asn Thr Thr Tyr Asn Phe Gly Lys Lys Phe Met Phe Lys Gln
    1205                1210                1215

Glu Tyr Arg Gly Asp Gly Asp Phe Leu Asp Ala Phe Leu Asn Tyr
    1220                1225                1230

Met Gln Ala Gln Asp Ile Ala Val
    1235                1240

<210> SEQ ID NO 4
<211> LENGTH: 1238
<212> TYPE: PRT
<213> ORGANISM: Candidatus Methanoplasma termitum

<400> SEQUENCE: 4

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
            20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Lys Phe Ile Asp Glu
    50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Val Phe Leu
                85                  90                  95

Ser Glu Gln Lys Arg Met Arg Gln Glu Ile Val Ser Glu Phe Lys Lys
            100                 105                 110

Asp Asp Arg Phe Lys Asp Leu Phe Ser Lys Lys Leu Phe Ser Glu Leu
        115                 120                 125

Leu Lys Glu Glu Ile Tyr Lys Lys Gly Asn His Gln Glu Ile Asp Ala
    130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
            180                 185                 190

Lys Tyr Gln Glu Ala Arg Lys Lys Tyr Pro Glu Trp Ile Ile Lys Ala
        195                 200                 205

Glu Ser Ala Leu Val Ala His Asn Ile Lys Met Asp Ile Val Phe Ser
    210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Gly Lys Ser Ser
            260                 265                 270

Lys Gly Arg Ile His Met Thr Pro Leu Phe Lys Gln Ile Leu Ser Glu
        275                 280                 285

Lys Glu Ser Phe Ser Tyr Ile Pro Asp Val Phe Thr Glu Asp Ser Gln
    290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335
```

-continued

Glu Tyr Asp Thr Glu Arg Ile Tyr Ile Arg Gln Ala Asp Ile Asn Arg
            340                 345                 350

Val Ser Asn Val Ile Phe Gly Glu Trp Gly Thr Leu Gly Gly Leu Met
            355                 360                 365

Arg Glu Tyr Lys Ala Asp Ser Ile Asn Asp Ile Asn Leu Glu Arg Thr
            370                 375                 380

Cys Lys Lys Val Asp Lys Trp Leu Asp Ser Lys Glu Phe Ala Leu Ser
385                 390                 395                 400

Asp Val Leu Glu Ala Ile Asp Arg Thr Gly Asn Asn Asp Ala Phe Asn
            405                 410                 415

Glu Tyr Ile Ser Lys Met Arg Thr Ala Arg Glu Lys Ile Asp Ala Ala
            420                 425                 430

Arg Lys Glu Met Lys Phe Ile Ser Glu Lys Ile Ser Gly Asp Glu Glu
            435                 440                 445

Ser Ile His Ile Ile Lys Thr Leu Leu Asp Ser Val Gln Gln Phe Leu
            450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
            485                 490                 495

Val Pro Leu Tyr Asn Lys Val Arg Asn Tyr Leu Thr Lys Asn Asn Leu
            500                 505                 510

Asn Thr Lys Lys Ile Lys Leu Asn Phe Lys Asn Pro Thr Leu Ala Asn
            515                 520                 525

Gly Trp Asp Gln Asn Lys Val Tyr Asp Tyr Ala Ser Leu Ile Phe Leu
            530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
            565                 570                 575

Met Val Tyr Lys Gln Ile Pro Gly Pro Asn Lys Asn Leu Arg Pro Val
            580                 585                 590

Phe Leu Thr Ser Thr Lys Gly Lys Lys Glu Tyr Lys Pro Ser Lys Glu
            595                 600                 605

Ile Ile Glu Gly Tyr Glu Ala Asp Lys His Ile Arg Gly Asp Lys Phe
            610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
            645                 650                 655

Glu Ser Tyr Gly Asp Ile Ser Glu Phe Tyr Leu Asp Val Glu Lys Gln
            660                 665                 670

Gly Tyr Arg Met His Phe Glu Asn Ile Ser Ala Glu Thr Ile Asp Glu
            675                 680                 685

Tyr Val Glu Lys Gly Asp Leu Phe Leu Phe Gln Ile Tyr Asn Lys Asp
            690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Lys Leu
            725                 730                 735

Asn Gly Glu Ala Glu Leu Phe Tyr Arg Asp Lys Ser Asp Ile Lys Glu
            740                 745                 750

```
Ile Val His Arg Glu Gly Glu Ile Leu Val Asn Arg Thr Tyr Asn Gly
            755                 760                 765

Arg Thr Pro Val Pro Asp Lys Ile His Lys Leu Thr Asp Tyr His
770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
                805                 810                 815

Leu Asn Asp Lys Ile Tyr Phe His Val Pro Leu Thr Leu Asn Phe Lys
            820                 825                 830

Ala Asn Gly Lys Lys Asn Leu Asn Lys Met Val Ile Glu Lys Phe Leu
            835                 840                 845

Ser Asp Glu Lys Ala His Ile Ile Gly Ile Asp Arg Gly Glu Arg Asn
850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
                900                 905                 910

Gly Lys Ile Lys Asp Leu Lys Glu Gly Tyr Leu Ser Lys Ala Val His
            915                 920                 925

Glu Ile Thr Lys Met Ala Ile Gln Tyr Asn Ala Ile Val Val Met Glu
            930                 935                 940

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
                965                 970                 975

Val Phe Lys Asp Ala Pro Asp Glu Ser Pro Gly Gly Val Leu Asn Ala
                980                 985                 990

Tyr Gln Leu Thr Asn Pro Leu Glu Ser Phe Ala Lys Leu Gly Lys Gln
            995                 1000                1005

Thr Gly Ile Leu Phe Tyr Val Pro Ala Ala Tyr Thr Ser Lys Ile
    1010                1015                1020

Asp Pro Thr Thr Gly Phe Val Asn Leu Phe Asn Thr Ser Ser Lys
    1025                1030                1035

Thr Asn Ala Gln Glu Arg Lys Glu Phe Leu Gln Lys Phe Glu Ser
    1040                1045                1050

Ile Ser Tyr Ser Ala Lys Asp Gly Gly Ile Phe Ala Phe Ala Phe
    1055                1060                1065

Asp Tyr Arg Lys Phe Gly Thr Ser Lys Thr Asp His Lys Asn Val
    1070                1075                1080

Trp Thr Ala Tyr Thr Asn Gly Glu Arg Met Arg Tyr Ile Lys Glu
    1085                1090                1095

Lys Lys Arg Asn Glu Leu Phe Asp Pro Ser Lys Glu Ile Lys Glu
    1100                1105                1110

Ala Leu Thr Ser Ser Gly Ile Lys Tyr Asp Gly Gly Gln Asn Ile
    1115                1120                1125

Leu Pro Asp Ile Leu Arg Ser Asn Asn Asn Gly Leu Ile Tyr Thr
    1130                1135                1140

Met Tyr Ser Ser Phe Ile Ala Ala Ile Gln Met Arg Val Tyr Asp
    1145                1150                1155

Gly Lys Glu Asp Tyr Ile Ile Ser Pro Ile Lys Asn Ser Lys Gly
```

```
              1160                1165                1170

Glu Phe Phe Arg Thr Asp Pro Lys Arg Arg Glu Leu Pro Ile Asp
    1175                1180                1185

Ala Asp Ala Asn Gly Ala Tyr Asn Ile Ala Leu Arg Gly Glu Leu
    1190                1195                1200

Thr Met Arg Ala Ile Ala Glu Lys Phe Asp Pro Asp Ser Glu Lys
    1205                1210                1215

Met Ala Lys Leu Glu Leu Lys His Lys Asp Trp Phe Glu Phe Met
    1220                1225                1230

Gln Thr Arg Gly Asp
    1235

<210> SEQ ID NO 5
<211> LENGTH: 1281
<212> TYPE: PRT
<213> ORGANISM: Eubacterium eligens

<400> SEQUENCE: 5

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
            20                  25                  30

Gln Glu His Ile Ile Gln Asn Gly Leu Ile Gln Glu Asp Glu Leu Arg
        35                  40                  45

Gln Glu Lys Ser Thr Glu Leu Lys Asn Ile Met Asp Asp Tyr Tyr Arg
    50                  55                  60

Glu Tyr Ile Asp Lys Ser Leu Ser Gly Val Thr Asp Leu Asp Phe Thr
65                  70                  75                  80

Leu Leu Phe Glu Leu Met Asn Leu Val Gln Ser Ser Pro Ser Lys Asp
                85                  90                  95

Asn Lys Lys Ala Leu Glu Lys Glu Gln Ser Lys Met Arg Glu Gln Ile
            100                 105                 110

Cys Thr His Leu Gln Ser Asp Ser Asn Tyr Lys Asn Ile Phe Asn Ala
        115                 120                 125

Lys Leu Leu Lys Glu Ile Leu Pro Asp Phe Ile Lys Asn Tyr Asn Gln
    130                 135                 140

Tyr Asp Val Lys Asp Lys Ala Gly Lys Leu Glu Thr Leu Ala Leu Phe
145                 150                 155                 160

Asn Gly Phe Ser Thr Tyr Phe Thr Asp Phe Phe Glu Lys Arg Lys Asn
                165                 170                 175

Val Phe Thr Lys Glu Ala Val Ser Thr Ser Ile Ala Tyr Arg Ile Val
            180                 185                 190

His Glu Asn Ser Leu Ile Phe Leu Ala Asn Met Thr Ser Tyr Lys Lys
        195                 200                 205

Ile Ser Glu Lys Ala Leu Asp Glu Ile Glu Val Ile Glu Lys Asn Asn
    210                 215                 220

Gln Asp Lys Met Gly Asp Trp Glu Leu Asn Gln Ile Phe Asn Pro Asp
225                 230                 235                 240

Phe Tyr Asn Met Val Leu Ile Gln Ser Gly Ile Asp Phe Tyr Asn Glu
                245                 250                 255

Ile Cys Gly Val Val Asn Ala His Met Asn Leu Tyr Cys Gln Gln Thr
            260                 265                 270

Lys Asn Asn Tyr Asn Leu Phe Lys Met Arg Lys Leu His Lys Gln Ile
        275                 280                 285
```

```
Leu Ala Tyr Thr Ser Thr Ser Phe Glu Val Pro Lys Met Phe Glu Asp
    290                 295                 300
Asp Met Ser Val Tyr Asn Ala Val Asn Ala Phe Ile Asp Glu Thr Glu
305                 310                 315                 320
Lys Gly Asn Ile Ile Gly Lys Leu Lys Asp Ile Val Asn Lys Tyr Asp
                325                 330                 335
Glu Leu Asp Glu Lys Arg Ile Tyr Ile Ser Lys Asp Phe Tyr Glu Thr
            340                 345                 350
Leu Ser Cys Phe Met Ser Gly Asn Trp Asn Leu Ile Thr Gly Cys Val
        355                 360                 365
Glu Asn Phe Tyr Asp Glu Asn Ile His Ala Lys Gly Lys Ser Lys Glu
    370                 375                 380
Glu Lys Val Lys Lys Ala Val Lys Glu Asp Lys Tyr Lys Ser Ile Asn
385                 390                 395                 400
Asp Val Asn Asp Leu Val Glu Lys Tyr Ile Asp Glu Lys Glu Arg Asn
                405                 410                 415
Glu Phe Lys Asn Ser Asn Ala Lys Gln Tyr Ile Arg Glu Ile Ser Asn
            420                 425                 430
Ile Ile Thr Asp Thr Glu Thr Ala His Leu Glu Tyr Asp Asp His Ile
        435                 440                 445
Ser Leu Ile Glu Ser Glu Glu Lys Ala Asp Glu Met Lys Lys Arg Leu
    450                 455                 460
Asp Met Tyr Met Asn Met Tyr His Trp Ala Lys Ala Phe Ile Val Asp
465                 470                 475                 480
Glu Val Leu Asp Arg Asp Glu Met Phe Tyr Ser Asp Ile Asp Asp Ile
                485                 490                 495
Tyr Asn Ile Leu Glu Asn Ile Val Pro Leu Tyr Asn Arg Val Arg Asn
            500                 505                 510
Tyr Val Thr Gln Lys Pro Tyr Asn Ser Lys Ile Lys Leu Asn Phe
        515                 520                 525
Gln Ser Pro Thr Leu Ala Asn Gly Trp Ser Gln Ser Lys Glu Phe Asp
    530                 535                 540
Asn Asn Ala Ile Ile Leu Ile Arg Asp Asn Lys Tyr Tyr Leu Ala Ile
545                 550                 555                 560
Phe Asn Ala Lys Asn Lys Pro Asp Lys Lys Ile Ile Gln Gly Asn Ser
                565                 570                 575
Asp Lys Lys Asn Asp Asn Asp Tyr Lys Lys Met Val Tyr Asn Leu Leu
            580                 585                 590
Pro Gly Ala Asn Lys Met Leu Pro Lys Val Phe Leu Ser Lys Lys Gly
        595                 600                 605
Ile Glu Thr Phe Lys Pro Ser Asp Tyr Ile Ile Ser Gly Tyr Asn Ala
    610                 615                 620
His Lys His Ile Lys Thr Ser Glu Asn Phe Asp Ile Ser Phe Cys Arg
625                 630                 635                 640
Asp Leu Ile Asp Tyr Phe Lys Asn Ser Ile Glu Lys His Ala Glu Trp
                645                 650                 655
Arg Lys Tyr Glu Phe Lys Phe Ser Ala Thr Asp Ser Tyr Ser Asp Ile
            660                 665                 670
Ser Glu Phe Tyr Arg Glu Val Glu Met Gln Gly Tyr Arg Ile Asp Trp
        675                 680                 685
Thr Tyr Ile Ser Glu Ala Asp Ile Asn Lys Leu Asp Glu Glu Gly Lys
    690                 695                 700
Ile Tyr Leu Phe Gln Ile Tyr Asn Lys Asp Phe Ala Glu Asn Ser Thr
```

-continued

```
          705                 710                 715                 720
Gly Lys Glu Asn Leu His Thr Met Tyr Phe Lys Asn Ile Phe Ser Glu
                  725                 730                 735
Glu Asn Leu Asp Lys Ile Ile Lys Leu Asn Gly Gln Ala Glu Leu Phe
                  740                 745                 750
Tyr Arg Arg Ala Ser Val Lys Asn Pro Val Lys His Lys Lys Asp Ser
                  755                 760                 765
Val Leu Val Asn Lys Thr Tyr Lys Asn Gln Leu Asp Asn Gly Asp Val
                  770                 775                 780
Val Arg Ile Pro Ile Pro Asp Asp Ile Tyr Asn Glu Ile Tyr Lys Met
785                 790                 795                 800
Tyr Asn Gly Tyr Ile Lys Glu Ser Asp Leu Ser Glu Ala Ala Lys Glu
                  805                 810                 815
Tyr Leu Asp Lys Val Glu Val Arg Thr Ala Gln Lys Asp Ile Val Lys
                  820                 825                 830
Asp Tyr Arg Tyr Thr Val Asp Lys Tyr Phe Ile His Thr Pro Ile Thr
                  835                 840                 845
Ile Asn Tyr Lys Val Thr Ala Arg Asn Asn Val Asn Asp Met Val Val
                  850                 855                 860
Lys Tyr Ile Ala Gln Asn Asp Asp Ile His Val Ile Gly Ile Asp Arg
865                 870                 875                 880
Gly Glu Arg Asn Leu Ile Tyr Ile Ser Val Ile Asp Ser His Gly Asn
                  885                 890                 895
Ile Val Lys Gln Lys Ser Tyr Asn Ile Leu Asn Asn Tyr Asp Tyr Lys
                  900                 905                 910
Lys Lys Leu Val Glu Lys Glu Lys Thr Arg Glu Tyr Ala Arg Lys Asn
                  915                 920                 925
Trp Lys Ser Ile Gly Asn Ile Lys Glu Leu Lys Glu Gly Tyr Ile Ser
                  930                 935                 940
Gly Val Val His Glu Ile Ala Met Leu Ile Val Glu Tyr Asn Ala Ile
945                 950                 955                 960
Ile Ala Met Glu Asp Leu Asn Tyr Gly Phe Lys Arg Gly Arg Phe Lys
                  965                 970                 975
Val Glu Arg Gln Val Tyr Gln Lys Phe Glu Ser Met Leu Ile Asn Lys
                  980                 985                 990
Leu Asn Tyr Phe Ala Ser Lys Glu Lys Ser Val Asp Glu Pro Gly Gly
                  995                 1000                1005
Leu Leu Lys Gly Tyr Gln Leu Thr Tyr Val Pro Asp Asn Ile Lys
                  1010                1015                1020
Asn Leu Gly Lys Gln Cys Gly Val Ile Phe Tyr Val Pro Ala Ala
                  1025                1030                1035
Phe Thr Ser Lys Ile Asp Pro Ser Thr Gly Phe Ile Ser Ala Phe
                  1040                1045                1050
Asn Phe Lys Ser Ile Ser Thr Asn Ala Ser Arg Lys Gln Phe Phe
                  1055                1060                1065
Met Gln Phe Asp Glu Ile Arg Tyr Cys Ala Glu Lys Asp Met Phe
                  1070                1075                1080
Ser Phe Gly Phe Asp Tyr Asn Asn Phe Asp Thr Tyr Asn Ile Thr
                  1085                1090                1095
Met Gly Lys Thr Gln Trp Thr Val Tyr Thr Asn Gly Glu Arg Leu
                  1100                1105                1110
Gln Ser Glu Phe Asn Asn Ala Arg Arg Thr Gly Lys Thr Lys Ser
                  1115                1120                1125
```

```
Ile Asn  Leu Thr Glu Thr Ile  Lys Leu Leu Leu Glu  Asp Asn Glu
    1130                 1135                 1140

Ile Asn  Tyr Ala Asp Gly His  Asp Ile Arg Ile Asp  Met Glu Lys
    1145                 1150                 1155

Met Asp  Glu Asp Lys Lys Ser  Glu Phe Phe Ala Gln  Leu Leu Ser
    1160                 1165                 1170

Leu Tyr  Lys Leu Thr Val Gln  Met Arg Asn Ser Tyr  Thr Glu Ala
    1175                 1180                 1185

Glu Glu  Gln Glu Asn Gly Ile  Ser Tyr Asp Lys Ile  Ile Ser Pro
    1190                 1195                 1200

Val Ile  Asn Asp Glu Gly Glu  Phe Phe Asp Ser Asp  Asn Tyr Lys
    1205                 1210                 1215

Glu Ser  Asp Asp Lys Glu Cys  Lys Met Pro Lys Asp  Ala Asp Ala
    1220                 1225                 1230

Asn Gly  Ala Tyr Cys Ile Ala  Leu Lys Gly Leu Tyr  Glu Val Leu
    1235                 1240                 1245

Lys Ile  Lys Ser Glu Trp Thr  Glu Asp Gly Phe Asp  Arg Asn Cys
    1250                 1255                 1260

Leu Lys  Leu Pro His Ala Glu  Trp Leu Asp Phe Ile  Gln Asn Lys
    1265                 1270                 1275

Arg Tyr  Glu
    1280
```

<210> SEQ ID NO 6
<211> LENGTH: 1300
<212> TYPE: PRT
<213> ORGANISM: Francisella novicida

<400> SEQUENCE: 6

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Val Asn Tyr Ser Ser
            180                 185                 190

Asn Asp Ile Pro Thr Ser Ile Ile Tyr Arg Ile Val Asp Asp Asn Leu
```

```
            195                 200                 205
Pro Lys Phe Leu Glu Asn Lys Ala Lys Tyr Glu Ser Leu Lys Asp Lys
210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
            245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
            325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
            370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
            405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
            435                 440                 445

Lys Tyr Leu Ser Leu Glu Thr Ile Lys Leu Ala Leu Glu Glu Phe Asn
450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
            485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
            515                 520                 525

Leu Leu Asp Gln Thr Asn Asn Leu Leu His Lys Leu Lys Ile Phe His
            530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
            565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
            610                 615                 620
```

```
Asp Asp Lys Tyr Tyr Leu Gly Val Met Asn Lys Asn Asn Lys Ile
625                 630                 635                 640

Phe Asp Asp Lys Ala Ile Lys Glu Asn Lys Gly Glu Gly Tyr Lys Lys
            645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
            725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
            805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
            885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010            1015               1020

Tyr Gln Lys Leu Glu Lys Met Leu Ile Glu Lys Leu Asn Tyr Leu
    1025            1030               1035
```

```
Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 7
<211> LENGTH: 1206
<212> TYPE: PRT
<213> ORGANISM: Unknown
<220> FEATURE:
<223> OTHER INFORMATION: Lachnospiraceae bacterium

<400> SEQUENCE: 7

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
                20                  25                  30

Asn Asn Ile Leu Glu Ser Asp Val Lys Arg Lys Gln Asn Tyr Glu His
            35                  40                  45

Val Lys Gly Ile Leu Asp Glu Tyr His Lys Gln Leu Ile Asn Glu Ala
        50                  55                  60

Leu Asp Asn Cys Thr Leu Pro Ser Leu Lys Ile Ala Ala Glu Ile Tyr
65                  70                  75                  80
```

-continued

```
Leu Lys Asn Gln Lys Glu Val Ser Asp Arg Glu Asp Phe Asn Lys Thr
                85                  90                  95
Gln Asp Leu Leu Arg Lys Glu Val Glu Lys Leu Lys Ala His Glu
            100                 105                 110
Asn Phe Thr Lys Ile Gly Lys Lys Asp Ile Leu Asp Leu Leu Glu Lys
            115                 120                 125
Leu Pro Ser Ile Ser Glu Asp Tyr Asn Ala Leu Glu Ser Phe Arg
        130                 135                 140
Asn Phe Tyr Thr Tyr Phe Thr Ser Tyr Asn Lys Val Arg Glu Asn Leu
145                 150                 155                 160
Tyr Ser Asp Lys Glu Lys Ser Ser Thr Val Ala Tyr Arg Leu Ile Asn
                165                 170                 175
Glu Asn Phe Pro Lys Phe Leu Asp Asn Val Lys Ser Tyr Arg Phe Val
            180                 185                 190
Lys Thr Ala Gly Ile Leu Ala Asp Gly Leu Gly Glu Glu Gln Asp
        195                 200                 205
Ser Leu Phe Ile Val Glu Thr Phe Asn Lys Thr Leu Thr Gln Asp Gly
        210                 215                 220
Ile Asp Thr Tyr Asn Ser Gln Val Gly Lys Ile Asn Ser Ser Ile Asn
225                 230                 235                 240
Leu Tyr Asn Gln Lys Asn Gln Lys Ala Asn Gly Phe Arg Lys Ile Pro
                245                 250                 255
Lys Met Lys Met Leu Tyr Lys Gln Ile Leu Ser Asp Arg Glu Glu Ser
            260                 265                 270
Phe Ile Asp Glu Phe Gln Ser Asp Glu Val Leu Ile Asp Asn Val Glu
            275                 280                 285
Ser Tyr Gly Ser Val Leu Ile Glu Ser Leu Lys Ser Ser Lys Val Ser
        290                 295                 300
Ala Phe Phe Asp Ala Leu Arg Glu Ser Lys Gly Lys Asn Val Tyr Val
305                 310                 315                 320
Lys Asn Asp Leu Ala Lys Thr Ala Met Ser Val Ile Val Phe Glu Asn
                325                 330                 335
Trp Arg Thr Phe Asp Asp Leu Leu Asn Gln Glu Tyr Asp Leu Ala Asn
            340                 345                 350
Glu Asn Lys Lys Lys Asp Asp Lys Tyr Phe Glu Lys Arg Gln Lys Glu
            355                 360                 365
Leu Lys Lys Asn Lys Ser Tyr Ser Leu Glu His Leu Cys Asn Leu Ser
        370                 375                 380
Glu Asp Ser Cys Asn Leu Ile Glu Asn Tyr Ile His Gln Ile Ser Asp
385                 390                 395                 400
Asp Ile Glu Asn Ile Ile Asn Asn Glu Thr Phe Leu Arg Ile Val
                405                 410                 415
Ile Asn Glu His Asp Arg Ser Arg Lys Leu Ala Lys Asn Arg Lys Ala
            420                 425                 430
Val Lys Ala Ile Lys Asp Phe Leu Asp Ser Ile Lys Val Leu Glu Arg
        435                 440                 445
Glu Leu Lys Leu Ile Asn Ser Ser Gly Gln Glu Leu Glu Lys Asp Leu
        450                 455                 460
Ile Val Tyr Ser Ala His Glu Glu Leu Leu Val Glu Leu Lys Gln Val
465                 470                 475                 480
Asp Ser Leu Tyr Asn Met Thr Arg Asn Tyr Leu Thr Lys Lys Pro Phe
                485                 490                 495
Ser Thr Glu Lys Val Lys Leu Asn Phe Asn Arg Ser Thr Leu Leu Asn
```

```
                500                 505                 510
Gly Trp Asp Arg Asn Lys Glu Thr Asp Asn Leu Gly Val Leu Leu Leu
            515                 520                 525

Lys Asp Gly Lys Tyr Tyr Leu Gly Ile Met Asn Thr Ser Ala Asn Lys
            530                 535                 540

Ala Phe Val Asn Pro Val Ala Lys Thr Glu Lys Val Phe Lys Lys
545                 550                 555                 560

Val Asp Tyr Lys Leu Leu Pro Val Pro Asn Gln Met Leu Pro Lys Val
                565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
            595                 600                 605

Leu Glu Asp Cys His Asn Leu Ile Asp Phe Phe Lys Glu Ser Ile Ser
    610                 615                 620

Lys His Glu Asp Trp Ser Lys Phe Gly Phe Lys Phe Asp Thr Gln Ala
625                 630                 635                 640

Ser Tyr Asn Asp Ile Ser Glu Phe Tyr Arg Glu Val Glu Lys Gln Gly
                645                 650                 655

Tyr Lys Leu Thr Tyr Thr Asp Ile Asp Glu Thr Tyr Ile Asn Asp Leu
                660                 665                 670

Ile Glu Arg Asn Glu Leu Tyr Leu Phe Gln Ile Tyr Asn Lys Asp Phe
            675                 680                 685

Ser Met Tyr Ser Lys Gly Lys Leu Asn Leu His Thr Leu Tyr Phe Met
            690                 695                 700

Met Leu Phe Asp Gln Arg Asn Ile Asp Asp Val Val Tyr Lys Leu Asn
705                 710                 715                 720

Gly Glu Ala Glu Val Phe Tyr Arg Pro Ala Ser Ile Ser Glu Asp Glu
                725                 730                 735

Leu Ile Ile His Lys Ala Gly Glu Glu Ile Lys Asn Lys Asn Pro Asn
                740                 745                 750

Arg Ala Arg Thr Lys Glu Thr Ser Thr Phe Ser Tyr Asp Ile Val Lys
            755                 760                 765

Asp Lys Arg Tyr Ser Lys Asp Lys Phe Thr Leu His Ile Pro Ile Thr
            770                 775                 780

Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
                805                 810                 815

Gly Glu Arg Asn Leu Leu Tyr Val Val Val Ile Asp Ser Lys Gly Asn
                820                 825                 830

Ile Leu Glu Gln Ile Ser Leu Asn Ser Ile Ile Asn Lys Glu Tyr Asp
            835                 840                 845

Ile Glu Thr Asp Tyr His Ala Leu Leu Asp Glu Arg Glu Gly Gly Arg
            850                 855                 860

Asp Lys Ala Arg Lys Asp Trp Asn Thr Val Glu Asn Ile Arg Asp Leu
865                 870                 875                 880

Lys Ala Gly Leu Tyr Leu Gln Val Val Asn Val Ala Lys Leu Val
                885                 890                 895

Leu Lys Tyr Asn Ala Ile Ile Cys Leu Glu Asp Leu Asn Phe Gly Phe
                900                 905                 910

Lys Arg Gly Arg Gln Lys Val Glu Lys Gln Val Tyr Gln Lys Phe Glu
            915                 920                 925
```

-continued

Lys Met Leu Ile Asp Lys Leu Asn Tyr Leu Val Ile Asp Lys Ser Arg
        930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
                965                 970                 975

Val Ile Tyr Tyr Val Pro Ala Tyr Leu Thr Ser Lys Ile Asp Pro Thr
            980                 985                 990

Thr Gly Phe Ala Asn Leu Phe Tyr Met Lys Cys Glu Asn Val Glu Lys
        995                1000                1005

Ser Lys Arg Phe Phe Asp Gly Phe Asp Phe Ile Arg Phe Asn Ala
    1010                1015                1020

Leu Glu Asn Val Phe Glu Gly Phe Asp Tyr Arg Ser Phe Thr
    1025                1030                1035

Gln Arg Ala Cys Gly Ile Asn Ser Lys Trp Thr Val Cys Thr Asn
    1040                1045                1050

Gly Glu Arg Ile Ile Lys Tyr Arg Asn Pro Asp Lys Asn Asn Met
    1055                1060                1065

Phe Asp Glu Lys Val Val Val Thr Asp Glu Met Lys Asn Leu
    1070                1075                1080

Phe Glu Gln Tyr Lys Ile Pro Tyr Glu Asp Gly Arg Asn Val Lys
    1085                1090                1095

Asp Met Ile Ile Ser Asn Glu Glu Ala Glu Phe Tyr Arg Arg Leu
    1100                1105                1110

Tyr Arg Leu Leu Gln Gln Thr Leu Gln Met Arg Asn Ser Thr Ser
    1115                1120                1125

Asp Gly Thr Arg Asp Tyr Ile Ile Ser Pro Val Lys Asn Lys Arg
    1130                1135                1140

Glu Ala Tyr Phe Asn Ser Glu Leu Ser Asp Gly Ser Val Pro Lys
    1145                1150                1155

Asp Ala Asp Ala Asn Gly Ala Tyr Asn Ile Ala Arg Lys Gly Leu
    1160                1165                1170

Trp Val Leu Glu Gln Ile Arg Gln Lys Ser Glu Gly Glu Lys Ile
    1175                1180                1185

Asn Leu Ala Met Thr Asn Ala Glu Trp Leu Glu Tyr Ala Gln Thr
    1190                1195                1200

His Leu Leu
    1205

<210> SEQ ID NO 8
<211> LENGTH: 1233
<212> TYPE: PRT
<213> ORGANISM: Unknown
<220> FEATURE:
<223> OTHER INFORMATION: Lachnospiraceae bacterium

<400> SEQUENCE: 8

Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
            20                  25                  30

Arg Glu Gln Lys Leu Leu Glu Gln Asp Ala Ala Phe Arg Lys Leu Val
        35                  40                  45

Glu Thr Val Thr Pro Ile Val Asp Asp Cys Ile Arg Lys Ile Ala Asp
    50                  55                  60

```
Asn Ala Leu Cys His Phe Gly Thr Glu Tyr Asp Phe Ser Cys Leu Gly
 65                  70                  75                  80

Asn Ala Ile Ser Lys Asn Asp Ser Lys Ala Ile Lys Lys Glu Thr Glu
             85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
        115                 120                 125

Thr Leu Thr Ser Phe Val Gln Asp Asp Ala Asp Lys Arg Val Leu Ile
130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
        275                 280                 285

Ser Asn Asp Ser Asp Ala Arg Ser Ile Leu Glu Lys Ile Leu Lys Asp
290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
            340                 345                 350

Glu Ser Lys Arg Ile Ser Glu Leu Met Glu Thr Leu Ser Pro Lys Glu
        355                 360                 365

Arg Lys Glu Ser Lys Lys Arg Leu Glu Gly Leu Glu Glu His Ile Arg
370                 375                 380

Lys Ser Thr Tyr Thr Phe Asp Glu Leu Asn Arg Tyr Ala Glu Lys Asn
385                 390                 395                 400

Val Met Ala Ala Tyr Ile Ala Ala Val Glu Glu Ser Cys Ala Glu Ile
                405                 410                 415

Met Arg Lys Glu Lys Asp Leu Arg Thr Leu Leu Ser Lys Glu Asp Val
            420                 425                 430

Lys Ile Arg Gly Asn Arg His Asn Thr Leu Ile Val Lys Asn Tyr Phe
        435                 440                 445

Asn Ala Trp Thr Val Phe Arg Asn Leu Ile Arg Ile Leu Arg Arg Lys
450                 455                 460

Ser Glu Ala Glu Ile Asp Ser Asp Phe Tyr Asp Val Leu Asp Asp Ser
465                 470                 475                 480
```

-continued

```
Val Glu Val Leu Ser Leu Thr Tyr Lys Gly Glu Asn Leu Cys Arg Ser
                485                 490                 495

Tyr Ile Thr Lys Lys Ile Gly Ser Asp Leu Lys Pro Glu Ile Ala Thr
            500                 505                 510

Tyr Gly Ser Ala Leu Arg Pro Asn Ser Arg Trp Trp Ser Pro Gly Glu
            515                 520                 525

Lys Phe Asn Val Lys Phe His Thr Ile Val Arg Arg Asp Gly Arg Leu
        530                 535                 540

Tyr Tyr Phe Ile Leu Pro Lys Gly Ala Lys Pro Val Glu Leu Glu Asp
545                 550                 555                 560

Met Asp Gly Asp Ile Glu Cys Leu Gln Met Arg Lys Ile Pro Asn Pro
                565                 570                 575

Thr Ile Phe Leu Pro Lys Leu Val Phe Lys Asp Pro Glu Ala Phe Phe
            580                 585                 590

Arg Asp Asn Pro Glu Ala Asp Glu Phe Val Phe Leu Ser Gly Met Lys
        595                 600                 605

Ala Pro Val Thr Ile Thr Arg Glu Thr Tyr Glu Ala Tyr Arg Tyr Lys
        610                 615                 620

Leu Tyr Thr Val Gly Lys Leu Arg Asp Gly Glu Val Ser Glu Glu Glu
625                 630                 635                 640

Tyr Lys Arg Ala Leu Leu Gln Val Leu Thr Ala Tyr Lys Glu Phe Leu
                645                 650                 655

Glu Asn Arg Met Ile Tyr Ala Asp Leu Asn Phe Gly Phe Lys Asp Leu
            660                 665                 670

Glu Glu Tyr Lys Asp Ser Ser Glu Phe Ile Lys Gln Val Glu Thr His
        675                 680                 685

Asn Thr Phe Met Cys Trp Ala Lys Val Ser Ser Gln Leu Asp Asp
        690                 695                 700

Leu Val Lys Ser Gly Asn Gly Leu Leu Phe Glu Ile Trp Ser Glu Arg
705                 710                 715                 720

Leu Glu Ser Tyr Tyr Lys Tyr Gly Asn Glu Lys Val Leu Arg Gly Tyr
                725                 730                 735

Glu Gly Val Leu Leu Ser Ile Leu Lys Asp Glu Asn Leu Val Ser Met
            740                 745                 750

Arg Thr Leu Leu Asn Ser Arg Pro Met Leu Val Tyr Arg Pro Lys Glu
        755                 760                 765

Ser Ser Lys Pro Met Val Val His Arg Asp Gly Ser Arg Val Val Asp
        770                 775                 780

Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
                805                 810                 815

Lys Ala Arg Lys Ile Leu Asp Asn Lys Lys Val Lys Val Lys Val Leu
            820                 825                 830

Glu Ser Glu Arg Val Lys Trp Ser Lys Phe Tyr Asp Glu Gln Phe Ala
        835                 840                 845

Val Thr Phe Ser Val Lys Lys Asn Ala Asp Cys Leu Asp Thr Thr Lys
        850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
                885                 890                 895

Lys Asn Gly Lys Val Leu Lys Gln Arg Ser Leu Asn Ile Ile Asn Asp
```

```
                    900             905                 910
Gly Ala Arg Asp Val Asp Trp Lys Glu Arg Phe Arg Gln Val Thr Lys
            915                 920             925
Asp Arg Asn Glu Gly Tyr Asn Glu Trp Asp Tyr Ser Arg Thr Ser Asn
        930                 935             940
Asp Leu Lys Glu Val Tyr Leu Asn Tyr Ala Leu Lys Glu Ile Ala Glu
945                 950             955                 960
Ala Val Ile Glu Tyr Asn Ala Ile Leu Ile Glu Lys Met Ser Asn
                965             970             975
Ala Phe Lys Asp Lys Tyr Ser Phe Leu Asp Asp Val Thr Phe Lys Gly
            980             985             990
Phe Glu Thr Lys Lys Leu Ala Lys Leu Ser Asp Leu His Phe Arg Gly
        995                 1000            1005
Ile Lys Asp Gly Glu Pro Cys Ser Phe Thr Asn Pro Leu Gln Leu
    1010            1015                1020
Cys Gln Asn Asp Ser Asn Lys Ile Leu Gln Asp Gly Val Ile Phe
1025                1030                1035
Met Val Pro Asn Ser Met Thr Arg Ser Leu Asp Pro Asp Thr Gly
    1040                1045            1050
Phe Ile Phe Ala Ile Asn Asp His Asn Ile Arg Thr Lys Lys Ala
    1055            1060                1065
Lys Leu Asn Phe Leu Ser Lys Phe Asp Gln Leu Lys Val Ser Ser
    1070            1075            1080
Glu Gly Cys Leu Ile Met Lys Tyr Ser Gly Asp Ser Leu Pro Thr
    1085            1090            1095
His Asn Thr Asp Asn Arg Val Trp Asn Cys Cys Cys Asn His Pro
    1100            1105            1110
Ile Thr Asn Tyr Asp Arg Glu Thr Lys Lys Val Glu Phe Ile Glu
    1115            1120            1125
Glu Pro Val Glu Glu Leu Ser Arg Val Leu Glu Glu Asn Gly Ile
    1130            1135            1140
Glu Thr Asp Thr Glu Leu Asn Lys Leu Asn Glu Arg Glu Asn Val
    1145            1150            1155
Pro Gly Lys Val Val Asp Ala Ile Tyr Ser Leu Val Leu Asn Tyr
    1160            1165            1170
Leu Arg Gly Thr Val Ser Gly Val Ala Gly Gln Arg Ala Val Tyr
    1175            1180            1185
Tyr Ser Pro Val Thr Gly Lys Lys Tyr Asp Ile Ser Phe Ile Gln
    1190            1195            1200
Ala Met Asn Leu Asn Arg Lys Cys Asp Tyr Tyr Arg Ile Gly Ser
    1205            1210            1215
Lys Glu Arg Gly Glu Trp Thr Asp Phe Val Ala Gln Leu Ile Asn
    1220            1225            1230
```

<210> SEQ ID NO 9
<211> LENGTH: 1227
<212> TYPE: PRT
<213> ORGANISM: Unknown
<220> FEATURE:
<223> OTHER INFORMATION: Lachnospiraceae bacterium

<400> SEQUENCE: 9

```
Met Ser Lys Leu Glu Lys Phe Thr Asn Cys Tyr Ser Leu Ser Lys Thr
1               5                   10                  15
Leu Arg Phe Lys Ala Ile Pro Val Gly Lys Thr Gln Glu Asn Ile Asp
```

```
                20              25              30
Asn Lys Arg Leu Leu Val Glu Asp Glu Lys Ala Glu Asp Tyr Lys
            35                  40                  45
Gly Val Lys Lys Leu Leu Asp Arg Tyr Tyr Leu Ser Phe Ile Asn Asp
        50                  55                  60
Val Leu His Ser Ile Lys Leu Lys Asn Leu Asn Asn Tyr Ile Ser Leu
 65                  70                  75                  80
Phe Arg Lys Lys Thr Arg Thr Glu Lys Glu Asn Lys Glu Leu Glu Asn
                85                  90                  95
Leu Glu Ile Asn Leu Arg Lys Glu Ile Ala Lys Ala Phe Lys Gly Asn
            100                 105                 110
Glu Gly Tyr Lys Ser Leu Phe Lys Lys Asp Ile Ile Glu Thr Ile Leu
        115                 120                 125
Pro Glu Phe Leu Asp Asp Lys Asp Glu Ile Ala Leu Val Asn Ser Phe
        130                 135                 140
Asn Gly Phe Thr Thr Ala Phe Thr Gly Phe Phe Asp Asn Arg Glu Asn
145                 150                 155                 160
Met Phe Ser Glu Glu Ala Lys Ser Thr Ser Ile Ala Phe Arg Cys Ile
                165                 170                 175
Asn Glu Asn Leu Thr Arg Tyr Ile Ser Asn Met Asp Ile Phe Glu Lys
            180                 185                 190
Val Asp Ala Ile Phe Asp Lys His Glu Val Gln Glu Ile Lys Glu Lys
        195                 200                 205
Ile Leu Asn Ser Asp Tyr Asp Val Glu Asp Phe Phe Glu Gly Glu Phe
        210                 215                 220
Phe Asn Phe Val Leu Thr Gln Glu Gly Ile Asp Val Tyr Asn Ala Ile
225                 230                 235                 240
Ile Gly Gly Phe Val Thr Glu Ser Gly Glu Lys Ile Lys Gly Leu Asn
                245                 250                 255
Glu Tyr Ile Asn Leu Tyr Asn Gln Lys Thr Lys Gln Lys Leu Pro Lys
            260                 265                 270
Phe Lys Pro Leu Tyr Lys Gln Val Leu Ser Asp Arg Glu Ser Leu Ser
        275                 280                 285
Phe Tyr Gly Glu Gly Tyr Thr Ser Asp Glu Glu Val Leu Glu Val Phe
        290                 295                 300
Arg Asn Thr Leu Asn Lys Asn Ser Glu Ile Phe Ser Ser Ile Lys Lys
305                 310                 315                 320
Leu Glu Lys Leu Phe Lys Asn Phe Asp Glu Tyr Ser Ser Ala Gly Ile
                325                 330                 335
Phe Val Lys Asn Gly Pro Ala Ile Ser Thr Ile Ser Lys Asp Ile Phe
            340                 345                 350
Gly Glu Trp Asn Val Ile Arg Asp Lys Trp Asn Ala Glu Tyr Asp Asp
        355                 360                 365
Ile His Leu Lys Lys Lys Ala Val Val Thr Glu Lys Tyr Glu Asp Asp
        370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
Ile Ile Ile Gln Lys Val Asp Glu Ile Tyr Lys Val Tyr Gly Ser Ser
            420                 425                 430
Glu Lys Leu Phe Asp Ala Asp Phe Val Leu Glu Lys Ser Leu Lys Lys
        435                 440                 445
```

```
Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
        530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
    595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
                675                 680                 685

Glu Val Asp Lys Leu Val Glu Glu Gly Lys Leu Tyr Met Phe Gln Ile
        690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Asn Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
                820                 825                 830

Asp Arg Gly Glu Arg Asn Leu Leu Tyr Ile Val Val Asp Gly Lys
        835                 840                 845

Gly Asn Ile Val Glu Gln Tyr Ser Leu Asn Glu Ile Ile Asn Asn Phe
850                 855                 860
```

```
Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
            885                 890                 895

Ile Lys Glu Leu Lys Ala Gly Tyr Ile Ser Gln Val Val His Lys Ile
        900                 905                 910

Cys Glu Leu Val Glu Lys Tyr Asp Ala Val Ile Ala Leu Glu Asp Leu
            915                 920                 925

Asn Ser Gly Phe Lys Asn Ser Arg Val Lys Val Glu Lys Gln Val Tyr
        930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
            965                 970                 975

Ile Thr Asn Lys Phe Glu Ser Phe Lys Ser Met Ser Thr Gln Asn Gly
        980                 985                 990

Phe Ile Phe Tyr Ile Pro Ala Trp Leu Thr Ser Lys Ile Asp Pro Ser
        995                 1000                1005

Thr Gly Phe Val Asn Leu Leu Lys Thr Lys Tyr Thr Ser Ile Ala
    1010                1015                1020

Asp Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ser Asn Lys Glu Trp Leu
    1205                1210                1215

Glu Tyr Ala Gln Thr Ser Val Lys His
    1220                1225

<210> SEQ ID NO 10
<211> LENGTH: 1264
<212> TYPE: PRT
<213> ORGANISM: Leptospira inadai

<400> SEQUENCE: 10
```

-continued

```
Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
            20                  25                  30

Lys Lys Gly Phe Leu Lys Asp Lys Ile Arg Ala Glu Asp Tyr Lys
        35                  40                  45

Ala Val Lys Lys Ile Ile Asp Lys Tyr His Arg Ala Tyr Ile Glu Glu
50                      55                  60

Val Phe Asp Ser Val Leu His Gln Lys Lys Lys Asp Lys Thr Arg
65                  70                  75                  80

Phe Ser Thr Gln Phe Ile Lys Glu Ile Lys Glu Phe Ser Glu Leu Tyr
                85                  90                  95

Tyr Lys Thr Glu Lys Asn Ile Pro Asp Lys Glu Arg Leu Glu Ala Leu
            100                 105                 110

Ser Glu Lys Leu Arg Lys Met Leu Val Gly Ala Phe Lys Gly Glu Phe
            115                 120                 125

Ser Glu Glu Val Ala Glu Lys Tyr Asn Lys Asn Leu Phe Ser Lys Glu
            130                 135                 140

Leu Ile Arg Asn Glu Ile Glu Lys Phe Cys Thr Asp Glu Glu Arg
145                 150                 155                 160

Lys Gln Val Ser Asn Phe Lys Ser Phe Thr Thr Tyr Phe Thr Gly Phe
                165                 170                 175

His Ser Asn Arg Gln Asn Ile Tyr Ser Asp Glu Lys Lys Ser Thr Ala
            180                 185                 190

Ile Gly Tyr Arg Ile Ile His Gln Asn Leu Pro Lys Phe Leu Asp Asn
            195                 200                 205

Leu Lys Ile Ile Glu Ser Ile Gln Arg Arg Phe Lys Asp Phe Pro Trp
210                 215                 220

Ser Asp Leu Lys Lys Asn Leu Lys Lys Ile Asp Lys Asn Ile Lys Leu
225                 230                 235                 240

Thr Glu Tyr Phe Ser Ile Asp Gly Phe Val Asn Val Leu Asn Gln Lys
                245                 250                 255

Gly Ile Asp Ala Tyr Asn Thr Ile Leu Gly Gly Lys Ser Glu Glu Ser
            260                 265                 270

Gly Glu Lys Ile Gln Gly Leu Asn Glu Tyr Ile Asn Leu Tyr Arg Gln
            275                 280                 285

Lys Asn Asn Ile Asp Arg Lys Asn Pro Leu Asn Val Lys Ile Leu Phe
            290                 295                 300

Lys Gln Ile Leu Gly Asp Arg Glu Thr Lys Ser Phe Ile Pro Glu Ala
305                 310                 315                 320

Phe Pro Asp Asp Gln Ser Val Leu Asn Ser Ile Thr Glu Phe Ala Lys
                325                 330                 335

Tyr Leu Lys Leu Asp Lys Lys Lys Ser Ile Ile Ala Glu Leu Lys
            340                 345                 350

Lys Phe Leu Ser Ser Phe Asn Arg Tyr Glu Leu Asp Gly Ile Tyr Leu
            355                 360                 365

Ala Asn Asp Asn Ser Leu Ala Ser Ile Ser Thr Phe Leu Phe Asp Asp
370                 375                 380

Trp Ser Phe Ile Lys Lys Ser Val Ser Phe Lys Tyr Asp Glu Ser Val
385                 390                 395                 400

Gly Asp Pro Lys Lys Lys Ile Lys Ser Pro Leu Lys Tyr Glu Lys Glu
            405                 410                 415
```

-continued

```
Lys Glu Lys Trp Leu Lys Gln Lys Tyr Tyr Thr Ile Ser Phe Leu Asn
                420                 425                 430
Asp Ala Ile Glu Ser Tyr Ser Lys Ser Gln Asp Glu Lys Arg Val Lys
                435                 440                 445
Ile Arg Leu Glu Ala Tyr Phe Ala Glu Phe Lys Ser Lys Asp Asp Ala
            450                 455                 460
Lys Lys Gln Phe Asp Leu Leu Glu Arg Ile Glu Glu Ala Tyr Ala Ile
465                 470                 475                 480
Val Glu Pro Leu Leu Gly Ala Glu Tyr Pro Arg Asp Arg Asn Leu Lys
                485                 490                 495
Ala Asp Lys Lys Glu Val Gly Lys Ile Lys Asp Phe Leu Asp Ser Ile
                500                 505                 510
Lys Ser Leu Gln Phe Phe Leu Lys Pro Leu Leu Ser Ala Glu Ile Phe
            515                 520                 525
Asp Glu Lys Asp Leu Gly Phe Tyr Asn Gln Leu Glu Gly Tyr Tyr Glu
                530                 535                 540
Glu Ile Asp Ile Ser Gly His Leu Tyr Asn Lys Val Arg Asn Tyr Leu
545                 550                 555                 560
Thr Gly Lys Ile Tyr Ser Lys Glu Lys Phe Lys Leu Asn Phe Glu Asn
                565                 570                 575
Ser Thr Leu Leu Lys Gly Trp Asp Glu Asn Arg Glu Val Ala Asn Leu
            580                 585                 590
Cys Val Ile Phe Arg Glu Asp Gln Lys Tyr Tyr Leu Gly Val Met Asp
                595                 600                 605
Lys Glu Asn Asn Thr Ile Leu Ser Asp Ile Pro Lys Val Lys Pro Asn
610                 615                 620
Glu Leu Phe Tyr Glu Lys Met Val Tyr Lys Leu Ile Pro Thr Pro His
625                 630                 635                 640
Met Gln Leu Pro Arg Ile Ile Phe Ser Ser Asp Asn Leu Ser Ile Tyr
                645                 650                 655
Asn Pro Ser Lys Ser Ile Leu Lys Ile Arg Glu Ala Lys Ser Phe Lys
            660                 665                 670
Glu Gly Lys Asn Phe Lys Leu Lys Asp Cys His Lys Phe Ile Asp Phe
            675                 680                 685
Tyr Lys Glu Ser Ile Ser Lys Asn Glu Asp Trp Ser Arg Phe Asp Phe
690                 695                 700
Lys Phe Ser Lys Thr Ser Ser Tyr Glu Asn Ile Ser Glu Phe Tyr Arg
705                 710                 715                 720
Glu Val Glu Arg Gln Gly Tyr Asn Leu Asp Phe Lys Lys Val Ser Lys
                725                 730                 735
Phe Tyr Ile Asp Ser Leu Val Glu Asp Gly Lys Leu Tyr Leu Phe Gln
                740                 745                 750
Ile Tyr Asn Lys Asp Phe Ser Ile Phe Ser Lys Gly Lys Pro Asn Leu
            755                 760                 765
His Thr Ile Tyr Phe Arg Ser Leu Phe Ser Lys Glu Asn Leu Lys Asp
            770                 775                 780
Val Cys Leu Lys Leu Asn Gly Glu Ala Glu Met Phe Phe Arg Lys Lys
785                 790                 795                 800
Ser Ile Asn Tyr Asp Glu Lys Lys Arg Glu Gly His His Pro Glu
                805                 810                 815
Leu Phe Glu Lys Leu Lys Tyr Pro Ile Leu Lys Asp Lys Arg Tyr Ser
                820                 825                 830
Glu Asp Lys Phe Gln Phe His Leu Pro Ile Ser Leu Asn Phe Lys Ser
```

```
                835              840              845
     Lys Glu Arg Leu Asn Phe Asn Leu Lys Val Asn Glu Phe Leu Lys Arg
         850              855              860

Asn Lys Asp Ile Asn Ile Ile Gly Ile Asp Arg Gly Glu Arg Asn Leu
865              870              875              880

Leu Tyr Leu Val Met Ile Asn Gln Lys Gly Glu Ile Leu Lys Gln Thr
                     885              890              895

Leu Leu Asp Ser Met Gln Ser Gly Lys Gly Arg Pro Glu Ile Asn Tyr
                 900              905              910

Lys Glu Lys Leu Gln Glu Lys Glu Ile Glu Arg Asp Lys Ala Arg Lys
                 915              920              925

Ser Trp Gly Thr Val Glu Asn Ile Lys Glu Leu Lys Glu Gly Tyr Leu
         930              935              940

Ser Ile Val Ile His Gln Ile Ser Lys Leu Met Val Glu Asn Asn Ala
945              950              955              960

Ile Val Val Leu Glu Asp Leu Asn Ile Gly Phe Lys Arg Gly Arg Gln
                 965              970              975

Lys Val Glu Arg Gln Val Tyr Gln Lys Phe Glu Lys Met Leu Ile Asp
                 980              985              990

Lys Leu Asn Phe Leu Val Phe Lys  Glu Asn Lys Pro Thr  Glu Pro Gly
                 995              1000             1005

Gly Val Leu Lys Ala Tyr Gln  Leu Thr Asp Glu Phe  Gln Ser Phe
         1010             1015             1020

Glu Lys Leu Ser Lys Gln Thr  Gly Phe Leu Phe Tyr  Val Pro Ser
         1025             1030             1035

Trp Asn Thr Ser Lys Ile Asp  Pro Arg Thr Gly Phe  Ile Asp Phe
         1040             1045             1050

Leu His Pro Ala Tyr Glu Asn  Ile Glu Lys Ala Lys  Gln Trp Ile
         1055             1060             1065

Asn Lys Phe Asp Ser Ile Arg  Phe Asn Ser Lys Met  Asp Trp Phe
         1070             1075             1080

Glu Phe Thr Ala Asp Thr Arg  Lys Phe Ser Glu Asn  Leu Met Leu
         1085             1090             1095

Gly Lys Asn Arg Val Trp Val  Ile Cys Thr Thr Asn  Val Glu Arg
         1100             1105             1110

Tyr Phe Thr Ser Lys Thr Ala  Asn Ser Ser Ile Gln  Tyr Asn Ser
         1115             1120             1125

Ile Gln Ile Thr Glu Lys Leu  Lys Glu Leu Phe Val  Asp Ile Pro
         1130             1135             1140

Phe Ser Asn Gly Gln Asp Leu  Lys Pro Glu Ile Leu  Arg Lys Asn
         1145             1150             1155

Asp Ala Val Phe Phe Lys Ser  Leu Leu Phe Tyr Ile  Lys Thr Thr
         1160             1165             1170

Leu Ser Leu Arg Gln Asn Asn  Gly Lys Lys Gly Glu  Glu Glu Lys
         1175             1180             1185

Asp Phe Ile Leu Ser Pro Val  Val Asp Ser Lys Gly  Arg Phe Phe
         1190             1195             1200

Asn Ser Leu Glu Ala Ser Asp  Asp Glu Pro Lys Asp  Ala Asp Ala
         1205             1210             1215

Asn Gly Ala Tyr His Ile Ala  Leu Lys Gly Leu Met  Asn Leu Leu
         1220             1225             1230

Val Leu Asn Glu Thr Lys Glu  Glu Asn Leu Ser Arg  Pro Lys Trp
         1235             1240             1245
```

```
Lys Ile Lys Asn Lys Asp Trp Leu Glu Phe Val Trp Glu Arg Asn
    1250                1255                1260

Arg

<210> SEQ ID NO 11
<211> LENGTH: 1373
<212> TYPE: PRT
<213> ORGANISM: Moraxella bovoculi

<400> SEQUENCE: 11

Met Leu Phe Gln Asp Phe Thr His Leu Tyr Pro Leu Ser Lys Thr Val
1               5                   10                  15

Arg Phe Glu Leu Phe Ile Asp Arg Thr Leu Glu His Ile His Ala Lys
                20                  25                  30

Asn Phe Leu Ser Gln Asp Glu Thr Met Ala Asp Met His Gln Lys Val
            35                  40                  45

Lys Val Ile Leu Asp Asp Tyr His Arg Asp Phe Ile Ala Asp Met Met
        50                  55                  60

Gly Glu Val Lys Leu Thr Lys Leu Ala Glu Phe Tyr Asp Val Tyr Leu
65                  70                  75                  80

Lys Phe Arg Lys Asn Pro Lys Asp Asp Glu Leu Gln Lys Ala Gln Leu
                85                  90                  95

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
    290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350
```

```
Tyr Val Glu His Lys Asn Leu Asn Glu Leu Ser Lys Gln Ala Phe Gly
            355                 360                 365

Asp Phe Ala Leu Leu Gly Arg Val Leu Asp Gly Tyr Tyr Val Asp Val
    370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
                420                 425                 430

His Asp Asp Glu Ser Val Gln Ala Gly Lys Leu Gly Gln Tyr Phe Lys
                435                 440                 445

His Gly Leu Ala Gly Val Asp Asn Pro Ile Gln Lys Ile His Asn Asn
450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
                500                 505                 510

Phe Ala Lys Leu Leu Thr Thr Lys Thr Thr Leu Asp Asn Gln Asp Gly
                515                 520                 525

Asn Phe Tyr Gly Glu Phe Gly Val Leu Tyr Asp Glu Leu Ala Lys Ile
                530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575

Gly Trp Asp Leu Asn Lys Glu Lys Asp Asn Phe Gly Val Ile Leu Gln
                580                 585                 590

Lys Asp Gly Cys Tyr Tyr Leu Ala Leu Leu Asp Lys Ala His Lys Lys
                595                 600                 605

Val Phe Asp Asn Ala Pro Asn Thr Gly Lys Ser Ile Tyr Gln Lys Met
610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
                660                 665                 670

Leu Tyr Arg Phe Ile Leu Glu Cys Leu Lys Ile His Pro Lys Tyr Asp
                675                 680                 685

Lys Lys Phe Glu Gly Ala Ile Gly Asp Ile Gln Leu Phe Lys Lys Asp
                690                 695                 700

Lys Lys Gly Arg Glu Val Pro Ile Ser Glu Lys Asp Leu Phe Lys Asp
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
                740                 745                 750

Gln Tyr Asn Ile Tyr Lys Lys Ile Asp Ser Asn Asp Asn Arg Lys Lys
                755                 760                 765
```

-continued

```
Glu Asn Phe Tyr Asn Asn His Pro Lys Phe Lys Lys Asp Leu Val Arg
770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
                805                 810                 815

Glu Leu Phe Thr Glu Ile Glu Thr Arg Arg Leu Asn Tyr Lys Ile Ser
                820                 825                 830

Phe Cys Asn Ile Asn Ala Asp Tyr Ile Asp Glu Leu Val Glu Gln Gly
                835                 840                 845

Gln Leu Tyr Leu Phe Gln Ile Tyr Asn Lys Asp Phe Ser Pro Lys Ala
850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
                900                 905                 910

Arg Ala Gly Glu Val Leu Glu Asn Lys Asn Pro Asp Asn Pro Lys Lys
                915                 920                 925

Arg Gln Phe Val Tyr Asp Ile Ile Lys Asp Lys Arg Tyr Thr Gln Lys
930                 935                 940

Asp Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
                980                 985                 990

Leu Tyr Leu Thr Val Ile Asn Ser Lys Gly Glu Ile Leu Glu Gln Cys
                995                1000                1005

Ser Leu Asn Asp Ile Thr Thr Ala Ser Ala Asn Gly Thr Gln Met
                1010               1015               1020

Thr Thr Pro Tyr His Lys Ile Leu Asp Lys Arg Glu Ile Glu Arg
                1025               1030               1035

Leu Asn Ala Arg Val Gly Trp Gly Glu Ile Glu Thr Ile Lys Glu
                1040               1045               1050

Leu Lys Ser Gly Tyr Leu Ser His Val Val His Gln Ile Ser Gln
                1055               1060               1065

Leu Met Leu Lys Tyr Asn Ala Ile Val Val Leu Glu Asp Leu Asn
                1070               1075               1080

Phe Gly Phe Lys Arg Gly Arg Phe Lys Val Glu Lys Gln Ile Tyr
                1085               1090               1095

Gln Asn Phe Glu Asn Ala Leu Ile Lys Lys Leu Asn His Leu Val
                1100               1105               1110

Leu Lys Asp Lys Ala Asp Asp Glu Ile Gly Ser Tyr Lys Asn Ala
                1115               1120               1125

Leu Gln Leu Thr Asn Asn Phe Thr Asp Leu Lys Ser Ile Gly Lys
                1130               1135               1140

Gln Thr Gly Phe Leu Phe Tyr Val Pro Ala Trp Asn Thr Ser Lys
                1145               1150               1155

Ile Asp Pro Glu Thr Gly Phe Val Asp Leu Leu Lys Pro Arg Tyr
                1160               1165               1170

Glu Asn Ile Gln Ala Ser Gln Ala Phe Phe Gly Lys Phe Asp Lys
```

```
                1175                1180                1185

Ile Cys Tyr Asn Ala Asp Lys Asp Tyr Phe Glu Phe His Ile Asp
    1190                1195                1200

Tyr Ala Lys Phe Thr Asp Lys Ala Lys Asn Ser Arg Gln Ile Trp
    1205                1210                1215

Thr Ile Cys Ser His Gly Asp Lys Arg Tyr Val Tyr Asp Lys Thr
    1220                1225                1230

Ala Asn Gln Asn Lys Gly Ala Ala Lys Gly Ile Asn Val Asn Asp
    1235                1240                1245

Ile Leu Lys Ser Leu Phe Ala Arg His His Ile Asn Glu Lys Gln
    1250                1255                1260

Pro Asn Leu Val Met Asp Ile Cys Gln Asn Asn Asp Lys Glu Phe
    1265                1270                1275

His Lys Ser Leu Met Tyr Leu Leu Lys Thr Leu Leu Ala Leu Arg
    1280                1285                1290

Tyr Ser Asn Ala Ser Ser Asp Glu Asp Phe Ile Leu Ser Pro Val
    1295                1300                1305

Ala Asn Asp Glu Gly Val Phe Phe Asn Ser Ala Leu Ala Asp Asp
    1310                1315                1320

Thr Gln Pro Gln Asn Ala Asp Ala Asn Gly Ala Tyr His Ile Ala
    1325                1330                1335

Leu Lys Gly Leu Trp Leu Leu Asn Glu Leu Lys Asn Ser Asp Asp
    1340                1345                1350

Leu Asn Lys Val Lys Leu Ala Ile Asp Asn Gln Thr Trp Leu Asn
    1355                1360                1365

Phe Ala Gln Asn Arg
    1370

<210> SEQ ID NO 12
<211> LENGTH: 1352
<212> TYPE: PRT
<213> ORGANISM: Parcubacteria bacterium

<400> SEQUENCE: 12

Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
                20                  25                  30

Lys Ile Asn Lys Val Phe Glu Lys Asp Gln Thr Ile Asp Asp Ser Tyr
            35                  40                  45

Asn Gln Ala Lys Phe Tyr Phe Asp Ser Leu His Gln Lys Phe Ile Asp
        50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
                100                 105                 110

Arg Leu Gln Lys Glu Ile Asn Asp Ala Glu Asp Ile Ile Gln Lys Glu
            115                 120                 125

Lys Glu Lys Ile Tyr Lys Asp Val Arg Thr Leu Phe Asp Asn Glu Ala
        130                 135                 140

Glu Ser Trp Lys Thr Tyr Tyr Gln Glu Arg Glu Val Asp Gly Lys Lys
145                 150                 155                 160
```

```
Ile Thr Glu Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
            180                 185                 190

Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
    210                 215                 220

Lys Phe Ala Gly Tyr Leu Thr Lys Phe Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
            260                 265                 270

Lys Asn Asn His Thr Asp Leu Gly Phe Asp Glu Glu Asn Ile Phe Glu
        275                 280                 285

Ile Glu Arg Tyr Lys Asn Cys Leu Leu Gln Arg Glu Ile Glu His Ile
    290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
    530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
```

-continued

```
                580                 585                 590
Ile Lys Tyr Tyr Asn Glu Phe Arg Asn Phe Ile Thr Lys Lys Pro Phe
            595                 600                 605

Asp Glu Asp Lys Ile Lys Leu Asn Phe Glu Asn Gly Ala Leu Leu Lys
        610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
            660                 665                 670

Gln Lys Met Ile Tyr Lys Gln Ile Ala Asp Ala Ser Lys Asp Val Pro
        675                 680                 685

Arg Leu Leu Leu Thr Ser Lys Lys Ala Met Glu Lys Phe Lys Pro Ser
        690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
            740                 745                 750

Gln Asp Thr Gly Lys Tyr Gln Asn Ile Lys Glu Phe Thr Asp Val
        755                 760                 765

Gln Lys Tyr Gly Tyr Lys Ile Ser Phe Arg Asp Ile Asp Glu Tyr
        770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815

Leu Tyr Phe Glu His Ile Leu Ser Ala Glu Asn Leu Asn Asp Pro Val
            820                 825                 830

Phe Lys Leu Ser Gly Met Ala Glu Ile Phe Gln Arg Gln Pro Ser Val
        835                 840                 845

Asn Glu Arg Glu Lys Ile Thr Thr Gln Lys Asn Gln Cys Ile Leu Asp
        850                 855                 860

Lys Gly Asp Arg Ala Tyr Lys Tyr Arg Arg Tyr Thr Glu Lys Lys Ile
865                 870                 875                 880

Met Phe His Met Ser Leu Val Leu Asn Thr Gly Lys Gly Glu Ile Lys
                885                 890                 895

Gln Val Gln Phe Asn Lys Ile Ile Asn Gln Arg Ile Ser Ser Ser Asp
            900                 905                 910

Asn Glu Met Arg Val Asn Val Ile Gly Ile Asp Arg Gly Glu Lys Asn
        915                 920                 925

Leu Leu Tyr Tyr Ser Val Val Lys Gln Asn Gly Glu Ile Ile Glu Gln
        930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
                965                 970                 975

Val Lys Ile Lys Asp Leu Lys Lys Gly Tyr Ile Ser His Val Ile His
            980                 985                 990

Lys Ile Cys Gln Leu Ile Glu Lys  Tyr Ser Ala Ile Val  Val Leu Glu
        995                 1000                1005
```

Asp Leu Asn Met Arg Phe Lys Gln Ile Arg Gly Gly Ile Glu Arg
            1010                1015                1020

Ser Val Tyr Gln Gln Phe Glu Lys Ala Leu Ile Asp Lys Leu Gly
        1025                1030                1035

Tyr Leu Val Phe Lys Asp Asn Arg Asp Leu Arg Ala Pro Gly Gly
    1040                1045                1050

Val Leu Asn Gly Tyr Gln Leu Ser Ala Pro Phe Val Ser Phe Glu
    1055                1060                1065

Lys Met Arg Lys Gln Thr Gly Ile Leu Phe Tyr Thr Gln Ala Glu
    1070                1075                1080

Tyr Thr Ser Lys Thr Asp Pro Ile Thr Gly Phe Arg Lys Asn Val
    1085                1090                1095

Tyr Ile Ser Asn Ser Ala Ser Leu Asp Lys Ile Lys Glu Ala Val
    1100                1105                1110

Lys Lys Phe Asp Ala Ile Gly Trp Asp Gly Lys Glu Gln Ser Tyr
    1115                1120                1125

Phe Phe Lys Tyr Asn Pro Tyr Asn Leu Ala Asp Glu Lys Tyr Lys
    1130                1135                1140

Asn Ser Thr Val Ser Lys Glu Trp Ala Ile Phe Ala Ser Ala Pro
    1145                1150                1155

Arg Ile Arg Arg Gln Lys Gly Glu Asp Gly Tyr Trp Lys Tyr Asp
    1160                1165                1170

Arg Val Lys Val Asn Glu Glu Phe Glu Lys Leu Leu Lys Val Trp
    1175                1180                1185

Asn Phe Val Asn Pro Lys Ala Thr Asp Ile Lys Gln Glu Ile Ile
    1190                1195                1200

Lys Lys Ile Lys Ala Gly Asp Leu Gln Gly Glu Lys Glu Leu Asp
    1205                1210                1215

Gly Arg Leu Arg Asn Phe Trp His Ser Phe Ile Tyr Leu Phe Asn
    1220                1225                1230

Leu Val Leu Glu Leu Arg Asn Ser Phe Ser Leu Gln Ile Lys Ile
    1235                1240                1245

Lys Ala Gly Glu Val Ile Ala Val Asp Glu Gly Val Asp Phe Ile
    1250                1255                1260

Ala Ser Pro Val Lys Pro Phe Phe Thr Thr Pro Asn Pro Tyr Ile
    1265                1270                1275

Pro Ser Asn Leu Cys Trp Leu Ala Val Glu Asn Ala Asp Ala Asn
    1280                1285                1290

Gly Ala Tyr Asn Ile Ala Arg Lys Gly Val Met Ile Leu Lys Lys
    1295                1300                1305

Ile Arg Glu His Ala Lys Lys Asp Pro Glu Phe Lys Lys Leu Pro
    1310                1315                1320

Asn Leu Phe Ile Ser Asn Ala Glu Trp Asp Glu Ala Ala Arg Asp
    1325                1330                1335

Trp Gly Lys Tyr Ala Gly Thr Thr Ala Leu Asn Leu Asp His
    1340                1345                1350

<210> SEQ ID NO 13
<211> LENGTH: 1260
<212> TYPE: PRT
<213> ORGANISM: Porphyromonas crevioricanis

<400> SEQUENCE: 13

Met Asp Ser Leu Lys Asp Phe Thr Asn Leu Tyr Pro Val Ser Lys Thr

-continued

```
1               5                   10                  15
Leu Arg Phe Glu Leu Lys Pro Val Gly Lys Thr Leu Glu Asn Ile Glu
            20                  25                  30
Lys Ala Gly Ile Leu Lys Glu Asp Glu His Arg Ala Glu Ser Tyr Arg
            35                  40                  45
Arg Val Lys Lys Ile Ile Asp Thr Tyr His Lys Val Phe Ile Asp Ser
50                      55                  60
Ser Leu Glu Asn Met Ala Lys Met Gly Ile Glu Asn Glu Ile Lys Ala
65                  70                  75                  80
Met Leu Gln Ser Phe Cys Glu Leu Tyr Lys Lys Asp His Arg Thr Glu
                85                  90                  95
Gly Glu Asp Lys Ala Leu Asp Lys Ile Arg Ala Val Leu Arg Gly Leu
                100                 105                 110
Ile Val Gly Ala Phe Thr Gly Val Cys Gly Arg Arg Glu Asn Thr Val
            115                 120                 125
Gln Asn Glu Lys Tyr Glu Ser Leu Phe Lys Glu Lys Leu Ile Lys Glu
130                 135                 140
Ile Leu Pro Asp Phe Val Leu Ser Thr Glu Ala Glu Ser Leu Pro Phe
145                 150                 155                 160
Ser Val Glu Glu Ala Thr Arg Ser Leu Lys Glu Phe Asp Ser Phe Thr
                165                 170                 175
Ser Tyr Phe Ala Gly Phe Tyr Glu Asn Arg Lys Asn Ile Tyr Ser Thr
            180                 185                 190
Lys Pro Gln Ser Thr Ala Ile Ala Tyr Arg Leu Ile His Glu Asn Leu
                195                 200                 205
Pro Lys Phe Ile Asp Asn Ile Leu Val Phe Gln Lys Ile Lys Glu Pro
            210                 215                 220
Ile Ala Lys Glu Leu Glu His Ile Arg Ala Asp Phe Ser Ala Gly Gly
225                 230                 235                 240
Tyr Ile Lys Lys Asp Glu Arg Leu Glu Asp Ile Phe Ser Leu Asn Tyr
                245                 250                 255
Tyr Ile His Val Leu Ser Gln Ala Gly Ile Glu Lys Tyr Asn Ala Leu
            260                 265                 270
Ile Gly Lys Ile Val Thr Glu Gly Asp Gly Glu Met Lys Gly Leu Asn
            275                 280                 285
Glu His Ile Asn Leu Tyr Asn Gln Gln Arg Gly Arg Glu Asp Arg Leu
            290                 295                 300
Pro Leu Phe Arg Pro Leu Tyr Lys Gln Ile Leu Ser Asp Arg Glu Gln
305                 310                 315                 320
Leu Ser Tyr Leu Pro Glu Ser Phe Glu Lys Asp Glu Glu Leu Leu Arg
                325                 330                 335
Ala Leu Lys Glu Phe Tyr Asp His Ile Ala Glu Asp Ile Leu Gly Arg
            340                 345                 350
Thr Gln Gln Leu Met Thr Ser Ile Ser Glu Tyr Asp Leu Ser Arg Ile
            355                 360                 365
Tyr Val Arg Asn Asp Ser Gln Leu Thr Asp Ile Ser Lys Lys Met Leu
            370                 375                 380
Gly Asp Trp Asn Ala Ile Tyr Met Ala Arg Glu Arg Ala Tyr Asp His
385                 390                 395                 400
Glu Gln Ala Pro Lys Arg Ile Thr Ala Lys Tyr Glu Arg Asp Arg Ile
                405                 410                 415
Lys Ala Leu Lys Gly Glu Glu Ser Ile Ser Leu Ala Asn Leu Asn Ser
            420                 425                 430
```

```
Cys Ile Ala Phe Leu Asp Asn Val Arg Asp Cys Arg Val Asp Thr Tyr
            435                 440                 445

Leu Ser Thr Leu Gly Gln Lys Glu Gly Pro His Gly Leu Ser Asn Leu
        450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
            500                 505                 510

Leu Lys Pro Leu Trp Gly Met Gly Asp Glu Pro Asp Lys Asp Glu Arg
        515                 520                 525

Phe Tyr Gly Glu Tyr Asn Tyr Ile Arg Gly Ala Leu Asp Gln Val Ile
        530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
            565                 570                 575

Trp Asp Arg Asn Lys Glu Lys Asp Asn Ser Cys Val Ile Leu Arg Lys
            580                 585                 590

Gly Gln Asn Phe Tyr Leu Ala Ile Met Asn Asn Arg His Lys Arg Ser
        595                 600                 605

Phe Glu Asn Lys Met Leu Pro Glu Tyr Lys Glu Gly Glu Pro Tyr Phe
        610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
            645                 650                 655

Lys Leu Leu Glu Gln Tyr Gly His Gly Thr His Lys Lys Gly Asp Thr
        660                 665                 670

Phe Ser Met Asp Asp Leu His Glu Leu Ile Asp Phe Phe Lys His Ser
        675                 680                 685

Ile Glu Ala His Glu Asp Trp Lys Gln Phe Gly Phe Lys Phe Ser Asp
        690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
            725                 730                 735

Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
            755                 760                 765

Trp Arg Met Leu Phe Asp Glu Arg Asn Leu Ala Asp Val Ile Tyr Lys
        770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Ser Arg
                805                 810                 815

Gln Lys Lys Gly Glu Glu Ser Leu Phe Glu Tyr Asp Leu Val Lys Asp
            820                 825                 830

Arg Arg Tyr Thr Met Asp Lys Phe Gln Phe His Val Pro Ile Thr Met
            835                 840                 845
```

```
Asn Phe Lys Cys Ser Ala Gly Ser Lys Val Asn Asp Met Val Asn Ala
850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
                900                 905                 910

Leu Leu Glu Ser Arg Asp Lys Asp Arg Gln Gln Glu His Arg Asn Trp
                915                 920                 925

Gln Thr Ile Glu Gly Ile Lys Glu Leu Lys Gln Gly Tyr Leu Ser Gln
930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
                980                 985                 990

Asn Tyr Leu Val Asp Lys Lys Lys Arg Pro Glu Asp Ile Gly Gly Leu
                995                 1000                1005

Leu Arg Ala Tyr Gln Phe Thr Ala Pro Phe Lys Ser Phe Lys Glu
1010                1015                1020

Met Gly Lys Gln Asn Gly Phe Leu Phe Tyr Ile Pro Ala Trp Asn
1025                1030                1035

Thr Ser Asn Ile Asp Pro Thr Gly Phe Val Asn Leu Phe His
1040                1045                1050

Val Gln Tyr Glu Asn Val Asp Lys Ala Lys Ser Phe Phe Gln Lys
1055                1060                1065

Phe Asp Ser Ile Ser Tyr Asn Pro Lys Lys Asp Trp Phe Glu Phe
1070                1075                1080

Ala Phe Asp Tyr Lys Asn Phe Thr Lys Lys Ala Glu Gly Ser Arg
1085                1090                1095

Ser Met Trp Ile Leu Cys Thr His Gly Ser Arg Ile Lys Asn Phe
1100                1105                1110

Arg Asn Ser Gln Lys Asn Gly Gln Trp Asp Ser Glu Glu Phe Ala
1115                1120                1125

Leu Thr Glu Ala Phe Lys Ser Leu Phe Val Arg Tyr Glu Ile Asp
1130                1135                1140

Tyr Thr Ala Asp Leu Lys Thr Ala Ile Val Asp Glu Lys Gln Lys
1145                1150                1155

Asp Phe Phe Val Asp Leu Leu Lys Leu Phe Lys Leu Thr Val Gln
1160                1165                1170

Met Arg Asn Ser Trp Lys Glu Lys Asp Leu Asp Tyr Leu Ile Ser
1175                1180                1185

Pro Val Ala Gly Ala Asp Gly Arg Phe Phe Asp Thr Arg Glu Gly
1190                1195                1200

Asn Lys Ser Leu Pro Lys Asp Ala Asp Ala Asn Gly Ala Tyr Asn
1205                1210                1215

Ile Ala Leu Lys Gly Leu Trp Ala Leu Arg Gln Ile Arg Gln Thr
1220                1225                1230

Ser Glu Gly Gly Lys Leu Lys Leu Ala Ile Ser Asn Lys Glu Trp
1235                1240                1245

Leu Gln Phe Val Gln Glu Arg Ser Tyr Glu Lys Asp
```

1250          1255          1260

<210> SEQ ID NO 14
<211> LENGTH: 1324
<212> TYPE: PRT
<213> ORGANISM: Prevotella disiens

<400> SEQUENCE: 14

Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Val Lys Lys Thr Ala Leu Arg
            100                 105                 110

Asn Lys Cys Thr Ser Ile Gln Arg Ala Met Arg Glu Ala Ile Ser Gln
            115                 120                 125

Ala Phe Leu Lys Ser Pro Gln Lys Lys Leu Leu Ala Ile Lys Asn Leu
    130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
        275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Asp Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
        355                 360                 365

```
Tyr Arg Asn Phe Ser Ile Asp Glu Ala Ile Asp Ala Gln Asn Ala Glu
370                 375                 380

Leu Gln Thr Phe Asn Asn Tyr Glu Leu Ile Ala Asn Ala Leu Arg Ala
385                 390                 395                 400

Lys Ile Lys Lys Glu Thr Lys Gln Gly Arg Lys Ser Phe Glu Lys Tyr
            405                 410                 415

Glu Glu Tyr Ile Asp Lys Lys Val Lys Ala Ile Asp Ser Leu Ser Ile
            420                 425                 430

Gln Glu Ile Asn Glu Leu Val Glu Asn Tyr Val Ser Glu Phe Asn Ser
            435                 440                 445

Asn Ser Gly Asn Met Pro Arg Lys Val Glu Asp Tyr Phe Ser Leu Met
450                 455                 460

Arg Lys Gly Asp Phe Gly Ser Asn Asp Leu Ile Glu Asn Ile Lys Thr
465                 470                 475                 480

Lys Leu Ser Ala Ala Glu Lys Leu Leu Gly Thr Lys Tyr Gln Glu Thr
            485                 490                 495

Ala Lys Asp Ile Phe Lys Lys Asp Glu Asn Ser Lys Leu Ile Lys Glu
            500                 505                 510

Leu Leu Asp Ala Thr Lys Gln Phe Gln His Phe Ile Lys Pro Leu Leu
            515                 520                 525

Gly Thr Gly Glu Glu Ala Asp Arg Asp Leu Val Phe Tyr Gly Asp Phe
530                 535                 540

Leu Pro Leu Tyr Glu Lys Phe Glu Glu Leu Thr Leu Leu Tyr Asn Lys
545                 550                 555                 560

Val Arg Asn Arg Leu Thr Gln Lys Pro Tyr Ser Lys Asp Lys Ile Arg
            565                 570                 575

Leu Cys Phe Asn Lys Pro Lys Leu Met Thr Gly Trp Val Asp Ser Lys
            580                 585                 590

Thr Glu Lys Ser Asp Asn Gly Thr Gln Tyr Gly Gly Tyr Leu Phe Arg
            595                 600                 605

Lys Lys Asn Glu Ile Gly Glu Tyr Asp Tyr Phe Leu Gly Ile Ser Ser
            610                 615                 620

Lys Ala Gln Leu Phe Arg Lys Asn Glu Ala Val Ile Gly Asp Tyr Glu
625                 630                 635                 640

Arg Leu Asp Tyr Tyr Gln Pro Lys Ala Asn Thr Ile Tyr Gly Ser Ala
            645                 650                 655

Tyr Glu Gly Glu Asn Ser Tyr Lys Glu Asp Lys Lys Arg Leu Asn Lys
            660                 665                 670

Val Ile Ile Ala Tyr Ile Glu Gln Ile Lys Gln Thr Asn Ile Lys Lys
            675                 680                 685

Ser Ile Ile Glu Ser Ile Ser Lys Tyr Pro Asn Ile Ser Asp Asp Asp
            690                 695                 700

Lys Val Thr Pro Ser Ser Leu Leu Glu Lys Ile Lys Lys Val Ser Ile
705                 710                 715                 720

Asp Ser Tyr Asn Gly Ile Leu Ser Phe Lys Ser Phe Gln Ser Val Asn
            725                 730                 735

Lys Glu Val Ile Asp Asn Leu Leu Lys Thr Ile Ser Pro Leu Lys Asn
            740                 745                 750

Lys Ala Glu Phe Leu Asp Leu Ile Asn Lys Asp Tyr Gln Ile Phe Thr
            755                 760                 765

Glu Val Gln Ala Val Ile Asp Glu Ile Cys Lys Gln Lys Thr Phe Ile
770                 775                 780

Tyr Phe Pro Ile Ser Asn Val Glu Leu Glu Lys Glu Met Gly Asp Lys
```

-continued

```
            785                 790                 795                 800
Asp Lys Pro Leu Cys Leu Phe Gln Ile Ser Asn Lys Asp Leu Ser Phe
                805                 810                 815

Ala Lys Thr Phe Ser Ala Asn Leu Arg Lys Arg Gly Ala Glu Asn
            820                 825                 830

Leu His Thr Met Leu Phe Lys Ala Leu Met Glu Gly Asn Gln Asp Asn
            835                 840                 845

Leu Asp Leu Gly Ser Gly Ala Ile Phe Tyr Arg Ala Lys Ser Leu Asp
            850                 855                 860

Gly Asn Lys Pro Thr His Pro Ala Asn Glu Ala Ile Lys Cys Arg Asn
865                 870                 875                 880

Val Ala Asn Lys Asp Lys Val Ser Leu Phe Thr Tyr Asp Ile Tyr Lys
                885                 890                 895

Asn Arg Arg Tyr Met Glu Asn Lys Phe Leu Phe His Leu Ser Ile Val
            900                 905                 910

Gln Asn Tyr Lys Ala Ala Asn Asp Ser Ala Gln Leu Asn Ser Ser Ala
            915                 920                 925

Thr Glu Tyr Ile Arg Lys Ala Asp Asp Leu His Ile Ile Gly Ile Asp
            930                 935                 940

Arg Gly Glu Arg Asn Leu Leu Tyr Tyr Ser Val Ile Asp Met Lys Gly
945                 950                 955                 960

Asn Ile Val Glu Gln Asp Ser Leu Asn Ile Ile Arg Asn Asn Asp Leu
                965                 970                 975

Glu Thr Asp Tyr His Asp Leu Leu Asp Lys Arg Glu Lys Glu Arg Lys
            980                 985                 990

Ala Asn Arg Gln Asn Trp Glu Ala Val Glu Gly Ile Lys Asp Leu Lys
            995                1000                1005

Lys Gly Tyr Leu Ser Gln Ala Val His Gln Ile Ala Gln Leu Met
            1010                1015                1020

Leu Lys Tyr Asn Ala Ile Ile Ala Leu Glu Asp Leu Gly Gln Met
            1025                1030                1035

Phe Val Thr Arg Gly Gln Lys Ile Glu Lys Ala Val Tyr Gln Gln
            1040                1045                1050

Phe Glu Lys Ser Leu Val Asp Lys Leu Ser Tyr Leu Val Asp Lys
            1055                1060                1065

Lys Arg Pro Tyr Asn Glu Leu Gly Gly Ile Leu Lys Ala Tyr Gln
            1070                1075                1080

Leu Ala Ser Ser Ile Thr Lys Asn Asn Ser Asp Lys Gln Asn Gly
            1085                1090                1095

Phe Leu Phe Tyr Val Pro Ala Trp Asn Thr Ser Lys Ile Asp Pro
            1100                1105                1110

Val Thr Gly Phe Thr Asp Leu Leu Arg Pro Lys Ala Met Thr Ile
            1115                1120                1125

Lys Glu Ala Gln Asp Phe Phe Gly Ala Phe Asp Asn Ile Ser Tyr
            1130                1135                1140

Asn Asp Lys Gly Tyr Phe Glu Phe Glu Thr Asn Tyr Asp Lys Phe
            1145                1150                1155

Lys Ile Arg Met Lys Ser Ala Gln Thr Arg Trp Thr Ile Cys Thr
            1160                1165                1170

Phe Gly Asn Arg Ile Lys Arg Lys Lys Asp Lys Asn Tyr Trp Asn
            1175                1180                1185

Tyr Glu Glu Val Glu Leu Thr Glu Glu Phe Lys Lys Leu Phe Lys
            1190                1195                1200
```

-continued

Asp Ser Asn Ile Asp Tyr Glu Asn Cys Asn Leu Lys Glu Glu Ile
1205                1210                1215

Gln Asn Lys Asp Asn Arg Lys Phe Phe Asp Asp Leu Ile Lys Leu
1220                1225                1230

Leu Gln Leu Thr Leu Gln Met Arg Asn Ser Asp Asp Lys Gly Asn
1235                1240                1245

Asp Tyr Ile Ile Ser Pro Val Ala Asn Ala Glu Gly Gln Phe Phe
1250                1255                1260

Asp Ser Arg Asn Gly Asp Lys Lys Leu Pro Leu Asp Ala Asp Ala
1265                1270                1275

Asn Gly Ala Tyr Asn Ile Ala Arg Lys Gly Leu Trp Asn Ile Arg
1280                1285                1290

Gln Ile Lys Gln Thr Lys Asn Lys Asp Asp Leu Asn Leu Ser Ile
1295                1300                1305

Ser Ser Thr Glu Trp Leu Asp Phe Val Arg Glu Lys Pro Tyr Leu
1310                1315                1320

Lys

<210> SEQ ID NO 15
<211> LENGTH: 1484
<212> TYPE: PRT
<213> ORGANISM: Peregrinibacteria bacterium
<220> FEATURE:
<221> NAME/KEY: misc_feature
<222> LOCATION: (1073)..(1073)
<223> OTHER INFORMATION: Xaa can be any naturally occurring amino acid

<400> SEQUENCE: 15

Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
                20                  25                  30

Lys Asp His Leu Glu Tyr Asp Glu Lys Leu Gln Thr Phe Leu Lys Asp
            35                  40                  45

Gln Asn Ile Asp Asp Ala Tyr Gln Ala Leu Lys Pro Gln Phe Asp Glu
        50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
        195                 200                 205

Phe Cys Asp Asn Val Ile Gln Phe Lys His Ile Ile Lys Arg Lys Lys

-continued

```
            210                 215                 220
Asp Gly Thr Val Glu Lys Thr Glu Arg Lys Thr Glu Tyr Leu Asn Ala
225                 230                 235                 240

Tyr Gln Tyr Leu Lys Asn Asn Lys Ile Thr Gln Ile Lys Asp Ala
                    245                 250                 255

Glu Thr Glu Lys Met Ile Glu Ser Thr Pro Ile Ala Glu Lys Ile Phe
                    260                 265                 270

Asp Val Tyr Tyr Phe Ser Ser Cys Leu Ser Gln Lys Gln Ile Glu Glu
                    275                 280                 285

Tyr Asn Arg Ile Ile Gly His Tyr Asn Leu Leu Ile Asn Leu Tyr Asn
            290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                    325                 330                 335

Gly Lys Lys Lys Asp Leu Phe Tyr Thr Ile Lys Cys Asp Thr Glu Glu
                    340                 345                 350

Glu Ala Asn Lys Ser Arg Asn Glu Gly Lys Glu Ser His Ser Val Glu
                    355                 360                 365

Glu Ile Ile Asn Lys Ala Gln Glu Ala Ile Asn Lys Tyr Phe Lys Ser
            370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
                    405                 410                 415

Met Asn Thr Ile Ser Asp Lys Tyr Phe Ala Asn Tyr His Asp Leu Gln
                    420                 425                 430

Asp Arg Leu Lys Glu Ala Lys Val Phe Gln Lys Ala Asp Lys Lys Ser
                    435                 440                 445

Glu Asp Asp Ile Lys Ile Pro Glu Ala Ile Glu Leu Ser Gly Leu Phe
                    450                 455                 460

Gly Val Leu Asp Ser Leu Ala Asp Trp Gln Thr Thr Leu Phe Lys Ser
465                 470                 475                 480

Ser Ile Leu Ser Asn Glu Lys Leu Lys Ile Ile Thr Asp Ser Gln Thr
                    485                 490                 495

Pro Ser Glu Ala Leu Leu Lys Met Ile Phe Asn Asp Ile Glu Lys Asn
                    500                 505                 510

Met Glu Ser Phe Leu Lys Glu Thr Asn Asp Ile Ile Thr Leu Lys Lys
                    515                 520                 525

Tyr Lys Gly Asn Lys Glu Gly Thr Glu Lys Ile Lys Gln Trp Phe Asp
                    530                 535                 540

Tyr Thr Leu Ala Ile Asn Arg Met Leu Lys Tyr Phe Leu Val Lys Glu
545                 550                 555                 560

Asn Lys Ile Lys Gly Asn Ser Leu Asp Thr Asn Ile Ser Glu Ala Leu
                    565                 570                 575

Lys Thr Leu Ile Tyr Ser Asp Asp Ala Glu Trp Phe Lys Trp Tyr Asp
                    580                 585                 590

Ala Leu Arg Asn Tyr Leu Thr Gln Lys Pro Gln Asp Glu Ala Lys Glu
                    595                 600                 605

Asn Lys Leu Lys Leu Asn Phe Asp Asn Pro Ser Leu Ala Gly Gly Trp
                    610                 615                 620

Asp Val Asn Lys Glu Cys Ser Asn Phe Cys Val Ile Leu Lys Asp Lys
625                 630                 635                 640
```

```
Asn Glu Lys Lys Tyr Leu Ala Met Ile Lys Lys Gly Glu Asn Thr Leu
            645                 650                 655

Phe Gln Lys Glu Trp Thr Glu Gly Arg Gly Lys Asn Leu Thr Lys Lys
            660                 665                 670

Ser Asn Pro Leu Phe Glu Ile Asn Asn Cys Glu Ile Leu Ser Lys Met
            675                 680                 685

Glu Tyr Asp Phe Trp Ala Asp Val Ser Lys Met Ile Pro Lys Cys Ser
690                 695                 700

Thr Gln Leu Lys Ala Val Val Asn His Phe Lys Gln Ser Asp Asn Glu
705                 710                 715                 720

Phe Ile Phe Pro Ile Gly Tyr Lys Val Thr Ser Gly Glu Lys Phe Arg
            725                 730                 735

Glu Glu Cys Lys Ile Ser Lys Gln Asp Phe Glu Leu Asn Asn Lys Val
            740                 745                 750

Phe Asn Lys Asn Glu Leu Ser Val Thr Ala Met Arg Tyr Asp Leu Ser
            755                 760                 765

Ser Thr Gln Glu Lys Gln Tyr Ile Lys Ala Phe Gln Lys Glu Tyr Trp
            770                 775                 780

Glu Leu Leu Phe Lys Gln Glu Lys Arg Asp Thr Lys Leu Thr Asn Asn
785                 790                 795                 800

Glu Ile Phe Asn Glu Trp Ile Asn Phe Cys Asn Lys Lys Tyr Ser Glu
            805                 810                 815

Leu Leu Ser Trp Glu Arg Lys Tyr Lys Asp Ala Leu Thr Asn Trp Ile
            820                 825                 830

Asn Phe Cys Lys Tyr Phe Leu Ser Lys Tyr Pro Lys Thr Thr Leu Phe
            835                 840                 845

Asn Tyr Ser Phe Lys Glu Ser Glu Asn Tyr Asn Ser Leu Asp Glu Phe
            850                 855                 860

Tyr Arg Asp Val Asp Ile Cys Ser Tyr Lys Leu Asn Ile Asn Thr Thr
865                 870                 875                 880

Ile Asn Lys Ser Ile Leu Asp Arg Leu Val Glu Glu Gly Lys Leu Tyr
            885                 890                 895

Leu Phe Glu Ile Lys Asn Gln Asp Ser Asn Asp Gly Lys Ser Ile Gly
            900                 905                 910

His Lys Asn Asn Leu His Thr Ile Tyr Trp Asn Ala Ile Phe Glu Asn
            915                 920                 925

Phe Asp Asn Arg Pro Lys Leu Asn Gly Glu Ala Glu Ile Phe Tyr Arg
930                 935                 940

Lys Ala Ile Ser Lys Asp Lys Leu Gly Ile Val Lys Gly Lys Lys Thr
945                 950                 955                 960

Lys Asn Gly Thr Trp Ile Ile Lys Asn Tyr Arg Phe Ser Lys Glu Lys
            965                 970                 975

Phe Ile Leu His Val Pro Ile Thr Leu Asn Phe Cys Ser Asn Asn Glu
            980                 985                 990

Tyr Val Asn Asp Ile Val Asn Thr Lys Phe Tyr Asn Phe Ser Asn Leu
            995                 1000                1005

His Phe Leu Gly Ile Asp Arg Gly Glu Lys His Leu Ala Tyr Tyr
        1010                1015                1020

Ser Leu Val Asn Lys Asn Gly Glu Ile Val Asp Gln Gly Thr Leu
        1025                1030                1035

Asn Leu Pro Phe Thr Asp Lys Asp Gly Asn Gln Arg Ser Ile Lys
        1040                1045                1050
```

```
Lys Glu Lys Tyr Phe Tyr Asn Lys Gln Glu Asp Lys Trp Glu Ala
1055                1060                1065

Lys Glu Val Asp Xaa Trp Asn Tyr Asn Asp Leu Leu Asp Ala Met
1070                1075                1080

Ala Ser Asn Arg Asp Met Ala Arg Lys Asn Trp Gln Arg Ile Gly
1085                1090                1095

Thr Ile Lys Glu Ala Lys Asn Gly Tyr Val Ser Leu Val Ile Arg
1100                1105                1110

Lys Ile Ala Asp Leu Ala Val Asn Asn Glu Arg Pro Ala Phe Ile
1115                1120                1125

Val Leu Glu Asp Leu Asn Thr Gly Phe Lys Arg Ser Arg Gln Lys
1130                1135                1140

Ile Asp Lys Ser Val Tyr Gln Lys Phe Glu Leu Ala Leu Ala Lys
1145                1150                1155

Lys Leu Asn Phe Leu Val Asp Lys Asn Ala Lys Arg Asp Glu Ile
1160                1165                1170

Gly Ser Pro Thr Lys Ala Leu Gln Leu Thr Pro Pro Val Asn Asn
1175                1180                1185

Tyr Gly Asp Ile Glu Asn Lys Lys Gln Ala Gly Ile Met Leu Tyr
1190                1195                1200

Thr Arg Ala Asn Tyr Thr Ser Gln Thr Asp Pro Ala Thr Gly Trp
1205                1210                1215

Arg Lys Thr Ile Tyr Leu Lys Ala Gly Pro Glu Glu Thr Thr Tyr
1220                1225                1230

Lys Lys Asp Gly Lys Ile Lys Asn Lys Ser Val Lys Asp Gln Ile
1235                1240                1245

Ile Glu Thr Phe Thr Asp Ile Gly Phe Asp Gly Lys Asp Tyr Tyr
1250                1255                1260

Phe Glu Tyr Asp Lys Gly Glu Phe Val Asp Glu Lys Thr Gly Glu
1265                1270                1275

Ile Lys Pro Lys Lys Trp Arg Leu Tyr Ser Gly Glu Asn Gly Lys
1280                1285                1290

Ser Leu Asp Arg Phe Arg Gly Glu Arg Glu Lys Asp Lys Tyr Glu
1295                1300                1305

Trp Lys Ile Asp Lys Ile Asp Ile Val Lys Ile Leu Asp Asp Leu
1310                1315                1320

Phe Val Asn Phe Asp Lys Asn Ile Ser Leu Leu Lys Gln Leu Lys
1325                1330                1335

Glu Gly Val Glu Leu Thr Arg Asn Asn Glu His Gly Thr Gly Glu
1340                1345                1350

Ser Leu Arg Phe Ala Ile Asn Leu Ile Gln Gln Ile Arg Asn Thr
1355                1360                1365

Gly Asn Asn Glu Arg Asp Asn Asp Phe Ile Leu Ser Pro Val Arg
1370                1375                1380

Asp Glu Asn Gly Lys His Phe Asp Ser Arg Glu Tyr Trp Asp Lys
1385                1390                1395

Glu Thr Lys Gly Glu Lys Ile Ser Met Pro Ser Ser Gly Asp Ala
1400                1405                1410

Asn Gly Ala Phe Asn Ile Ala Arg Lys Gly Ile Ile Met Asn Ala
1415                1420                1425

His Ile Leu Ala Asn Ser Asp Ser Lys Asp Leu Ser Leu Phe Val
1430                1435                1440

Ser Asp Glu Glu Trp Asp Leu His Leu Asn Asn Lys Thr Glu Trp
```

```
              1445           1450           1455
Lys Lys Gln Leu Asn Ile Phe Ser Ser Arg Lys Ala Met Ala Lys
            1460           1465           1470

Arg Lys Lys Lys Arg Pro Ala Ala Thr Lys Lys
            1475           1480

<210> SEQ ID NO 16
<211> LENGTH: 1245
<212> TYPE: PRT
<213> ORGANISM: Porphyromonas macacae

<400> SEQUENCE: 16

Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
            20                  25                  30

Asn Ile Lys Lys Asn Gly Leu Ile Arg Arg Asp Glu Gln Arg Leu Asp
        35                  40                  45

Asp Tyr Glu Lys Leu Lys Lys Val Ile Asp Glu Tyr His Glu Asp Phe
    50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Ile Ser Glu Ala Arg Ala Lys Ile Glu
                85                  90                  95

Lys Thr Met Arg Asp Thr Leu Ala Lys Ala Phe Ser Glu Asp Glu Arg
            100                 105                 110

Tyr Lys Ser Ile Phe Lys Lys Glu Leu Val Lys Lys Asp Ile Pro Val
        115                 120                 125

Trp Cys Pro Ala Tyr Lys Ser Leu Cys Lys Lys Phe Asp Asn Phe Thr
130                 135                 140

Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
            180                 185                 190

Met Gly Ala Asp Leu Tyr Leu Glu Met Met Glu Asn Leu Arg Asn Val
        195                 200                 205

Trp Pro Ser Phe Val Lys Thr Pro Asp Asp Leu Cys Asn Leu Lys Thr
210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
        275                 280                 285

Ser Phe Ile Ser Asp Thr Leu Glu Asn Asp Asp Gln Val Phe Cys Val
    290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335
```

-continued

```
Asp Pro Glu Ala Ile Tyr Val Ser Asp Ala His Leu Ala Thr Ile Ser
            340                 345                 350

Lys Asn Ile Phe Asp Arg Trp Asn Tyr Ile Ser Asp Ala Ile Arg Arg
        355                 360                 365

Lys Thr Glu Val Leu Met Pro Arg Lys Lys Glu Ser Val Glu Arg Tyr
    370                 375                 380

Ala Glu Lys Ile Ser Lys Gln Ile Lys Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
            420                 425                 430

Tyr Leu Val Ser Asp Gly Glu Val Ile Leu Tyr Glu Glu Gly Ser Asn
        435                 440                 445

Ile Trp Asp Glu Val Leu Ile Ala Phe Arg Asp Leu Gln Val Ile Leu
    450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
                485                 490                 495

Phe Asp Leu Leu Ser Gly Thr Gly Ala Glu Ile Arg Arg Asp Ser Ser
            500                 505                 510

Phe Tyr Ala Leu Tyr Thr Asp Arg Met Asp Lys Leu Lys Gly Leu Leu
        515                 520                 525

Lys Met Tyr Asp Lys Val Arg Asn Tyr Leu Thr Lys Lys Pro Tyr Ser
    530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
        595                 600                 605

Met Glu Tyr Lys Gln Ile Ala Glu Pro Met Leu Met Leu Pro Lys Val
    610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
            660                 665                 670

Thr Val His Glu Trp Lys Leu Phe Asn Phe Ser Phe Ser Pro Thr Glu
        675                 680                 685

Gln Tyr Arg Asn Ile Gly Glu Phe Phe Asp Glu Val Arg Glu Gln Ala
    690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
```

```
              755                 760                 765
Gly Gly Glu Leu Phe Tyr Arg Lys Ala Ser Leu His Met Gln Asp Thr
770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe His Val Pro Ile Ser Ile Asn Tyr
                820                 825                 830

Lys Asn Lys Lys Ile Thr Asn Val Asn Gln Met Val Arg Asp Tyr Ile
                835                 840                 845

Ala Gln Asn Asp Asp Leu Gln His Gly Ile Asp Arg Gly Glu Arg Asn
850                 855                 860

Leu Leu Tyr Ile Ser Arg Ile Asp Thr Arg Gly Asn Leu Leu Glu Gln
865                 870                 875                 880

Phe Ser Leu Asn Val Ile Glu Ser Asp Lys Gly Asp Leu Arg Thr Asp
                885                 890                 895

Tyr Gln Lys Ile Leu Gly Asp Arg Glu Gln Glu Arg Leu Arg Arg Arg
                900                 905                 910

Gln Glu Trp Lys Ser Ile Glu Ser Ile Lys Asp Leu Lys Asp Gly Tyr
                915                 920                 925

Met Ser Gln Val Val His Lys Ile Cys Asn Met Val Val Glu His Lys
930                 935                 940

Ala Ile Val Val Leu Glu Asn Leu Asn Leu Ser Phe Met Lys Gly Arg
945                 950                 955                 960

Lys Lys Val Glu Lys Ser Val Tyr Glu Lys Phe Glu Arg Met Leu Val
                965                 970                 975

Asp Lys Leu Asn Tyr Leu Val Val Asp Lys Lys Asn Leu Ser Asn Glu
                980                 985                 990

Pro Gly Gly Leu Tyr Ala Ala Tyr Gln Leu Thr Asn Pro Leu Phe Ser
                995                 1000                1005

Phe Glu Glu Leu His Arg Tyr Pro Gln Ser Gly Ile Leu Phe Phe
   1010                1015                1020

Val Asp Pro Trp Asn Thr Ser Leu Thr Asp Pro Ser Thr Gly Phe
   1025                1030                1035

Val Asn Leu Leu Gly Arg Ile Asn Tyr Thr Asn Val Gly Asp Ala
   1040                1045                1050

Arg Lys Phe Phe Asp Arg Phe Asn Ala Ile Arg Tyr Asp Gly Lys
   1055                1060                1065

Gly Asn Ile Leu Phe Asp Leu Asp Leu Ser Arg Phe Asp Val Arg
   1070                1075                1080

Val Glu Thr Gln Arg Lys Leu Trp Thr Leu Thr Thr Phe Gly Ser
   1085                1090                1095

Arg Ile Ala Lys Ser Lys Lys Ser Gly Lys Trp Met Val Glu Arg
   1100                1105                1110

Ile Glu Asn Leu Ser Leu Cys Phe Leu Glu Leu Phe Glu Gln Phe
   1115                1120                1125

Asn Ile Gly Tyr Arg Val Glu Lys Asp Leu Lys Lys Ala Ile Leu
   1130                1135                1140

Ser Gln Asp Arg Lys Glu Phe Tyr Val Arg Leu Ile Tyr Leu Phe
   1145                1150                1155

Asn Leu Met Met Gln Ile Arg Asn Ser Asp Gly Glu Glu Asp Tyr
   1160                1165                1170
```

-continued

```
Ile Leu Ser Pro Ala Leu Asn Glu Lys Asn Leu Gln Phe Asp Ser
    1175                1180                1185

Arg Leu Ile Glu Ala Lys Asp Leu Pro Val Asp Ala Asp Ala Asn
    1190                1195                1200

Gly Ala Tyr Asn Val Ala Arg Lys Gly Leu Met Val Val Gln Arg
    1205                1210                1215

Ile Lys Arg Gly Asp His Glu Ser Ile His Arg Ile Gly Arg Ala
    1220                1225                1230

Gln Trp Leu Arg Tyr Val Gln Glu Gly Ile Val Glu
    1235                1240                1245

<210> SEQ ID NO 17
<211> LENGTH: 1250
<212> TYPE: PRT
<213> ORGANISM: Smithella sp.

<400> SEQUENCE: 17

Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
            20                  25                  30

Glu Gln Lys Gly Leu Leu Lys Lys Asp Glu Asp Arg Ala Glu Lys Tyr
        35                  40                  45

Lys Lys Val Lys Asn Ile Ile Asp Glu Tyr His Lys Asp Phe Ile Glu
    50                  55                  60

Lys Ser Leu Asn Gly Leu Lys Leu Asp Gly Leu Glu Lys Tyr Lys Thr
65                  70                  75                  80

Leu Tyr Leu Lys Gln Glu Lys Asp Asp Lys Asp Lys Lys Ala Phe Asp
                85                  90                  95

Lys Glu Lys Glu Asn Leu Arg Lys Gln Ile Ala Asn Ala Phe Arg Asn
            100                 105                 110

Asn Glu Lys Phe Lys Thr Leu Phe Ala Lys Glu Leu Ile Lys Asn Asp
        115                 120                 125

Leu Met Ser Phe Ala Cys Glu Glu Asp Lys Lys Asn Val Lys Glu Phe
    130                 135                 140

Glu Ala Phe Thr Thr Tyr Phe Thr Gly Phe His Gln Asn Arg Ala Asn
145                 150                 155                 160

Met Tyr Val Ala Asp Glu Lys Arg Thr Ala Ile Ala Ser Arg Leu Ile
                165                 170                 175

His Glu Asn Leu Pro Lys Phe Ile Asp Asn Ile Lys Ile Phe Glu Lys
            180                 185                 190

Met Lys Lys Glu Ala Pro Glu Leu Leu Ser Pro Phe Asn Gln Thr Leu
        195                 200                 205

Lys Asp Met Lys Asp Val Ile Lys Gly Thr Thr Leu Glu Glu Ile Phe
    210                 215                 220

Ser Leu Asp Tyr Phe Asn Lys Thr Leu Thr Gln Ser Gly Ile Asp Ile
225                 230                 235                 240

Tyr Asn Ser Val Ile Gly Gly Arg Thr Pro Glu Glu Gly Lys Thr Lys
                245                 250                 255

Ile Lys Gly Leu Asn Glu Tyr Ile Asn Thr Asp Phe Asn Gln Lys Gln
            260                 265                 270

Thr Asp Lys Lys Lys Arg Gln Pro Lys Phe Lys Gln Leu Tyr Lys Gln
        275                 280                 285

Ile Leu Ser Asp Arg Gln Ser Leu Ser Phe Ile Ala Glu Ala Phe Lys
```

-continued

```
                290                 295                 300
Asn Asp Thr Glu Ile Leu Glu Ala Ile Glu Lys Phe Tyr Val Asn Glu
305                 310                 315                 320

Leu Leu His Phe Ser Asn Glu Gly Lys Ser Thr Asn Val Leu Asp Ala
                325                 330                 335

Ile Lys Asn Ala Val Ser Asn Leu Glu Ser Phe Asn Leu Thr Lys Met
                340                 345                 350

Tyr Phe Arg Ser Gly Ala Ser Leu Thr Asp Val Ser Arg Lys Val Phe
                355                 360                 365

Gly Glu Trp Ser Ile Ile Asn Arg Ala Leu Asp Asn Tyr Tyr Ala Thr
                370                 375                 380

Thr Tyr Pro Ile Lys Pro Arg Glu Lys Ser Glu Lys Tyr Glu Glu Arg
385                 390                 395                 400

Lys Glu Lys Trp Leu Lys Gln Asp Phe Asn Val Ser Leu Ile Gln Thr
                405                 410                 415

Ala Ile Asp Glu Tyr Asp Asn Glu Thr Val Lys Gly Lys Asn Ser Gly
                420                 425                 430

Lys Val Ile Ala Asp Tyr Phe Ala Lys Phe Cys Asp Asp Lys Glu Thr
                435                 440                 445

Asp Leu Ile Gln Lys Val Asn Glu Gly Tyr Ile Ala Val Lys Asp Leu
                450                 455                 460

Leu Asn Thr Pro Cys Pro Glu Asn Glu Lys Leu Gly Ser Asn Lys Asp
465                 470                 475                 480

Gln Val Lys Gln Ile Lys Ala Phe Met Asp Ser Ile Met Asp Ile Met
                485                 490                 495

His Phe Val Arg Pro Leu Ser Leu Lys Asp Thr Asp Lys Glu Lys Asp
                500                 505                 510

Glu Thr Phe Tyr Ser Leu Phe Thr Pro Leu Tyr Asp His Leu Thr Gln
                515                 520                 525

Thr Ile Ala Leu Tyr Asn Lys Val Arg Asn Tyr Leu Thr Gln Lys Pro
                530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                565                 570                 575

Arg Lys Asp Asn Leu Tyr Tyr Leu Gly Ile Met Asp Lys Arg His Asn
                580                 585                 590

Arg Ile Phe Arg Asn Val Pro Lys Ala Asp Lys Lys Asp Phe Cys Tyr
                595                 600                 605

Glu Lys Met Val Tyr Lys Leu Leu Pro Gly Ala Asn Lys Met Leu Pro
610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                645                 650                 655

Phe Asn Leu Asn His Cys His Lys Leu Ile Asp Phe Phe Lys Asp Ser
                660                 665                 670

Ile Asn Lys His Glu Asp Trp Lys Asn Phe Asp Phe Arg Phe Ser Ala
                675                 680                 685

Thr Ser Thr Tyr Ala Asp Leu Ser Gly Phe Tyr His Glu Val Glu His
                690                 695                 700

Gln Gly Tyr Lys Ile Ser Phe Gln Ser Val Ala Asp Ser Phe Ile Asp
705                 710                 715                 720
```

-continued

Asp Leu Val Asn Glu Gly Lys Leu Tyr Leu Phe Gln Ile Tyr Asn Lys
            725                 730                 735

Asp Phe Ser Pro Phe Ser Lys Gly Lys Pro Asn Leu His Thr Leu Tyr
            740                 745                 750

Trp Lys Met Leu Phe Asp Glu Asn Asn Leu Lys Asp Val Val Tyr Lys
            755                 760                 765

Leu Asn Gly Glu Ala Glu Val Phe Tyr Arg Lys Lys Ser Ile Ala Glu
        770                 775                 780

Lys Asn Thr Thr Ile His Lys Ala Asn Glu Ser Ile Ile Asn Lys Asn
785                 790                 795                 800

Pro Asp Asn Pro Lys Ala Thr Ser Thr Phe Asn Tyr Asp Ile Val Lys
            805                 810                 815

Asp Lys Arg Tyr Thr Ile Asp Lys Phe Gln Phe His Ile Pro Ile Thr
            820                 825                 830

Met Asn Phe Lys Ala Glu Gly Ile Phe Asn Met Asn Gln Arg Val Asn
            835                 840                 845

Gln Phe Leu Lys Ala Asn Pro Asp Ile Asn Ile Ile Gly Ile Asp Arg
        850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
            885                 890                 895

Val Asp Tyr His Asn Leu Leu Asp Lys Lys Glu Gly Asp Arg Ala Thr
        900                 905                 910

Ala Arg Gln Glu Trp Gly Val Ile Glu Thr Ile Lys Glu Leu Lys Glu
            915                 920                 925

Gly Tyr Leu Ser Gln Val Ile His Lys Leu Thr Asp Leu Met Ile Glu
        930                 935                 940

Asn Asn Ala Ile Ile Val Met Glu Asp Leu Asn Phe Gly Phe Lys Arg
945                 950                 955                 960

Gly Arg Gln Lys Val Glu Lys Gln Val Tyr Gln Lys Phe Glu Lys Met
            965                 970                 975

Leu Ile Asp Lys Leu Asn Tyr Leu Val Asp Lys Asn Lys Lys Ala Asn
            980                 985                 990

Glu Leu Gly Gly Leu Leu Asn Ala Phe Gln Leu Ala Asn Lys Phe Glu
        995                 1000                1005

Ser Phe Gln Lys Met Gly Lys Gln Asn Gly Phe Ile Phe Tyr Val
        1010                1015                1020

Pro Ala Trp Asn Thr Ser Lys Thr Asp Pro Ala Thr Gly Phe Ile
        1025                1030                1035

Asp Phe Leu Lys Pro Arg Tyr Glu Asn Leu Asn Gln Ala Lys Asp
        1040                1045                1050

Phe Phe Glu Lys Phe Asp Ser Ile Arg Leu Asn Ser Lys Ala Asp
        1055                1060                1065

Tyr Phe Glu Phe Ala Phe Asp Phe Lys Asn Phe Thr Glu Lys Ala
        1070                1075                1080

Asp Gly Gly Arg Thr Lys Trp Thr Val Cys Thr Thr Asn Glu Asp
        1085                1090                1095

Arg Tyr Gln Trp Asn Arg Ala Leu Asn Asn Asn Arg Gly Ser Gln
        1100                1105                1110

Glu Lys Tyr Asp Ile Thr Ala Glu Leu Lys Ser Leu Phe Asp Gly
        1115                1120                1125

```
Lys Val Asp Tyr Lys Ser Gly Lys Asp Leu Lys Gln Gln Ile Ala
    1130            1135            1140

Ser Gln Glu Ser Ala Asp Phe Phe Lys Ala Leu Met Lys Asn Leu
    1145            1150            1155

Ser Ile Thr Leu Ser Leu Arg His Asn Asn Gly Glu Lys Gly Asp
    1160            1165            1170

Asn Glu Gln Asp Tyr Ile Leu Ser Pro Val Ala Asp Ser Lys Gly
    1175            1180            1185

Arg Phe Phe Asp Ser Arg Lys Ala Asp Asp Met Pro Lys Asn
    1190            1195            1200

Ala Asp Ala Asn Gly Ala Tyr His Ile Ala Leu Lys Gly Leu Trp
    1205            1210            1215

Cys Leu Glu Gln Ile Ser Lys Thr Asp Asp Leu Lys Lys Val Lys
    1220            1225            1230

Leu Ala Ile Ser Asn Lys Glu Trp Leu Glu Phe Val Gln Thr Leu
    1235            1240            1245

Lys Gly
    1250
```

<210> SEQ ID NO 18
<211> LENGTH: 3987
<212> TYPE: DNA
<213> ORGANISM: Artificial
<220> FEATURE:
<223> OTHER INFORMATION: enAsCpf1

<400> SEQUENCE: 18

```
atggccggga gcaagaagcg ccggataaag caggacacgc agttcgaggg cttcaccaac      60
ctgtaccaag tctccaagac gctccggttc gagcttatcc cgcaagggaa gaccctgaaa     120
cacatccagg aacaaggttt catcgaggag acaaggccc gcaacgacca ctacaaggag      180
ctcaagccca taatcgatcg gatctacaag acgtacgccg accagtgcct ccaactggtg     240
cagctcgact gggagaacct gagcgccgcc attgacagct accgcaagga aaagacggag     300
gagacgcgca acgcccttat tgaggagcaa gccacctacc gcaacgccat ccacgactac     360
ttcatcgggc gcaccgacaa cctgacggac gcgatcaaca agcgccacgc ggaaatctac     420
aagggccttt tcaaggccga gctcttcaac gggaaggtcc taaaacagct cgggactgtc     480
acgacaaccg agcatgagaa cgccctcctt cgcagcttcg acaagttcac cacatacttc     540
tcgggcttct accggaaccg caagaacgtt ttcagcgccg aggacatctc caccgccatc     600
ccgcacagga tcgtccagga caacttcccc aagttcaagg agaactgcca catcttcacg     660
cgcctgatta cagccgtacc ttcacttcgt gagcacttcg agaacgtcaa aaaggccatc     720
gggatcttcg tctccacgtc catcgaggag gtattctctt cccgttccta taccagctc     780
ctgacccaga cgcagatcga cctctacaac cagctactgg cggcatcag ccggggaggcc    840
gggaccgaga aaataaaggg cctcaacgaa gttctcaacc tggccatcca agaacgac      900
gagaccgcgc atatcatcgc atccctgccg catcgcttca ttcctttgtt caagcagata     960
ttgagcgacc ggaacaccct ctcgttcatc ctcgaagaat tcaagagcga cgaggaggtc    1020
attcagtctt tctgcaagta caagacgctc tacggaatg agaatgtgct ggagaccgcg    1080
gaggcactct tcaatgagct gaactccatt gacctgaccc acatcttcat tagccacaag   1140
aaactggaga cgatctccag cgccctgtgc gaccactggg acactctccg caacgccctc   1200
tacgaacgcc ggatctccga acttaccggc aagataacta gtcggctaa ggagaaggtg   1260
```

```
caacggagcc tcaagcacga ggacatcaac cttcaggaaa tcatctcagc cgcgggcaag    1320
gagctgagcg aggcgtttaa gcagaaaaca tcggagatac tgagccacgc gcacgcggcc    1380
ctggatcaac cgctgccgac gactctcaag aagcaagagg agaaggaaat ccttaagtcc    1440
cagctcgact cgctgctcgg cctctatcac ttgctcgact ggttcgcggt tgatgagtcc    1500
aacgaggtgg acccggagtt ctccgcgcgc ctcacgggta ttaagctgga gatggagcca    1560
agcttaagct tctacaacaa ggcccgcaac tacgcgacca aaaaaccgta ctcagtcgag    1620
aaattcaagc tgaatttcca gatgcctaca ttggcgaggg ggtgggacgt gaaccgcgag    1680
aagaacaatg gagccatcct gttcgtcaaa aatgggttgt actacctggg catcatgccc    1740
aagcagaagg gccgttacaa ggccctgtca ttcgagccta ccgagaagac ctcggagggc    1800
ttcgacaaga tgtactacga ctatttcccg gacgccgcca agatgatccc gaagtgctcc    1860
acgcagctca agccgtcac ggcccacttc cagacgcata ccacgccgat acttctgagc     1920
aacaacttca ttgagccgct agagatcacg aaggagatat acgacctaaa caaccccgaa    1980
aaggagccca agaagttcca gacagcctac gctaagaaga caggtgatca aagggatat     2040 agggaggcac tctgcaagtg gatcgacttc acgcgcgact ccctgtcgaa atatacaaag    2100
acgaccagca ttgacctaag ttctctccgc ccatcctccc agtacaagga tctgggcgag    2160
tattatgcgg agctgaaccc attgctgtac cacatcagct tccagaggat cgccgagaag    2220
gagattatgg acgcggtgga gacggggaaa ctatacctgt tccaaatata taacaaggac    2280
ttcgctaaag ggcaccacgg gaagcccaac ctgcacacac tctactggac gggcttgttt    2340
tcgccagaaa atttggccaa gacttcgatc aagctcaacg gccaggcgga gttgtttttac    2400 cgtcccaagt ctcgcatgaa gcgcatggcg catcgcctcg agagaaaat gcttaacaag     2460 aagctcaagg atcagaagac gcccatacct gatacgttgt accaggaatt gtacgactac    2520
gtgaaccacc gcctatcgca cgacctctca gacgaggccc gcgccctcct cccaaacgtg    2580
attactaagg aggtttccca tgaaataatc aaggaccgac ggttcaccag cgacaaattt    2640
tttttccacg tgcctatcac gctcaattac caggcggcca actccccatc gaagttcaac    2700
cagcgcgtga acgcctacct taaggagcac ccggagaccc caatcatcgg gatcgaccgt    2760
ggcgagcgga acctgatcta tattacggtg atcgatagca ccgggaagat cctggagcag    2820 cgctcctga acacaatcca gcagtttgac taccagaaga aactcgacaa ccgggagaag    2880
gagcgcgtcg cagcccggca agcatggagt gtggtcggca ccataaagga cctgaaacag    2940
ggttacctaa gtcaagttat ccacgagatc gttgacctga tgatacacta tcaagccgta    3000
gtcgtgctgg agaacctcaa cttcgggttt aagtccaagc gcaccggcat cgcggagaag    3060
gcggtgtacc agcagttcga aagatgctg atcgacaagc tgaactgcct ggtgctcaag     3120
gactaccctg cggagaaggt cggcgggtc ttgaacccgt accagctaac cgaccagttc     3180
acgagcttcg ccaaaatggg cacgcagtcc ggattcttgt tttatgtccc ggctccatat    3240
acaagtaaga tcgacccgct gacagggttt gttgacccat tcgtgtggaa gaccatcaag    3300
aaccacgaga gcaggaaaca cttcttagag ggcttcgact tcctgcatta cgacgttaag    3360
acaggcgact tcatcctgca cttcaagatg aaccgcaacc gtcgttcca gaggggcctg    3420 cccggcttca tgcccgcctg ggatatcgtc tttgagaaga tgagacgca gttcgacgcg     3480 aaggggacgc cgttcatcgc tggaaagcgg atcgtgccgg tcatcgagaa ccaccgcttc    3540
acgggtcgct accgagattt ataccccgcc aacgaactaa ttgcgctgct ggaggagaag    3600
gggatcgtgt tccgagatgg cagcaacatt ctcccgaagc tgctggagaa cgacgactcg    3660
```

```
cacgctattg acacgatggt cgccctcata cggagcgtgc ttcagatgcg aacagtaac     3720 gctgccacgg gcgaggacta cattaactcc cccgtccgcg acctcaacgg ggtctgcttc     3780
gatagccgct tccagaaccc ggagtggcct atggatgcgg acgcgaacgg ggcctaccac     3840
atcgccctca agggccaact cctgctcaac cacttgaagg aaagcaaaga cctcaaattg     3900
cagaatggca tcagtaacca ggactggctc gcgtacatcc aggaactgag aaacgggtcc     3960
aagaagcggc gtatcaagca agattga                                         3987
```

<210> SEQ ID NO 19
<211> LENGTH: 3987
<212> TYPE: DNA
<213> ORGANISM: Artificial
<220> FEATURE:
<223> OTHER INFORMATION: enAsCpf1

<400> SEQUENCE: 19

```
atggcgggaa gcaaaaagcg ccggattaag caagacacgc agttcgaggg cttcacgaac       60
ctctaccaag tcagcaagac cctccggttc gagctgatac acagggaaa gacgctcaag       120 cacatccagg aacagggctt catcgaggag acaaggcgc gcaacgacca ctacaaggag        180
ttgaaaccga tcatcgaccg catctacaag acgtacgccg accagtgcct ccagctcgtg       240
cagctcgact gggagaacct ctccgccgcc attgactcgt accggaagga gaagactgag       300
gagacccgca acgccctgat cgaggagcaa gcaacctacc ggaacgccat ccacgactac       360
ttcatcggcc gcaccgacaa cctcaccgac gcgatcaaca gcggcacgc ggagatatac        420 aaagggctgt tcaaggcgga gctgttcaac ggcaaggtgc tcaagcagct agggacggtg       480
accacgaccg agcacgagaa cgcgctcctc gcagcttcg acaagttcac cacctacttc        540
agcggcttct accggaaccg caagaatgtg ttcagcgcgg aggacatcag cacggccatc       600
ccgcaccgca tcgtccagga caacttcccg aagttcaagg agaactgcca catcttcacc       660
cgcctgataa ccgccgtccc ctccctgcgg gagcacttcg agaacgtcaa aaaggcaatt       720
gggatcttcg tctcgaccag cattgaggag gtgttcagct tccccttcta caaccagctc       780
ctcacccaga cgcagatcga cctgtacaat cagttgctcg gcgggataag ccgcgaggcg       840
ggaaccgaaa aaatcaaggg gctgaacgaa gtgttgaacc tcgccatcca gaagaacgac       900
gagaccgcgc acatcatcgc ctcccgcc caccggttca tcccgctgtt caagcagatc         960
ctctctgacc ggaacaccct gtccttcatt cttgaggagt tcaagtcgga cgaggaggtc      1020
atccagagct tctgcaagta caagacgctg ctacggaacg agaacgtgct ggagacggcg      1080
gaggcactgt tcaacgagct aaacagcatc gacctcacgc acatcttcat cagtcacaag      1140
aaactggaga ccatctcctc cgcgctgtgc gaccactggg acacgctcag gaacgcgctc      1200
tacgagcgcc gaatcagtga gctgacgggc aagatcacga gtccgcgaa ggagaaggtg      1260 cagcggtccc tcaagcacga ggacatcaac tccaggaga tcatctcagc ggctgggaaa      1320
gagctgtccg aggcgttcaa gcagaaaacg agcgaaatcc tgtcccacgc gcacgcggcc      1380
ctggatcagc tctgtgccgac gaccctcaag aaacaagaag aaaaggaaat cctcaagtcg      1440
cagctcgact cgctgctggg cctgtaccat tcctcgact ggttcgccgt ggacgagagc       1500
aacgaggtgg accccgagtt ctccgcgcgg cttacgggga tcaagctgga gatggagccc     1560
agcctgtcct tctacaacaa ggcgcgcaac tacgccacca agaagccca cagcgtggag      1620 aagttcaagc tcaacttcca gatgcccact ctcgcacgtg gtgggacgt caaccgcgaa      1680
```

```
aaaaataatg gggcgatcct gttcgtcaag aacggcctgt actacttggg catcatgccg    1740
aaacagaagg gccgctacaa ggccctgagc ttcgaaccga ccgagaaaac gagcgagggg    1800
ttcgacaaga tgtactacga ctacttcccc gacgccgcga agatgattcc aaagtgctcc    1860
acgcagctta aggccgtgac ggcccacttc cagacgcaca cgaccccgat cctcctcagc    1920
aacaacttca tcgagcccct ggagatcacg aaggagatat acgacctgaa caacccggag    1980
aaggagccca agaaattcca gaccgcctac gccaagaaga caggcgacca aaagggttac    2040
agggaggccc tctgcaagtg gatcgacttc actagggact tcctgtccaa gtacaccaag    2100
actacctcta tcgacctgtc cagcctccgc ccgtcgtccc agtacaaaga tttgggcgag    2160
tattacgcgg agctgaaccc actgctctac cacatcagct tccagcgcat cgcggagaag    2220
gagatcatgg acgcagtgga gacgggcaag ctatacctat ttcagatata caacaaagac    2280
ttcgctaagg gacaccacgg caagcctaac ctgcacaccc tctactggac ggggctcttc    2340
agcccggaga acctcgccaa gacctcgatc aagctcaacg gccaggccga gctgttctac    2400
cggcccaagt cccgcatgaa gcggatggcc caccggctcg gggagaaaat gctcaacaag    2460
aaattgaagg accaaaaaac gccgataccc gacaccctat accaggagct gtacgactat    2520
gtgaaccacc gcctgagcca cgacctcagc gacgaggcgc gggccctcct gccgaacgtc    2580
atcacaaagg aggtcagcca cgagatcatc aaggaccggc gcttcacctc cgacaagttt    2640
ttctttcacg tgcccatcac gctcaactac caggccgcca actcgccgtc caagttcaac    2700
cagcgcgtga cgcctacct caaggagcac cccgagaccc cgatcatcgg gattgaccga    2760
ggggagcgga acctcatcta catcaccgtc atcgacagca ccgggaagat ccttgaacag    2820
cggtcgctca acaccatcca gcagttcgac taccagaaga aactcgacaa ccgggagaag    2880
gagagagtgg cggcccgcca ggcttggtcc gtcgtcggga cgattaagga cttgaaacaa    2940
ggttacctgt cgcaagtgat ccacgagatc gttgacctga tgatccacta ccaagccgtc    3000
gtggtcctgg agaacctcaa cttcggcttc aagagcaaac gaaccggcat cgcggagaag    3060
gccgtgtacc agcagttcga aaaaatgctg atcgacaagc tgaactgcct cgtgctcaag    3120 gactacccg ctgagaaggt cggcggggtg ctgaacccgt accagctcac tgaccagttc    3180
accagcttcg caaagatggg cacccagtcc ggcttcctgt tctacgtgcc tgcgccatac    3240
acctcgaaga tcgacccgct caccgggttc gtggaccccct tcgtctggaa gaccatcaag    3300
aaccacgaga gccgcaagca cttcctggag ggcttcgact tcctccacta cgacgtcaag    3360
accggggact tcatcctgca cttcaagatg aaccgcaacc tcagtttcca gcgcggcctg    3420
ccggggttca tgcccgcttg ggatatagtc ttcgagaaga atgagacgca gttcgacgcg    3480
aagggcaccc cgttcatcgc cgggaagcgc atcgtgccgg tcatcgagaa ccaccggttc    3540
accgggcgct accgcgacct atacccggcg aacgagttga tcgccctcct ggaggagaag    3600
ggcatcgtgt tccgcgacgg ctccaacatc ctcccgaagc tgctcgaaaa cgacgactcc    3660
cacgccatcg acacgatggt cgcgctgatc cggtcggtgc tccagatgcg gaactccaac    3720
gccgcgacgg gcgaggacta catcaacagt ccggtccgcg atctgaacgg cgtctgcttc    3780
gactcccggt tccagaaccc cgagtggccg atggacgcgg acgcgaacgg cgcataccac    3840
atcgccctaa aagggcaatt gctgctcaac cacctcaagg aatccaaaga cctaaagctc    3900
cagaacggca tctccaacca ggactggctg gcgtacatcc aggaactgcg gaacgggagc    3960
aaaaaacgtc ggatcaagca agattga                                       3987
```

<210> SEQ ID NO 20
<211> LENGTH: 3987
<212> TYPE: DNA
<213> ORGANISM: Artificial
<220> FEATURE:
<223> OTHER INFORMATION: enAsCpf1

<400> SEQUENCE: 20

| | | | | | | |
|---|---|---|---|---|---|---|
| atggcgggct | ccaagaaacg | ccggattaag | caagatacccc | agttcgaggg | gttcacgaac | 60 |
| ctctaccaag | tgagcaagac | cctccgattc | gaactgattc | ctcaggggaa | gaccctcaag | 120 |
| cacatccagg | agcaagggtt | catcgaggag | acaaggcgc | ggaacgacca | ctacaaggaa | 180 |
| ctcaaaccca | tcatcgaccg | catctacaag | acctacgccg | atcagtgcct | ccagctcgtg | 240 |
| cagttggact | gggagaacct | cagcgcggcc | attgactcct | accggaagga | gaaaacggag | 300 |
| gagacgcgca | acgcgctcat | cgaggaacag | gcaacctatc | gcaacgccat | ccacgactac | 360 |
| ttcatcggga | ggactgacaa | cctcactgac | gcgattaaca | gcgccacgc | ggagatatac | 420 |
| aagggactct | caaagcgga | gctgtttaac | ggcaaggttc | tcaagcaact | cggcactgtg | 480 |
| accacgaccg | agcatgagaa | cgccctgctc | cgctccttcg | acaagttcac | cacctacttc | 540 |
| tccggggttct | accgcaaccg | caagaatgtc | ttcagcgcgg | aggacatcag | cacggccatt | 600 |
| ccacatcgaa | tcgtccaaga | taacttcccg | aagttcaagg | agaactgcca | tcttcacc | 660 |
| cgactcatta | ctgctgtacc | gtcgttacgc | gaacacttcg | agaacgtcaa | gaaggcaatt | 720 |
| ggaatcttcg | tctctacgtc | aatagaggag | gtgttcagct | tcccttttcta | caaccagctc | 780 |
| cttacgcaga | cccagataga | cctgtacaat | cagctcctcg | gtgggatcag | ccgggaggcg | 840 |
| gggactgaga | agattaaagg | gctcaacgag | gtcttgaacc | tggccatcca | aaaaaacgat | 900 |
| gagacggcgc | acatcatcgc | ctcgctgccc | caccggttca | tcccgctgtt | caagcagatc | 960 |
| ctcagtgaca | ggaacaccctt | gagctttatc | ctagaggagt | caagagcga | cgaggaggtg | 1020 |
| atccagagct | tctgcaagta | caaaaccctg | ctgaggaacg | agaacgtcct | ggagacggcg | 1080 |
| gaggcgctgt | tcaacgagct | gaactctatc | gacttaactc | acatattcat | ctcgcacaag | 1140 |
| aagctggaga | ctattagctc | tgcactctgc | gaccactggg | acaccctccg | caacgcgctc | 1200 |
| tacgagcgcc | gcatctcgga | gctgaccggg | aagatcacca | atccgcgaa | ggaaaaggtc | 1260 |
| cagcgttccc | tcaaacacga | ggatattaac | ttacaggaga | ttatctcagc | ggctgggaag | 1320 |
| gagttgtcag | aggcgttcaa | gcagaaaact | tccgagatcc | tgagccacgc | gcacgcagcg | 1380 |
| ctcgaccagc | ctctgcccac | cacccctcaaa | aagcaggaag | aaaagagat | cctcaagagc | 1440 |
| cagttggact | ccctgctggg | gctctatcac | cttctcgact | ggttcgccgt | cgatgagtcg | 1500 |
| aacgaggtgg | accccgagtt | ctccgcccgg | ctgaccggca | tcaagctaga | gatggagccg | 1560 |
| tccctcagct | tctacaataa | ggcccgcaac | tacgcgacca | aaaaacccta | cagcgtggag | 1620 |
| aagttcaagc | tgaacttcca | gatgccgacc | ttagcacgcg | gttgggacgt | aaacagggag | 1680 |
| aagaacaatg | gagccatcct | gttcgtcaag | aacgggcttt | actacctcgg | gataatgccc | 1740 |
| aagcagaagg | gccgctacaa | ggcccttttcc | ttcgagccga | cggagaaaac | ctccgagggg | 1800 |
| ttcgacaaga | tgtactacga | ctacttccccc | gacgccgcca | gatgatcccc | gaagtgctca | 1860 |
| acgcagctaa | aagccgtgac | cgcccacttc | cagacccaca | cgacgccgat | cctgctgagc | 1920 |
| aacaacttca | tcgagcccct | tgagatcact | aaggagatat | acgacctgaa | caaccccgag | 1980 |
| aaggagccca | agaagtttca | aaccgcctac | gccaaaaaaa | ctggcgacca | aaagggctac | 2040 |
| agggaggcgc | tgtgtaagtg | gatcgacttc | acacgcgact | tcctttcgaa | gtatacgaag | 2100 |

```
acaacctcta ttgacctgag cagcctgcgt cctagctccc agtacaaaga tttgggcgag    2160
tactacgcgg agcttaatcc actactctac cacatctcat tccagcgcat cgctgagaag    2220
gaaatcatgg acgcggtgga gacaggcaaa ctgtacctct tccagatata caacaaagac    2280
ttcgctaagg ggcaccacgg gaagcccaac cttcatacgc tctactggac gggcctattc    2340
agccccgaaa atctggccaa gacctccatc aagctgaacg gccaagcgga gctgttctac    2400
agacccaaga gccggatgaa gcggatggcc cacaggctcg gcgagaaaat gcttaacaaa    2460
aagttgaagg accagaaaac ccctatcccc gacaccctct accaggaact gtacgactac    2520
gtgaaccaca ggctctcgca cgacctttcc gacgaggccc gtgccctact cccgaacgtc    2580
attaccaaag aggtttcgca cgagatcatc aaggaccggc ggttcacgag cgacaagttt    2640
ttctttcacg tccccatcac ccttaactac caggcggcca actccccatc caagttcaac    2700
cagcgtgtga atgcctacct caaggagcac ccagagaccc cgatcattgg gatcgaccgg    2760
ggcgagcgga acctgatcta catcaccgtc atcgactcga cgggcaagat tcttgagcag    2820
agatcgttga ataccataca gcagttcgac taccagaaga aactcgacaa ccgcgagaag    2880
gagcgcgtgg cggcccgcca ggcgtggtcc gtcgttggga cgattaagga cttgaaacaa    2940
ggttatctgt cccaagtcat ccacgagatc gttgatctga tgatccacta tcaggcagtg    3000
gtggtgctgg agaatctcaa cttcggcttc aagagtaagc ggacgggaat cgccgagaag    3060
gccgtgtacc agcagttcga agagatgctg atcgacaagc tcaactgcct tgtgctgaaa    3120
gactacccgg ccgagaaggt cggcggcgtc ctcaacccgt accaacttac cgaccagttc    3180
acctccttcg ccaagatggg cactcagtcc gggttcttgt tctacgtccc cgcaccttac    3240
acctctaaga tcgaccctct gactggcttc gtagatccat tcgtgtggaa gaccattaag    3300
aaccacgaga gccgcaagca cttcctggag ggcttcgact tcctgcacta cgacgtgaag    3360
accggggact tcatccttca cttcaagatg aaccggaacc tcagcttcca gcggggcctg    3420
ccggggttca tgcccgcctg ggacatcgtg ttcgagaaga acgagaccca gttcgacgcg    3480
aagggcacgc ccttcatcgc cgggaagcgt atcgtgccgg tgatcgagaa ccatcgtttc    3540
acgggtcgct accgtgacct ctaccccgcg aacgagctta tcgcactcct ggaggagaag    3600
ggcatcgtct tccgggacgg ctccaacatc ctcccgaaac tgctggaaaa cgacgactct    3660
cacgccatcg acacgatggt ggccctcatc cggtccgtgc tccaaatgcg gaacagcaac    3720
gccgccaccg gtgaggacta catcaacagc ccggtccggg atctgaacgg ggtgtgcttc    3780
gattcgcggt tccagaatcc tgagtggccg atggacgcgg atgcaaacgg ggcgtaccac    3840
atcgcgctca agggccagtt acttctgaac caccttaagg agtctaaaga tttgaaactc    3900
cagaacggga tctcgaacca ggactggctg gcctacatcc aagagttgcg gaacggcagc    3960
aagaagcggc ggattaagca agattag                                        3987
```

<210> SEQ ID NO 21
<211> LENGTH: 1592
<212> TYPE: DNA
<213> ORGANISM: Medicago truncatula

<400> SEQUENCE: 21

```
actgttaata attttaaac gtcagcgcac taaaaaaacg aaaagacgga cacgtgaaaa     60
taaaaaacac acactagttt atgacgcaat actatttac ttatgatttg ggtacattag    120
acaaaaccgt gaaagagatg tatcagctat gaaacctgta tacttcaata cagagactta    180
ctcatatcgg atacgtacgc acgaagtatc atattaatta tttaatttt taataaatat    240
```

```
tttatcggat acttatgtga tactctacat atacacaagg atatttctaa gatactttat    300
agatacgtat cctagaaaaa catgaagagt aaaaaagtga gacaatgttg taaaaattca    360
ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttcttttaa tgatgtttct ctcaatatca catcatatga    540
aaatgtaata tgatttataa gaaaattttt aaaaaattta ttttaataat cacatgtact    600 atttttttaaa aattgtatct tttataataa tacaataata aagagtaatc agtgttaatt    660
tttcttcaaa tataagtttt attataaatc attgttaacg tatcataagt cattaccgta    720
tcgtatctta attttttttt aaaaaccgct aattcacgta cccgtattgt attgtacccg    780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagg tgccgttggc gtaatataac    960
agccaatcga tttttgctat aaaagcaaat caggtaaact aaacttcttc attcttttct   1020
tccccatcgc tacaaaaccg gttcctttgg aaaagagatt cattcaaacc tagcacccaa   1080
ttccgtttca aggtataatc tactttctat tcttcgatta ttttattatt attagctact   1140
atcgtttaat cgatcttttc ttttgatccg tcaaatttaa attcaattag ggttttgttc   1200
ttttctttca tctgattgaa atccttctga attgaaccgt ttacttgatt ttactgttta   1260
ttgtatgatt taatccttg ttttttcaaag acagtcttta gattgtgatt aggggttcat   1320
ataaattttt agatttggat ttttgtattg tatgattcaa aaaatacgtc ctttaattag   1380
attagtacat ggatattttt tacccgattt attgattgtc agggagaatt tgatgagcaa   1440 gttttttga tgtctgttgt aaattgaatt gattataatt gctgatctgc tgcttccagt   1500
tttcataacc catattcttt taaccttgtt gtacacacaa tgaaaaattg gtgattgatt   1560
catttgtttt tctttgtttt ggattataca gg                                 1592

<210> SEQ ID NO 22
<211> LENGTH: 2000
<212> TYPE: DNA
<213> ORGANISM: Zea mays

<400> SEQUENCE: 22
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatcttttt agtgtgcatg tgatctctct gttttttttg caaatagctt gacctatata    300
atacttcatc catttattta gtacatccat ttaggattta gggttgatgg tttctataga    360 ctaatttta gtacatccat tttattcttt ttagtctcta aattttttaa aactaaaact    420
ctattttagt tttttatttta ataatttaga tataaaatga aataaaataa attgactaca    480
aataaaacaa ataccctta agaaataaaa aaactaagca acatttttc ttgtttcgag    540 tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
```

```
gcgtggcgga gcggcagacg tgaggcggca cggcaggcgg cctcttcctc ctctcacggc    780
accggcagct acgggggatt cctttcccac cgctccttcg cttccccttc ctcgcccgcc    840
gtaataaata gacaccccct ccacaccctc tttccccaac ctcgtgttcg ttcggagcgc    900
acacacacgc aaccagatct cccccaaatc cagccgtcgg cacctccgct tcaaggtacg    960
ccgctcatcc tcccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt taagatgatg gatggaaata tcgatctagg ataggtatac atgttgatgc   1260
gggttttact gatgcatata cagagatgct ttttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc ttttttcgc ttggttgtga tgatgtggtc tggttgggcg gtcgttctag   1620
atcggagtag aatactgttt caaactacct ggtggattta ttaattttgt atctttatgt   1680
gtgtgccata catcttcata gttacgagtt taagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggattttt    1920
agccctgcct tcatacgcta tttatttgct tggtactgtt tcttttgtcc gatgctcacc   1980
ctgttgtttg gtgatacttc                                              2000
```

<210> SEQ ID NO 23
<211> LENGTH: 24
<212> TYPE: PRT
<213> ORGANISM: Artificial
<220> FEATURE:
<223> OTHER INFORMATION: GCN4 sequence

<400> SEQUENCE: 23

Glu Glu Leu Leu Ser Lys Asn Tyr His Leu Glu Asn Glu Val Ala Arg
1               5                   10                  15

Leu Lys Lys Gly Ser Gly Ser Gly
            20

<210> SEQ ID NO 24
<211> LENGTH: 241
<212> TYPE: PRT
<213> ORGANISM: Artificial
<220> FEATURE:
<223> OTHER INFORMATION: 10-mer GCN4 sequence

<400> SEQUENCE: 24

Glu Glu Glu Leu Leu Ser Lys Asn Tyr His Leu Glu Asn Glu Val Ala
1               5                   10                  15

Arg Leu Lys Lys Gly Ser Gly Ser Gly Glu Glu Leu Leu Ser Lys Asn
            20                  25                  30

Tyr His Leu Glu Asn Glu Val Ala Arg Leu Lys Lys Gly Ser Gly Ser
        35                  40                  45

```
Gly Glu Glu Leu Leu Ser Lys Asn Tyr His Leu Glu Asn Glu Val Ala
 50                  55                  60

Arg Leu Lys Lys Gly Ser Gly Ser Gly Glu Glu Leu Leu Ser Lys Asn
 65                  70                  75                  80

Tyr His Leu Glu Asn Glu Val Ala Arg Leu Lys Lys Gly Ser Gly Ser
                 85                  90                  95

Gly Glu Glu Leu Leu Ser Lys Asn Tyr His Leu Glu Asn Glu Val Ala
            100                 105                 110

Arg Leu Lys Lys Gly Ser Gly Ser Gly Glu Glu Leu Leu Ser Lys Asn
            115                 120                 125

Tyr His Leu Glu Asn Glu Val Ala Arg Leu Lys Lys Gly Ser Gly Ser
            130                 135                 140

Gly Glu Glu Leu Leu Ser Lys Asn Tyr His Leu Glu Asn Glu Val Ala
145                 150                 155                 160

Arg Leu Lys Lys Gly Ser Gly Ser Gly Glu Glu Leu Leu Ser Lys Asn
                165                 170                 175

Tyr His Leu Glu Asn Glu Val Ala Arg Leu Lys Lys Gly Ser Gly Ser
                180                 185                 190

Gly Glu Glu Leu Leu Ser Lys Asn Tyr His Leu Glu Asn Glu Val Ala
            195                 200                 205

Arg Leu Lys Lys Gly Ser Gly Ser Gly Glu Glu Leu Leu Ser Lys Asn
            210                 215                 220

Tyr His Leu Glu Asn Glu Val Ala Arg Leu Lys Lys Gly Ser Gly Ser
225                 230                 235                 240

Gly
```

<210> SEQ ID NO 25
<211> LENGTH: 277
<212> TYPE: PRT
<213> ORGANISM: Artificial
<220> FEATURE:
<223> OTHER INFORMATION: ScFv antibody

<400> SEQUENCE: 25

```
Met Gly Pro Asp Ile Val Met Thr Gln Ser Pro Ser Ser Leu Ser Ala
1                   5                  10                  15

Ser Val Gly Asp Arg Val Thr Ile Thr Cys Arg Ser Ser Thr Gly Ala
                 20                  25                  30

Val Thr Thr Ser Asn Tyr Ala Ser Trp Val Gln Glu Lys Pro Gly Lys
             35                  40                  45

Leu Phe Lys Gly Leu Ile Gly Gly Thr Asn Asn Arg Ala Pro Gly Val
 50                  55                  60

Pro Ser Arg Phe Ser Gly Ser Leu Ile Gly Asp Lys Ala Thr Leu Thr
 65                  70                  75                  80

Ile Ser Ser Leu Gln Pro Glu Asp Phe Ala Thr Tyr Phe Cys Ala Leu
                 85                  90                  95

Trp Tyr Ser Asn His Trp Val Phe Gly Gln Gly Thr Lys Val Glu Leu
            100                 105                 110

Lys Arg Gly Gly Gly Gly Ser Gly Gly Gly Gly Ser Gly Gly Gly Gly
            115                 120                 125

Ser Ser Gly Gly Gly Ser Glu Val Lys Leu Leu Glu Ser Gly Gly Gly
            130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
```

```
                    165                 170                 175
Arg Gly Leu Glu Trp Ile Gly Val Ile Trp Gly Asp Gly Ile Thr Asp
            180                 185                 190

Tyr Asn Ser Ala Leu Lys Asp Arg Phe Ile Ile Ser Lys Asp Asn Gly
        195                 200                 205

Lys Asn Thr Val Tyr Leu Gln Met Ser Lys Val Arg Ser Asp Asp Thr
    210                 215                 220

Ala Leu Tyr Tyr Cys Val Thr Gly Leu Phe Asp Tyr Trp Gly Gln Gly
225                 230                 235                 240

Thr Leu Val Thr Val Ser Ser Tyr Pro Tyr Asp Val Pro Asp Tyr Ala
                245                 250                 255

Gly Gly Gly Gly Gly Ser Gly Gly Gly Ser Gly Gly Gly Gly Ser
                260                 265                 270

Gly Gly Gly Gly Ser
            275

<210> SEQ ID NO 26
<211> LENGTH: 66
<212> TYPE: DNA
<213> ORGANISM: Saccharomyces bayanus

<400> SEQUENCE: 26
ttcttgtcgt acttatagat cgctacgtta tttcaatttt gaaaatctga gtcctgggag    60
tgcgga                                                               66

<210> SEQ ID NO 27
<211> LENGTH: 605
<212> TYPE: PRT
<213> ORGANISM: Homo sapiens

<400> SEQUENCE: 27

Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
                20                  25                  30

Ser Gly Arg Asp Ser Leu Ile Phe Leu Val Asp Ala Ser Lys Ala Met
            35                  40                  45

Phe Glu Ser Gln Ser Glu Asp Glu Leu Thr Pro Phe Asp Met Ser Ile
    50                  55                  60

Gln Cys Ile Gln Ser Val Tyr Ile Ser Lys Ile Ile Ser Ser Asp Arg
65                  70                  75                  80

Asp Leu Leu Ala Trp Phe Tyr Gly Thr Glu Lys Asp Lys Asn Ser Val
                85                  90                  95

Asn Phe Lys Ile Tyr Val Leu Gln Glu Leu Asp Asn Pro Gly Ala Lys
                100                 105                 110

Arg Ile Leu Glu Leu Asp Gln Phe Lys Gly Gln Gln Gly Gln Lys Arg
            115                 120                 125

Phe Gln Asp Met Met Gly His Gly Ser Asp Tyr Ser Leu Ser Glu Val
    130                 135                 140

Leu Trp Val Cys Ala Asn Leu Phe Ser Asp Val Gln Phe Lys Met Ser
145                 150                 155                 160

His Lys Arg Ile Met Leu Phe Thr Asn Glu Asp Asn Pro His Gly Asn
                165                 170                 175

Asp Ser Ala Lys Ala Ser Arg Ala Arg Thr Lys Ala Gly Asp Leu Arg
                180                 185                 190
```

```
Asp Thr Gly Ile Phe Leu Asp Leu His Leu Lys Lys Pro Gly Gly Phe
        195                 200                 205
Asp Ile Ser Leu Phe Tyr Arg Asp Ile Ser Ile Ala Glu Asp Glu
    210                 215                 220
Asp Leu Arg Val His Phe Glu Glu Ser Ser Lys Leu Glu Asp Leu Leu
225                 230                 235                 240
Arg Lys Val Arg Ala Lys Glu Thr Arg Lys Arg Ala Leu Ser Arg Leu
                245                 250                 255
Lys Leu Lys Leu Asn Lys Asp Ile Val Ile Ser Val Gly Ile Tyr Asn
                260                 265                 270
Leu Val Gln Lys Ala Leu Lys Pro Pro Ile Lys Leu Tyr Arg Glu
            275                 280                 285
Thr Asn Glu Pro Val Lys Thr Lys Thr Arg Thr Phe Asn Thr Ser Thr
    290                 295                 300
Gly Gly Leu Leu Leu Pro Ser Asp Thr Lys Arg Ser Gln Ile Tyr Gly
305                 310                 315                 320
Ser Arg Gln Ile Ile Leu Glu Lys Glu Thr Glu Glu Leu Lys Arg
                325                 330                 335
Phe Asp Asp Pro Gly Leu Met Leu Met Gly Phe Lys Pro Leu Val Leu
            340                 345                 350
Leu Lys Lys His His Tyr Leu Arg Pro Ser Leu Phe Val Tyr Pro Glu
        355                 360                 365
Glu Ser Leu Val Ile Gly Ser Ser Thr Leu Phe Ser Ala Leu Leu Ile
    370                 375                 380
Lys Cys Leu Glu Lys Glu Val Ala Ala Leu Cys Arg Tyr Thr Pro Arg
385                 390                 395                 400
Arg Asn Ile Pro Pro Tyr Phe Val Ala Leu Val Pro Gln Glu Glu
            405                 410                 415
Leu Asp Asp Gln Lys Ile Gln Val Thr Pro Gly Phe Gln Leu Val
            420                 425                 430
Phe Leu Pro Phe Ala Asp Asp Lys Arg Lys Met Pro Phe Thr Glu Lys
        435                 440                 445
Ile Met Ala Thr Pro Glu Gln Val Gly Lys Met Lys Ala Ile Val Glu
450                 455                 460
Lys Leu Arg Phe Thr Tyr Arg Ser Asp Ser Phe Glu Asn Pro Val Leu
465                 470                 475                 480
Gln Gln His Phe Arg Asn Leu Glu Ala Leu Ala Leu Asp Leu Met Glu
                485                 490                 495
Pro Glu Gln Ala Val Asp Leu Thr Leu Pro Lys Val Glu Ala Met Asn
            500                 505                 510
Lys Arg Leu Gly Ser Leu Val Asp Glu Phe Lys Glu Leu Val Tyr Pro
        515                 520                 525
Pro Asp Tyr Asn Pro Glu Gly Lys Val Thr Lys Arg Lys His Asp Asn
    530                 535                 540
Glu Gly Ser Gly Ser Lys Arg Pro Lys Val Glu Tyr Ser Glu Glu
545                 550                 555                 560
Leu Lys Thr His Ile Ser Lys Gly Thr Leu Gly Lys Phe Thr Val Pro
                565                 570                 575
Leu Lys Glu Ala Cys Arg Ala Tyr Gly Leu Lys Ser Gly Leu Lys Lys
            580                 585                 590
Gln Glu Leu Leu Glu Ala Leu Thr Lys His Phe Gln Asp
        595                 600                 605
```

```
<210> SEQ ID NO 28
<211> LENGTH: 482
<212> TYPE: PRT
<213> ORGANISM: Artificial
<220> FEATURE:
<223> OTHER INFORMATION: polypeptide

<400> SEQUENCE: 28

Met Val Arg Ser Gly Asn Lys Ala Ala Trp Leu Cys Met Asp Val Gly
1               5                   10                  15

Phe Thr Met Ser Asn Ser Ile Pro Gly Ile Glu Ser Pro Phe Glu Gln
            20                  25                  30

Ala Lys Lys Val Ile Thr Met Phe Val Gln Arg Gln Val Phe Ala Glu
        35                  40                  45

Asn Lys Asp Glu Ile Ala Leu Val Leu Phe Gly Thr Asp Gly Thr Asp
    50                  55                  60

Asn Pro Leu Ser Gly Gly Asp Gln Tyr Gln Asn Ile Thr Val His Arg
65                  70                  75                  80

His Leu Met Leu Pro Asp Phe Asp Leu Leu Glu Asp Ile Glu Ser Lys
                85                  90                  95

Ile Gln Pro Gly Ser Gln Gln Ala Asp Phe Leu Asp Ala Leu Ile Val
            100                 105                 110

Ser Met Asp Val Ile Gln His Glu Thr Ile Gly Lys Lys Phe Glu Lys
        115                 120                 125

Arg His Ile Glu Ile Phe Thr Asp Leu Ser Ser Arg Phe Ser Lys Ser
    130                 135                 140

Gln Leu Asp Ile Ile His Ser Leu Lys Lys Cys Asp Ile Ser Glu
145                 150                 155                 160

Arg His Ser Ile His Trp Pro Cys Arg Leu Thr Ile Gly Ser Asn Leu
                165                 170                 175

Ser Ile Arg Ile Ala Ala Tyr Lys Ser Ile Leu Gln Glu Arg Val Lys
            180                 185                 190

Lys Thr Thr Trp Asp Ala Lys Thr Leu Lys Lys Glu Asp Ile Gln Lys
        195                 200                 205

Glu Thr Val Tyr Cys Leu Asn Asp Asp Asp Glu Thr Glu Val Leu Lys
    210                 215                 220

Glu Asp Ile Ile Gln Gly Phe Arg Tyr Gly Ser Asp Ile Val Pro Phe
225                 230                 235                 240

Ser Lys Val Asp Glu Glu Gln Met Lys Tyr Lys Ser Glu Gly Lys Cys
                245                 250                 255

Phe Ser Val Leu Gly Phe Cys Lys Ser Ser Gln Val Gln Arg Arg Phe
            260                 265                 270

Phe Met Gly Asn Gln Val Leu Lys Val Phe Ala Ala Arg Asp Asp Glu
        275                 280                 285

Ala Ala Val Ala Leu Ser Ser Leu Ile His Ala Leu Asp Asp Leu
    290                 295                 300

Asp Ile Trp Ala Ile Val Arg Tyr Ala Tyr Asp Lys Arg Ala Asn Pro
305                 310                 315                 320

Gln Val Gly Val Ala Phe Pro His Ile Lys His Asn Tyr Glu Cys Leu
                325                 330                 335

Val Tyr Val Gln Leu Pro Phe Met Glu Asp Leu Arg Gln Tyr Met Phe
            340                 345                 350

Ser Ser Leu Lys Asn Ser Lys Lys Tyr Ala Pro Thr Glu Ala Gln Leu
        355                 360                 365

Asn Ala Val Asp Ala Leu Ile Asp Ser Met Ser Leu Ala Lys Lys Asp
```

```
            370                 375                 380
Glu Lys Thr Asp Thr Leu Glu Asp Leu Phe Pro Thr Thr Lys Ile Pro
385                 390                 395                 400

Asn Pro Arg Phe Gln Arg Leu Phe Gln Cys Leu Leu His Arg Ala Leu
                405                 410                 415

His Pro Arg Glu Pro Leu Pro Pro Ile Gln Gln His Ile Trp Asn Met
            420                 425                 430

Leu Asn Pro Pro Ala Glu Val Thr Thr Lys Ser Gln Ile Pro Leu Ser
                435                 440                 445

Lys Ile Lys Thr Leu Phe Pro Leu Ile Glu Ala Lys Lys Lys Asp Gln
            450                 455                 460

Val Thr Ala Gln Glu Ile Phe Gln Asp Asn His Glu Asp Gly Pro Thr
465                 470                 475                 480

Ala Lys

<210> SEQ ID NO 29
<211> LENGTH: 10
<212> TYPE: DNA
<213> ORGANISM: Methanobacterium thermoautotrophicum

<400> SEQUENCE: 29
aatttttgga                                                           10

<210> SEQ ID NO 30
<211> LENGTH: 83
<212> TYPE: PRT
<213> ORGANISM: Methanobacterium thermoautotrophicum

<400> SEQUENCE: 30

Gly Ser Val Ile Asp Val Ser Ser Gln Arg Val Asn Val Gln Arg Pro
1               5                   10                  15

Leu Asp Ala Leu Gly Asn Ser Leu Asn Ser Pro Val Ile Ile Lys Leu
            20                  25                  30

Lys Gly Asp Arg Glu Phe Arg Gly Val Leu Lys Ser Phe Asp Leu His
        35                  40                  45

Met Asn Leu Val Leu Asn Asp Ala Glu Glu Leu Glu Asp Gly Glu Val
    50                  55                  60

Thr Arg Arg Leu Gly Thr Val Leu Ile Arg Gly Asp Asn Ile Val Tyr
65                  70                  75                  80

Ile Ser Pro

<210> SEQ ID NO 31
<211> LENGTH: 25
<212> TYPE: DNA
<213> ORGANISM: Bacteriophage MS2

<400> SEQUENCE: 31
gcgcacatga ggatcaccca tgtgc                                          25

<210> SEQ ID NO 32
<211> LENGTH: 116
<212> TYPE: PRT
<213> ORGANISM: Bacteriophage MS2

<400> SEQUENCE: 32

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
```

-continued

```
                20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
        50                  55                  60

Pro Lys Gly Ala Trp Arg Ser Tyr Leu Asn Met Glu Leu Thr Ile Pro
65                  70                  75                  80

Ile Phe Ala Thr Asn Ser Asp Cys Glu Leu Ile Val Lys Ala Met Gln
                85                  90                  95

Gly Leu Leu Lys Asp Gly Asn Pro Ile Pro Ser Ala Ile Ala Ala Asn
            100                 105                 110

Ser Gly Ile Tyr
        115

<210> SEQ ID NO 33
<211> LENGTH: 26
<212> TYPE: DNA
<213> ORGANISM: Bacteriophage PP7

<400> SEQUENCE: 33
ataaggagtt tatatggaaa ccctta                                           26

<210> SEQ ID NO 34
<211> LENGTH: 127
<212> TYPE: PRT
<213> ORGANISM: Bacteriophage PP7

<400> SEQUENCE: 34

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
                20                  25                  30

Gly Pro Leu Val Gly Arg Leu Arg Leu Thr Ala Ser Leu Arg Gln Asn
            35                  40                  45

Gly Ala Lys Thr Ala Tyr Arg Val Asn Leu Lys Leu Asp Gln Ala Asp
        50                  55                  60

Trp Asp Cys Ser Thr Ser Val Cys Gly Glu Leu Pro Lys Val Arg Tyr
65                  70                  75                  80

Thr Gln Val Trp Ser His Asp Val Thr Ile Val Ala Asn Ser Thr Glu
                85                  90                  95

Ala Ser Arg Lys Ser Leu Tyr Asp Leu Thr Lys Ser Leu Val Ala Thr
            100                 105                 110

Ser Gln Val Glu Asp Leu Val Val Asn Leu Val Pro Leu Gly Arg
        115                 120                 125

<210> SEQ ID NO 35
<211> LENGTH: 19
<212> TYPE: DNA
<213> ORGANISM: Shigella phage

<400> SEQUENCE: 35
ctgaatgcct gcgagcatc                                                   19

<210> SEQ ID NO 36
<211> LENGTH: 62
<212> TYPE: PRT
<213> ORGANISM: Shigella phage

<400> SEQUENCE: 36
```

```
Met Lys Ser Ile Arg Cys Lys Asn Cys Asn Lys Leu Leu Phe Lys Ala
1               5                   10                  15

Asp Ser Phe Asp His Ile Glu Ile Arg Cys Pro Arg Cys Lys Arg His
            20                  25                  30

Ile Ile Met Leu Asn Ala Cys Glu His Pro Thr Glu Lys His Cys Gly
        35                  40                  45

Lys Arg Glu Lys Ile Thr His Ser Asp Glu Thr Val Arg Tyr
    50                  55                  60

<210> SEQ ID NO 37
<211> LENGTH: 19
<212> TYPE: DNA
<213> ORGANISM: Artificial
<220> FEATURE:
<223> OTHER INFORMATION: Spacer
<220> FEATURE:
<221> NAME/KEY: misc_feature
<222> LOCATION: (1)..(19)
<223> OTHER INFORMATION: wherein n is A, C, T or G

<400> SEQUENCE: 37 nnnnnnnnn nnnnnnnnn                                              19

<210> SEQ ID NO 38
<211> LENGTH: 22
<212> TYPE: DNA
<213> ORGANISM: Artificial
<220> FEATURE:
<223> OTHER INFORMATION: Target strand
<220> FEATURE:
<221> NAME/KEY: misc_feature
<222> LOCATION: (4)..(22)
<223> OTHER INFORMATION: wherein n is A, C, T or G

<400> SEQUENCE: 38
aaannnnnnn nnnnnnnnnn nn                                         22

<210> SEQ ID NO 39
<211> LENGTH: 22
<212> TYPE: DNA
<213> ORGANISM: Artificial
<220> FEATURE:
<223> OTHER INFORMATION: Non-target strand
<220> FEATURE:
<221> NAME/KEY: misc_feature
<222> LOCATION: (4)..(22)
<223> OTHER INFORMATION: wherein n is A, C, T or G

<400> SEQUENCE: 39
tttnnnnnnn nnnnnnnnnn nn                                         22

<210> SEQ ID NO 40
<211> LENGTH: 15
<212> TYPE: DNA
<213> ORGANISM: Unknown
<220> FEATURE:
<223> OTHER INFORMATION: Porcine circovirus

<400> SEQUENCE: 40
aagtattacc agaaa                                                 15

<210> SEQ ID NO 41
<211> LENGTH: 15
<212> TYPE: DNA
<213> ORGANISM: Unknown
<220> FEATURE:
```

```
<223> OTHER INFORMATION: Duck circovirus

<400> SEQUENCE: 41
aagtattacc agaaa                                                        15

<210> SEQ ID NO 42
<211> LENGTH: 15
<212> TYPE: DNA
<213> ORGANISM: Fava bean necrosis yellows virus

<400> SEQUENCE: 42
aagtattacc agaaa                                                        15

<210> SEQ ID NO 43
<211> LENGTH: 23
<212> TYPE: DNA
<213> ORGANISM: Streptococcus agalactiae

<400> SEQUENCE: 43
tgcttccgta ctacgacccc cca                                               23

<210> SEQ ID NO 44
<211> LENGTH: 23
<212> TYPE: DNA
<213> ORGANISM: Fructobacillus tropaeoli

<400> SEQUENCE: 44
tgcttccgta ctacgacccc cca                                               23

<210> SEQ ID NO 45
<211> LENGTH: 22
<212> TYPE: DNA
<213> ORGANISM: Escherichia coli

<400> SEQUENCE: 45
tttgcgtggg gtgtggtgct tt                                                22

<210> SEQ ID NO 46
<211> LENGTH: 38
<212> TYPE: DNA
<213> ORGANISM: Escherichia coli

<400> SEQUENCE: 46
ccagtttctc gaagagaaac cggtaagtgc accctccc                               38

<210> SEQ ID NO 47
<211> LENGTH: 45
<212> TYPE: DNA
<213> ORGANISM: Staphylococcus aureus

<400> SEQUENCE: 47
acgcgaacgg aacgttcgca taagtgcgcc cttacgggat ttaac                       45

<210> SEQ ID NO 48
<211> LENGTH: 2286
<212> TYPE: PRT
<213> ORGANISM: Homo sapiens

<400> SEQUENCE: 48

Met Ser Leu Arg Ser Gly Gly Arg Arg Ala Asp Pro Gly Ala Asp
1               5                   10                  15

Gly Glu Ala Ser Arg Asp Asp Gly Ala Thr Ser Ser Val Ser Ala Leu
            20                  25                  30
```

-continued

```
Lys Arg Leu Glu Arg Ser Gln Trp Thr Asp Lys Met Asp Leu Arg Phe
         35                  40                  45
Gly Phe Glu Arg Leu Lys Glu Pro Gly Glu Lys Thr Gly Trp Leu Ile
 50                  55                  60
Asn Met His Pro Thr Glu Ile Leu Asp Glu Asp Lys Arg Leu Gly Ser
 65                  70                  75                  80
Ala Val Asp Tyr Tyr Phe Ile Gln Asp Gly Ser Arg Phe Lys Val
                 85                  90                  95
Ala Leu Pro Tyr Lys Pro Tyr Phe Tyr Ile Ala Thr Arg Lys Gly Cys
                100                 105                 110
Glu Arg Glu Val Ser Ser Phe Leu Ser Lys Lys Phe Gln Gly Lys Ile
                115                 120                 125
Ala Lys Val Glu Thr Val Pro Lys Glu Asp Leu Asp Leu Pro Asn His
                130                 135                 140
Leu Val Gly Leu Lys Arg Asn Tyr Ile Arg Leu Ser Phe His Thr Val
145                 150                 155                 160
Glu Asp Leu Val Lys Val Arg Lys Glu Ile Ser Pro Ala Val Lys Lys
                165                 170                 175
Asn Arg Glu Gln Asp His Ala Ser Asp Ala Tyr Thr Ala Leu Leu Ser
                180                 185                 190
Ser Val Leu Gln Arg Gly Gly Val Ile Thr Asp Glu Glu Thr Ser
                195                 200                 205
Lys Lys Ile Ala Asp Gln Leu Asp Asn Ile Val Asp Met Arg Glu Tyr
                210                 215                 220
Asp Val Pro Tyr His Ile Arg Leu Ser Ile Asp Leu Lys Ile His Val
225                 230                 235                 240
Ala His Trp Tyr Asn Val Arg Tyr Arg Gly Asn Ala Phe Pro Val Glu
                245                 250                 255
Ile Thr Arg Arg Asp Asp Leu Val Glu Arg Pro Asp Pro Val Val Leu
                260                 265                 270
Ala Phe Asp Ile Glu Thr Thr Lys Leu Pro Leu Lys Phe Pro Asp Ala
                275                 280                 285
Glu Thr Asp Gln Ile Met Met Ile Ser Tyr Met Ile Asp Gly Gln Gly
                290                 295                 300
Tyr Leu Ile Thr Asn Arg Glu Ile Val Ser Glu Asp Ile Glu Asp Phe
305                 310                 315                 320
Glu Phe Thr Pro Lys Pro Glu Tyr Glu Gly Pro Phe Cys Val Phe Asn
                325                 330                 335
Glu Pro Asp Glu Ala His Leu Ile Gln Arg Trp Phe Glu His Val Gln
                340                 345                 350
Glu Thr Lys Pro Thr Ile Met Val Thr Tyr Asn Gly Asp Phe Phe Asp
                355                 360                 365
Trp Pro Phe Val Glu Ala Arg Ala Ala Val His Gly Leu Ser Met Gln
370                 375                 380
Gln Glu Ile Gly Phe Gln Lys Asp Ser Gln Gly Glu Tyr Lys Ala Pro
385                 390                 395                 400
Gln Cys Ile His Met Asp Cys Leu Arg Trp Val Lys Arg Asp Ser Tyr
                405                 410                 415
Leu Pro Val Gly Ser His Asn Leu Lys Ala Ala Lys Ala Lys Leu
                420                 425                 430
Gly Tyr Asp Pro Val Glu Leu Asp Pro Glu Asp Met Cys Arg Met Ala
                435                 440                 445
```

```
Thr Glu Gln Pro Gln Thr Leu Ala Thr Tyr Ser Val Ser Asp Ala Val
    450                 455                 460

Ala Thr Tyr Tyr Leu Tyr Met Lys Tyr Val His Pro Phe Ile Phe Ala
465                 470                 475                 480

Leu Cys Thr Ile Ile Pro Met Glu Pro Asp Glu Val Leu Arg Lys Gly
                485                 490                 495

Ser Gly Thr Leu Cys Glu Ala Leu Leu Met Val Gln Ala Phe His Ala
                500                 505                 510

Asn Ile Ile Phe Pro Asn Lys Gln Glu Gln Phe Asn Lys Leu Thr
            515                 520                 525

Asp Asp Gly His Val Leu Asp Ser Glu Thr Tyr Val Gly Gly His Val
530                 535                 540

Glu Ala Leu Glu Ser Gly Val Phe Arg Ser Asp Ile Pro Cys Arg Phe
545                 550                 555                 560

Arg Met Asn Pro Ala Ala Phe Asp Phe Leu Leu Gln Arg Val Glu Lys
                565                 570                 575

Thr Leu Arg His Ala Leu Glu Glu Glu Lys Val Pro Val Glu Gln
                580                 585                 590

Val Thr Asn Phe Glu Glu Val Cys Asp Glu Ile Lys Ser Lys Leu Ala
    595                 600                 605

Ser Leu Lys Asp Val Pro Ser Arg Ile Glu Cys Pro Leu Ile Tyr His
    610                 615                 620

Leu Asp Val Gly Ala Met Tyr Pro Asn Ile Ile Leu Thr Asn Arg Leu
625                 630                 635                 640

Gln Pro Ser Ala Met Val Asp Glu Ala Thr Cys Ala Ala Cys Asp Phe
                645                 650                 655

Asn Lys Pro Gly Ala Asn Cys Gln Arg Lys Met Ala Trp Gln Trp Arg
                660                 665                 670

Gly Glu Phe Met Pro Ala Ser Arg Ser Glu Tyr His Arg Ile Gln His
                675                 680                 685

Gln Leu Glu Ser Glu Lys Phe Pro Pro Leu Phe Pro Glu Gly Pro Ala
    690                 695                 700

Arg Ala Phe His Glu Leu Ser Arg Glu Glu Gln Ala Lys Tyr Glu Lys
705                 710                 715                 720

Arg Arg Leu Ala Asp Tyr Cys Arg Lys Ala Tyr Lys Lys Ile His Ile
                725                 730                 735

Thr Lys Val Glu Glu Arg Leu Thr Thr Ile Cys Gln Arg Glu Asn Ser
                740                 745                 750

Phe Tyr Val Asp Thr Val Arg Ala Phe Arg Asp Arg Tyr Glu Phe
                755                 760                 765

Lys Gly Leu His Lys Val Trp Lys Lys Leu Ser Ala Ala Val Glu
770                 775                 780

Val Gly Asp Ala Ala Glu Val Lys Arg Cys Lys Asn Met Glu Val Leu
785                 790                 795                 800

Tyr Asp Ser Leu Gln Leu Ala His Lys Cys Ile Leu Asn Ser Phe Tyr
                805                 810                 815

Gly Tyr Val Met Arg Lys Gly Ala Arg Trp Tyr Ser Met Glu Met Ala
                820                 825                 830

Gly Ile Val Cys Phe Thr Gly Ala Asn Ile Ile Thr Gln Ala Arg Glu
                835                 840                 845

Leu Ile Glu Gln Ile Gly Arg Pro Leu Glu Leu Asp Thr Asp Gly Ile
850                 855                 860

Trp Cys Val Leu Pro Asn Ser Phe Pro Glu Asn Phe Val Phe Lys Thr
```

```
                865                 870                 875                 880
            Thr Asn Val Lys Lys Pro Lys Val Thr Ile Ser Tyr Pro Gly Ala Met
                            885                 890                 895
            Leu Asn Ile Met Val Lys Glu Gly Phe Thr Asn Asp Gln Tyr Gln Glu
                            900                 905                 910
            Leu Ala Glu Pro Ser Ser Leu Thr Tyr Val Thr Arg Ser Glu Asn Ser
                            915                 920                 925
            Ile Phe Phe Glu Val Asp Gly Pro Tyr Leu Ala Met Ile Leu Pro Ala
                            930                 935                 940
            Ser Lys Glu Glu Gly Lys Lys Leu Lys Arg Tyr Ala Val Phe Asn
            945                 950                 955                 960
            Glu Asp Gly Ser Leu Ala Glu Leu Lys Gly Phe Glu Val Lys Arg Arg
                            965                 970                 975
            Gly Glu Leu Gln Leu Ile Lys Ile Phe Gln Ser Ser Val Phe Glu Ala
                            980                 985                 990
            Phe Leu Lys Gly Ser Thr Leu Glu  Glu Val Tyr Gly Ser  Val Ala Lys
                            995                 1000                1005
            Val Ala  Asp Tyr Trp Leu Asp  Val Leu Tyr Ser Lys  Ala Ala Asn
                1010                1015                1020
            Met Pro  Asp Ser Glu Leu Phe  Glu Leu Ile Ser Glu  Asn Arg Ser
                1025                1030                1035
            Met Ser  Arg Lys Leu Glu Asp  Tyr Gly Glu Gln Lys  Ser Thr Ser
                1040                1045                1050
            Ile Ser  Thr Ala Lys Arg Leu  Ala Glu Phe Leu Gly  Asp Gln Met
                1055                1060                1065
            Val Lys  Asp Ala Gly Leu Ser  Cys Arg Tyr Ile Ile  Ser Arg Lys
                1070                1075                1080
            Pro Glu  Gly Ser Pro Val Thr  Glu Arg Ala Ile Pro  Leu Ala Ile
                1085                1090                1095
            Phe Gln  Ala Glu Pro Thr Val  Arg Lys His Phe Leu  Arg Lys Trp
                1100                1105                1110
            Leu Lys  Ser Ser Ser Leu Gln  Asp Phe Asp Ile Arg  Ala Ile Leu
                1115                1120                1125
            Asp Trp  Asp Tyr Tyr Ile Glu  Arg Leu Gly Ser Ala  Ile Gln Lys
                1130                1135                1140
            Ile Ile  Thr Ile Pro Ala Ala  Leu Gln Gln Val Lys  Asn Pro Val
                1145                1150                1155
            Pro Arg  Val Lys His Pro Asp  Trp Leu His Lys Lys  Leu Leu Glu
                1160                1165                1170
            Lys Asn  Asp Val Tyr Lys Gln  Lys Lys Ile Ser Glu  Leu Phe Thr
                1175                1180                1185
            Leu Glu  Gly Arg Arg Gln Val  Thr Met Ala Glu Ala  Ser Glu Asp
                1190                1195                1200
            Ser Pro  Arg Pro Ser Ala Pro  Asp Met Glu Asp Phe  Gly Leu Val
                1205                1210                1215
            Lys Leu  Pro His Pro Ala Ala  Pro Val Thr Val Lys  Arg Lys Arg
                1220                1225                1230
            Val Leu  Trp Glu Ser Gln Glu  Ser Gln Asp Leu Thr  Pro Thr
                1235                1240                1245
            Val Pro  Trp Gln Glu Ile Leu  Gly Gln Pro Pro Ala  Leu Gly Thr
                1250                1255                1260
            Ser Gln  Glu Glu Trp Leu Val  Trp Leu Arg Phe His  Lys Lys Lys
                1265                1270                1275
```

-continued

Trp Gln Leu Gln Ala Arg Gln Arg Leu Ala Arg Arg Lys Arg Gln
    1280            1285            1290

Arg Leu Glu Ser Ala Glu Gly Val Leu Arg Pro Gly Ala Ile Arg
    1295            1300            1305

Asp Gly Pro Ala Thr Gly Leu Gly Ser Phe Leu Arg Arg Thr Ala
    1310            1315            1320

Arg Ser Ile Leu Asp Leu Pro Trp Gln Ile Val Gln Ile Ser Glu
    1325            1330            1335

Thr Ser Gln Ala Gly Leu Phe Arg Leu Trp Ala Leu Val Gly Ser
    1340            1345            1350

Asp Leu His Cys Ile Arg Leu Ser Ile Pro Arg Val Phe Tyr Val
    1355            1360            1365

Asn Gln Arg Val Ala Lys Ala Glu Glu Gly Ala Ser Tyr Arg Lys
    1370            1375            1380

Val Asn Arg Val Leu Pro Arg Ser Asn Met Val Tyr Asn Leu Tyr
    1385            1390            1395

Glu Tyr Ser Val Pro Glu Asp Met Tyr Gln Glu His Ile Asn Glu
    1400            1405            1410

Ile Asn Ala Glu Leu Ser Ala Pro Asp Ile Glu Gly Val Tyr Glu
    1415            1420            1425

Thr Gln Val Pro Leu Leu Phe Arg Ala Leu Val His Leu Gly Cys
    1430            1435            1440

Val Cys Val Val Asn Lys Gln Leu Val Arg His Leu Ser Gly Trp
    1445            1450            1455

Glu Ala Glu Thr Phe Ala Leu Glu His Leu Glu Met Arg Ser Leu
    1460            1465            1470

Ala Gln Phe Ser Tyr Leu Glu Pro Gly Ser Ile Arg His Ile Tyr
    1475            1480            1485

Leu Tyr His His Ala Gln Ala His Lys Ala Leu Phe Gly Ile Phe
    1490            1495            1500

Ile Pro Ser Gln Arg Arg Ala Ser Val Phe Val Leu Asp Thr Val
    1505            1510            1515

Arg Ser Asn Gln Met Pro Ser Leu Gly Ala Leu Tyr Ser Ala Glu
    1520            1525            1530

His Gly Leu Leu Leu Glu Lys Val Gly Pro Glu Leu Leu Pro Pro
    1535            1540            1545

Pro Lys His Thr Phe Glu Val Arg Ala Glu Thr Asp Leu Lys Thr
    1550            1555            1560

Ile Cys Arg Ala Ile Gln Arg Phe Leu Leu Ala Tyr Lys Glu Glu
    1565            1570            1575

Arg Arg Gly Pro Thr Leu Ile Ala Val Gln Ser Ser Trp Glu Leu
    1580            1585            1590

Lys Arg Leu Ala Ser Glu Ile Pro Val Leu Glu Glu Phe Pro Leu
    1595            1600            1605

Val Pro Ile Cys Val Ala Asp Lys Ile Asn Tyr Gly Val Leu Asp
    1610            1615            1620

Trp Gln Arg His Gly Ala Arg Arg Met Ile Arg His Tyr Leu Asn
    1625            1630            1635

Leu Asp Thr Cys Leu Ser Gln Ala Phe Glu Met Ser Arg Tyr Phe
    1640            1645            1650

His Ile Pro Ile Gly Asn Leu Pro Glu Asp Ile Ser Thr Phe Gly
    1655            1660            1665

-continued

Ser Asp Leu Phe Phe Ala Arg His Leu Gln Arg His Asn His Leu
1670              1675              1680

Leu Trp Leu Ser Pro Thr Ala Arg Pro Asp Leu Gly Gly Lys Glu
1685              1690              1695

Ala Asp Asp Asn Cys Leu Val Met Glu Phe Asp Gln Ala Thr
1700              1705              1710

Val Glu Ile Asn Ser Ser Gly Cys Tyr Ser Thr Val Cys Val Glu
1715              1720              1725

Leu Asp Leu Gln Asn Leu Ala Val Asn Thr Ile Leu Gln Ser His
1730              1735              1740

His Val Asn Asp Met Glu Gly Ala Asp Ser Met Gly Ile Ser Phe
1745              1750              1755

Asp Val Ile Gln Gln Ala Ser Leu Glu Asp Met Ile Thr Gly Gly
1760              1765              1770

Gln Ala Ala Ser Ala Pro Ala Ser Tyr Asp Glu Thr Ala Leu Cys
1775              1780              1785

Ser Asn Thr Phe Arg Ile Leu Lys Ser Met Val Val Gly Trp Val
1790              1795              1800

Lys Glu Ile Thr Gln Tyr His Asn Ile Tyr Ala Asp Asn Gln Val
1805              1810              1815

Met His Phe Tyr Arg Trp Leu Arg Ser Pro Ser Ser Leu Leu His
1820              1825              1830

Asp Pro Ala Leu His Arg Thr Leu His Asn Met Met Lys Lys Leu
1835              1840              1845

Phe Leu Gln Leu Ile Ala Glu Phe Lys Arg Leu Gly Ser Ser Val
1850              1855              1860

Ile Tyr Ala Asn Phe Asn Arg Ile Ile Leu Cys Thr Lys Lys Arg
1865              1870              1875

Arg Val Glu Asp Ala Ile Ala Tyr Val Glu Tyr Ile Thr Ser Ser
1880              1885              1890

Ile His Ser Lys Glu Thr Phe His Ser Leu Thr Ile Ser Phe Ser
1895              1900              1905

Arg Cys Trp Glu Phe Leu Leu Trp Met Asp Pro Ser Asn Tyr Gly
1910              1915              1920

Gly Ile Lys Gly Lys Val Ser Ser Arg Ile His Cys Gly Leu Gln
1925              1930              1935

Asp Ser Gln Lys Ala Gly Gly Ala Glu Asp Glu Gln Glu Asn Glu
1940              1945              1950

Asp Asp Glu Glu Glu Arg Asp Gly Glu Glu Glu Glu Ala Glu
1955              1960              1965

Glu Ser Asn Val Glu Asp Leu Leu Glu Asn Asn Trp Asn Ile Leu
1970              1975              1980

Gln Phe Leu Pro Gln Ala Ala Ser Cys Gln Asn Tyr Phe Leu Met
1985              1990              1995

Ile Val Ser Ala Tyr Ile Val Ala Val Tyr His Cys Met Lys Asp
2000              2005              2010

Gly Leu Arg Arg Ser Ala Pro Gly Ser Thr Pro Val Arg Arg Arg
2015              2020              2025

Gly Ala Ser Gln Leu Ser Gln Glu Ala Glu Gly Ala Val Gly Ala
2030              2035              2040

Leu Pro Gly Met Ile Thr Phe Ser Gln Asp Tyr Val Ala Asn Glu
2045              2050              2055

Leu Thr Gln Ser Phe Phe Thr Ile Thr Gln Lys Ile Gln Lys Lys

```
                    2060                2065                2070
Val Thr Gly Ser Arg Asn Ser Thr Glu Leu Ser Glu Met Phe Pro
    2075                2080                2085
Val Leu Pro Gly Ser His Leu Leu Leu Asn Asn Pro Ala Leu Glu
    2090                2095                2100
Phe Ile Lys Tyr Val Cys Lys Val Leu Ser Leu Asp Thr Asn Ile
    2105                2110                2115
Thr Asn Gln Val Asn Lys Leu Asn Arg Asp Leu Leu Arg Leu Val
    2120                2125                2130
Asp Val Gly Glu Phe Ser Glu Glu Ala Gln Phe Arg Asp Pro Cys
    2135                2140                2145
Arg Ser Tyr Val Leu Pro Glu Val Ile Cys Arg Ser Cys Asn Phe
    2150                2155                2160
Cys Arg Asp Leu Asp Leu Cys Lys Asp Ser Ser Phe Ser Glu Asp
    2165                2170                2175
Gly Ala Val Leu Pro Gln Trp Leu Cys Ser Asn Cys Gln Ala Pro
    2180                2185                2190
Tyr Asp Ser Ser Ala Ile Glu Met Thr Leu Val Glu Val Leu Gln
    2195                2200                2205
Lys Lys Leu Met Ala Phe Thr Leu Gln Asp Leu Val Cys Leu Lys
    2210                2215                2220
Cys Arg Gly Val Lys Glu Thr Ser Met Pro Val Tyr Cys Ser Cys
    2225                2230                2235
Ala Gly Asp Phe Ala Leu Thr Ile His Thr Gln Val Phe Met Glu
    2240                2245                2250
Gln Ile Gly Ile Phe Arg Asn Ile Ala Gln His Tyr Gly Met Ser
    2255                2260                2265
Tyr Leu Leu Glu Thr Leu Glu Trp Leu Leu Gln Lys Asn Pro Gln
    2270                2275                2280
Leu Gly His
    2285

<210> SEQ ID NO 49
<211> LENGTH: 1462
<212> TYPE: PRT
<213> ORGANISM: Homo sapiens

<400> SEQUENCE: 49

Met Ala Pro Val His Gly Asp Asp Ser Leu Ser Asp Ser Gly Ser Phe
1               5                   10                  15
Val Ser Ser Arg Ala Arg Arg Glu Lys Lys Ser Lys Lys Gly Arg Gln
            20                  25                  30
Glu Ala Leu Glu Arg Leu Lys Lys Ala Lys Ala Gly Glu Lys Tyr Lys
        35                  40                  45
Tyr Glu Val Glu Asp Phe Thr Gly Val Tyr Glu Glu Val Asp Glu Glu
    50                  55                  60
Gln Tyr Ser Lys Leu Val Gln Ala Arg Gln Asp Asp Asp Trp Ile Val
65                  70                  75                  80
Asp Asp Asp Gly Ile Gly Tyr Val Glu Asp Gly Arg Glu Ile Phe Asp
                85                  90                  95
Asp Asp Leu Glu Asp Asp Ala Leu Asp Ala Asp Glu Lys Gly Lys Asp
            100                 105                 110
Gly Lys Ala Arg Asn Lys Asp Lys Arg Asn Val Lys Lys Leu Ala Val
        115                 120                 125
```

```
Thr Lys Pro Asn Asn Ile Lys Ser Met Phe Ile Ala Cys Ala Gly Lys
    130                 135                 140

Lys Thr Ala Asp Lys Ala Val Asp Leu Ser Lys Asp Gly Leu Leu Gly
145                 150                 155                 160

Asp Ile Leu Gln Asp Leu Asn Thr Glu Thr Pro Gln Ile Thr Pro Pro
                165                 170                 175

Pro Val Met Ile Leu Lys Lys Arg Ser Ile Gly Ala Ser Pro Asn
            180                 185                 190

Pro Phe Ser Val His Thr Ala Thr Ala Val Pro Ser Gly Lys Ile Ala
        195                 200                 205

Ser Pro Val Ser Arg Lys Glu Pro Pro Leu Thr Pro Val Pro Leu Lys
210                 215                 220

Arg Ala Glu Phe Ala Gly Asp Asp Val Gln Val Glu Ser Thr Glu Glu
225                 230                 235                 240

Glu Gln Glu Ser Gly Ala Met Glu Phe Glu Asp Gly Asp Phe Asp Glu
                245                 250                 255

Pro Met Glu Val Glu Val Asp Leu Glu Pro Met Ala Ala Lys Ala
            260                 265                 270

Trp Asp Lys Glu Ser Glu Pro Ala Glu Glu Val Lys Gln Glu Ala Asp
            275                 280                 285

Ser Gly Lys Gly Thr Val Ser Tyr Leu Gly Ser Phe Leu Pro Asp Val
    290                 295                 300

Ser Cys Trp Asp Ile Asp Gln Glu Gly Asp Ser Ser Phe Ser Val Gln
305                 310                 315                 320

Glu Val Gln Val Asp Ser Ser His Leu Pro Leu Val Lys Gly Ala Asp
                325                 330                 335

Glu Glu Gln Val Phe His Phe Tyr Trp Leu Asp Ala Tyr Glu Asp Gln
            340                 345                 350

Tyr Asn Gln Pro Gly Val Val Phe Leu Phe Gly Lys Val Trp Ile Glu
        355                 360                 365

Ser Ala Glu Thr His Val Ser Cys Cys Val Met Val Lys Asn Ile Glu
    370                 375                 380

Arg Thr Leu Tyr Phe Leu Pro Arg Glu Met Lys Ile Asp Leu Asn Thr
385                 390                 395                 400

Gly Lys Glu Thr Gly Thr Pro Ile Ser Met Lys Asp Val Tyr Glu Glu
                405                 410                 415

Phe Asp Glu Lys Ile Ala Thr Lys Tyr Lys Ile Met Lys Phe Lys Ser
            420                 425                 430

Lys Pro Val Glu Lys Asn Tyr Ala Phe Glu Ile Pro Asp Val Pro Glu
        435                 440                 445

Lys Ser Glu Tyr Leu Glu Val Lys Tyr Ser Ala Glu Met Pro Gln Leu
    450                 455                 460

Pro Gln Asp Leu Lys Gly Glu Thr Phe Ser His Val Phe Gly Thr Asn
465                 470                 475                 480

Thr Ser Ser Leu Glu Leu Phe Leu Met Asn Arg Lys Ile Lys Gly Pro
                485                 490                 495

Cys Trp Leu Glu Val Lys Ser Pro Gln Leu Leu Asn Gln Pro Val Ser
            500                 505                 510

Trp Cys Lys Val Glu Ala Met Ala Leu Lys Pro Asp Leu Val Asn Val
        515                 520                 525

Ile Lys Asp Val Ser Pro Pro Pro Leu Val Val Met Ala Phe Ser Met
    530                 535                 540

Lys Thr Met Gln Asn Ala Lys Asn His Gln Asn Glu Ile Ile Ala Met
```

-continued

```
            545                 550                 555                 560
        Ala Ala Leu Val His His Ser Phe Ala Leu Asp Lys Ala Ala Pro Lys
                        565                 570                 575

Pro Pro Phe Gln Ser His Phe Cys Val Val Ser Lys Pro Lys Asp Cys
                        580                 585                 590

Ile Phe Pro Tyr Ala Phe Lys Glu Val Ile Glu Lys Lys Asn Val Lys
                        595                 600                 605

Val Glu Val Ala Ala Thr Glu Arg Thr Leu Leu Gly Phe Phe Leu Ala
                        610                 615                 620

Lys Val His Lys Ile Asp Pro Asp Ile Ile Val Gly His Asn Ile Tyr
        625                 630                 635                 640

Gly Phe Glu Leu Glu Val Leu Leu Gln Arg Ile Asn Val Cys Lys Ala
                        645                 650                 655

Pro His Trp Ser Lys Ile Gly Arg Leu Lys Arg Ser Asn Met Pro Lys
                        660                 665                 670

Leu Gly Gly Arg Ser Gly Phe Gly Glu Arg Asn Ala Thr Cys Gly Arg
                        675                 680                 685

Met Ile Cys Asp Val Glu Ile Ser Ala Lys Glu Leu Ile Arg Cys Lys
                        690                 695                 700

Ser Tyr His Leu Ser Glu Leu Val Gln Gln Ile Leu Lys Thr Glu Arg
        705                 710                 715                 720

Val Val Ile Pro Met Glu Asn Ile Gln Asn Met Tyr Ser Glu Ser Ser
                        725                 730                 735

Gln Leu Leu Tyr Leu Leu Glu His Thr Trp Lys Asp Ala Lys Phe Ile
                        740                 745                 750

Leu Gln Ile Met Cys Glu Leu Asn Val Leu Pro Leu Ala Leu Gln Ile
                        755                 760                 765

Thr Asn Ile Ala Gly Asn Ile Met Ser Arg Thr Leu Met Gly Gly Arg
                        770                 775                 780

Ser Glu Arg Asn Glu Phe Leu Leu His Ala Phe Tyr Glu Asn Asn
        785                 790                 795                 800

Tyr Ile Val Pro Asp Lys Gln Ile Phe Arg Lys Pro Gln Gln Lys Leu
                        805                 810                 815

Gly Asp Glu Asp Glu Ile Asp Gly Asp Thr Asn Lys Tyr Lys Lys
                        820                 825                 830

Gly Arg Lys Lys Ala Ala Tyr Ala Gly Gly Leu Val Leu Asp Pro Lys
                        835                 840                 845

Val Gly Phe Tyr Asp Lys Phe Ile Leu Leu Leu Asp Phe Asn Ser Leu
                        850                 855                 860

Tyr Pro Ser Ile Ile Gln Glu Phe Asn Ile Cys Phe Thr Thr Val Gln
        865                 870                 875                 880

Arg Val Ala Ser Glu Ala Gln Lys Val Thr Glu Asp Gly Glu Gln Glu
                        885                 890                 895

Gln Ile Pro Glu Leu Pro Asp Pro Ser Leu Glu Met Gly Ile Leu Pro
                        900                 905                 910

Arg Glu Ile Arg Lys Leu Val Glu Arg Arg Lys Gln Val Lys Gln Leu
                        915                 920                 925

Met Lys Gln Gln Asp Leu Asn Pro Asp Leu Ile Leu Gln Tyr Asp Ile
        930                 935                 940

Arg Gln Lys Ala Leu Lys Leu Thr Ala Asn Ser Met Tyr Gly Cys Leu
        945                 950                 955                 960

Gly Phe Ser Tyr Ser Arg Phe Tyr Ala Lys Pro Leu Ala Ala Leu Val
                        965                 970                 975
```

```
Thr Tyr Lys Gly Arg Glu Ile Leu Met His Thr Lys Glu Met Val Gln
                980                 985                 990

Lys Met Asn Leu Glu Val Ile Tyr Gly Asp Thr Asp Ser Ile Met Ile
        995                 1000                1005

Asn Thr Asn Ser Thr Asn Leu Glu Glu Val Phe Lys Leu Gly Asn
    1010                1015                1020

Lys Val Lys Ser Glu Val Asn Lys Leu Tyr Lys Leu Leu Glu Ile
    1025                1030                1035

Asp Ile Asp Gly Val Phe Lys Ser Leu Leu Leu Lys Lys Lys
    1040                1045                1050

Lys Tyr Ala Ala Leu Val Val Glu Pro Thr Ser Asp Gly Asn Tyr
    1055                1060                1065

Val Thr Lys Gln Glu Leu Lys Gly Leu Asp Ile Val Arg Arg Asp
    1070                1075                1080

Trp Cys Asp Leu Ala Lys Asp Thr Gly Asn Phe Val Ile Gly Gln
    1085                1090                1095

Ile Leu Ser Asp Gln Ser Arg Asp Thr Ile Val Glu Asn Ile Gln
    1100                1105                1110

Lys Arg Leu Ile Glu Ile Gly Glu Asn Val Leu Asn Gly Ser Val
    1115                1120                1125

Pro Val Ser Gln Phe Glu Ile Asn Lys Ala Leu Thr Lys Asp Pro
    1130                1135                1140

Gln Asp Tyr Pro Asp Lys Lys Ser Leu Pro His Val His Val Ala
    1145                1150                1155

Leu Trp Ile Asn Ser Gln Gly Gly Arg Lys Val Lys Ala Gly Asp
    1160                1165                1170

Thr Val Ser Tyr Val Ile Cys Gln Asp Gly Ser Asn Leu Thr Ala
    1175                1180                1185

Ser Gln Arg Ala Tyr Ala Pro Glu Gln Leu Gln Lys Gln Asp Asn
    1190                1195                1200

Leu Thr Ile Asp Thr Gln Tyr Tyr Leu Ala Gln Gln Ile His Pro
    1205                1210                1215

Val Val Ala Arg Ile Cys Glu Pro Ile Asp Gly Ile Asp Ala Val
    1220                1225                1230

Leu Ile Ala Thr Trp Leu Gly Leu Asp Pro Thr Gln Phe Arg Val
    1235                1240                1245

His His Tyr His Lys Asp Glu Glu Asn Asp Ala Leu Leu Gly Gly
    1250                1255                1260

Pro Ala Gln Leu Thr Asp Glu Glu Lys Tyr Arg Asp Cys Glu Arg
    1265                1270                1275

Phe Lys Cys Pro Cys Pro Thr Cys Gly Thr Glu Asn Ile Tyr Asp
    1280                1285                1290

Asn Val Phe Asp Gly Ser Gly Thr Asp Met Glu Pro Ser Leu Tyr
    1295                1300                1305

Arg Cys Ser Asn Ile Asp Cys Lys Ala Ser Pro Leu Thr Phe Thr
    1310                1315                1320

Val Gln Leu Ser Asn Lys Leu Ile Met Asp Ile Arg Arg Phe Ile
    1325                1330                1335

Lys Lys Tyr Tyr Asp Gly Trp Leu Ile Cys Glu Glu Pro Thr Cys
    1340                1345                1350

Arg Asn Arg Thr Arg His Leu Pro Leu Gln Phe Ser Arg Thr Gly
    1355                1360                1365
```

```
Pro Leu Cys Pro Ala Cys Met Lys Ala Thr Leu Gln Pro Glu Tyr
    1370            1375            1380

Ser Asp Lys Ser Leu Tyr Thr Gln Leu Cys Phe Tyr Arg Tyr Ile
    1385            1390            1395

Phe Asp Ala Glu Cys Ala Leu Glu Lys Leu Thr Thr Asp His Glu
    1400            1405            1410

Lys Asp Lys Leu Lys Lys Gln Phe Phe Thr Pro Lys Val Leu Gln
    1415            1420            1425

Asp Tyr Arg Lys Leu Lys Asn Thr Ala Glu Gln Phe Leu Ser Arg
    1430            1435            1440

Ser Gly Tyr Ser Glu Val Asn Leu Ser Lys Leu Phe Ala Gly Cys
    1445            1450            1455

Ala Val Lys Ser
    1460

<210> SEQ ID NO 50
<211> LENGTH: 335
<212> TYPE: PRT
<213> ORGANISM: Homo sapiens

<400> SEQUENCE: 50

Met Ser Lys Arg Lys Ala Pro Gln Glu Thr Leu Asn Gly Gly Ile Thr
1               5                   10                  15

Asp Met Leu Thr Glu Leu Ala Asn Phe Glu Lys Asn Val Ser Gln Ala
                20                  25                  30

Ile His Lys Tyr Asn Ala Tyr Arg Lys Ala Ala Ser Val Ile Ala Lys
            35                  40                  45

Tyr Pro His Lys Ile Lys Ser Gly Ala Glu Ala Lys Lys Leu Pro Gly
    50                  55                  60

Val Gly Thr Lys Ile Ala Glu Lys Ile Asp Glu Phe Leu Ala Thr Gly
65                  70                  75                  80

Lys Leu Arg Lys Leu Glu Lys Ile Arg Gln Asp Asp Thr Ser Ser Ser
                85                  90                  95

Ile Asn Phe Leu Thr Arg Val Ser Gly Ile Gly Pro Ser Ala Ala Arg
            100                 105                 110

Lys Phe Val Asp Glu Gly Ile Lys Thr Leu Glu Asp Leu Arg Lys Asn
        115                 120                 125

Glu Asp Lys Leu Asn His His Gln Arg Ile Gly Leu Lys Tyr Phe Gly
    130                 135                 140

Asp Phe Glu Lys Arg Ile Pro Arg Glu Glu Met Leu Gln Met Gln Asp
145                 150                 155                 160

Ile Val Leu Asn Glu Val Lys Lys Val Asp Ser Glu Tyr Ile Ala Thr
                165                 170                 175

Val Cys Gly Ser Phe Arg Arg Gly Ala Glu Ser Ser Gly Asp Met Asp
            180                 185                 190

Val Leu Leu Thr His Pro Ser Phe Thr Ser Glu Ser Thr Lys Gln Pro
        195                 200                 205

Lys Leu Leu His Gln Val Val Glu Gln Leu Gln Lys Val His Phe Ile
    210                 215                 220

Thr Asp Thr Leu Ser Lys Gly Asp Thr Lys Phe Met Gly Val Cys Gln
225                 230                 235                 240

Leu Pro Ser Lys Asn Asp Glu Lys Glu Tyr Pro His Arg Arg Ile Asp
                245                 250                 255

Ile Arg Leu Ile Pro Lys Asp Gln Tyr Tyr Cys Gly Val Leu Tyr Phe
            260                 265                 270
```

```
Thr Gly Ser Asp Ile Phe Asn Lys Asn Met Arg Ala His Ala Leu Glu
            275                 280                 285

Lys Gly Phe Thr Ile Asn Glu Tyr Thr Ile Arg Pro Leu Gly Val Thr
    290                 295                 300

Gly Val Ala Gly Glu Pro Leu Pro Val Asp Ser Glu Lys Asp Ile Phe
305                 310                 315                 320

Asp Tyr Ile Gln Trp Lys Tyr Arg Glu Pro Lys Asp Arg Ser Glu
                325                 330                 335

<210> SEQ ID NO 51
<211> LENGTH: 1239
<212> TYPE: PRT
<213> ORGANISM: Homo sapiens

<400> SEQUENCE: 51

Met Ser Arg Leu Leu Trp Arg Lys Val Ala Gly Ala Thr Val Gly Pro
1               5                   10                  15

Gly Pro Val Pro Ala Pro Gly Arg Trp Val Ser Ser Val Pro Ala
            20                  25                  30

Ser Asp Pro Ser Asp Gly Gln Arg Arg Gln Gln Gln Gln Gln Gln
            35                  40                  45

Gln Gln Gln Gln Gln Gln Pro Gln Pro Gln Val Leu Ser Ser
50                  55                  60

Glu Gly Gly Gln Leu Arg His Asn Pro Leu Asp Ile Gln Met Leu Ser
65                  70                  75                  80

Arg Gly Leu His Glu Gln Ile Phe Gly Gln Gly Glu Met Pro Gly
                85                  90                  95

Glu Ala Ala Val Arg Arg Ser Val Glu His Leu Gln Lys His Gly Leu
                100                 105                 110

Trp Gly Gln Pro Ala Val Pro Leu Pro Asp Val Glu Leu Arg Leu Pro
            115                 120                 125

Pro Leu Tyr Gly Asp Asn Leu Asp Gln His Phe Arg Leu Leu Ala Gln
    130                 135                 140

Lys Gln Ser Leu Pro Tyr Leu Glu Ala Ala Asn Leu Leu Leu Gln Ala
145                 150                 155                 160

Gln Leu Pro Pro Lys Pro Pro Ala Trp Ala Trp Ala Glu Gly Trp Thr
                165                 170                 175

Arg Tyr Gly Pro Glu Gly Glu Ala Val Pro Val Ala Ile Pro Glu Glu
            180                 185                 190

Arg Ala Leu Val Phe Asp Val Glu Val Cys Leu Ala Glu Gly Thr Cys
        195                 200                 205

Pro Thr Leu Ala Val Ala Ile Ser Pro Ser Ala Trp Tyr Ser Trp Cys
    210                 215                 220

Ser Gln Arg Leu Val Glu Glu Arg Tyr Ser Trp Thr Ser Gln Leu Ser
225                 230                 235                 240

Pro Ala Asp Leu Ile Pro Leu Glu Val Pro Thr Gly Ala Ser Ser Pro
                245                 250                 255

Thr Gln Arg Asp Trp Gln Glu Gln Leu Val Val Gly His Asn Val Ser
            260                 265                 270

Phe Asp Arg Ala His Ile Arg Glu Gln Tyr Leu Ile Gln Gly Ser Arg
    275                 280                 285

Met Arg Phe Leu Asp Thr Met Ser Met His Met Ala Ile Ser Gly Leu
290                 295                 300

Ser Ser Phe Gln Arg Ser Leu Trp Ile Ala Ala Lys Gln Gly Lys His
```

```
                305                 310                 315                 320
Lys Val Gln Pro Pro Thr Lys Gln Gly Gln Lys Ser Gln Arg Lys Ala
                    325                 330                 335

Arg Arg Gly Pro Ala Ile Ser Ser Trp Asp Trp Leu Asp Ile Ser Ser
                    340                 345                 350

Val Asn Ser Leu Ala Glu Val His Arg Leu Tyr Val Gly Gly Pro Pro
                    355                 360                 365

Leu Glu Lys Glu Pro Arg Glu Leu Phe Val Lys Gly Thr Met Lys Asp
            370                 375                 380

Ile Arg Glu Asn Phe Gln Asp Leu Met Gln Tyr Cys Ala Gln Asp Val
385                 390                 395                 400

Trp Ala Thr His Glu Val Phe Gln Gln Gln Leu Pro Leu Phe Leu Glu
                    405                 410                 415

Arg Cys Pro His Pro Val Thr Leu Ala Gly Met Leu Glu Met Gly Val
                    420                 425                 430

Ser Tyr Leu Pro Val Asn Gln Asn Trp Glu Arg Tyr Leu Ala Glu Ala
                    435                 440                 445

Gln Gly Thr Tyr Glu Glu Leu Gln Arg Glu Met Lys Lys Ser Leu Met
            450                 455                 460

Asp Leu Ala Asn Asp Ala Cys Gln Leu Leu Ser Gly Glu Arg Tyr Lys
465                 470                 475                 480

Glu Asp Pro Trp Leu Trp Asp Leu Glu Trp Asp Leu Gln Glu Phe Lys
                    485                 490                 495

Gln Lys Lys Ala Lys Lys Val Lys Lys Glu Pro Ala Thr Ala Ser Lys
                    500                 505                 510

Leu Pro Ile Glu Gly Ala Gly Ala Pro Gly Asp Pro Met Asp Gln Glu
            515                 520                 525

Asp Leu Gly Pro Cys Ser Glu Glu Glu Phe Gln Gln Asp Val Met
                    535                 540

Ala Arg Ala Cys Leu Gln Lys Leu Lys Gly Thr Thr Glu Leu Leu Pro
545                 550                 555                 560

Lys Arg Pro Gln His Leu Pro Gly His Pro Gly Trp Tyr Arg Lys Leu
                    565                 570                 575

Cys Pro Arg Leu Asp Asp Pro Ala Trp Thr Pro Gly Pro Ser Leu Leu
                    580                 585                 590

Ser Leu Gln Met Arg Val Thr Pro Lys Leu Met Ala Leu Thr Trp Asp
            595                 600                 605

Gly Phe Pro Leu His Tyr Ser Glu Arg His Gly Trp Gly Tyr Leu Val
            610                 615                 620

Pro Gly Arg Arg Asp Asn Leu Ala Lys Leu Pro Thr Gly Thr Thr Leu
625                 630                 635                 640

Glu Ser Ala Gly Val Val Cys Pro Tyr Arg Ala Ile Glu Ser Leu Tyr
                    645                 650                 655

Arg Lys His Cys Leu Glu Gln Gly Lys Gln Gln Leu Met Pro Gln Glu
                    660                 665                 670

Ala Gly Leu Ala Glu Glu Phe Leu Leu Thr Asp Asn Ser Ala Ile Trp
            675                 680                 685

Gln Thr Val Glu Glu Leu Asp Tyr Leu Glu Val Glu Ala Glu Ala Lys
            690                 695                 700

Met Glu Asn Leu Arg Ala Ala Val Pro Gly Gln Pro Leu Ala Leu Thr
705                 710                 715                 720

Ala Arg Gly Gly Pro Lys Asp Thr Gln Pro Ser Tyr His His Gly Asn
                    725                 730                 735
```

```
Gly Pro Tyr Asn Asp Val Asp Ile Pro Gly Cys Trp Phe Lys Leu
                740                 745                 750

Pro His Lys Asp Gly Asn Ser Cys Asn Val Gly Ser Pro Phe Ala Lys
        755                 760                 765

Asp Phe Leu Pro Lys Met Glu Asp Gly Thr Leu Gln Ala Gly Pro Gly
770                 775                 780

Gly Ala Ser Gly Pro Arg Ala Leu Glu Ile Asn Lys Met Ile Ser Phe
785                 790                 795                 800

Trp Arg Asn Ala His Lys Arg Ile Ser Ser Gln Met Val Val Trp Leu
                805                 810                 815

Pro Arg Ser Ala Leu Pro Arg Ala Val Ile Arg His Pro Asp Tyr Asp
        820                 825                 830

Glu Glu Gly Leu Tyr Gly Ala Ile Leu Pro Gln Val Val Thr Ala Gly
                835                 840                 845

Thr Ile Thr Arg Arg Ala Val Glu Pro Thr Trp Leu Thr Ala Ser Asn
        850                 855                 860

Ala Arg Pro Asp Arg Val Gly Ser Glu Leu Lys Ala Met Val Gln Ala
865                 870                 875                 880

Pro Pro Gly Tyr Thr Leu Val Gly Ala Asp Val Asp Ser Gln Glu Leu
                885                 890                 895

Trp Ile Ala Ala Val Leu Gly Asp Ala His Phe Ala Gly Met His Gly
                900                 905                 910

Cys Thr Ala Phe Gly Trp Met Thr Leu Gln Gly Arg Lys Ser Arg Gly
        915                 920                 925

Thr Asp Leu His Ser Lys Thr Ala Thr Thr Val Gly Ile Ser Arg Glu
        930                 935                 940

His Ala Lys Ile Phe Asn Tyr Gly Arg Ile Tyr Gly Ala Gly Gln Pro
945                 950                 955                 960

Phe Ala Glu Arg Leu Leu Met Gln Phe Asn His Arg Leu Thr Gln Gln
                965                 970                 975

Glu Ala Ala Glu Lys Ala Gln Gln Met Tyr Ala Ala Thr Lys Gly Leu
        980                 985                 990

Arg Trp Tyr Arg Leu Ser Asp Glu  Gly Glu Trp Leu Val  Arg Glu Leu
        995                 1000                1005

Asn Leu  Pro Val Asp Arg Thr  Glu Gly Gly Trp Ile  Ser Leu Gln
    1010                1015                1020

Asp Leu  Arg Lys Val Gln Arg  Glu Thr Ala Arg Lys  Ser Gln Trp
    1025                1030                1035

Lys Lys  Trp Glu Val Val Ala  Glu Arg Ala Trp Lys  Gly Gly Thr
    1040                1045                1050

Glu Ser  Glu Met Phe Asn Lys  Leu Glu Ser Ile Ala  Thr Ser Asp
    1055                1060                1065

Ile Pro  Arg Thr Pro Val Leu  Gly Cys Cys Ile Ser  Arg Ala Leu
    1070                1075                1080

Glu Pro  Ser Ala Val Gln Glu  Glu Phe Met Thr Ser  Arg Val Asn
    1085                1090                1095

Trp Val  Val Gln Ser Ser Ala  Val Asp Tyr Leu His  Leu Met Leu
    1100                1105                1110

Val Ala  Met Lys Trp Leu Phe  Glu Glu Phe Ala Ile  Asp Gly Arg
    1115                1120                1125

Phe Cys  Ile Ser Ile His Asp  Glu Val Arg Tyr Leu  Val Arg Glu
    1130                1135                1140
```

```
Glu Asp Arg Tyr Arg Ala Ala Leu Ala Leu Gln Ile Thr Asn Leu
    1145                1150                1155

Leu Thr Arg Cys Met Phe Ala Tyr Lys Leu Gly Leu Asn Asp Leu
    1160                1165                1170

Pro Gln Ser Val Ala Phe Phe Ser Ala Val Asp Ile Asp Arg Cys
    1175                1180                1185

Leu Arg Lys Glu Val Thr Met Asp Cys Lys Thr Pro Ser Asn Pro
    1190                1195                1200

Thr Gly Met Glu Arg Arg Tyr Gly Ile Pro Gln Gly Glu Ala Leu
    1205                1210                1215

Asp Ile Tyr Gln Ile Ile Glu Leu Thr Lys Gly Ser Leu Glu Lys
    1220                1225                1230

Arg Ser Gln Pro Gly Pro
    1235

<210> SEQ ID NO 52
<211> LENGTH: 1187
<212> TYPE: PRT
<213> ORGANISM: Saccharomyces cerevisiae

<400> SEQUENCE: 52

Met Met Phe Gly Lys Lys Lys Asn Asn Gly Gly Ser Ser Thr Ala Arg
1               5                   10                  15

Tyr Ser Ala Gly Asn Lys Tyr Asn Thr Leu Ser Asn Asn Tyr Ala Leu
                20                  25                  30

Ser Ala Gln Gln Leu Leu Asn Ala Ser Lys Ile Asp Asp Ile Asp Ser
            35                  40                  45

Met Met Gly Phe Glu Arg Tyr Val Pro Pro Gln Tyr Asn Gly Arg Phe
    50                  55                  60

Asp Ala Lys Asp Ile Asp Gln Ile Pro Gly Arg Val Gly Trp Leu Thr
65                  70                  75                  80

Asn Met His Ala Thr Leu Val Ser Gln Glu Thr Leu Ser Ser Gly Ser
                85                  90                  95

Asn Gly Gly Gly Asn Ser Asn Asp Gly Glu Arg Val Thr Thr Asn Gln
            100                 105                 110

Gly Ile Ser Gly Val Asp Phe Tyr Phe Leu Asp Glu Glu Gly Gly Ser
        115                 120                 125

Phe Lys Ser Thr Val Val Tyr Asp Pro Tyr Phe Phe Ile Ala Cys Asn
    130                 135                 140

Asp Glu Ser Arg Val Asn Asp Val Glu Glu Leu Val Lys Lys Tyr Leu
145                 150                 155                 160

Glu Ser Cys Leu Lys Ser Leu Gln Ile Ile Arg Lys Glu Asp Leu Thr
                165                 170                 175

Met Asp Asn His Leu Leu Gly Leu Gln Lys Thr Leu Ile Lys Leu Ser
            180                 185                 190

Phe Val Asn Ser Asn Gln Leu Phe Glu Ala Arg Lys Leu Leu Arg Pro
        195                 200                 205

Ile Leu Gln Asp Asn Ala Asn Asn Val Gln Arg Asn Ile Tyr Asn
    210                 215                 220

Val Ala Ala Asn Gly Ser Glu Lys Val Asp Ala Lys His Leu Ile Glu
225                 230                 235                 240

Asp Ile Arg Glu Tyr Asp Val Pro Tyr His Val Arg Val Ser Ile Asp
                245                 250                 255

Lys Asp Ile Arg Val Gly Lys Trp Tyr Lys Val Thr Gln Gln Gly Phe
            260                 265                 270
```

```
Ile Glu Asp Thr Arg Lys Ile Ala Phe Ala Asp Pro Val Met Ala
            275                 280                 285
Phe Asp Ile Glu Thr Thr Lys Pro Pro Leu Lys Phe Pro Asp Ser Ala
    290                 295                 300
Val Asp Gln Ile Met Met Ile Ser Tyr Met Ile Asp Gly Gly Phe
305                 310                 315                 320
Leu Ile Thr Asn Arg Glu Ile Ile Ser Glu Asp Ile Glu Asp Phe Glu
                325                 330                 335
Tyr Thr Pro Lys Pro Glu Tyr Pro Gly Phe Phe Thr Ile Phe Asn Glu
            340                 345                 350
Asn Asp Glu Val Ala Leu Leu Gln Arg Phe Phe Glu His Ile Arg Asp
        355                 360                 365
Val Arg Pro Thr Val Ile Ser Thr Phe Asn Gly Asp Phe Phe Asp Trp
    370                 375                 380
Pro Phe Ile His Asn Arg Ser Lys Ile His Gly Leu Asp Met Phe Asp
385                 390                 395                 400
Glu Ile Gly Phe Ala Pro Asp Ala Glu Gly Glu Tyr Lys Ser Ser Tyr
                405                 410                 415
Cys Ser His Met Asp Cys Phe Arg Trp Val Lys Arg Asp Ser Tyr Leu
            420                 425                 430
Pro Gln Gly Ser Gln Gly Leu Lys Ala Val Thr Gln Ser Lys Leu Gly
        435                 440                 445
Tyr Asn Pro Ile Glu Leu Asp Pro Glu Leu Met Thr Pro Tyr Ala Phe
    450                 455                 460
Glu Lys Pro Gln His Leu Ser Glu Tyr Ser Val Ser Asp Ala Val Ala
465                 470                 475                 480
Thr Tyr Tyr Leu Tyr Met Lys Tyr Val His Pro Phe Ile Phe Ser Leu
                485                 490                 495
Cys Thr Ile Ile Pro Leu Asn Pro Asp Glu Thr Leu Arg Lys Gly Thr
            500                 505                 510
Gly Thr Leu Cys Glu Met Leu Leu Met Val Gln Ala Tyr Gln His Asn
        515                 520                 525
Ile Leu Leu Pro Asn Lys His Thr Asp Pro Ile Glu Arg Phe Tyr Asp
    530                 535                 540
Gly His Leu Leu Glu Ser Glu Thr Tyr Val Gly Gly His Val Glu Ser
545                 550                 555                 560
Leu Glu Ala Gly Val Phe Arg Ser Asp Leu Lys Asn Glu Phe Lys Ile
                565                 570                 575
Asp Pro Ser Ala Ile Asp Glu Leu Leu Gln Glu Leu Pro Glu Ala Leu
            580                 585                 590
Lys Phe Ser Val Glu Val Glu Asn Lys Ser Ser Val Asp Lys Val Thr
        595                 600                 605
Asn Phe Glu Glu Ile Lys Asn Gln Ile Thr Gln Lys Leu Leu Glu Leu
    610                 615                 620
Lys Glu Asn Asn Ile Arg Asn Glu Leu Pro Leu Ile Tyr His Val Asp
625                 630                 635                 640
Val Ala Ser Met Tyr Pro Asn Ile Met Thr Thr Asn Arg Leu Gln Pro
                645                 650                 655
Asp Ser Ile Lys Ala Glu Arg Asp Cys Ala Ser Cys Asp Phe Asn Arg
            660                 665                 670
Pro Gly Lys Thr Cys Ala Arg Lys Leu Lys Trp Ala Trp Arg Gly Glu
        675                 680                 685
```

```
Phe Phe Pro Ser Lys Met Asp Glu Tyr Asn Met Ile Lys Arg Ala Leu
        690             695                 700

Gln Asn Glu Thr Phe Pro Asn Lys Asn Lys Phe Ser Lys Lys Val
705             710                 715                 720

Leu Thr Phe Asp Glu Leu Ser Tyr Ala Asp Gln Val Ile His Ile Lys
                725                 730                 735

Lys Arg Leu Thr Glu Tyr Ser Arg Lys Val Tyr His Arg Val Lys Val
            740                 745                 750

Ser Glu Ile Val Glu Arg Glu Ala Ile Val Cys Gln Arg Glu Asn Pro
                755                 760                 765

Phe Tyr Val Asp Thr Val Lys Ser Phe Arg Asp Arg Arg Tyr Glu Phe
770                 775                 780

Lys Gly Leu Ala Lys Thr Trp Lys Gly Asn Leu Ser Lys Ile Asp Pro
785             790                 795                 800

Ser Asp Lys His Ala Arg Asp Glu Ala Lys Lys Met Ile Val Leu Tyr
                805                 810                 815

Asp Ser Leu Gln Leu Ala His Lys Val Ile Leu Asn Ser Phe Tyr Gly
            820                 825                 830

Tyr Val Met Arg Lys Gly Ser Arg Trp Tyr Ser Met Glu Met Ala Gly
            835                 840                 845

Ile Thr Cys Leu Thr Gly Ala Thr Ile Ile Gln Met Ala Arg Ala Leu
850                 855                 860

Val Glu Arg Val Gly Arg Pro Leu Glu Leu Asp Thr Asp Gly Ile Trp
865                 870                 875                 880

Cys Ile Leu Pro Lys Ser Phe Pro Glu Thr Tyr Phe Phe Thr Leu Glu
                885                 890                 895

Asn Gly Lys Lys Leu Tyr Leu Ser Tyr Pro Cys Ser Met Leu Asn Tyr
            900                 905                 910

Arg Val His Gln Lys Phe Thr Asn His Gln Tyr Gln Glu Leu Lys Asp
            915                 920                 925

Pro Leu Asn Tyr Ile Tyr Glu Thr His Ser Glu Asn Thr Ile Phe Phe
    930                 935                 940

Glu Val Asp Gly Pro Tyr Lys Ala Met Ile Leu Pro Ser Ser Lys Glu
945                 950                 955                 960

Glu Gly Lys Gly Ile Lys Lys Arg Tyr Ala Val Phe Asn Glu Asp Gly
                965                 970                 975

Ser Leu Ala Glu Leu Lys Gly Phe Glu Leu Lys Arg Arg Gly Glu Leu
            980                 985                 990

Gln Leu Ile Lys Asn Phe Gln Ser Asp Ile Phe Lys Val Phe Leu Glu
        995                 1000                1005

Gly Asp Thr Leu Glu Gly Cys Tyr Ser Ala Val Ala Ser Val Cys
    1010                1015                1020

Asn Arg Trp Leu Asp Val Leu Asp Ser His Gly Leu Met Leu Glu
    1025                1030                1035

Asp Glu Asp Leu Val Ser Leu Ile Cys Glu Asn Arg Ser Met Ser
    1040                1045                1050

Lys Thr Leu Lys Glu Tyr Glu Gly Gln Lys Ser Thr Ser Ile Thr
    1055                1060                1065

Thr Ala Arg Arg Leu Gly Asp Phe Leu Gly Glu Asp Met Val Lys
    1070                1075                1080

Asp Lys Gly Leu Gln Cys Lys Tyr Ile Ile Ser Ser Lys Pro Phe
    1085                1090                1095

Asn Ala Pro Val Thr Glu Arg Ala Ile Pro Val Ala Ile Phe Ser
```

```
                1100                1105                1110
Ala Asp Ile Pro Ile Lys Arg Ser Phe Leu Arg Arg Trp Thr Leu
    1115                1120                1125

Asp Pro Ser Leu Glu Asp Leu Asp Ile Arg Thr Ile Ile Asp Trp
    1130                1135                1140

Gly Tyr Tyr Arg Glu Arg Leu Gly Ser Ala Ile Gln Lys Ile Ile
    1145                1150                1155

Thr Ile Pro Ala Ala Leu Gln Gly Val Ser Asn Pro Val Pro Arg
    1160                1165                1170

Val Glu His Pro Asp Trp Leu Lys Arg Lys Ile Ala Thr Lys
    1175                1180                1185

<210> SEQ ID NO 53
<211> LENGTH: 632
<212> TYPE: PRT
<213> ORGANISM: Saccharomyces cerevisiae

<400> SEQUENCE: 53

Met Ser Lys Phe Thr Trp Lys Glu Leu Ile Gln Leu Gly Ser Pro Ser
1               5                   10                  15

Lys Ala Tyr Glu Ser Ser Leu Ala Cys Ile Ala His Ile Asp Met Asn
            20                  25                  30

Ala Phe Phe Ala Gln Val Glu Gln Met Arg Cys Gly Leu Ser Lys Glu
        35                  40                  45

Asp Pro Val Val Cys Val Gln Trp Asn Ser Ile Ile Ala Val Ser Tyr
    50                  55                  60

Ala Ala Arg Lys Tyr Gly Ile Ser Arg Met Asp Thr Ile Gln Glu Ala
65                  70                  75                  80

Leu Lys Lys Cys Ser Asn Leu Ile Pro Ile His Thr Ala Val Phe Lys
                85                  90                  95

Lys Gly Glu Asp Phe Trp Gln Tyr His Asp Gly Cys Gly Ser Trp Val
            100                 105                 110

Gln Asp Pro Ala Lys Gln Ile Ser Val Glu Asp His Lys Val Ser Leu
        115                 120                 125

Glu Pro Tyr Arg Arg Glu Ser Arg Lys Ala Leu Lys Ile Phe Lys Ser
    130                 135                 140

Ala Cys Asp Leu Val Glu Arg Ala Ser Ile Asp Glu Val Phe Leu Asp
145                 150                 155                 160

Leu Gly Arg Ile Cys Phe Asn Met Leu Met Phe Asp Asn Glu Tyr Glu
                165                 170                 175

Leu Thr Gly Asp Leu Lys Leu Lys Asp Ala Leu Ser Asn Ile Arg Glu
            180                 185                 190

Ala Phe Ile Gly Gly Asn Tyr Asp Ile Asn Ser His Leu Pro Leu Ile
        195                 200                 205

Pro Glu Lys Ile Lys Ser Leu Lys Phe Glu Gly Asp Val Phe Asn Pro
    210                 215                 220

Glu Gly Arg Asp Leu Ile Thr Asp Trp Asp Asp Val Ile Leu Ala Leu
225                 230                 235                 240

Gly Ser Gln Val Cys Lys Gly Ile Arg Asp Ser Ile Lys Asp Ile Leu
                245                 250                 255

Gly Tyr Thr Thr Ser Cys Gly Leu Ser Ser Thr Lys Asn Val Cys Lys
            260                 265                 270

Leu Ala Ser Asn Tyr Lys Lys Pro Asp Ala Gln Thr Ile Val Lys Asn
        275                 280                 285
```

Asp Cys Leu Leu Asp Phe Leu Asp Cys Gly Lys Phe Glu Ile Thr Ser
            290                 295                 300

Phe Trp Thr Leu Gly Gly Val Leu Gly Lys Glu Leu Ile Asp Val Leu
305                 310                 315                 320

Asp Leu Pro His Glu Asn Ser Ile Lys His Ile Arg Glu Thr Trp Pro
            325                 330                 335

Asp Asn Ala Gly Gln Leu Lys Glu Phe Leu Asp Ala Lys Val Lys Gln
            340                 345                 350

Ser Asp Tyr Asp Arg Ser Thr Ser Asn Ile Asp Pro Leu Lys Thr Ala
        355                 360                 365

Asp Leu Ala Glu Lys Leu Phe Lys Leu Ser Arg Gly Arg Tyr Gly Leu
370                 375                 380

Pro Leu Ser Ser Arg Pro Val Val Lys Ser Met Met Ser Asn Lys Asn
385                 390                 395                 400

Leu Arg Gly Lys Ser Cys Asn Ser Ile Val Asp Cys Ile Ser Trp Leu
                405                 410                 415

Glu Val Phe Cys Ala Glu Leu Thr Ser Arg Ile Gln Asp Leu Glu Gln
            420                 425                 430

Glu Tyr Asn Lys Ile Val Ile Pro Arg Thr Val Ser Ile Ser Leu Lys
        435                 440                 445

Thr Lys Ser Tyr Glu Val Tyr Arg Lys Ser Gly Pro Val Ala Tyr Lys
450                 455                 460

Gly Ile Asn Phe Gln Ser His Glu Leu Leu Lys Val Gly Ile Lys Phe
465                 470                 475                 480

Val Thr Asp Leu Asp Ile Lys Gly Lys Asn Lys Ser Tyr Tyr Pro Leu
                485                 490                 495

Thr Lys Leu Ser Met Thr Ile Thr Asn Phe Asp Ile Ile Asp Leu Gln
            500                 505                 510

Lys Thr Val Val Asp Met Phe Gly Asn Gln Val His Thr Phe Lys Ser
        515                 520                 525

Ser Ala Gly Lys Glu Asp Glu Leu Lys Thr Thr Ser Ser Lys Ala Asp
530                 535                 540

Glu Lys Thr Pro Lys Leu Glu Cys Cys Lys Tyr Gln Val Thr Phe Thr
545                 550                 555                 560

Asp Gln Lys Ala Leu Gln Glu His Ala Asp Tyr His Leu Ala Leu Lys
                565                 570                 575

Leu Ser Glu Gly Leu Asn Gly Ala Glu Glu Ser Ser Lys Asn Leu Ser
            580                 585                 590

Phe Gly Glu Lys Arg Leu Leu Phe Ser Arg Lys Arg Pro Asn Ser Gln
        595                 600                 605

His Thr Ala Thr Pro Gln Lys Lys Gln Val Thr Ser Ser Lys Asn Ile
610                 615                 620

Leu Ser Phe Phe Thr Arg Lys Lys
625                 630

<210> SEQ ID NO 54
<211> LENGTH: 928
<212> TYPE: PRT
<213> ORGANISM: Escherichia coli

<400> SEQUENCE: 54

Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
            20                  25                  30

```
Gly Glu Pro Thr Gly Ala Met Tyr Gly Val Leu Asn Met Leu Arg Ser
            35                  40                  45

Leu Ile Met Gln Tyr Lys Pro Thr His Ala Ala Val Val Phe Asp Ala
 50                  55                  60

Lys Gly Lys Thr Phe Arg Asp Glu Leu Phe Glu His Tyr Lys Ser His
 65                  70                  75                  80

Arg Pro Pro Met Pro Asp Asp Leu Arg Ala Gln Ile Glu Pro Leu His
                 85                  90                  95

Ala Met Val Lys Ala Met Gly Leu Pro Leu Leu Ala Val Ser Gly Val
             100                 105                 110

Glu Ala Asp Asp Val Ile Gly Thr Leu Ala Arg Glu Ala Glu Lys Ala
             115                 120                 125

Gly Arg Pro Val Leu Ile Ser Thr Gly Asp Lys Asp Met Ala Gln Leu
 130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                 165                 170                 175

Ile Asp Phe Leu Ala Leu Met Gly Asp Ser Ser Asp Asn Ile Pro Gly
             180                 185                 190

Val Pro Gly Val Gly Glu Lys Thr Ala Gln Ala Leu Leu Gln Gly Leu
             195                 200                 205

Gly Gly Leu Asp Thr Leu Tyr Ala Glu Pro Glu Lys Ile Ala Gly Leu
 210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                 245                 250                 255

Glu Leu Glu Leu Thr Cys Glu Gln Leu Glu Val Gln Gln Pro Ala Ala
             260                 265                 270

Glu Glu Leu Leu Gly Leu Phe Lys Lys Tyr Glu Phe Lys Arg Trp Thr
             275                 280                 285

Ala Asp Val Glu Ala Gly Lys Trp Leu Gln Ala Lys Gly Ala Lys Pro
 290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                 325                 330                 335

Glu Thr Leu Lys Ala Trp Ile Ala Lys Leu Glu Lys Ala Pro Val Phe
             340                 345                 350

Ala Phe Asp Thr Glu Thr Asp Ser Leu Asp Asn Ile Ser Ala Asn Leu
             355                 360                 365

Val Gly Leu Ser Phe Ala Ile Glu Pro Gly Val Ala Ala Tyr Ile Pro
 370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Glu Lys Ala Leu Lys
                 405                 410                 415

Val Gly Gln Asn Leu Lys Tyr Asp Arg Gly Ile Leu Ala Asn Tyr Gly
             420                 425                 430

Ile Glu Leu Arg Gly Ile Ala Phe Asp Thr Met Leu Glu Ser Tyr Ile
             435                 440                 445
```

-continued

```
Leu Asn Ser Val Ala Gly Arg His Asp Met Asp Ser Leu Ala Glu Arg
    450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
                485                 490                 495

Tyr Ala Ala Glu Asp Ala Asp Val Thr Leu Gln Leu His Leu Lys Met
                500                 505                 510

Trp Pro Asp Leu Gln Lys His Lys Gly Pro Leu Asn Val Phe Glu Asn
                515                 520                 525

Ile Glu Met Pro Leu Val Pro Val Leu Ser Arg Ile Glu Arg Asn Gly
530                 535                 540

Val Lys Ile Asp Pro Lys Val Leu His Asn His Ser Glu Glu Leu Thr
545                 550                 555                 560

Leu Arg Leu Ala Glu Leu Gly Lys Lys Ala His Glu Ile Ala Gly Glu
                565                 570                 575

Glu Phe Asn Leu Ser Ser Thr Lys Gln Leu Gln Thr Ile Leu Phe Glu
                580                 585                 590

Lys Gln Gly Ile Lys Pro Leu Lys Lys Thr Pro Gly Gly Ala Pro Ser
            595                 600                 605

Thr Ser Glu Glu Val Leu Glu Glu Leu Ala Leu Asp Tyr Pro Leu Pro
    610                 615                 620

Lys Val Ile Leu Glu Tyr Arg Gly Leu Ala Lys Leu Lys Ser Thr Tyr
625                 630                 635                 640

Thr Asp Lys Leu Pro Leu Met Ile Asn Pro Lys Thr Gly Arg Val His
                645                 650                 655

Thr Ser Tyr His Gln Ala Val Thr Ala Thr Gly Arg Leu Ser Ser Thr
                660                 665                 670

Asp Pro Asn Leu Gln Asn Ile Pro Val Arg Asn Glu Glu Gly Arg Arg
            675                 680                 685

Ile Arg Gln Ala Phe Ile Ala Pro Glu Asp Tyr Val Ile Val Ser Ala
    690                 695                 700

Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
                725                 730                 735

Thr Ala Ala Glu Val Phe Gly Leu Pro Leu Glu Thr Val Thr Ser Glu
                740                 745                 750

Gln Arg Arg Ser Ala Lys Ala Ile Asn Phe Gly Leu Ile Tyr Gly Met
            755                 760                 765

Ser Ala Phe Gly Leu Ala Arg Gln Leu Asn Ile Pro Arg Lys Glu Ala
    770                 775                 780

Gln Lys Tyr Met Asp Leu Tyr Phe Glu Arg Tyr Pro Gly Val Leu Glu
785                 790                 795                 800

Tyr Met Glu Arg Thr Arg Ala Gln Ala Lys Glu Gln Gly Tyr Val Glu
                805                 810                 815

Thr Leu Asp Gly Arg Arg Leu Tyr Leu Pro Asp Ile Lys Ser Ser Asn
                820                 825                 830

Gly Ala Arg Arg Ala Ala Ala Glu Arg Ala Ala Ile Asn Ala Pro Met
            835                 840                 845

Gln Gly Thr Ala Ala Asp Ile Ile Lys Arg Ala Met Ile Ala Val Asp
    850                 855                 860

Ala Trp Leu Gln Ala Glu Gln Pro Arg Val Arg Met Ile Met Gln Val
```

```
                865                 870                 875                 880
His Asp Glu Leu Val Phe Glu Val His Lys Asp Asp Val Asp Ala Val
                        885                 890                 895

Ala Lys Gln Ile His Gln Leu Met Glu Asn Cys Thr Arg Leu Asp Val
            900                 905                 910

Pro Leu Leu Val Glu Val Gly Ser Gly Glu Asn Trp Asp Gln Ala His
            915                 920                 925

<210> SEQ ID NO 55
<211> LENGTH: 783
<212> TYPE: PRT
<213> ORGANISM: Escherichia coli

<400> SEQUENCE: 55

Met Ala Gln Ala Gly Phe Ile Leu Thr Arg His Trp Arg Asp Thr Pro
1               5                   10                  15

Gln Gly Thr Glu Val Ser Phe Trp Leu Ala Thr Asp Asn Gly Pro Leu
            20                  25                  30

Gln Val Thr Leu Ala Pro Gln Glu Ser Val Ala Phe Ile Pro Ala Asp
        35                  40                  45

Gln Val Pro Arg Ala Gln His Ile Leu Gln Gly Glu Gln Gly Phe Arg
    50                  55                  60

Leu Thr Pro Leu Ala Leu Lys Asp Phe His Arg Gln Pro Val Tyr Gly
65                  70                  75                  80

Leu Tyr Cys Arg Ala His Arg Gln Leu Met Asn Tyr Glu Lys Arg Leu
                85                  90                  95

Arg Glu Gly Gly Val Thr Val Tyr Glu Ala Asp Val Arg Pro Pro Glu
            100                 105                 110

Arg Tyr Leu Met Glu Arg Phe Ile Thr Ser Pro Val Trp Val Glu Gly
        115                 120                 125

Asp Met His Asn Gly Thr Ile Val Asn Ala Arg Leu Lys Pro His Pro
    130                 135                 140

Asp Tyr Arg Pro Pro Leu Lys Trp Val Ser Ile Asp Ile Glu Thr Thr
145                 150                 155                 160

Arg His Gly Glu Leu Tyr Cys Ile Gly Leu Glu Gly Cys Gly Gln Arg
                165                 170                 175

Ile Val Tyr Met Leu Gly Pro Glu Asn Gly Asp Ala Ser Ser Leu Asp
            180                 185                 190

Phe Glu Leu Glu Tyr Val Ala Ser Arg Pro Gln Leu Leu Glu Lys Leu
        195                 200                 205

Asn Ala Trp Phe Ala Asn Tyr Asp Pro Asp Val Ile Ile Gly Trp Asn
    210                 215                 220

Val Val Gln Phe Asp Leu Arg Met Leu Gln Lys His Ala Glu Arg Tyr
225                 230                 235                 240

Arg Leu Pro Leu Arg Leu Gly Arg Asp Asn Ser Glu Leu Glu Trp Arg
                245                 250                 255

Glu His Gly Phe Lys Asn Gly Val Phe Phe Ala Gln Ala Lys Gly Arg
            260                 265                 270

Leu Ile Ile Asp Gly Ile Glu Ala Leu Lys Ser Ala Phe Trp Asn Phe
        275                 280                 285

Ser Ser Phe Ser Leu Glu Thr Val Ala Gln Glu Leu Leu Gly Glu Gly
    290                 295                 300

Lys Ser Ile Asp Asn Pro Trp Asp Arg Met Asp Glu Ile Asp Arg Arg
305                 310                 315                 320
```

```
Phe Ala Glu Asp Lys Pro Ala Leu Ala Thr Tyr Asn Leu Lys Asp Cys
                325                 330                 335

Glu Leu Val Thr Gln Ile Phe His Lys Thr Glu Ile Met Pro Phe Leu
        340                 345                 350

Leu Glu Arg Ala Thr Val Asn Gly Leu Pro Val Asp Arg His Gly Gly
            355                 360                 365

Ser Val Ala Ala Phe Gly His Leu Tyr Phe Pro Arg Met His Arg Ala
370                 375                 380

Gly Tyr Val Ala Pro Asn Leu Gly Glu Val Pro His Ala Ser Pro
385                 390                 395                 400

Gly Gly Tyr Val Met Asp Ser Arg Pro Gly Leu Tyr Asp Ser Val Leu
                405                 410                 415

Val Leu Asp Tyr Lys Ser Leu Tyr Pro Ser Ile Ile Arg Thr Phe Leu
            420                 425                 430

Ile Asp Pro Val Gly Leu Val Glu Gly Met Ala Gln Pro Asp Pro Glu
        435                 440                 445

His Ser Thr Glu Gly Phe Leu Asp Ala Trp Phe Ser Arg Glu Lys His
    450                 455                 460

Cys Leu Pro Glu Ile Val Thr Asn Ile Trp His Gly Arg Asp Glu Ala
465                 470                 475                 480

Lys Arg Gln Gly Asn Lys Pro Leu Ser Gln Ala Leu Lys Ile Ile Met
                485                 490                 495

Asn Ala Phe Tyr Gly Val Leu Gly Thr Thr Ala Cys Arg Phe Phe Asp
            500                 505                 510

Pro Arg Leu Ala Ser Ser Ile Thr Met Arg Gly His Gln Ile Met Arg
        515                 520                 525

Gln Thr Lys Ala Leu Ile Glu Ala Gln Gly Tyr Asp Val Ile Tyr Gly
    530                 535                 540

Asp Thr Asp Ser Thr Phe Val Trp Leu Lys Gly Ala His Ser Glu Glu
545                 550                 555                 560

Glu Ala Ala Lys Ile Gly Arg Ala Leu Val Gln His Val Asn Ala Trp
                565                 570                 575

Trp Ala Glu Thr Leu Gln Lys Gln Arg Leu Thr Ser Ala Leu Glu Leu
            580                 585                 590

Glu Tyr Glu Thr His Phe Cys Arg Phe Leu Met Pro Thr Ile Arg Gly
        595                 600                 605

Ala Asp Thr Gly Ser Lys Lys Arg Tyr Ala Gly Leu Ile Gln Glu Gly
    610                 615                 620

Asp Lys Gln Arg Met Val Phe Lys Gly Leu Glu Thr Val Arg Thr Asp
625                 630                 635                 640

Trp Thr Pro Leu Ala Gln Gln Phe Gln Gln Glu Leu Tyr Leu Arg Ile
                645                 650                 655

Phe Arg Asn Glu Pro Tyr Gln Glu Tyr Val Arg Glu Thr Ile Asp Lys
            660                 665                 670

Leu Met Ala Gly Glu Leu Asp Ala Arg Leu Val Tyr Arg Lys Arg Leu
        675                 680                 685

Arg Arg Pro Leu Ser Glu Tyr Gln Arg Asn Val Pro Pro His Val Arg
    690                 695                 700

Ala Ala Arg Leu Ala Asp Glu Glu Asn Gln Lys Arg Gly Arg Pro Leu
705                 710                 715                 720

Gln Tyr Gln Asn Arg Gly Thr Ile Lys Tyr Val Trp Thr Thr Asn Gly
                725                 730                 735

Pro Glu Pro Leu Asp Tyr Gln Arg Ser Pro Leu Asp Tyr Glu His Tyr
```

-continued

```
                740                 745                 750
Leu Thr Arg Gln Leu Gln Pro Val Ala Glu Gly Ile Leu Pro Phe Ile
                755                 760                 765
Glu Asp Asn Phe Ala Thr Leu Met Thr Gly Gln Leu Gly Leu Phe
            770                 775                 780

<210> SEQ ID NO 56
<211> LENGTH: 1160
<212> TYPE: PRT
<213> ORGANISM: Escherichia coli

<400> SEQUENCE: 56

Met Ser Glu Pro Arg Phe Val His Leu Arg Val His Ser Asp Tyr Ser
1               5                   10                  15
Met Ile Asp Gly Leu Ala Lys Thr Ala Pro Leu Val Lys Lys Ala Ala
                20                  25                  30
Ala Leu Gly Met Pro Ala Leu Ala Ile Thr Asp Phe Thr Asn Leu Cys
            35                  40                  45
Gly Leu Val Lys Phe Tyr Gly Ala Gly His Gly Ala Gly Ile Lys Pro
        50                  55                  60
Ile Val Gly Ala Asp Phe Asn Val Gln Cys Asp Leu Leu Gly Asp Glu
65                  70                  75                  80
Leu Thr His Leu Thr Val Leu Ala Ala Asn Asn Thr Gly Tyr Gln Asn
                85                  90                  95
Leu Thr Leu Leu Ile Ser Lys Ala Tyr Gln Arg Gly Tyr Gly Ala Ala
                100                 105                 110
Gly Pro Ile Ile Asp Arg Asp Trp Leu Ile Glu Leu Asn Glu Gly Leu
            115                 120                 125
Ile Leu Leu Ser Gly Gly Arg Met Gly Asp Val Gly Arg Ser Leu Leu
130                 135                 140
Arg Gly Asn Ser Ala Leu Val Asp Glu Cys Val Ala Phe Tyr Glu Glu
145                 150                 155                 160
His Phe Pro Asp Arg Tyr Phe Leu Glu Leu Ile Arg Thr Gly Arg Pro
                165                 170                 175
Asp Glu Glu Ser Tyr Leu His Ala Ala Val Glu Leu Ala Glu Ala Arg
            180                 185                 190
Gly Leu Pro Val Val Ala Thr Asn Asp Val Arg Phe Ile Asp Ser Ser
        195                 200                 205
Asp Phe Asp Ala His Glu Ile Arg Val Ala Ile His Asp Gly Phe Thr
210                 215                 220
Leu Asp Asp Pro Lys Arg Pro Arg Asn Tyr Ser Pro Gln Gln Tyr Met
225                 230                 235                 240
Arg Ser Glu Glu Glu Met Cys Glu Leu Phe Ala Asp Ile Pro Glu Ala
                245                 250                 255
Leu Ala Asn Thr Val Glu Ile Ala Lys Arg Cys Asn Val Thr Val Arg
            260                 265                 270
Leu Gly Glu Tyr Phe Leu Pro Gln Phe Pro Thr Gly Asp Met Ser Thr
        275                 280                 285
Glu Asp Tyr Leu Val Lys Arg Ala Lys Glu Gly Leu Glu Glu Arg Leu
    290                 295                 300
Ala Phe Leu Phe Pro Asp Glu Glu Arg Leu Lys Arg Arg Pro Glu
305                 310                 315                 320
Tyr Asp Glu Arg Leu Glu Thr Glu Leu Gln Val Ile Asn Gln Met Gly
                325                 330                 335
```

```
Phe Pro Gly Tyr Phe Leu Ile Val Met Glu Phe Ile Gln Trp Ser Lys
                340                 345                 350

Asp Asn Gly Val Pro Val Gly Pro Gly Arg Gly Ser Gly Ala Gly Ser
            355                 360                 365

Leu Val Ala Tyr Ala Leu Lys Ile Thr Asp Leu Asp Pro Leu Glu Phe
        370                 375                 380

Asp Leu Leu Phe Glu Arg Phe Leu Asn Pro Glu Arg Val Ser Met Pro
385                 390                 395                 400

Asp Phe Asp Val Asp Phe Cys Met Glu Lys Arg Asp Gln Val Ile Glu
                405                 410                 415

His Val Ala Asp Met Tyr Gly Arg Asp Ala Val Ser Gln Ile Ile Thr
            420                 425                 430

Phe Gly Thr Met Ala Ala Lys Ala Val Ile Arg Asp Val Gly Arg Val
        435                 440                 445

Leu Gly His Pro Tyr Gly Phe Val Asp Arg Ile Ser Lys Leu Ile Pro
    450                 455                 460

Pro Asp Pro Gly Met Thr Leu Ala Lys Ala Phe Glu Ala Glu Pro Gln
465                 470                 475                 480

Leu Pro Glu Ile Tyr Glu Ala Asp Glu Val Lys Ala Leu Ile Asp
                485                 490                 495

Met Ala Arg Lys Leu Glu Gly Val Thr Arg Asn Ala Gly Lys His Ala
            500                 505                 510

Gly Gly Val Val Ile Ala Pro Thr Lys Ile Thr Asp Phe Ala Pro Leu
        515                 520                 525

Tyr Cys Asp Glu Glu Gly Lys His Pro Val Thr Gln Phe Asp Lys Ser
    530                 535                 540

Asp Val Glu Tyr Ala Gly Leu Val Lys Phe Asp Phe Leu Gly Leu Arg
545                 550                 555                 560

Thr Leu Thr Ile Ile Asn Trp Ala Leu Glu Met Ile Asn Lys Arg Arg
                565                 570                 575

Ala Lys Asn Gly Glu Pro Pro Leu Asp Ile Ala Ala Ile Pro Leu Asp
            580                 585                 590

Asp Lys Lys Ser Phe Asp Met Leu Gln Arg Ser Glu Thr Thr Ala Val
        595                 600                 605

Phe Gln Leu Glu Ser Arg Gly Met Lys Asp Leu Ile Lys Arg Leu Gln
    610                 615                 620

Pro Asp Cys Phe Glu Asp Met Ile Ala Leu Val Ala Leu Phe Arg Pro
625                 630                 635                 640

Gly Pro Leu Gln Ser Gly Met Val Asp Asn Phe Ile Asp Arg Lys His
                645                 650                 655

Gly Arg Glu Glu Ile Ser Tyr Pro Asp Val Gln Trp Gln His Glu Ser
            660                 665                 670

Leu Lys Pro Val Leu Glu Pro Thr Tyr Gly Ile Ile Leu Tyr Gln Glu
        675                 680                 685

Gln Val Met Gln Ile Ala Gln Val Leu Ser Gly Tyr Thr Leu Gly Gly
    690                 695                 700

Ala Asp Met Leu Arg Arg Ala Met Gly Lys Lys Pro Glu Glu Met
705                 710                 715                 720

Ala Lys Gln Arg Ser Val Phe Ala Glu Gly Ala Glu Lys Asn Gly Ile
                725                 730                 735

Asn Ala Glu Leu Ala Met Lys Ile Phe Asp Leu Val Glu Lys Phe Ala
            740                 745                 750

Gly Tyr Gly Phe Asn Lys Ser His Ser Ala Ala Tyr Ala Leu Val Ser
```

-continued

```
            755                 760                 765
Tyr Gln Thr Leu Trp Leu Lys Ala His Tyr Pro Ala Glu Phe Met Ala
770                 775                 780

Ala Val Met Thr Ala Asp Met Asp Asn Thr Glu Lys Val Val Gly Leu
785                 790                 795                 800

Val Asp Glu Cys Trp Arg Met Gly Leu Lys Ile Leu Pro Pro Asp Ile
                805                 810                 815

Asn Ser Gly Leu Tyr His Phe His Val Asn Asp Asp Gly Glu Ile Val
                820                 825                 830

Tyr Gly Ile Gly Ala Ile Lys Gly Val Gly Glu Gly Pro Ile Glu Ala
                835                 840                 845

Ile Ile Glu Ala Arg Asn Lys Gly Gly Tyr Phe Arg Glu Leu Phe Asp
850                 855                 860

Leu Cys Ala Arg Thr Asp Thr Lys Lys Leu Asn Arg Arg Val Leu Glu
865                 870                 875                 880

Lys Leu Ile Met Ser Gly Ala Phe Asp Arg Leu Gly Pro His Arg Ala
                885                 890                 895

Ala Leu Met Asn Ser Leu Gly Asp Ala Leu Lys Ala Ala Asp Gln His
                900                 905                 910

Ala Lys Ala Glu Ala Ile Gly Gln Ala Asp Met Phe Gly Val Leu Ala
                915                 920                 925

Glu Glu Pro Glu Gln Ile Glu Gln Ser Tyr Ala Ser Cys Gln Pro Trp
930                 935                 940

Pro Glu Gln Val Val Leu Asp Gly Glu Arg Glu Thr Leu Gly Leu Tyr
945                 950                 955                 960

Leu Thr Gly His Pro Ile Asn Gln Tyr Leu Lys Glu Ile Glu Arg Tyr
                965                 970                 975

Val Gly Gly Val Arg Leu Lys Asp Met His Pro Thr Glu Arg Gly Lys
                980                 985                 990

Val Ile Thr Ala Ala Gly Leu Val  Val Ala Ala Arg Val  Met Val Thr
                995                 1000                1005

Lys Arg  Gly Asn Arg Ile Gly  Ile Cys Thr Leu Asp  Asp Arg Ser
1010                 1015                1020

Gly Arg  Leu Glu Val Met Leu  Phe Thr Asp Ala Leu  Asp Lys Tyr
1025                 1030                1035

Gln Gln  Leu Leu Glu Lys Asp  Arg Ile Leu Ile Val  Ser Gly Gln
1040                 1045                1050

Val Ser  Phe Asp Asp Phe Ser  Gly Gly Leu Lys Met  Thr Ala Arg
1055                 1060                1065

Glu Val  Met Asp Ile Asp Glu  Ala Arg Glu Lys Tyr  Ala Arg Gly
1070                 1075                1080

Leu Ala  Ile Ser Leu Thr Asp  Arg Gln Ile Asp Asp  Gln Leu Leu
1085                 1090                1095

Asn Arg  Leu Arg Gln Ser Leu  Glu Pro His Arg Ser  Gly Thr Ile
1100                 1105                1110

Pro Val  His Leu Tyr Tyr Gln  Arg Ala Asp Ala Arg  Ala Arg Leu
1115                 1120                1125

Arg Phe  Gly Ala Thr Trp Arg  Val Ser Pro Ser Asp  Arg Leu Leu
1130                 1135                1140

Asn Asp  Leu Arg Gly Leu Ile  Gly Ser Glu Gln Val  Glu Leu Glu
1145                 1150                1155

Phe Asp
1160
```

<210> SEQ ID NO 57
<211> LENGTH: 775
<212> TYPE: PRT
<213> ORGANISM: Thermococcus guaymasensis

<400> SEQUENCE: 57

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Arg Thr Ile Val Lys
50                  55                  60

Val Lys Arg Ala Glu Lys Val Gln Lys Lys Phe Leu Arg Arg Pro Ile
65                  70                  75                  80

Glu Val Trp Lys Leu Tyr Phe Asn His Pro Gln Asp Val Pro Ala Ile
                85                  90                  95

Arg Asp Lys Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Lys Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Thr Glu Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Glu Ser Tyr
```

```
                370             375             380
Ala Gly Gly Tyr Val Lys Glu Pro Glu Arg Gly Leu Trp Glu Asn Ile
385                 390                 395                 400
Val Tyr Leu Asp Phe Met Ser Leu Tyr Pro Ser Ile Ile Thr His
            405                 410                 415
Asn Val Ser Pro Asp Thr Leu Asn Arg Glu Gly Cys Arg Glu Tyr Asp
            420                 425                 430
Val Ala Pro Glu Val Gly His Lys Phe Cys Lys Asp Phe Pro Gly Phe
            435                 440                 445
Ile Pro Ser Leu Leu Gly Asp Leu Leu Glu Glu Arg Gln Lys Ile Lys
            450                 455                 460
Arg Lys Met Lys Ala Thr Ile Asp Pro Leu Glu Lys Lys Ile Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Lys Ala Arg Trp Tyr Cys Arg Glu Cys Ala Glu Ser
            500                 505                 510
Val Thr Ala Trp Gly Arg Glu Tyr Ile Glu Thr Thr Ile Arg Glu Ile
            515                 520                 525
Glu Glu Lys Phe Gly Phe Lys Val Leu Tyr Ala Asp Thr Asp Gly Phe
            530                 535                 540
Phe Ala Thr Ile Pro Gly Ala Asn Ala Glu Thr Val Lys Lys Lys Ala
545                 550                 555                 560
Arg Glu Phe Leu Lys Tyr Ile Asn Ala Lys Leu Pro Gly Leu Leu Glu
                565                 570                 575
Leu Glu Tyr Glu Gly Phe Tyr Leu Arg Gly Phe Phe Val Thr Lys Lys
            580                 585                 590
Lys Tyr Ala Leu Ile Asp Glu Glu Gly Lys Ile Thr Thr Arg Gly Leu
            595                 600                 605
Glu Ile Val Arg Arg Asp Trp Ser Glu Ile Ala Lys Glu Thr Gln Ala
            610                 615                 620
Arg Val Leu Glu Ala Ile Leu Lys His Gly Asp Ile Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
            660                 665                 670
Tyr Lys Ala Thr Gly Pro His Val Ala Val Ala Lys Arg Leu Ala Ala
            675                 680                 685
Arg Gly Val Lys Ile Arg Pro Gly Thr Val Ile Ser Tyr Ile Val Leu
            690                 695                 700
Arg Gly Ser Gly Arg Ile Gly Asp Arg Ala Ile Pro Ala Asp Glu Phe
705                 710                 715                 720
Asp Pro Thr Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Lys Gln Val Gly Leu Gly Ala Trp
            755                 760                 765
Leu Lys Val Lys Gly Arg Lys
770                 775

<210> SEQ ID NO 58
```

```
<211> LENGTH: 775
<212> TYPE: PRT
<213> ORGANISM: Pyrococcus furiosus

<400> SEQUENCE: 58

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
```

```
                385                 390                 395                 400
        Ile Val Tyr Leu Asp Phe Arg Ala Leu Tyr Pro Ser Ile Ile Ile Thr
                            405                 410                 415

His Asn Val Ser Pro Asp Thr Leu Asn Leu Glu Gly Cys Lys Asn Tyr
                            420                 425                 430

Asp Ile Ala Pro Gln Val Gly His Lys Phe Cys Lys Asp Ile Pro Gly
                            435                 440                 445

Phe Ile Pro Ser Leu Leu Gly His Leu Leu Glu Arg Gln Lys Ile
            450                 455                 460

Lys Thr Lys Met Lys Glu Thr Gln Asp Pro Ile Glu Lys Ile Leu Leu
        465                 470                 475                 480

Asp Tyr Arg Gln Lys Ala Ile Lys Leu Leu Ala Asn Ser Phe Tyr Gly
                            485                 490                 495

Tyr Tyr Gly Tyr Ala Lys Ala Arg Trp Tyr Cys Lys Glu Cys Ala Glu
                        500                 505                 510

Ser Val Thr Ala Trp Gly Arg Lys Tyr Ile Glu Leu Val Trp Lys Glu
                        515                 520                 525

Leu Glu Glu Lys Phe Gly Phe Lys Val Leu Tyr Ile Asp Thr Asp Gly
                    530                 535                 540

Leu Tyr Ala Thr Ile Pro Gly Gly Glu Ser Glu Glu Ile Lys Lys Lys
        545                 550                 555                 560

Ala Leu Glu Phe Val Lys Tyr Ile Asn Ser Lys Leu Pro Gly Leu Leu
                            565                 570                 575

Glu Leu Glu Tyr Glu Gly Phe Tyr Lys Arg Gly Phe Phe Val Thr Lys
                        580                 585                 590

Lys Arg Tyr Ala Val Ile Asp Glu Glu Gly Lys Val Ile Thr Arg Gly
                    595                 600                 605

Leu Glu Ile Val Arg Arg Asp Trp Ser Glu Ile Ala Lys Glu Thr Gln
                    610                 615                 620

Ala Arg Val Leu Glu Thr Ile Leu Lys His Gly Asp Val Glu Glu Ala
        625                 630                 635                 640

Val Arg Ile Val Lys Glu Val Ile Gln Lys Leu Ala Asn Tyr Glu Ile
                            645                 650                 655

Pro Pro Glu Lys Leu Ala Ile Tyr Glu Gln Ile Thr Arg Pro Leu His
                        660                 665                 670

Glu Tyr Lys Ala Ile Gly Pro His Val Ala Val Ala Lys Lys Leu Ala
                        675                 680                 685

Ala Lys Gly Val Lys Ile Lys Pro Gly Met Val Ile Gly Tyr Ile Val
                    690                 695                 700

Leu Arg Gly Asp Gly Pro Ile Ser Asn Arg Ala Ile Leu Ala Glu Glu
        705                 710                 715                 720

Tyr Asp Pro Lys Lys His Lys Tyr Asp Ala Glu Tyr Tyr Ile Glu Asn
                            725                 730                 735

Gln Val Leu Pro Ala Val Leu Arg Ile Leu Glu Gly Phe Gly Tyr Arg
                        740                 745                 750

Lys Glu Asp Leu Arg Tyr Gln Lys Thr Arg Gln Val Gly Leu Thr Ser
                    755                 760                 765

Trp Leu Asn Ile Lys Lys Ser
            770                 775

<210> SEQ ID NO 59
<211> LENGTH: 4101
<212> TYPE: DNA
<213> ORGANISM: Artificial
```

```
<220> FEATURE:
<223> OTHER INFORMATION: Cas9

<400> SEQUENCE: 59
gacaagaagt acagcatcgg cctggacatc ggcaccaact ctgtgggctg ggccgtgatc    60
accgacgagt acaaggtgcc cagcaagaaa ttcaaggtgc tgggcaacac cgaccggcac   120
agcatcaaga agaacctgat cggagccctg ctgttcgaca cggcgaaac agccgaggcc    180 acccggctga agagaaccgc cagaagaaga tacaccagac ggaagaaccg gatctgctat   240
ctgcaagaga tcttcagcaa cgagatggcc aaggtggacg acagcttctt ccacagactg   300
gaagagtcct tcctggtgga agaggataag aagcacgagc ggcaccccat cttcggcaac   360
atcgtggacg aggtggccta ccacgagaag taccccacca tctaccacct gagaaagaaa   420 ctggtgtgaca gcaccgacaa ggccgacctg cggctgatct atctggccct ggcccacatg   480
atcaagttcc ggggccactt cctgatcgag ggcgacctga ccccgacaa cagcgacgtg    540 gacaagctgt tcatccagct ggtgcagacc tacaaccagc tgttcgagga aaacccatc    600 aacgccagcg gcgtggacgc caaggccatc ctgtctgcca gactgagcaa gagcagacgg   660
ctggaaaatc tgatcgccca gctgcccggc gagaagaaga tggcctgtt cggaaacctg    720 attgccctga gcctgggcct gacccccaac ttcaagagca cttcgacct ggccgaggat    780 gccaaactgc agctgagcaa ggacacctac gacgacgacc tggacaacct gctggcccag   840
atcggcgacc agtacgccga cctgtttctg gccgccaaga acctgtccga cgccatcctg   900
ctgagcgaca tcctgagagt gaacaccgag atcaccaagg ccccctgag cgcctctatg    960 atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga tttttaccca ttcctgaagg acaaccggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct cgactccgt ggaaatctcc    1740 ggcgtggaag atcggttcaa cgcctccctg ggcacatacc acgatctgct gaaaattatc   1800
aaggacaagg acttcctgga caatgaggaa acgaggaca ttctggaaga tatcgtgctg    1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100
ctgaccttta aagaggacat ccagaaagcc caggtgtccg gccagggcga tagcctgcac   2160
gagcacattg ccaatctggc cggcagcccc gccattaaga agggcatcct gcagacagtg   2220
```

| | |
|---|---|
| aaggtggtgg acgagctcgt gaaagtgatg ggccggcaca agcccgagaa catcgtgatc | 2280 |
| gaaatggcca gagagaacca gaccacccag aagggacaga agaacagccg cgagagaatg | 2340 |
| aagcggatcg aagagggcat caaagagctg ggcagccaga tcctgaaaga caccccgtg | 2400 |
| gaaaacaccc agctgcagaa cgagaagctg tacctgtact acctgcagaa tgggcgggat | 2460 |
| atgtacgtgg accaggaact ggacatcaac cggctgtccg actacgatgt ggaccatatc | 2520 |
| gtgcctcaga gctttctgaa ggacgactcc atcgacaaca aggtgctgac cagaagcgac | 2580 |
| aagaaccggg gcaagagcga caacgtgccc tccgaagagg tcgtgaagaa gatgaagaac | 2640 |
| tactggcggc agctgctgaa cgccaagctg attacccaga gaaagttcga caatctgacc | 2700 |
| aaggccgaga gaggcggcct gagcgaactg gataaggccg gcttcatcaa gagacagctg | 2760 |
| gtggaaaccc ggcagatcac aaagcacgtg gcacagatcc tggactcccg gatgaacact | 2820 |
| aagtacgacg agaatgacaa gctgatccgg gaagtgaaag tgatcaccct gaagtccaag | 2880 |
| ctggtgtccg atttccggaa ggatttccag ttttacaaag tgcgcgagat caacaactac | 2940 |
| caccacgccc acgacgccta cctgaacgcc gtcgtgggaa ccgccctgat caaaaagtac | 3000 |
| cctaagctgg aaagcgagtt cgtgtacggc gactacaagg tgtacgacgt gcggaagatg | 3060 |
| atcgccaaga gcgagcagga aatcggcaag gctaccgcca gtacttctt ctacagcaac | 3120 |
| atcatgaact ttttcaagac cgagattacc ctggccaacg gcgagatccg gaagcggcct | 3180 |
| ctgatcgaga caaacggcga aaccggggag atcgtgtggg ataagggccg ggattttgcc | 3240 |
| accgtgcgga aagtgctgag catgccccaa gtgaatatcg tgaaaaagac cgaggtgcag | 3300 |
| acaggcggct tcagcaaaga gtctatcctg cccaagagga cagcgataaa gctgatcgcc | 3360 |
| agaaagaagg actgggaccc taagaagtac ggcggcttcg acagccccac cgtggcctat | 3420 |
| tctgtgctgg tggtggccaa agtggaaaag ggcaagtcca agaaactgaa gagtgtgaaa | 3480 |
| gagctgctgg ggatcaccat catggaaaga agcagcttcg agaagaatcc catcgacttt | 3540 |
| ctggaagcca agggctacaa agaagtgaaa aaggacctga tcatcaagct gcctaagtac | 3600 |
| tccctgttcg agctggaaaa cggccggaag agaatgctgg cctctgccgg cgaactgcag | 3660 |
| aagggaaacg aactggccct gccctccaaa tatgtgaact tcctgtacct ggccagccac | 3720 |
| tatgagaagc tgaagggctc ccccgaggat aatgagcaga acagctgtt tgtggaacag | 3780 |
| cacaagcact acctggacga gatcatcgag cagatcagcg agttctccaa gagagtgatc | 3840 |
| ctggccgacg ctaatctgga caaagtgctg tccgcctaca acaagcaccg ggataagccc | 3900 |
| atcagagagc aggccgagaa tatcatccac ctgtttaccc tgaccaatct gggagcccct | 3960 |
| gccgccttca gtactttga caccaccatc gaccggaaga ggtacaccag caccaaagag | 4020 |
| gtgctggacg ccaccctgat ccaccagagc atcaccggcc tgtacgagac acggatcgac | 4080 |
| ctgtctcagc tgggaggtga c | 4101 |

<210> SEQ ID NO 60
<211> LENGTH: 4101
<212> TYPE: DNA
<213> ORGANISM: Artificial
<220> FEATURE:
<223> OTHER INFORMATION: nCas9

<400> SEQUENCE: 60

| | |
|---|---|
| gacaagaagt acagcatcgg cctggacatc ggcaccaact ctgtgggctg ggccgtgatc | 60 |
| accgacgagt acaaggtgcc cagcaagaaa ttcaaggtgc tgggcaacac cgaccggcac | 120 |
| agcatcaaga gaacctgat cggagccctg ctgttcgaca cggcgaaac agccgaggcc | 180 |

```
acccggctga agagaaccgc cagaagaaga tacaccagac ggaagaaccg gatctgctat      240
ctgcaagaga tcttcagcaa cgagatggcc aaggtggacg acagcttctt ccacagactg      300
gaagagtcct tcctggtgga agaggataag aagcacgagc ggcaccccat cttcggcaac      360
atcgtggacg aggtggccta ccacgagaag tacccacca tctaccacct gagaaagaaa       420
ctggtggaca gcaccgacaa ggccgacctg cggctgatct atctggccct ggcccacatg      480
atcaagttcc ggggccactt cctgatcgag ggcgacctga ccccgacaa cagcgacgtg       540 gacaagctgt tcatccagct ggtgcagacc tacaaccagc tgttcgagga aaaccccatc      600
aacgccagcg gcgtggacgc caaggccatc ctgtctgcca gactgagcaa gagcagacgg      660
ctggaaaatc tgatcgccca gctgcccggc gagaagaaga atggcctgtt cggaaacctg      720
attgccctga gctgggcct gaccccaac ttcaagagca cttcgacct ggccgaggat         780 gccaaactgc agctgagcaa ggacacctac gacgacgacc tggacaacct gctggcccag      840
atcggcgacc agtacgccga cctgtttctg gccgccaaga acctgtccga cgccatcctg      900
ctgagcgaca tcctgagagt gaacaccgag atcaccaagg ccccctgag cgcctctatg       960 atcaagagat acgacgagca ccaccaggac ctgaccctgc tgaaagctct cgtgcggcag     1020
cagctgcctg agaagtacaa agagatttc ttcgaccaga gcaagaacgg ctacgccggc      1080
tacattgacg gcgagccag ccaggaagag ttctacaagt tcatcaagcc catcctggaa      1140
aagatggacg gcaccgagga actgctcgtg aagctgaaca gagaggacct gctgcggaag    1200
cagcggacct tcgacaacgg cagcatcccc caccagatcc acctgggaga gctgcacgcc    1260
attctgcggc ggcaggaaga tttttaccca ttcctgaagg acaaccggga aaagatcgag    1320
aagatcctga cctccgcat cccctactac gtgggccctc tggccagggg aaacagcaga      1380
ttcgcctgga tgaccagaaa gagcgaggaa accatcaccc cctggaactt cgaggaagtg    1440
gtggacaagg gcgcttccgc ccagagcttc atcgagcgga tgaccaactt cgataagaac    1500
ctgcccaacg agaaggtgct gcccaagcac agcctgctgt acgagtactt caccgtgtat    1560
aacgagctga ccaaagtgaa atacgtgacc gagggaatga gaaagcccgc cttcctgagc    1620
ggcgagcaga aaaaggccat cgtggacctg ctgttcaaga ccaaccggaa agtgaccgtg    1680
aagcagctga aagaggacta cttcaagaaa atcgagtgct tcgactccgt ggaaatctcc    1740
ggcgtggaag atcggttcaa cgcctccctg ggcacatacc acgatctgct gaaaattatc    1800
aaggacaagg acttcctgga caatgaggaa aacgaggaca ttctggaaga tatcgtgctg    1860
accctgacac tgtttgagga cagagagatg atcgaggaac ggctgaaaac ctatgcccac    1920
ctgttcgacg acaaagtgat gaagcagctg aagcggcgga gatacaccgg ctggggcagg    1980
ctgagccgga agctgatcaa cggcatccgg gacaagcagt ccggcaagac aatcctggat    2040
ttcctgaagt ccgacggctt cgccaacaga aacttcatgc agctgatcca cgacgacagc    2100 ctgacctta aagaggacat ccagaaagcc caggtgtccg gccagggcga tagcctgcac    2160
gagcacattg ccaatctggc cggcagcccc gccattaaga agggcatcct gcagacagtg    2220
aaggtggtgg acgagctcgt gaaagtgatg ggccggcaca gcccgagaa catcgtgatc    2280 gaaatggcca gagagaacca gaccaccag aagggacaga gaacagccg cgagagaatg    2340 aagcggatcg aagagggcat caaagagctg ggcagccaga tcctgaaaga caccccgtg    2400 gaaaacaccc agctgcagaa cgagaagctg tacctgtact acctgcagaa tgggcggat    2460 atgtacgtgg accaggaact ggacatcaac cggctgtccg actacgatgt ggaccatatc    2520
```

-continued

```
gtgcctcaga gctttctggc cgacgactcc atcgacaaca aggtgctgac cagaagcgac    2580
aagaaccggg gcaagagcga caacgtgccc tccgaagagg tcgtgaagaa gatgaagaac    2640
tactggcggc agctgctgaa cgccaagctg attacccaga gaaagttcga caatctgacc    2700
aaggccgaga gaggcggcct gagcgaactg gataaggccg gcttcatcaa gagacagctg    2760
gtggaaaccc ggcagatcac aaagcacgtg gcacagatcc tggactcccg gatgaacact    2820
aagtacgacg agaatgacaa gctgatccgg gaagtgaaag tgatcaccct gaagtccaag    2880
ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctgccctgg aaagcgagtt cgtgtacggc gactacaagg tgtacgacgt gcggaagatg    3060
atcgccaaga gcgagcagga aatcggcaag gctaccgcca gtacttctt ctacagcaac     3120
atcatgaact tttcaagac cgagattacc ctggccaacg gcgagatccg gaaggcccct    3180
ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagaa acagcgataa gctgatcgcc    3360
agaaagaagg actgggaccc taagaagtac ggcggcttcg acagcccac cgtggcctat    3420
tctgtgctgg tggtggccaa agtggaaaag ggcaagtcca agaaactgaa gagtgtgaaa    3480
gagctgctgg gatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtggaacag    3780
cacaagcact acctggacga gatcatcgag cagatcagcg agttctccaa gagagtgatc    3840
ctggccgacg ctaatctgga caaagtgctg tccgcctaca acaagcaccg ggataagccc    3900
atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccacccctgat ccaccagagc atcaccggcc tgtacgagac acggatcgac    4080
ctgtctcagc tgggaggtga c                                             4101
```

<210> SEQ ID NO 61
<211> LENGTH: 4101
<212> TYPE: DNA
<213> ORGANISM: Artificial
<220> FEATURE:
<223> OTHER INFORMATION: nCas9(D10A)

<400> SEQUENCE: 61

```
gacaagaagt acagcatcgg cctggccatc ggcaccaact ctgtgggctg ggccgtgatc      60
accgacgagt acaaggtgcc cagcaagaaa ttcaaggtgc tgggcaacac cgaccggcac     120
agcatcaaga gaacctgat cggagccctg ctgttcgaca cggcgaaac agccgaggcc      180
acccggctga agaaccgcc agaagaaga tacaccagac ggaagaaccg gatctgctat      240
ctgcaagaga tcttcagcaa cgagatggcc aaggtggacg acagcttctt ccacagactg    300
gaagagtcct tcctggtgga agaggataag aagcacgagc ggcaccccat cttcggcaac    360
atcgtggacg aggtggccta ccacgagaag taccccacca tctaccacct gagaaagaaa    420
ctggtggaca gcaccgacaa ggccgacctg cggctgatct atctggccct ggcccacatg    480
```

| | | |
|---|---|---|
| atcaagttcc ggggccactt cctgatcgag ggcgacctga accccgacaa cagcgacgtg | 540 | |
| gacaagctgt tcatccagct ggtgcagacc tacaaccagc tgttcgagga aaacccatc | 600 | |
| aacgccagcg gcgtggacgc caaggccatc ctgtctgcca gactgagcaa gagcagacgg | 660 | |
| ctggaaaatc tgatcgccca gctgcccggc gagaagaaga atggcctgtt cggaaacctg | 720 | |
| attgccctga gcctgggcct gacccccaac ttcaagagca acttcgacct ggccgaggat | 780 | |
| gccaaactgc agctgagcaa ggacacctac gacgacgacc tggacaacct gctggcccag | 840 | |
| atcggcgacc agtacgccga cctgtttctg gccgccaaga acctgtccga cgccatcctg | 900 | |
| ctgagcgaca tcctgagagt gaacaccgag atcaccaagg ccccctgag cgcctctatg | 960 | |
| atcaagagat acgacgagca ccaccaggac ctgaccctgc tgaaagctct cgtgcggcag | 1020 | |
| cagctgcctg agaagtacaa agagattttc ttcgaccaga gcaagaacgg ctacgccggc | 1080 | |
| tacattgacg gcggagccag ccaggaagag ttctacaagt tcatcaagcc catcctggaa | 1140 | |
| aagatggacg gcaccgagga actgctcgtg aagctgaaca gagaggacct gctgcggaag | 1200 | |
| cagcggacct tcgacaacgg cagcatcccc caccagatcc acctgggaga gctgcacgcc | 1260 | |
| attctgcggc ggcaggaaga ttttacccca ttcctgaagg acaaccggga aaagatcgag | 1320 | |
| aagatcctga ccttccgcat cccctactac gtgggccctc tggccagggg aaacagcaga | 1380 | |
| ttcgcctgga tgaccagaaa gagcgaggaa accatcaccc cctggaactt cgaggaagtg | 1440 | |
| gtggacaagg gcgcttccgc ccagagcttc atcgagcgga tgaccaactt cgataagaac | 1500 | |
| ctgcccaacg agaaggtgct gcccaagcac agcctgctgt acgagtactt caccgtgtat | 1560 | |
| aacgagctga ccaaagtgaa atacgtgacc gagggaatga gaaagcccgc cttcctgagc | 1620 | |
| ggcgagcaga aaaaggccat cgtggacctg ctgttcaaga ccaaccggaa agtgaccgtg | 1680 | |
| aagcagctga aagaggacta cttcaagaaa atcgagtgct tcgactccgt ggaaatctcc | 1740 | |
| ggcgtggaag atcggttcaa cgcctccctg ggcacatacc acgatctgct gaaaattatc | 1800 | |
| aaggacaagg acttcctgga caatgaggaa aacgaggaca ttctggaaga tatcgtgctg | 1860 | |
| accctgacac tgtttgagga cagagagatg atcgaggaac ggctgaaaac ctatgcccac | 1920 | |
| ctgttcgacg acaaagtgat gaagcagctg aagcggcgga gatacaccgg ctggggcagg | 1980 | |
| ctgagccgga agctgatcaa cggcatccgg gacaagcagt ccggcaagac aatcctggat | 2040 | |
| ttcctgaagt ccgacggctt cgccaacaga aacttcatgc agctgatcca cgacgacagc | 2100 | |
| ctgaccttta agaggacat ccagaaagcc caggtgtccg ccagggcga tagcctgcac | 2160 | |
| gagcacattg ccaatctggc cggcagcccc gccattaaga agggcatcct gcagacagtg | 2220 | |
| aaggtggtgg acgagctcgt gaaagtgatg ggccggcaca gcccgagaa catcgtgatc | 2280 | |
| gaaatggcca gagagaacca gaccacccag aagggacaga gaacagccg cgagagaatg | 2340 | |
| aagcggatcg aagagggcat caaagagctg ggcagccaga tcctgaaaga cacccccgtg | 2400 | |
| gaaaacaccc agctgcagaa cgagaagctg tacctgtact acctgcagaa tgggcgggat | 2460 | |
| atgtacgtgg accaggaact ggacatcaac cggctgtccg actacgatgt ggaccatatc | 2520 | |
| gtgcctcaga gctttctgaa ggacgactcc atcgacaaca aggtgctgac cagaagcgac | 2580 | |
| aagaaccggg gcaagagcga caacgtgccc tccgaagagg tcgtgaagaa gatgaagaac | 2640 | |
| tactggcggc agctgctgaa cgccaagctg attacccaga gaaagttcga caatctgacc | 2700 | |
| aaggccgaga gaggcggcct gagcgaactg gataaggccg gcttcatcaa gagacagctg | 2760 | |
| gtggaaaccc ggcagatcac aaagcacgtg gcacagatcc tggactcccg gatgaacact | 2820 | |

```
aagtacgacg agaatgacaa gctgatccgg gaagtgaaag tgatcaccct gaagtccaag    2880
ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga aatcggcaag gctaccgcca agtacttctt ctacagcaac    3120
atcatgaact ttttcaagac cgagattacc ctggccaacg cgagatccg gaagcggcct    3180 ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagga cagcgataa gctgatcgcc    3360 agaaagaagg actgggaccc taagaagtac ggcggcttcg acagcccac cgtggcctat    3420 tctgtgctgg tggtggccaa agtggaaaag ggcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc cccccgaggat aatgagcaga acagctgtt tgtggaacag    3780 cacaagcact acctggacga gatcatcgag cagatcagcg agttctccaa gagagtgatc    3840
ctggccgacg ctaatctgga caaagtgctg tccgcctaca acaagcaccg ggataagccc    3900
atcagagagc aggccgagaa tatcatccac ctgtttaccc tgaccaatct gggagccct    3960 gccgccttca gtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggtga c                                              4101
```

<210> SEQ ID NO 62
<211> LENGTH: 4101
<212> TYPE: DNA
<213> ORGANISM: Artificial
<220> FEATURE:
<223> OTHER INFORMATION: nCas9(H840A)

<400> SEQUENCE: 62

```
gacaagaagt acagcatcgg cctggacatc ggcaccaact ctgtgggctg ggccgtgatc      60
accgacgagt acaaggtgcc cagcaagaaa ttcaaggtgc tgggcaacac cgaccggcac     120
agcatcaaga gaacctgat cggagccctg ctgttcgaca cggcgaaac agccgaggcc      180 acccggctga agaaccgc cagaagaaga tacaccagac ggaagaaccg gatctgctat      240
ctgcaagaga tcttcagcaa cgagatggcc aaggtggacg acagcttctt ccacagactg     300
gaagagtcct tcctggtgga agaggataag aagcacgagc ggcacccat cttcggcaac      360 atcgtggacg aggtggccta ccacgagaag taccccacca tctaccacct gagaaagaaa     420
ctggtggaca gcaccgacaa ggccgacctg cggctgatct atctggccct ggcccacatg     480
atcaagttcc ggggccactt cctgatcgag ggcgacctga accccgacaa cagcgacgtg     540
gacaagctgt tcatccagct ggtgcagacc tacaaccagc tgttcgagga aaaccccatc     600
aacgccagcg gcgtggacgc caaggccatc ctgtctgcca gactgagcaa gagcagacgg     660
ctggaaaatc tgatcgccca gctgccccgc gagaagaaga tggcctgtt cggaaacctg     720 attgccctga gctgggcct gaccccaac ttcaagagca acttcgacct ggccgaggat     780
```

```
gccaaactgc agctgagcaa ggacacctac gacgacgacc tggacaacct gctggcccag      840
atcggcgacc agtacgccga cctgtttctg gccgccaaga acctgtccga cgccatcctg      900
ctgagcgaca tcctgagagt gaacaccgag atcaccaagg ccccctgag cgcctctatg       960 atcaagagat acgacgagca ccaccaggac ctgaccctgc tgaaagctct cgtgcggcag     1020
cagctgcctg agaagtacaa agagattttc ttcgaccaga gcaagaacgg ctacgccggc     1080
tacattgacg gcggagccag ccaggaagag ttctacaagt tcatcaagcc catcctggaa     1140
aagatggacg gcaccgagga actgctcgtg aagctgaaca gagaggacct gctgcggaag     1200
cagcggacct tcgacaacgg cagcatcccc caccagatcc acctgggaga gctgcacgcc     1260
attctgcggc ggcaggaaga ttttacccca ttcctgaagg acaaccggga aaagatcgag     1320
aagatcctga ccttccgcat cccctactac gtgggccctc tggccagggg aaacagcaga     1380
ttcgcctgga tgaccagaaa gagcgaggaa accatcaccc cctggaactt cgaggaagtg     1440
gtggacaagg gcgcttccgc ccagagcttc atcgagcgga tgaccaactt cgataagaac     1500
ctgcccaacg agaaggtgct gcccaagcac agcctgctgt acgagtactt caccgtgtat     1560
aacgagctga ccaaagtgaa atacgtgacc gagggaatga gaaagcccgc cttcctgagc     1620
ggcgagcaga aaaaggccat cgtggacctg ctgttcaaga ccaaccggaa agtgaccgtg     1680
aagcagctga aagaggacta cttcaagaaa atcgagtgct tcgactccgt ggaaatctcc     1740
ggcgtggaag atcggttcaa cgcctccctg ggcacatacc acgatctgct gaaaattatc     1800
aaggacaagg acttcctgga caatgaggaa aacgaggaca ttctggaaga tatcgtgctg     1860
accctgacac tgtttgagga cagagagatg atcgaggaac ggctgaaaac ctatgcccac     1920
ctgttcgacg acaaagtgat gaagcagctg aagcggcgga gatacaccgg ctggggcagg     1980
ctgagccgga agctgatcaa cggcatccgg gacaagcagt ccggcaagac aatcctggat     2040
ttcctgaagt ccgacggctt cgccaacaga aacttcatgc agctgatcca cgacgacagc     2100 ctgacctttta aagaggacat ccagaaagcc caggtgtccg gccagggcga tagcctgcac     2160
gagcacattg ccaatctggc cggcagcccc gccattaaga agggcatcct gcagacagtg     2220
aaggtggtgg acgagctcgt gaaagtgatg ggccggcaca gcccgagaa catcgtgatc     2280 gaaatggcca gagagaacca gaccacccag aagggacaga agaacagccg cgagagaatg     2340
aagcggatcg aagagggcat caaagagctg ggcagccaga tcctgaagga acaccccgtg     2400
gaaaacaccc agctgcagaa cgagaagctg tacctgtact acctgcagaa tgggcgggat     2460
atgtacgtgg accaggaact ggacatcaac cggctgtccg actacgatgt ggacgccatc     2520
gtgcctcaga gctttctgaa ggacgactcc atcgacaaca aggtgctgac cagaagcgac     2580
aagaaccggg gcaagagcga caacgtgccc tccgaagagg tcgtgaagaa gatgaagaac     2640
tactggcggc agctgctgaa cgccaagctg attacccaga gaaagttcga caatctgacc     2700
aaggccgaga gaggcggcct gagcgaactg gataaggccg gcttcatcaa gagacagctg     2760
gtggaaaccc ggcagatcac aaagcacgtg gcacagatcc tggactcccg gatgaacact     2820
aagtacgacg agaatgacaa gctgatccgg gaagtgaaag tgatcaccct gaagtccaag     2880
ctggtgtccg atttccggaa ggatttccag ttttacaaag tgcgcgagat caacaactac     2940
caccacgccc acgacgccta cctgaacgcc gtcgtgggaa ccgccctgat caaaaagtac     3000
cctaagctgg aaagcgagtt cgtgtacggc gactacaagg tgtacgacgt gcggaagatg     3060
atcgccaaga gcgagcagga aatcggcaag gctaccgcca agtacttctt ctacagcaac     3120
```

```
atcatgaact tttcaagac cgagattacc ctggccaacg gcgagatccg gaagcggcct    3180
ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagga acagcgataa gctgatcgcc    3360
agaaagaagg actgggaccc taagaagtac ggcggcttcg acagcccac cgtggcctat    3420 tctgtgctgg tggtggccaa agtggaaaag ggcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gcccctccaaa tatgtgaact tcctgtacct ggccagccac    3720
tatgagaagc tgaagggctc ccccgaggat aatgagcaga acagctgtt tgtggaacag    3780 cacaagcact acctggacga gatcatcgag cagatcagcg agttctccaa gagagtgatc    3840
ctggccgacg ctaatctgga caaagtgctg tccgcctaca caagcaccg gataagccc    3900 atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggtga c                                              4101

<210> SEQ ID NO 63
<211> LENGTH: 1761
<212> TYPE: DNA
<213> ORGANISM: Escherichia coli

<400> SEQUENCE: 63
atgacaaaaa catctaaact tgacgcactt agggctgcta cttcacgtga agacttggct      60
aaaattttag atattaagtt ggtatttta actaacgttc tatatagaat cggctcggat     120
aatcaataca ctcaatttac aataccgaag aaaggaaaag gggtaaggac tatttctgca     180
cctacagacc ggttgaagga catccaacga agaatatgtg acttactttc tgattgtaga     240
gatgagatct ttgctataag gaaaattagt aacaactatt cctttggttt tgagagggga     300
aaatcaataa tcctaaatgc ttataagcat agaggcaaac aaataatatt aaatatagat     360
cttaaggatt tttttgaaag ctttaattt ggacgagtta gaggatattt tctttccaat     420
caggattttt tattaaatcc tgtggtggca acgacacttg caaaagctgc atgctataat     480
ggaaccctcc cccaaggaag tccatgttct cctattatct caaatctaat ttgcaatatt     540
atggatatga gattagctaa gctggctaaa aatatggat gtacttatag cagatatgct     600
gatgatataa caatttctac aaataaaaat acatttccgt tagaaatggc tactgtgcaa     660
cctgaagggg ttgttttggg aaaagttttg gtaaaagaaa tagaaaactc tggattcgaa     720
ataaatgatt caaagactag gcttacgtat aagacatcaa ggcaagaagt aacgggactt     780
acagttaaca gaatcgttaa tattgataga tgttattata aaaaaactcg ggcgttggca     840
catgctttgt atcgtacagg tgaatataaa gtgccagatg aaaatggtgt tttagtttca     900
ggaggtctgg ataaacttga ggggatgttt ggttttattg atcaagttga taagttaaac     960
aatataaaga aaaactgaa caagcaacct gatagatatg tattgactaa tgcgactttg    1020
catggtttta aattaaagtt gaatgcgcga gaaaaagcat atagtaaatt tatttactat    1080 aaatttttc atggcaacac ctgtcctacg ataattacag aagggaagac tgatcggata    1140
```

```
tatttgaagg ctgctttgca ttctttggag acatcatatc ctgagttgtt tagagaaaaa    1200
acagatagta aaagaaaga aataaatctt aatatattta aatctaatga aaagaccaaa     1260 tatttttag atctttctgg gggaactgca gatctgaaaa aatttgtaga gcgttataaa     1320
aataattatg cttcttatta tggttctgtt ccaaaacagc cagtgattat ggttcttgat    1380
aatgatacag gtccaagcga tttacttaat tttctgcgca ataaagttaa aagctgccca    1440
gacgatgtaa ctgaaatgag aaagatgaaa tatattcatg ttttctataa tttatatata   1500
gttctcacac cattgagtcc ttccggcgaa caaacttcaa tggaggatct tttccctaaa    1560
gatattttag atatcaagat tgatggtaag aaattcaaca aaaataatga tggagactca    1620
aaaacggaat atgggaagca tattttttcc atgagggttg ttagagataa aaagcggaaa   1680
atagatttta aggcattttg ttgtattttt gatgctataa agatataaa ggaacattat    1740 aaattaatgt taaatagcta a                                              1761

<210> SEQ ID NO 64
<211> LENGTH: 132
<212> TYPE: DNA
<213> ORGANISM: Escherichia coli

<400> SEQUENCE: 64
cacgcatgta ggcagatttg ttggttgtga atcgcaacca gtggccttaa tggcaggagg    60
aatcgcctcc ctaaaatcct tgattcagag ctatacggca ggtgtgctgt gcgaaggagt   120
gcctgcatgc gt                                                       132

<210> SEQ ID NO 65
<211> LENGTH: 99
<212> TYPE: DNA
<213> ORGANISM: Escherichia coli

<400> SEQUENCE: 65
atgaaatcgc atgatcgatt gaggatcgtc tttgctcaga tccgccagaa ctggcggctt    60
ttgctcatgt tatgcatgtg catgaaaacc actgcataa                           99

<210> SEQ ID NO 66
<211> LENGTH: 170
<212> TYPE: DNA
<213> ORGANISM: Escherichia coli

<400> SEQUENCE: 66
atgcgcaccc ttagcgagag gtttatcatt aaggtcaacc tctggatgtt gtttcggcat    60
cctgcattga atctgagtta ctgtctgttt tccttgttgg aacggagagc atcgcctgat   120
gctctccgag ccaaccagga aacccgtttt ttctgacgta agggtgcgca               170

<210> SEQ ID NO 67
<211> LENGTH: 960
<212> TYPE: DNA
<213> ORGANISM: Escherichia coli

<400> SEQUENCE: 67
atggatgcta cccggacaac ccttctggcg ctcgatttgt tcggctcgcc gggctggagc    60
gccgataaag aaatacagcg actgcatgcg ctcagtaatc atgccggacg ccattaccga   120
cgcattattc tttctaaacg ccacggtggt cagcggctgg tgttagcccc tgattacttg   180
ctcaaaaccg tacagcgcaa cattcttaag aacgtccttt cacaatttcc gctttcccct   240
```

| | |
|---|---:|
| tttgctacag cctaccgacc aggttgccca atcgtcagca acgcgcagcc acactgccaa | 300 |
| cagccgcaga tcctgaaact cgatatcgaa aacttttcg atagcattag ctggttacag | 360 |
| gtctggcgtg tgtttcgcca ggcccagttg ccacgtaatg tggtaaccat gctgacctgg | 420 |
| atttgttgtt ataacgacgc gttaccgcag ggggcaccaa cttcgccagc catttccaat | 480 |
| cttgtgatgc gccgttttga tgaacgcata ggggaatggt gtcaggctcg ggaattacc | 540 |
| tacacccgct actgcgatga catgaccttt tcaggtcact tcaatgcccg ccaggttaaa | 600 |
| aataaagtgt gcggattgtt agcggagctg ggcctgagcc tcaataaacg caaaggctgc | 660 |
| ctgatagctg cctgtaagcg ccagcaagta accgggattg ttgttaatca aagccacag | 720 |
| cttgcccgtg aagcgcgccg ggcgctgcgt caggaggtgc atttgtgcca aaaatatggc | 780 |
| gttatttcgc atcttagtca tcgtggtgaa cttgatcctt ctggcgatct ccacgcacag | 840 |
| gcaacggcgt atctttatgc tttgcaggga agaataaact ggttattgca aatcaaccct | 900 |
| gaggatgagg cctttcaaca ggcgagagag agtgtaaagc gaatgctggt tgcatggtaa | 960 |

<210> SEQ ID NO 68
<211> LENGTH: 176
<212> TYPE: DNA
<213> ORGANISM: Escherichia coli

<400> SEQUENCE: 68

| | |
|---|---:|
| cgccagcagt ggcaatagcg tttccggcct tttgtgccgg gagggtcggc gagtcgctga | 60 |
| cttaacgcca gtagtatgtc catatacca aagtcgcttc attgtacctg agtacgcttc | 120 |
| gcgtacgtcg cgctgacgcg ctcagtacag ttacgcgcct tcgggatggt ttaatg | 176 |

<210> SEQ ID NO 69
<211> LENGTH: 1458
<212> TYPE: DNA
<213> ORGANISM: Myxococcus xanthus

<400> SEQUENCE: 69

| | |
|---|---:|
| atgaccgcca ggctggaccc gttcgtcccc gcagcttcgc cgcaggccgt gcccacgccc | 60 |
| gagctcaccg ctccgtcgtc agacgcggcc gcgaagcgtg aagcccgccg gctcgcgcac | 120 |
| gaagcgttgc tcgtccgcgc gaaggccatc gacgaagcgg gcggcgccga cgactgggtg | 180 |
| caggcgcagc tcgtctccaa gggcctcgcg gtggaggacc tggacttctc cagcgcctcc | 240 |
| gagaaggaca agaaggcctg gaaggagaag aagaaggccg aggccaccga cgccgcgcg | 300 |
| ctgaagcgtc aggcgcacga ggcgtggaag gccacgcacg tgggccacct gggcgcgggc | 360 |
| gtgcactggg cggaggaccg cctggccgac gcgttcgacg tgccccaccg cgaggagcgc | 420 |
| gcccgggcca acggcctgac ggagctggac tcggcgagg cgctggccaa ggcgctgggg | 480 |
| ctgagcgtgt ccaagctgcg ctggttcgcg ttccaccgcg aggtggacac ggccacgcac | 540 |
| tacgtgagct ggacgattcc gaagcgggac ggcagcaagc gcacgattac gtcccccaag | 600 |
| cctgagctga aggcagcgca gcgctgggtg ctgtccaacg tcgtggagcg gctgccggtg | 660 |
| cacggcgcgg cgcacggctt cgtggcggga cgctccatcc tcaccaacgc gctggcccac | 720 |
| cagggcgcg acgtggtggt gaaggtggac ctcaaggact tcttccctc cgtcacctgg | 780 |
| cgccgggtga agggcctgtt gcgcaagggc ggcctgcggg agggcacgtc cacgctgctg | 840 |
| tcgctgctct ccacggaagc gccgcgggag gcggtgcagt tccggggcaa gctgctgcac | 900 |
| gtggccaagg gccgcgcgc gctgcccag ggcgcgccca cgtcgccggg catcaccaac | 960 |
| gcgctgtgcc tgaagctgga caagcggctg tccgcgctcg cgaagcggct gggcttcacg | 1020 |

```
tacacgcgct acgcggacga cctgaccttc tcgtggacga aggcgaagca gcccaagccg    1080
cggcggacgc agcgtccccc ggtggcggtg ctgctgtctc gcgtgcagga agtggtggag    1140
gcggagggct tccgcgtgca cccggacaag acgcgcgtgg cgcgcaaggg cacgcggcag    1200
cgggtgacgg ggctggtcgt gaatgcggcg ggcaaggacg cgccggcggc ccgagtcccg    1260
cgcgacgtgg tgcgccagct ccgcgccgcc atccacaacc ggaagaaggg caagccgggc    1320
cgcgagggcg agtcgctgga gcagctcaag ggcatggccg ccttcatcca catgacggac    1380
ccggccaagg gccgcgcctt cctggctcag ctcacggagc tggagtccac ggcgagcgcg    1440
gctccgcagg cggagtga                                                  1458

<210> SEQ ID NO 70
<211> LENGTH: 231
<212> TYPE: DNA
<213> ORGANISM: Myxococcus xanthus

<400> SEQUENCE: 70
agaggtccgg agtgcatcag cctgagcgcc tcgagcggcg gagcggcgtt gcgccgctcc      60
ggttggaatg caggacactc tccgcaaggt agcctgttct tggctctctc cctcctaggc     120
actacggcca gggtgggtag cggagccaac gacgcgaccg ccgtttaccc accccggccg     180
tagtgcctag gaggggagag ccggtgaggc taccgtgccc caggtaagat g              231

<210> SEQ ID NO 71
<211> LENGTH: 334
<212> TYPE: DNA
<213> ORGANISM: Artificial
<220> FEATURE:
<223> OTHER INFORMATION: Chimeric guide nucleic acid sequences (guide
      DNA)

<400> SEQUENCE: 71
cacgcatgta ggcagatttg ttggttgtga atcgcaacca gtggccttaa tggcaggagg      60
aatcgcctcc agagtcgccg tctccaaggt gaaagcggaa gtagggcctt cgcgcacctc     120
atggaatccc ttctgcagca cctagatcgc ttttctgaac tcctagcagt atctagcact     180
acctacgtca gcacctggga ccccgcggtg tgctgtgcga aggagtgcct gcatgcgtgg     240
aatcccttct gcagcaccgt tttagagcta gaaatagcaa gttaaaataa ggctagtccg     300
ttatcaactt gaaaaagtgg caccgagtcg gtgc                                 334

<210> SEQ ID NO 72
<211> LENGTH: 361
<212> TYPE: DNA
<213> ORGANISM: Artificial
<220> FEATURE:
<223> OTHER INFORMATION: Chimeric guide nucleic acid sequences (guide
      DNA)

<400> SEQUENCE: 72
atgcgcaccc ttagcgagag gtttatcatt aaggtcaacc tctggatgtt gtttcggcat      60
cctgcattga atctgagtta ctgtctgttt tcctagagtc gccgtctcca aggtgaaagc     120
ggaagtaggg ccttcgcgca cctcatggaa tcccttctgc agcacctaga tcgcttttct     180
gaactcctag cagtatctag cactacctac gtcagcacct gggaccccgc aggaaaccc     240 gttttttctg acgtaagggt gcgcaggaat cccttctgca gcaccgtttt agagctagaa     300
atagcaagtt aaaataaggc tagtccgtta tcaacttgaa aaagtggcac cgagtcggtg     360
```

<210> SEQ ID NO 73
<211> LENGTH: 345
<212> TYPE: DNA
<213> ORGANISM: Artificial
<220> FEATURE:
<223> OTHER INFORMATION: Chimeric guide nucleic acid sequences (guide DNA)

<400> SEQUENCE: 73

```
gccagcagtg gcaatagcgt ttccggcctt ttgtgccggg agggtcggcg agtcgctgac      60
ttaacgccag tagtatgtcc atatacccaa gagtcgccgt ctccaaggtg aaagcggaag     120
tagggccttc gcgcacctca tggaatccct tctgcagcac ctagatcgct tttctgaact     180
cctagcagta tctagcacta cctacgtcag cacctgggac cccgcgggat ggtttaatgg     240
tattgccgcg gaatcccttc tgcagcaccg ttttagagct agaaatagca agttaaaata     300
aggctagtcc gttatcaact tgaaaaagtg gcaccgagtc ggtgc                     345
```

<210> SEQ ID NO 74
<211> LENGTH: 364
<212> TYPE: DNA
<213> ORGANISM: Artificial
<220> FEATURE:
<223> OTHER INFORMATION: Chimeric guide nucleic acid sequences (guide DNA)

<400> SEQUENCE: 74

```
agaggtccgg agtgcatcag cctgagcgcc tcgagcggcg gagcggcgtt gcgccgctcc      60
ggttggaatg caggacactc tccgcaaggt agagtcgccg tctccaaggt gaaagcggaa     120
gtagggcctt cgcgcacctc atggaatccc ttctgcagca cctagatcgc ttttctgaac     180
tcctagcagt atctagcact acctacgtca gcacctggga ccccgctgag ctaccgtgc      240
cccaggtaag atggtggtgc tttcccgggg aatcccttct gcagcaccgt tttagagcta     300
gaaatagcaa gttaaaataa ggctagtccg ttatcaactt gaaaaagtgg caccgagtcg     360
gtgc                                                                  364
```

<210> SEQ ID NO 75
<211> LENGTH: 1244
<212> TYPE: PRT
<213> ORGANISM: Artificial
<220> FEATURE:
<223> OTHER INFORMATION: Cas12a RNP protein sequence

<400> SEQUENCE: 75

```
Met Gly Ser Lys Leu Glu Lys Phe Thr Asn Cys Tyr Ser Leu Ser Lys
1               5                   10                  15

Thr Leu Arg Phe Lys Ala Ile Pro Val Gly Lys Thr Gln Glu Asn Ile
            20                  25                  30

Asp Asn Lys Arg Leu Leu Val Glu Asp Glu Lys Arg Ala Glu Asp Tyr
        35                  40                  45

Lys Gly Val Lys Lys Leu Leu Asp Arg Tyr Tyr Leu Ser Phe Ile Asn
    50                  55                  60

Asp Val Leu His Ser Ile Lys Leu Lys Asn Leu Asn Asn Tyr Ile Ser
65                  70                  75                  80

Leu Phe Arg Lys Lys Thr Arg Thr Glu Lys Glu Asn Lys Glu Leu Glu
                85                  90                  95

Asn Leu Glu Ile Asn Leu Arg Lys Glu Ile Ala Lys Ala Phe Lys Gly
```

```
                100                 105                 110
Asn Glu Gly Tyr Lys Ser Leu Phe Lys Lys Asp Ile Ile Glu Thr Ile
            115                 120                 125
Leu Pro Glu Phe Leu Asp Asp Lys Asp Glu Ile Ala Leu Val Asn Ser
            130                 135                 140
Phe Asn Gly Phe Thr Thr Ala Phe Thr Gly Phe Asp Asn Arg Glu
145             150                 155                 160
Asn Met Phe Ser Glu Glu Ala Lys Ser Thr Ser Ile Ala Phe Arg Cys
            165                 170                 175
Ile Asn Glu Asn Leu Thr Arg Tyr Ile Ser Asn Met Asp Ile Phe Glu
            180                 185                 190
Lys Val Asp Ala Ile Phe Asp Lys His Glu Val Gln Glu Ile Lys Glu
            195                 200                 205
Lys Ile Leu Asn Ser Asp Tyr Asp Val Glu Asp Phe Phe Glu Gly Glu
            210                 215                 220
Phe Phe Asn Phe Val Leu Thr Gln Glu Gly Ile Asp Val Tyr Asn Ala
225             230                 235                 240
Ile Ile Gly Gly Phe Val Thr Glu Ser Gly Glu Lys Ile Lys Gly Leu
                245                 250                 255
Asn Glu Tyr Ile Asn Leu Tyr Asn Gln Lys Thr Lys Gln Lys Leu Pro
                260                 265                 270
Lys Phe Lys Pro Leu Tyr Lys Gln Val Leu Ser Asp Arg Glu Ser Leu
                275                 280                 285
Ser Phe Tyr Gly Glu Gly Tyr Thr Ser Asp Glu Glu Val Leu Glu Val
                290                 295                 300
Phe Arg Asn Thr Leu Asn Lys Asn Ser Glu Ile Phe Ser Ser Ile Lys
305                 310                 315                 320
Lys Leu Glu Lys Leu Phe Lys Asn Phe Asp Glu Tyr Ser Ser Ala Gly
                325                 330                 335
Ile Phe Val Lys Asn Gly Pro Ala Ile Ser Thr Ile Ser Lys Asp Ile
                340                 345                 350
Phe Gly Glu Trp Asn Val Ile Arg Asp Lys Trp Asn Ala Glu Tyr Asp
                355                 360                 365
Asp Ile His Leu Lys Lys Lys Ala Val Val Thr Glu Lys Tyr Glu Asp
                370                 375                 380
Asp Arg Arg Lys Ser Phe Lys Lys Ile Gly Ser Phe Ser Leu Glu Gln
385                 390                 395                 400
Leu Gln Glu Tyr Ala Asp Ala Asp Leu Ser Val Val Glu Lys Leu Lys
                    405                 410                 415
Glu Ile Ile Ile Gln Lys Val Asp Glu Ile Tyr Lys Val Tyr Gly Ser
                420                 425                 430
Ser Glu Lys Leu Phe Asp Ala Asp Phe Val Leu Glu Lys Ser Leu Lys
                435                 440                 445
Lys Asn Asp Ala Val Val Ala Ile Met Lys Asp Leu Leu Asp Ser Val
                450                 455                 460
Lys Ser Phe Glu Asn Tyr Ile Lys Ala Phe Phe Gly Glu Gly Lys Glu
465                 470                 475                 480
Thr Asn Arg Asp Glu Ser Phe Tyr Gly Asp Phe Val Leu Ala Tyr Asp
                    485                 490                 495
Ile Leu Leu Lys Val Asp His Ile Tyr Asp Ala Ile Arg Asn Tyr Val
                500                 505                 510
Thr Gln Lys Pro Tyr Ser Lys Asp Lys Phe Lys Leu Tyr Phe Gln Asn
                515                 520                 525
```

```
Pro Gln Phe Met Gly Gly Trp Asp Lys Asp Lys Glu Thr Asp Tyr Arg
    530                 535                 540

Ala Thr Ile Leu Arg Tyr Gly Ser Lys Tyr Tyr Leu Ala Ile Met Asp
545                 550                 555                 560

Lys Lys Tyr Ala Lys Cys Leu Gln Lys Ile Asp Lys Asp Asp Val Asn
                565                 570                 575

Gly Asn Tyr Glu Lys Ile Asn Tyr Lys Leu Leu Pro Gly Pro Asn Lys
                580                 585                 590

Met Leu Pro Lys Val Phe Phe Ser Lys Lys Trp Met Ala Tyr Tyr Asn
            595                 600                 605

Pro Ser Glu Asp Ile Gln Lys Ile Tyr Lys Asn Gly Thr Phe Lys Lys
    610                 615                 620

Gly Asp Met Phe Asn Leu Asn Asp Cys His Lys Leu Ile Asp Phe Phe
625                 630                 635                 640

Lys Asp Ser Ile Ser Arg Tyr Pro Lys Trp Ser Asn Ala Tyr Asp Phe
                645                 650                 655

Asn Phe Ser Glu Thr Glu Lys Tyr Lys Asp Ile Ala Gly Phe Tyr Arg
                660                 665                 670

Glu Val Glu Glu Gln Gly Tyr Lys Val Ser Phe Glu Ser Ala Ser Lys
            675                 680                 685

Lys Glu Val Asp Lys Leu Val Glu Glu Gly Lys Leu Tyr Met Phe Gln
    690                 695                 700

Ile Tyr Asn Lys Asp Phe Ser Asp Lys Ser His Gly Thr Pro Asn Leu
705                 710                 715                 720

His Thr Met Tyr Phe Lys Leu Leu Phe Asp Glu Asn Asn His Gly Gln
                725                 730                 735

Ile Arg Leu Ser Gly Gly Ala Glu Leu Phe Met Arg Arg Ala Ser Leu
                740                 745                 750

Lys Lys Glu Glu Leu Val Val His Pro Ala Asn Ser Pro Ile Ala Asn
    755                 760                 765

Lys Asn Pro Asp Asn Pro Lys Lys Thr Thr Thr Leu Ser Tyr Asp Val
770                 775                 780

Tyr Lys Asp Lys Arg Phe Ser Glu Asp Gln Tyr Glu Leu His Ile Pro
785                 790                 795                 800

Ile Ala Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
                820                 825                 830

Asp Arg Gly Glu Arg Asn Leu Leu Tyr Ile Val Val Val Asp Gly Lys
            835                 840                 845

Gly Asn Ile Val Glu Gln Tyr Ser Leu Asn Glu Ile Ile Asn Asn Phe
850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
    915                 920                 925

Asn Ser Gly Phe Lys Asn Ser Arg Val Lys Val Glu Lys Gln Val Tyr
930                 935                 940
```

-continued

```
Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
            965                 970                 975

Ile Thr Asn Lys Phe Glu Ser Phe Lys Ser Met Ser Thr Gln Asn Gly
            980                 985                 990

Phe Ile Phe Tyr Ile Pro Ala Trp Leu Thr Ser Lys Ile Asp Pro Ser
        995                 1000                1005

Thr Gly Phe Val Asn Leu Leu Lys Thr Lys Tyr Thr Ser Ile Ala
    1010                1015                1020

Asp Ser Lys Lys Phe Ile Ser Ser Phe Asp Arg Ile Met Tyr Val
    1025                1030                1035

Pro Glu Glu Asp Leu Phe Glu Phe Ala Leu Asp Tyr Lys Asn Phe
    1040                1045                1050

Ser Arg Thr Asp Ala Asp Tyr Ile Lys Lys Trp Lys Leu Tyr Ser
    1055                1060                1065

Tyr Gly Asn Arg Ile Arg Ile Phe Arg Asn Pro Lys Lys Asn Asn
    1070                1075                1080

Val Phe Asp Trp Glu Glu Val Cys Leu Thr Ser Ala Tyr Lys Glu
    1085                1090                1095

Leu Phe Asn Lys Tyr Gly Ile Asn Tyr Gln Gln Gly Asp Ile Arg
    1100                1105                1110

Ala Leu Leu Cys Glu Gln Ser Asp Lys Ala Phe Tyr Ser Ser Phe
    1115                1120                1125

Met Ala Leu Met Ser Leu Met Leu Gln Met Arg Asn Ser Ile Thr
    1130                1135                1140

Gly Arg Thr Asp Val Asp Phe Leu Ile Ser Pro Val Lys Asn Ser
    1145                1150                1155

Asp Gly Ile Phe Tyr Asp Ser Arg Asn Tyr Glu Ala Gln Glu Asn
    1160                1165                1170

Ala Ile Leu Pro Lys Asn Ala Asp Ala Asn Gly Ala Tyr Asn Ile
    1175                1180                1185

Ala Arg Lys Val Leu Trp Ala Ile Gly Gln Phe Lys Lys Ala Glu
    1190                1195                1200

Asp Glu Lys Leu Asp Lys Val Lys Ile Ala Ile Ser Asn Lys Glu
    1205                1210                1215

Trp Leu Glu Tyr Ala Gln Thr Ser Val Lys His Pro Lys Lys Lys
    1220                1225                1230

Arg Lys Val Leu Glu His His His His His His
    1235                1240
```

```
<210> SEQ ID NO 76
<211> LENGTH: 23
<212> TYPE: RNA
<213> ORGANISM: Artificial
<220> FEATURE:
<223> OTHER INFORMATION: PWsp137 Target Sequence

<400> SEQUENCE: 76
ccucacuccu gcucggugaa uuu                                            23

<210> SEQ ID NO 77
<211> LENGTH: 43
<212> TYPE: RNA
<213> ORGANISM: Artificial
<220> FEATURE:
<223> OTHER INFORMATION: PWsp137 crRNA
```

<400> SEQUENCE: 77
aauuucuacu aaguguagau ccucacuccu gcucggugaa uuu    43

<210> SEQ ID NO 78
<211> LENGTH: 103
<212> TYPE: DNA
<213> ORGANISM: Artificial
<220> FEATURE:
<223> OTHER INFORMATION: PWsp137 crRNA - PBS 24bp; RTT 36bp

<400> SEQUENCE: 78
aauuucuacu aaguguagau ccucacuccu gcucggugaa uuuctggggc cgtaaccctc    60
actcctgctc ggtgaatttg gctcagcagg cacctgcctc agc    103

<210> SEQ ID NO 79
<211> LENGTH: 115
<212> TYPE: DNA
<213> ORGANISM: Artificial
<220> FEATURE:
<223> OTHER INFORMATION: PWsp137 crRNA - PBS 36bp; RTT 36bp

<400> SEQUENCE: 79
aauuucuacu aaguguagau ccucacuccu gcucggugaa uuuctggggc cgtaaccctc    60
actcctgctc ggtgaatttg gctcagcagg cacctgcctc agctgctcac ttgag    115

<210> SEQ ID NO 80
<211> LENGTH: 23
<212> TYPE: RNA
<213> ORGANISM: Artificial
<220> FEATURE:
<223> OTHER INFORMATION: PWsp453 Target Sequence

<400> SEQUENCE: 80
uaugaguuac aacgaacacc uca    23

<210> SEQ ID NO 81
<211> LENGTH: 43
<212> TYPE: RNA
<213> ORGANISM: Artificial
<220> FEATURE:
<223> OTHER INFORMATION: PWsp453 crRNA

<400> SEQUENCE: 81
aauuucuacu aaguguagau uaugaguuac aacgaacacc uca    43

<210> SEQ ID NO 82
<211> LENGTH: 103
<212> TYPE: DNA
<213> ORGANISM: Artificial
<220> FEATURE:
<223> OTHER INFORMATION: PWsp453 crRNA - PBS 24bp; RTT 36bp

<400> SEQUENCE: 82
aauuucuacu aaguguagau uaugaguuac aacgaacacc ucaggaactc agtaaatatg    60
agttacaacg aacacctcag gtaatgacta agatgactgc caa    103

<210> SEQ ID NO 83
<211> LENGTH: 115
<212> TYPE: DNA
<213> ORGANISM: Artificial
<220> FEATURE:
<223> OTHER INFORMATION: PWsp453 crRNA - PBS 36bp; RTT 36bp

```
<400> SEQUENCE: 83
aauuucuacu aaguguagau uaugaguuac aacgaacacc ucaggaacuc agtaaatatg      60
agttacaacg aacacctcag gtaatgacta agatgactgc aaggggcat atgag           115

<210> SEQ ID NO 84
<211> LENGTH: 23
<212> TYPE: RNA
<213> ORGANISM: Artificial
<220> FEATURE:
<223> OTHER INFORMATION: PWsp454 Target Sequence

<400> SEQUENCE: 84
cacgucucau augccccuug gca                                              23

<210> SEQ ID NO 85
<211> LENGTH: 43
<212> TYPE: RNA
<213> ORGANISM: Artificial
<220> FEATURE:
<223> OTHER INFORMATION: PWsp454 crRNA

<400> SEQUENCE: 85
aauuucuacu aaguguagau cacgucucau augccccuug gca                        43

<210> SEQ ID NO 86
<211> LENGTH: 103
<212> TYPE: DNA
<213> ORGANISM: Artificial
<220> FEATURE:
<223> OTHER INFORMATION: PWsp454 crRNA - PBS 24bp; RTT 36bp

<400> SEQUENCE: 86
aauuucuacu aaguguagau cacgucucau augccccuug gcagtatccc agtaaacacg      60
tctcatatgc cccttggcag tcatcttagt cattacctga ggt                        103

<210> SEQ ID NO 87
<211> LENGTH: 115
<212> TYPE: DNA
<213> ORGANISM: Artificial
<220> FEATURE:
<223> OTHER INFORMATION: PWsp454 crRNA - PBS 36bp; RTT 36bp

<400> SEQUENCE: 87
aauuucuacu aaguguagau cacgucucau augccccuug gcagtatccc agtaaacacg      60
tctcatatgc cccttggcag tcatcttagt cattacctga ggtgttcgtt gtaac           115

<210> SEQ ID NO 88
<211> LENGTH: 579
<212> TYPE: PRT
<213> ORGANISM: Artificial
<220> FEATURE:
<223> OTHER INFORMATION: Klentaq aa

<400> SEQUENCE: 88

Met Ser Gly Gly Ser Lys Arg Thr Ala Asp Gly Ser Glu Phe Glu Pro
1               5                   10                  15

Lys Lys Lys Arg Lys Val Gly Ser Gly Gly Leu Leu His Glu Phe
            20                  25                  30

Gly Leu Leu Glu Ser Pro Lys Ala Leu Glu Glu Ala Pro Trp Pro Pro
        35                  40                  45

Pro Glu Gly Ala Phe Val Gly Phe Val Leu Ser Arg Lys Glu Pro Met
    50                  55                  60
```

```
Trp Ala Asp Leu Leu Ala Leu Ala Ala Arg Gly Arg Val His
 65                  70                  75                  80

Arg Ala Pro Glu Pro Tyr Lys Ala Leu Arg Asp Leu Lys Glu Ala Arg
                 85                  90                  95

Gly Leu Leu Ala Lys Asp Leu Ser Val Leu Ala Leu Arg Glu Gly Leu
            100                 105                 110

Gly Leu Pro Pro Gly Asp Asp Pro Met Leu Leu Ala Tyr Leu Leu Asp
            115                 120                 125

Pro Ser Asn Thr Thr Pro Glu Gly Val Ala Arg Arg Tyr Gly Gly Glu
130                 135                 140

Trp Thr Glu Glu Ala Gly Glu Arg Ala Ala Leu Ser Glu Arg Leu Phe
145                 150                 155                 160

Ala Asn Leu Trp Gly Arg Leu Glu Gly Glu Arg Leu Leu Trp Leu
                165                 170                 175

Tyr Arg Glu Val Glu Arg Pro Leu Ser Ala Val Leu Ala His Met Glu
                180                 185                 190

Ala Thr Gly Val Arg Leu Asp Val Ala Tyr Leu Arg Ala Leu Ser Leu
            195                 200                 205

Glu Val Ala Glu Glu Ile Ala Arg Leu Glu Ala Glu Val Phe Arg Leu
210                 215                 220

Ala Gly His Pro Phe Asn Leu Asn Ser Arg Asp Gln Leu Glu Arg Val
225                 230                 235                 240

Leu Phe Asp Glu Leu Gly Leu Pro Ala Ile Gly Lys Thr Glu Lys Thr
                245                 250                 255

Gly Lys Arg Ser Thr Ser Ala Ala Val Leu Glu Ala Leu Arg Glu Ala
                260                 265                 270

His Pro Ile Val Glu Lys Ile Leu Gln Tyr Arg Glu Leu Thr Lys Leu
            275                 280                 285

Lys Ser Thr Tyr Ile Asp Pro Leu Pro Asp Leu Ile His Pro Arg Thr
290                 295                 300

Gly Arg Leu His Thr Arg Phe Asn Gln Thr Ala Thr Ala Thr Gly Arg
305                 310                 315                 320

Leu Ser Ser Ser Asp Pro Asn Leu Gln Asn Ile Pro Val Arg Thr Pro
                325                 330                 335

Leu Gly Gln Arg Ile Arg Arg Ala Phe Ile Ala Glu Glu Gly Trp Leu
            340                 345                 350

Leu Val Ala Leu Asp Tyr Ser Gln Ile Glu Leu Arg Val Leu Ala His
            355                 360                 365

Leu Ser Gly Asp Glu Asn Leu Ile Arg Val Phe Gln Glu Gly Arg Asp
370                 375                 380

Ile His Thr Glu Thr Ala Ser Trp Met Phe Gly Val Pro Arg Glu Ala
385                 390                 395                 400

Val Asp Pro Leu Met Arg Arg Ala Ala Lys Thr Ile Asn Phe Gly Val
                405                 410                 415

Leu Tyr Gly Met Ser Ala His Arg Leu Ser Gln Glu Leu Ala Ile Pro
            420                 425                 430

Tyr Glu Glu Ala Gln Ala Phe Ile Glu Arg Tyr Phe Gln Ser Phe Pro
            435                 440                 445

Lys Val Arg Ala Trp Ile Glu Lys Thr Leu Glu Glu Gly Arg Arg Arg
            450                 455                 460

Gly Tyr Val Glu Thr Leu Phe Gly Arg Arg Tyr Val Pro Asp Leu
465                 470                 475                 480
```

```
Glu Ala Arg Val Lys Ser Val Arg Glu Ala Glu Arg Met Ala Phe
                485                 490                 495

Asn Met Pro Val Gln Gly Thr Ala Ala Asp Leu Met Lys Leu Ala Met
                500                 505                 510

Val Lys Leu Phe Pro Arg Leu Glu Glu Met Gly Ala Arg Met Leu Leu
                515                 520                 525

Gln Val His Asp Glu Leu Val Leu Glu Ala Pro Lys Glu Arg Ala Glu
                530                 535                 540

Ala Val Ala Arg Leu Ala Lys Glu Val Met Glu Gly Val Tyr Pro Leu
545                 550                 555                 560

Ala Val Pro Leu Glu Val Glu Val Gly Ile Gly Glu Asp Trp Leu Ser
                565                 570                 575

Ala Lys Glu

<210> SEQ ID NO 89
<211> LENGTH: 800
<212> TYPE: PRT
<213> ORGANISM: Artificial
<220> FEATURE:
<223> OTHER INFORMATION: Therminator aa

<400> SEQUENCE: 89

Met Ser Gly Gly Ser Lys Arg Thr Ala Asp Gly Ser Glu Phe Glu Pro
1               5                   10                  15

Lys Lys Lys Arg Lys Val Gly Ser Ser Gly Ile Leu Asp Thr Asp Tyr
                20                  25                  30

Ile Thr Glu Asn Gly Lys Pro Val Ile Arg Val Phe Lys Lys Glu Asn
                35                  40                  45

Gly Glu Phe Lys Ile Glu Tyr Asp Arg Thr Phe Glu Pro Tyr Phe Tyr
            50                  55                  60

Ala Leu Leu Lys Asp Asp Ser Ala Ile Glu Asp Val Lys Lys Val Thr
65                  70                  75                  80

Ala Lys Arg His Gly Thr Val Val Lys Val Lys Arg Ala Glu Lys Val
                85                  90                  95

Gln Lys Lys Phe Leu Gly Arg Pro Ile Glu Val Trp Lys Leu Tyr Phe
                100                 105                 110

Asn His Pro Gln Asp Val Pro Ala Ile Arg Asp Arg Ile Arg Ala His
                115                 120                 125

Pro Ala Val Val Asp Ile Tyr Glu Tyr Asp Ile Pro Phe Ala Lys Arg
            130                 135                 140

Tyr Leu Ile Asp Lys Gly Leu Ile Pro Met Glu Gly Asp Glu Glu Leu
145                 150                 155                 160

Thr Met Leu Ala Phe Ala Ile Ala Thr Leu Tyr His Glu Gly Glu Glu
                165                 170                 175

Phe Gly Thr Gly Pro Ile Leu Met Ile Ser Tyr Ala Asp Gly Ser Glu
                180                 185                 190

Ala Arg Val Ile Thr Trp Lys Lys Ile Asp Leu Pro Tyr Val Asp Val
                195                 200                 205

Val Ser Thr Glu Lys Glu Met Ile Lys Arg Phe Leu Arg Val Val Arg
            210                 215                 220

Glu Lys Asp Pro Asp Val Leu Ile Thr Tyr Asn Gly Asp Asn Phe Asp
225                 230                 235                 240

Phe Ala Tyr Leu Lys Lys Arg Cys Glu Glu Leu Gly Ile Lys Phe Thr
                245                 250                 255

Leu Gly Arg Asp Gly Ser Glu Pro Lys Ile Gln Arg Met Gly Asp Arg
```

-continued

```
                260                 265                 270
Phe Ala Val Glu Val Lys Gly Arg Ile His Phe Asp Leu Tyr Pro Val
            275                 280                 285
Ile Arg Arg Thr Ile Asn Leu Pro Thr Tyr Thr Leu Glu Ala Val Tyr
            290                 295                 300
Glu Ala Val Phe Gly Lys Pro Lys Glu Lys Val Tyr Ala Glu Glu Ile
305                 310                 315                 320
Ala Gln Ala Trp Glu Ser Gly Glu Gly Leu Glu Arg Val Ala Arg Tyr
            325                 330                 335
Ser Met Glu Asp Ala Lys Val Thr Tyr Glu Leu Gly Arg Glu Phe Phe
            340                 345                 350
Pro Met Glu Ala Gln Leu Ser Arg Leu Ile Gly Gln Ser Leu Trp Asp
            355                 360                 365
Val Ser Arg Ser Ser Thr Gly Asn Leu Val Glu Trp Phe Leu Leu Arg
            370                 375                 380
Lys Ala Tyr Lys Arg Asn Glu Leu Ala Pro Asn Lys Pro Asp Glu Arg
385                 390                 395                 400
Glu Leu Ala Arg Arg Arg Gly Tyr Ala Gly Gly Tyr Val Lys Glu
            405                 410                 415
Pro Glu Arg Gly Leu Trp Asp Asn Ile Val Tyr Leu Asp Phe Arg Ser
            420                 425                 430
Leu Tyr Pro Ser Ile Ile Ile Thr His Asn Val Ser Pro Asp Thr Leu
            435                 440                 445
Asn Arg Glu Gly Cys Lys Glu Tyr Asp Val Ala Pro Glu Val Gly His
            450                 455                 460
Lys Phe Cys Lys Asp Phe Pro Gly Phe Ile Pro Ser Leu Leu Gly Asp
465                 470                 475                 480
Leu Leu Glu Glu Arg Gln Lys Ile Lys Arg Lys Met Lys Ala Thr Val
            485                 490                 495
Asp Pro Leu Glu Lys Lys Leu Leu Asp Tyr Arg Gln Arg Leu Ile Lys
            500                 505                 510
Ile Leu Ala Asn Ser Phe Tyr Gly Tyr Tyr Gly Tyr Ala Lys Ala Arg
            515                 520                 525
Trp Tyr Cys Lys Glu Cys Ala Glu Ser Val Thr Ala Trp Gly Arg Glu
            530                 535                 540
Tyr Ile Glu Met Val Ile Arg Glu Leu Glu Glu Lys Phe Gly Phe Lys
545                 550                 555                 560
Val Leu Tyr Ala Asp Thr Asp Gly Leu His Ala Thr Ile Pro Gly Ala
            565                 570                 575
Asp Ala Glu Thr Val Lys Lys Lys Ala Lys Glu Phe Leu Lys Tyr Ile
            580                 585                 590
Asn Pro Lys Leu Pro Gly Leu Leu Glu Leu Glu Tyr Glu Gly Phe Tyr
            595                 600                 605
Val Arg Gly Phe Phe Val Thr Lys Lys Tyr Ala Val Ile Asp Glu
            610                 615                 620
Glu Gly Lys Ile Thr Thr Arg Gly Leu Glu Ile Val Arg Arg Asp Trp
625                 630                 635                 640
Ser Glu Ile Ala Lys Glu Thr Gln Ala Arg Val Leu Glu Ala Ile Leu
            645                 650                 655
Lys His Gly Asp Val Glu Glu Ala Val Arg Ile Val Lys Glu Val Thr
            660                 665                 670
Glu Lys Leu Ser Lys Tyr Glu Val Pro Pro Glu Lys Leu Val Ile His
            675                 680                 685
```

```
Glu Gln Ile Thr Arg Asp Leu Arg Asp Tyr Lys Ala Thr Gly Pro His
    690                 695                 700
Val Ala Val Ala Lys Arg Leu Ala Ala Arg Gly Val Lys Ile Arg Pro
705                 710                 715                 720
Gly Thr Val Ile Ser Tyr Ile Val Leu Lys Gly Ser Gly Arg Ile Gly
                725                 730                 735
Asp Arg Ala Ile Pro Ala Asp Glu Phe Asp Pro Thr Lys His Arg Tyr
            740                 745                 750
Asp Ala Glu Tyr Tyr Ile Glu Asn Gln Val Leu Pro Ala Val Glu Arg
        755                 760                 765
Ile Leu Lys Ala Phe Gly Tyr Arg Lys Glu Asp Leu Arg Tyr Gln Lys
    770                 775                 780
Thr Lys Gln Val Gly Leu Gly Ala Trp Leu Lys Val Lys Gly Lys Lys
785                 790                 795                 800

<210> SEQ ID NO 90
<211> LENGTH: 876
<212> TYPE: PRT
<213> ORGANISM: Artificial
<220> FEATURE:
<223> OTHER INFORMATION: Pfu-Ssod7 aa

<400> SEQUENCE: 90

Met Ser Gly Gly Ser Lys Arg Thr Ala Asp Gly Ser Glu Phe Glu Pro
1               5                   10                  15
Lys Lys Lys Arg Lys Val Gly Ser Ser Gly His Ile Glu Gly Arg His
                20                  25                  30
Met Ile Leu Asp Val Asp Tyr Ile Thr Glu Glu Gly Lys Pro Val Ile
            35                  40                  45
Arg Leu Phe Lys Lys Glu Asn Gly Lys Phe Lys Ile Glu His Asp Arg
    50                  55                  60
Thr Phe Arg Pro Tyr Ile Tyr Ala Leu Leu Arg Asp Asp Ser Lys Ile
65                  70                  75                  80
Glu Glu Val Lys Lys Ile Thr Gly Glu Arg His Gly Lys Ile Val Arg
                85                  90                  95
Ile Val Asp Val Glu Lys Val Glu Lys Lys Phe Leu Gly Lys Pro Ile
            100                 105                 110
Thr Val Trp Lys Leu Tyr Leu Glu His Pro Gln Asp Val Pro Thr Ile
        115                 120                 125
Arg Glu Lys Val Arg Glu His Pro Ala Val Val Asp Ile Phe Glu Tyr
    130                 135                 140
Asp Ile Pro Phe Ala Lys Arg Tyr Leu Ile Asp Lys Gly Leu Ile Pro
145                 150                 155                 160
Met Glu Gly Glu Glu Leu Lys Ile Leu Ala Phe Asp Ile Glu Thr
                165                 170                 175
Leu Tyr His Glu Gly Glu Glu Phe Gly Lys Gly Pro Ile Ile Met Ile
            180                 185                 190
Ser Tyr Ala Asp Glu Asn Glu Ala Lys Val Ile Thr Trp Lys Asn Ile
        195                 200                 205
Asp Leu Pro Tyr Val Glu Val Val Ser Ser Glu Arg Glu Met Ile Lys
    210                 215                 220
Arg Phe Leu Arg Ile Ile Arg Glu Lys Asp Pro Asp Ile Ile Val Thr
225                 230                 235                 240
Tyr Asn Gly Asp Ser Phe Asp Phe Pro Tyr Leu Ala Lys Arg Ala Glu
                245                 250                 255
```

```
Lys Leu Gly Ile Lys Leu Thr Ile Gly Arg Asp Gly Ser Glu Pro Lys
            260                 265                 270

Met Gln Arg Ile Gly Asp Met Thr Ala Val Glu Val Lys Gly Arg Ile
        275                 280                 285

His Phe Asp Leu Tyr His Val Ile Thr Arg Thr Ile Asn Leu Pro Thr
    290                 295                 300

Tyr Thr Leu Glu Ala Val Tyr Glu Ala Ile Phe Gly Lys Pro Lys Glu
305                 310                 315                 320

Lys Val Tyr Ala Asp Glu Ile Ala Lys Ala Trp Ser Gly Glu Asn
                325                 330                 335

Leu Glu Arg Val Ala Lys Tyr Ser Met Glu Asp Ala Lys Ala Thr Tyr
                340                 345                 350

Glu Leu Gly Lys Glu Phe Leu Pro Met Glu Ile Gln Leu Ser Arg Leu
            355                 360                 365

Val Gly Gln Pro Leu Trp Asp Val Ser Arg Ser Thr Gly Asn Leu
        370                 375                 380

Val Glu Trp Phe Leu Leu Arg Lys Ala Tyr Glu Arg Asn Glu Val Ala
385                 390                 395                 400

Pro Asn Lys Pro Ser Glu Glu Tyr Gln Arg Arg Leu Arg Glu Ser
                405                 410                 415

Tyr Thr Gly Gly Phe Val Lys Glu Pro Glu Lys Gly Leu Trp Glu Asn
                420                 425                 430

Ile Val Tyr Leu Asp Phe Arg Ala Leu Tyr Pro Ser Ile Ile Ile Thr
            435                 440                 445

His Asn Val Ser Pro Asp Thr Leu Asn Leu Glu Gly Cys Lys Asn Tyr
    450                 455                 460

Asp Ile Ala Pro Gln Val Gly His Lys Phe Cys Lys Asp Ile Pro Gly
465                 470                 475                 480

Phe Ile Pro Ser Leu Leu Gly His Leu Leu Glu Glu Arg Gln Lys Ile
                485                 490                 495

Lys Thr Lys Met Lys Glu Thr Gln Asp Pro Ile Glu Lys Ile Leu Leu
            500                 505                 510

Asp Tyr Arg Gln Lys Ala Ile Lys Leu Leu Ala Asn Ser Phe Tyr Gly
        515                 520                 525

Tyr Tyr Gly Tyr Ala Lys Ala Arg Trp Tyr Cys Lys Glu Cys Ala Glu
    530                 535                 540

Ser Val Thr Ala Trp Gly Arg Lys Tyr Ile Glu Leu Val Trp Lys Glu
545                 550                 555                 560

Leu Glu Glu Lys Phe Gly Phe Lys Val Leu Tyr Ile Asp Thr Asp Gly
                565                 570                 575

Leu Tyr Ala Thr Ile Pro Gly Gly Glu Ser Glu Glu Ile Lys Lys Lys
            580                 585                 590

Ala Leu Glu Phe Val Lys Tyr Ile Asn Ser Lys Leu Pro Gly Leu Leu
        595                 600                 605

Glu Leu Glu Tyr Glu Gly Phe Tyr Lys Arg Gly Phe Phe Val Thr Lys
    610                 615                 620

Lys Arg Tyr Ala Val Ile Asp Glu Glu Gly Lys Val Ile Thr Arg Gly
625                 630                 635                 640

Leu Glu Ile Val Arg Arg Asp Trp Ser Glu Ile Ala Lys Glu Thr Gln
                645                 650                 655

Ala Arg Val Leu Glu Thr Ile Leu Lys His Gly Asp Val Glu Glu Ala
            660                 665                 670
```

Val Arg Ile Val Lys Glu Val Ile Gln Lys Leu Ala Asn Tyr Glu Ile
            675                 680                 685

Pro Pro Glu Lys Leu Ala Ile Tyr Glu Gln Ile Thr Arg Pro Leu His
690                 695                 700

Glu Tyr Lys Ala Ile Gly Pro His Val Ala Val Ala Lys Lys Leu Ala
705                 710                 715                 720

Ala Lys Gly Val Lys Ile Lys Pro Gly Met Val Ile Gly Tyr Ile Val
            725                 730                 735

Leu Arg Gly Asp Gly Pro Ile Ser Asn Arg Ala Ile Leu Ala Glu Glu
            740                 745                 750

Tyr Asp Pro Lys Lys His Lys Tyr Asp Ala Glu Tyr Tyr Ile Glu Asn
755                 760                 765

Gln Val Leu Pro Ala Val Leu Arg Ile Leu Glu Gly Phe Gly Tyr Arg
770                 775                 780

Lys Glu Asp Leu Arg Tyr Gln Lys Thr Arg Gln Val Gly Leu Thr Ser
785                 790                 795                 800

Trp Leu Asn Ile Lys Lys Ser Gly Thr Gly Gly Gly Ala Thr Val
            805                 810                 815

Lys Phe Lys Tyr Lys Gly Glu Glu Lys Glu Val Asp Ile Ser Lys Ile
            820                 825                 830

Lys Lys Val Trp Arg Val Gly Lys Met Ile Ser Phe Thr Tyr Asp Glu
            835                 840                 845

Gly Gly Gly Lys Thr Gly Arg Gly Ala Val Ser Glu Lys Asp Ala Pro
            850                 855                 860

Lys Glu Leu Leu Gln Met Leu Glu Lys Gln Lys Lys
865                 870                 875

<210> SEQ ID NO 91
<211> LENGTH: 648
<212> TYPE: PRT
<213> ORGANISM: Artificial
<220> FEATURE:
<223> OTHER INFORMATION: Klenow aa

<400> SEQUENCE: 91

Met Ser Gly Gly Ser Lys Arg Thr Ala Asp Gly Ser Glu Phe Glu Pro
1               5                   10                  15

Lys Lys Lys Arg Lys Val Val Ile Ser Tyr Asp Asn Tyr Val Thr Ile
            20                  25                  30

Leu Asp Glu Glu Thr Leu Lys Ala Trp Ile Ala Lys Leu Glu Lys Ala
            35                  40                  45

Pro Val Phe Ala Phe Asp Thr Glu Thr Asp Ser Leu Asp Asn Ile Ser
50                  55                  60

Ala Asn Leu Val Gly Leu Ser Phe Ala Ile Glu Pro Gly Val Ala Ala
65                  70                  75                  80

Tyr Ile Pro Val Ala His Asp Tyr Leu Asp Ala Pro Asp Gln Ile Ser
            85                  90                  95

Arg Glu Arg Ala Leu Glu Leu Leu Lys Pro Leu Leu Glu Asp Glu Lys
            100                 105                 110

Ala Leu Lys Val Gly Gln Asn Leu Lys Tyr Asp Arg Gly Ile Leu Ala
            115                 120                 125

Asn Tyr Gly Ile Glu Leu Arg Gly Ile Ala Phe Asp Thr Met Leu Glu
            130                 135                 140

Ser Tyr Ile Leu Asn Ser Val Ala Gly Arg His Asp Met Asp Ser Leu
145                 150                 155                 160

-continued

Ala Glu Arg Trp Leu Lys His Lys Thr Ile Thr Phe Glu Glu Ile Ala
                165                 170                 175

Gly Lys Gly Lys Asn Gln Leu Thr Phe Asn Gln Ile Ala Leu Glu Glu
            180                 185                 190

Ala Gly Arg Tyr Ala Ala Glu Asp Ala Asp Val Thr Leu Gln Leu His
        195                 200                 205

Leu Lys Met Trp Pro Asp Leu Gln Lys His Lys Gly Pro Leu Asn Val
    210                 215                 220

Phe Glu Asn Ile Glu Met Pro Leu Val Pro Val Leu Ser Arg Ile Glu
225                 230                 235                 240

Arg Asn Gly Val Lys Ile Asp Pro Lys Val Leu His Asn His Ser Glu
            245                 250                 255

Glu Leu Thr Leu Arg Leu Ala Glu Leu Glu Lys Lys Ala His Glu Ile
        260                 265                 270

Ala Gly Glu Glu Phe Asn Leu Ser Ser Thr Lys Gln Leu Gln Thr Ile
    275                 280                 285

Leu Phe Glu Lys Gln Gly Ile Lys Pro Leu Lys Lys Thr Pro Gly Gly
    290                 295                 300

Ala Pro Ser Thr Ser Glu Glu Val Leu Glu Glu Leu Ala Leu Asp Tyr
305                 310                 315                 320

Pro Leu Pro Lys Val Ile Leu Glu Tyr Arg Gly Leu Ala Lys Leu Lys
            325                 330                 335

Ser Thr Tyr Thr Asp Lys Leu Pro Leu Met Ile Asn Pro Lys Thr Gly
        340                 345                 350

Arg Val His Thr Ser Tyr His Gln Ala Val Thr Ala Thr Gly Arg Leu
    355                 360                 365

Ser Ser Thr Asp Pro Asn Leu Gln Asn Ile Pro Val Arg Asn Glu Glu
    370                 375                 380

Gly Arg Arg Ile Arg Gln Ala Phe Ile Ala Pro Glu Asp Tyr Val Ile
385                 390                 395                 400

Val Ser Ala Asp Tyr Ser Gln Ile Glu Leu Arg Ile Met Ala His Leu
            405                 410                 415

Ser Arg Asp Lys Gly Leu Leu Thr Ala Phe Ala Glu Gly Lys Asp Ile
        420                 425                 430

His Arg Ala Thr Ala Ala Glu Val Phe Gly Leu Pro Leu Glu Thr Val
    435                 440                 445

Thr Ser Glu Gln Arg Arg Ser Ala Lys Ala Ile Asn Phe Gly Leu Ile
    450                 455                 460

Tyr Gly Met Ser Ala Phe Gly Leu Ala Arg Gln Leu Asn Ile Pro Arg
465                 470                 475                 480

Lys Glu Ala Gln Lys Tyr Met Asp Leu Tyr Phe Glu Arg Tyr Pro Gly
            485                 490                 495

Val Leu Glu Tyr Met Glu Arg Thr Arg Ala Gln Ala Lys Glu Gln Gly
        500                 505                 510

Tyr Val Glu Thr Leu Asp Gly Arg Arg Leu Tyr Leu Pro Asp Ile Lys
    515                 520                 525

Ser Ser Asn Gly Ala Arg Arg Ala Ala Ala Glu Arg Ala Ala Ile Asn
    530                 535                 540

Ala Pro Met Gln Gly Thr Ala Ala Asp Ile Ile Lys Arg Ala Met Ile
545                 550                 555                 560

Ala Val Asp Ala Trp Leu Gln Ala Glu Gln Pro Arg Val Arg Met Ile
            565                 570                 575

Met Gln Val His Asp Glu Leu Val Phe Glu Val His Lys Asp Asp Val

```
                580             585             590
Asp Ala Val Ala Lys Gln Ile His Gln Leu Met Glu Asn Cys Thr Arg
            595                 600             605

Leu Asp Val Pro Leu Leu Val Glu Val Gly Ser Gly Glu Asn Trp Asp
            610                 615             620

Gln Ala His Ser Gly Gly Ser Lys Arg Thr Ala Asp Gly Ser Glu Phe
625                 630                 635                 640

Glu Pro Lys Lys Lys Arg Lys Val
                645

<210> SEQ ID NO 92
<211> LENGTH: 970
<212> TYPE: PRT
<213> ORGANISM: Escherichia coli

<400> SEQUENCE: 92

Met Ser Gly Gly Ser Lys Arg Thr Ala Asp Gly Ser Glu Phe Glu Pro
1               5                   10                  15

Lys Lys Lys Arg Lys Val Val Gln Ile Pro Gln Asn Pro Leu Ile Leu
                20                  25                  30

Val Asp Gly Ser Ser Tyr Leu Tyr Arg Ala Tyr His Ala Phe Pro Pro
            35                  40                  45

Leu Thr Asn Ser Ala Gly Glu Pro Thr Gly Ala Met Tyr Gly Val Leu
        50                  55                  60

Asn Met Leu Arg Ser Leu Ile Met Gln Tyr Lys Pro Thr His Ala Ala
65              70                  75                  80

Val Val Phe Asp Ala Lys Gly Lys Thr Phe Arg Asp Glu Leu Phe Glu
                85                  90                  95

His Tyr Lys Ser His Arg Pro Pro Met Pro Asp Asp Leu Arg Ala Gln
            100                 105                 110

Ile Glu Pro Leu His Ala Met Val Lys Ala Met Gly Leu Pro Leu Leu
        115                 120                 125

Ala Val Ser Gly Val Glu Ala Asp Asp Val Ile Gly Thr Leu Ala Arg
    130                 135                 140

Glu Ala Glu Lys Ala Gly Arg Pro Val Leu Ile Ser Thr Gly Asp Lys
145                 150                 155                 160

Asp Met Ala Gln Leu Val Thr Pro Asn Ile Thr Leu Ile Asn Thr Met
                165                 170                 175

Thr Asn Thr Ile Leu Gly Pro Glu Glu Val Val Asn Lys Tyr Gly Val
            180                 185                 190

Pro Pro Glu Leu Ile Ile Asp Phe Leu Ala Leu Met Gly Asp Ser Ser
        195                 200                 205

Asp Asn Ile Pro Gly Val Pro Gly Val Gly Glu Lys Thr Ala Gln Ala
    210                 215                 220

Leu Leu Gln Gly Leu Gly Gly Leu Asp Thr Leu Tyr Ala Glu Pro Glu
225                 230                 235                 240

Lys Ile Ala Gly Leu Ser Phe Arg Gly Ala Lys Thr Met Ala Ala Lys
                245                 250                 255

Leu Glu Gln Asn Lys Glu Val Ala Tyr Leu Ser Tyr Gln Leu Ala Thr
            260                 265                 270

Ile Lys Thr Asp Val Glu Leu Glu Leu Thr Cys Glu Gln Leu Glu Val
        275                 280                 285

Gln Gln Pro Ala Ala Glu Glu Leu Leu Gly Leu Phe Lys Lys Tyr Glu
    290                 295                 300
```

```
Phe Lys Arg Trp Thr Ala Asp Val Glu Ala Gly Lys Trp Leu Gln Ala
305                 310                 315                 320

Lys Gly Ala Lys Pro Ala Ala Lys Pro Gln Glu Thr Ser Val Ala Asp
                325                 330                 335

Glu Ala Pro Glu Val Thr Ala Thr Val Ile Ser Tyr Asp Asn Tyr Val
                340                 345                 350

Thr Ile Leu Asp Glu Glu Thr Leu Lys Ala Trp Ile Ala Lys Leu Glu
                355                 360                 365

Lys Ala Pro Val Phe Ala Phe Asp Thr Glu Thr Asp Ser Leu Asp Asn
    370                 375                 380

Ile Ser Ala Asn Leu Val Gly Leu Ser Phe Ala Ile Glu Pro Gly Val
385                 390                 395                 400

Ala Ala Tyr Ile Pro Val Ala His Asp Tyr Leu Asp Ala Pro Asp Gln
                405                 410                 415

Ile Ser Arg Glu Arg Ala Leu Glu Leu Leu Lys Pro Leu Leu Glu Asp
                420                 425                 430

Glu Lys Ala Leu Lys Val Gly Gln Asn Leu Lys Tyr Asp Arg Gly Ile
    435                 440                 445

Leu Ala Asn Tyr Gly Ile Glu Leu Arg Gly Ile Ala Phe Asp Thr Met
450                 455                 460

Leu Glu Ser Tyr Ile Leu Asn Ser Val Ala Gly Arg His Asp Met Asp
465                 470                 475                 480

Ser Leu Ala Glu Arg Trp Leu Lys His Lys Thr Ile Thr Phe Glu Glu
                485                 490                 495

Ile Ala Gly Lys Gly Lys Asn Gln Leu Thr Phe Asn Gln Ile Ala Leu
                500                 505                 510

Glu Glu Ala Gly Arg Tyr Ala Ala Glu Asp Ala Asp Val Thr Leu Gln
                515                 520                 525

Leu His Leu Lys Met Trp Pro Asp Leu Gln Lys His Lys Gly Pro Leu
                530                 535                 540

Asn Val Phe Glu Asn Ile Glu Met Pro Leu Val Pro Val Leu Ser Arg
545                 550                 555                 560

Ile Glu Arg Asn Gly Val Lys Ile Asp Pro Lys Val Leu His Asn His
                565                 570                 575

Ser Glu Glu Leu Thr Leu Arg Leu Ala Glu Leu Glu Lys Lys Ala His
                580                 585                 590

Glu Ile Ala Gly Glu Glu Phe Asn Leu Ser Ser Thr Lys Gln Leu Gln
                595                 600                 605

Thr Ile Leu Phe Glu Lys Gln Gly Ile Lys Pro Leu Lys Lys Thr Pro
    610                 615                 620

Gly Gly Ala Pro Ser Thr Ser Glu Glu Val Leu Glu Glu Leu Ala Leu
625                 630                 635                 640

Asp Tyr Pro Leu Pro Lys Val Ile Leu Glu Tyr Arg Gly Leu Ala Lys
                645                 650                 655

Leu Lys Ser Thr Tyr Thr Asp Lys Leu Pro Leu Met Ile Asn Pro Lys
                660                 665                 670

Thr Gly Arg Val His Thr Ser Tyr His Gln Ala Val Thr Ala Thr Gly
                675                 680                 685

Arg Leu Ser Ser Thr Asp Pro Asn Leu Gln Asn Ile Pro Val Arg Asn
                690                 695                 700

Glu Glu Gly Arg Arg Ile Arg Gln Ala Phe Ile Ala Pro Glu Asp Tyr
705                 710                 715                 720

Val Ile Val Ser Ala Asp Tyr Ser Gln Ile Glu Leu Arg Ile Met Ala
```

```
                725                 730                 735
His Leu Ser Arg Asp Lys Gly Leu Leu Thr Ala Phe Ala Glu Gly Lys
            740                 745                 750

Asp Ile His Arg Ala Thr Ala Ala Glu Val Phe Gly Leu Pro Leu Glu
            755                 760                 765

Thr Val Thr Ser Glu Gln Arg Arg Ser Ala Lys Ala Ile Asn Phe Gly
            770                 775                 780

Leu Ile Tyr Gly Met Ser Ala Phe Gly Leu Ala Arg Gln Leu Asn Ile
785                 790                 795                 800

Pro Arg Lys Glu Ala Gln Lys Tyr Met Asp Leu Tyr Phe Glu Arg Tyr
                805                 810                 815

Pro Gly Val Leu Glu Tyr Met Glu Arg Thr Arg Ala Gln Ala Lys Glu
            820                 825                 830

Gln Gly Tyr Val Glu Thr Leu Asp Gly Arg Arg Leu Tyr Leu Pro Asp
            835                 840                 845

Ile Lys Ser Ser Asn Gly Ala Arg Arg Ala Ala Ala Glu Arg Ala Ala
850                 855                 860

Ile Asn Ala Pro Met Gln Gly Thr Ala Ala Asp Ile Ile Lys Arg Ala
865                 870                 875                 880

Met Ile Ala Val Asp Ala Trp Leu Gln Ala Glu Gln Pro Arg Val Arg
                885                 890                 895

Met Ile Met Gln Val His Asp Glu Leu Val Phe Glu Val His Lys Asp
            900                 905                 910

Asp Val Asp Ala Val Ala Lys Gln Ile His Gln Leu Met Glu Asn Cys
            915                 920                 925

Thr Arg Leu Asp Val Pro Leu Leu Val Glu Val Gly Ser Gly Glu Asn
930                 935                 940

Trp Asp Gln Ala His Ser Gly Gly Ser Lys Arg Thr Ala Asp Gly Ser
945                 950                 955                 960

Glu Phe Glu Pro Lys Lys Lys Arg Lys Val
                965                 970

<210> SEQ ID NO 93
<211> LENGTH: 1654
<212> TYPE: PRT
<213> ORGANISM: Homo sapiens

<400> SEQUENCE: 93

Met Lys Arg Thr Ala Asp Gly Ser Glu Phe Glu Ser Pro Lys Lys Lys
1               5                   10                  15

Arg Lys Val Gly Arg Ser Arg Leu Leu Glu Asp Phe Arg Asn Asn Arg
            20                  25                  30

Tyr Pro Asn Leu Gln Leu Arg Glu Ile Ala Gly His Ile Met Glu Phe
        35                  40                  45

Ser Gln Asp Gln His Gly Ser Arg Phe Ile Gln Leu Lys Leu Glu Arg
    50                  55                  60

Ala Thr Pro Ala Glu Arg Gln Leu Val Phe Asn Glu Ile Leu Gln Ala
65                  70                  75                  80

Ala Tyr Gln Leu Met Val Asp Val Phe Gly Asn Tyr Val Ile Gln Lys
                85                  90                  95

Phe Phe Glu Phe Gly Ser Leu Glu Gln Lys Leu Ala Leu Ala Glu Arg
            100                 105                 110

Ile Arg Gly His Val Leu Ser Leu Ala Leu Gln Met Tyr Gly Ser Arg
        115                 120                 125
```

-continued

```
Val Ile Glu Lys Ala Leu Glu Phe Ile Pro Ser Asp Gln Gln Asn Glu
    130                 135                 140

Met Val Arg Glu Leu Asp Gly His Val Leu Lys Cys Val Lys Asp Gln
145                 150                 155                 160

Asn Gly Asn His Val Val Gln Lys Cys Ile Glu Cys Val Gln Pro Gln
                165                 170                 175

Ser Leu Gln Phe Ile Ile Asp Ala Phe Lys Gly Gln Val Phe Ala Leu
                180                 185                 190

Ser Thr His Pro Tyr Gly Cys Arg Val Ile Gln Arg Ile Leu Glu His
            195                 200                 205

Cys Leu Pro Asp Gln Thr Leu Pro Ile Leu Glu Glu Leu His Gln His
    210                 215                 220

Thr Glu Gln Leu Val Gln Asp Gln Tyr Gly Asn Tyr Val Ile Gln His
225                 230                 235                 240

Val Leu Glu His Gly Arg Pro Glu Asp Lys Ser Lys Ile Val Ala Glu
                245                 250                 255

Ile Arg Gly Asn Val Leu Val Leu Ser Gln His Lys Phe Ala Ser Asn
            260                 265                 270

Val Val Glu Lys Cys Val Thr His Ala Ser Arg Thr Glu Arg Ala Val
    275                 280                 285

Leu Ile Asp Glu Val Cys Thr Met Asn Asp Gly Pro His Ser Ala Leu
290                 295                 300

Tyr Thr Met Met Lys Asp Gln Tyr Ala Asn Tyr Val Val Gln Lys Met
305                 310                 315                 320

Ile Asp Val Ala Glu Pro Gly Gln Arg Lys Ile Val Met His Lys Ile
                325                 330                 335

Arg Pro His Ile Ala Thr Leu Arg Lys Tyr Thr Tyr Gly Lys His Ile
            340                 345                 350

Leu Ala Lys Leu Glu Lys Tyr Tyr Met Lys Asn Gly Val Asp Leu Gly
    355                 360                 365

Ser Gly Gly Ser Ser Gly Gly Ser Ser Gly Ser Glu Thr Pro Gly Thr
    370                 375                 380

Ser Glu Ser Ala Thr Pro Glu Ser Ser Gly Gly Ser Ser Gly Gly Ser
385                 390                 395                 400

Met Ser Leu Arg Ser Gly Gly Arg Arg Arg Ala Asp Pro Gly Ala Asp
                405                 410                 415

Gly Glu Ala Ser Arg Asp Asp Gly Ala Thr Ser Ser Val Ser Ala Leu
            420                 425                 430

Lys Arg Leu Glu Arg Ser Gln Trp Thr Asp Lys Met Asp Leu Arg Phe
    435                 440                 445

Gly Phe Glu Arg Leu Lys Glu Pro Gly Glu Lys Thr Gly Trp Leu Ile
    450                 455                 460

Asn Met His Pro Thr Glu Ile Leu Asp Glu Asp Lys Arg Leu Gly Ser
465                 470                 475                 480

Ala Val Asp Tyr Tyr Phe Ile Gln Asp Asp Gly Ser Arg Phe Lys Val
                485                 490                 495

Ala Leu Pro Tyr Lys Pro Tyr Phe Tyr Ile Ala Thr Arg Lys Gly Cys
            500                 505                 510

Glu Arg Glu Val Ser Ser Phe Leu Ser Lys Lys Phe Gln Gly Lys Ile
    515                 520                 525

Ala Lys Val Glu Thr Val Pro Lys Glu Asp Leu Asp Leu Pro Asn His
    530                 535                 540

Leu Val Gly Leu Lys Arg Asn Tyr Ile Arg Leu Ser Phe His Thr Val
```

-continued

```
545                 550                 555                 560
Glu Asp Leu Val Lys Val Arg Lys Glu Ile Ser Pro Ala Val Lys Lys
                565                 570                 575
Asn Arg Glu Gln Asp His Ala Ser Asp Ala Tyr Thr Ala Leu Leu Ser
                580                 585                 590
Ser Val Leu Gln Arg Gly Gly Val Ile Thr Asp Glu Glu Thr Ser
                595                 600                 605
Lys Lys Ile Ala Asp Gln Leu Asp Asn Ile Val Asp Met Arg Glu Tyr
                610                 615                 620
Asp Val Pro Tyr His Ile Arg Leu Ser Ile Asp Leu Lys Ile His Val
625                 630                 635                 640
Ala His Trp Tyr Asn Val Arg Tyr Arg Gly Asn Ala Phe Pro Val Glu
                645                 650                 655
Ile Thr Arg Arg Asp Asp Leu Val Glu Arg Pro Asp Pro Val Val Leu
                660                 665                 670
Ala Phe Asp Ile Glu Thr Thr Lys Leu Pro Leu Lys Phe Pro Asp Ala
                675                 680                 685
Glu Thr Asp Gln Ile Met Met Ile Ser Tyr Met Ile Asp Gly Gln Gly
                690                 695                 700
Tyr Leu Ile Thr Asn Arg Glu Ile Val Ser Glu Asp Ile Glu Asp Phe
705                 710                 715                 720
Glu Phe Thr Pro Lys Pro Glu Tyr Glu Gly Pro Phe Cys Val Phe Asn
                725                 730                 735
Glu Pro Asp Glu Ala His Leu Ile Gln Arg Trp Phe Glu His Val Gln
                740                 745                 750
Glu Thr Lys Pro Thr Ile Met Val Thr Tyr Asn Gly Asp Phe Phe Asp
                755                 760                 765
Trp Pro Phe Val Glu Ala Arg Ala Ala Val His Gly Leu Ser Met Gln
                770                 775                 780
Gln Glu Ile Gly Phe Gln Lys Asp Ser Gln Gly Glu Tyr Lys Ala Pro
785                 790                 795                 800
Gln Cys Ile His Met Asp Cys Leu Arg Trp Val Lys Arg Asp Ser Tyr
                805                 810                 815
Leu Pro Val Gly Ser His Asn Leu Lys Ala Ala Lys Ala Lys Leu
                820                 825                 830
Gly Tyr Asp Pro Val Glu Leu Asp Pro Glu Asp Met Cys Arg Met Ala
                835                 840                 845
Thr Glu Gln Pro Gln Thr Leu Ala Thr Tyr Ser Val Ser Asp Ala Val
850                 855                 860
Ala Thr Tyr Tyr Leu Tyr Met Lys Tyr Val His Pro Phe Ile Phe Ala
865                 870                 875                 880
Leu Cys Thr Ile Ile Pro Met Glu Pro Asp Glu Val Leu Arg Lys Gly
                885                 890                 895
Ser Gly Thr Leu Cys Glu Ala Leu Leu Met Val Gln Ala Phe His Ala
                900                 905                 910
Asn Ile Ile Phe Pro Asn Lys Gln Glu Gln Glu Phe Asn Lys Leu Thr
                915                 920                 925
Asp Asp Gly His Val Leu Asp Ser Glu Thr Tyr Val Gly Gly His Val
                930                 935                 940
Glu Ala Leu Glu Ser Gly Val Phe Arg Ser Asp Ile Pro Cys Arg Phe
945                 950                 955                 960
Arg Met Asn Pro Ala Ala Phe Asp Phe Leu Leu Gln Arg Val Glu Lys
                965                 970                 975
```

```
Thr Leu Arg His Ala Leu Glu Glu Glu Lys Val Pro Val Glu Gln
            980             985                 990

Val Thr Asn Phe Glu Glu Val Cys Asp Glu Ile Lys Ser Lys Leu Ala
        995                1000                1005

Ser Leu Lys Asp Val Pro Ser Arg Ile Glu Cys Pro Leu Ile Tyr
    1010            1015                1020

His Leu Asp Val Gly Ala Met Tyr Pro Asn Ile Ile Leu Thr Asn
    1025            1030                1035

Arg Leu Gln Pro Ser Ala Met Val Asp Glu Ala Thr Cys Ala Ala
    1040            1045                1050

Cys Asp Phe Asn Lys Pro Gly Ala Asn Cys Gln Arg Lys Met Ala
    1055            1060                1065

Trp Gln Trp Arg Gly Glu Phe Met Pro Ala Ser Arg Ser Glu Tyr
    1070            1075                1080

His Arg Ile Gln His Gln Leu Glu Ser Glu Lys Phe Pro Pro Leu
    1085            1090                1095

Phe Pro Glu Gly Pro Ala Arg Ala Phe His Glu Leu Ser Arg Glu
    1100            1105                1110

Glu Gln Ala Lys Tyr Glu Lys Arg Arg Leu Ala Asp Tyr Cys Arg
    1115            1120                1125

Lys Ala Tyr Lys Lys Ile His Ile Thr Lys Val Glu Glu Arg Leu
    1130            1135                1140

Thr Thr Ile Cys Gln Arg Glu Asn Ser Phe Tyr Val Asp Thr Val
    1145            1150                1155

Arg Ala Phe Arg Asp Arg Arg Tyr Glu Phe Lys Gly Leu His Lys
    1160            1165                1170

Val Trp Lys Lys Lys Leu Ser Ala Ala Val Glu Val Gly Asp Ala
    1175            1180                1185

Ala Glu Val Lys Arg Cys Lys Asn Met Glu Val Leu Tyr Asp Ser
    1190            1195                1200

Leu Gln Leu Ala His Lys Cys Ile Leu Asn Ser Phe Tyr Gly Tyr
    1205            1210                1215

Val Met Arg Lys Gly Ala Arg Trp Tyr Ser Met Glu Met Ala Gly
    1220            1225                1230

Ile Val Cys Phe Thr Gly Ala Asn Ile Ile Thr Gln Ala Arg Glu
    1235            1240                1245

Leu Ile Glu Gln Ile Gly Arg Pro Leu Glu Leu Asp Thr Asp Gly
    1250            1255                1260

Ile Trp Cys Val Leu Pro Asn Ser Phe Pro Glu Asn Phe Val Phe
    1265            1270                1275

Lys Thr Thr Asn Val Lys Lys Pro Lys Val Thr Ile Ser Tyr Pro
    1280            1285                1290

Gly Ala Met Leu Asn Ile Met Val Lys Glu Gly Phe Thr Asn Asp
    1295            1300                1305

Gln Tyr Gln Glu Leu Ala Glu Pro Ser Ser Leu Thr Tyr Val Thr
    1310            1315                1320

Arg Ser Glu Asn Ser Ile Phe Phe Glu Val Asp Gly Pro Tyr Leu
    1325            1330                1335

Ala Met Ile Leu Pro Ala Ser Lys Glu Glu Gly Lys Lys Leu Lys
    1340            1345                1350

Lys Arg Tyr Ala Val Phe Asn Glu Asp Gly Ser Leu Ala Glu Leu
    1355            1360                1365
```

```
Lys Gly Phe Glu Val Lys Arg Arg Gly Glu Leu Gln Leu Ile Lys
    1370                1375                1380

Ile Phe Gln Ser Ser Val Phe Glu Ala Phe Leu Lys Gly Ser Thr
    1385                1390                1395

Leu Glu Glu Val Tyr Gly Ser Val Ala Lys Val Ala Asp Tyr Trp
    1400                1405                1410

Leu Asp Val Leu Tyr Ser Lys Ala Ala Asn Met Pro Asp Ser Glu
    1415                1420                1425

Leu Phe Glu Leu Ile Ser Glu Asn Arg Ser Met Ser Arg Lys Leu
    1430                1435                1440

Glu Asp Tyr Gly Glu Gln Lys Ser Thr Ser Ile Ser Thr Ala Lys
    1445                1450                1455

Arg Leu Ala Glu Phe Leu Gly Asp Gln Met Val Lys Asp Ala Gly
    1460                1465                1470

Leu Ser Cys Arg Tyr Ile Ile Ser Arg Lys Pro Glu Gly Ser Pro
    1475                1480                1485

Val Thr Glu Arg Ala Ile Pro Leu Ala Ile Phe Gln Ala Glu Pro
    1490                1495                1500

Thr Val Arg Lys His Phe Leu Arg Lys Trp Leu Lys Ser Ser Ser
    1505                1510                1515

Leu Gln Asp Phe Asp Ile Arg Ala Ile Leu Asp Trp Asp Tyr Tyr
    1520                1525                1530

Ile Glu Arg Leu Gly Ser Ala Ile Gln Lys Ile Ile Thr Ile Pro
    1535                1540                1545

Ala Ala Leu Gln Gln Val Lys Asn Pro Val Pro Arg Val Lys His
    1550                1555                1560

Pro Asp Trp Leu His Lys Lys Leu Leu Glu Lys Asn Asp Val Tyr
    1565                1570                1575

Lys Gln Lys Lys Ile Ser Glu Leu Phe Thr Leu Glu Gly Arg Arg
    1580                1585                1590

Gln Val Thr Met Ala Glu Ala Ser Gly Gly Ser Lys Arg Thr Ala
    1595                1600                1605

Asp Gly Ser Glu Phe Glu Pro Lys Lys Lys Arg Lys Val Gly Ser
    1610                1615                1620

Gly Ala Thr Asn Phe Ser Leu Leu Lys Gln Ala Gly Asp Val Glu
    1625                1630                1635

Glu Asn Pro Gly Pro Ser Gly Gly Ser Pro Lys Lys Lys Arg Lys
    1640                1645                1650

Val

<210> SEQ ID NO 94
<211> LENGTH: 1233
<212> TYPE: PRT
<213> ORGANISM: Saccharomyces cerevisiae

<400> SEQUENCE: 94

Met Ser Gly Gly Ser Lys Arg Thr Ala Asp Gly Ser Glu Phe Glu Pro
1               5                   10                  15

Lys Lys Lys Arg Lys Val Gly Ser Ser Gly Met Phe Gly Lys Lys Lys
                20                  25                  30

Asn Asn Gly Gly Ser Ser Thr Ala Arg Tyr Ser Ala Gly Asn Lys Tyr
            35                  40                  45

Asn Thr Leu Ser Asn Asn Tyr Ala Leu Ser Ala Gln Gln Leu Leu Asn
        50                  55                  60
```

```
Ala Ser Lys Ile Asp Asp Ile Asp Ser Met Met Gly Phe Glu Arg Tyr
 65                  70                  75                  80

Val Pro Pro Gln Tyr Asn Gly Arg Phe Asp Ala Lys Asp Ile Asp Gln
                 85                  90                  95

Ile Pro Gly Arg Val Gly Trp Leu Thr Asn Met His Ala Thr Leu Val
            100                 105                 110

Ser Gln Glu Thr Leu Ser Ser Gly Ser Asn Gly Gly Asn Ser Asn
        115                 120                 125

Asp Gly Glu Arg Val Thr Thr Asn Gln Gly Ile Ser Gly Val Asp Phe
    130                 135                 140

Tyr Phe Leu Asp Glu Glu Gly Gly Ser Phe Lys Ser Thr Val Val Tyr
145                 150                 155                 160

Asp Pro Tyr Phe Phe Ile Ala Cys Asn Asp Glu Ser Arg Val Asn Asp
                165                 170                 175

Val Glu Glu Leu Val Lys Lys Tyr Leu Glu Ser Cys Leu Lys Ser Leu
            180                 185                 190

Gln Ile Ile Arg Lys Glu Asp Leu Thr Met Asp Asn His Leu Leu Gly
        195                 200                 205

Leu Gln Lys Thr Leu Ile Lys Leu Ser Phe Val Asn Ser Asn Gln Leu
210                 215                 220

Phe Glu Ala Arg Lys Leu Leu Arg Pro Ile Leu Gln Asp Asn Ala Asn
225                 230                 235                 240

Asn Asn Val Gln Arg Asn Ile Tyr Asn Val Ala Ala Asn Gly Ser Glu
                245                 250                 255

Lys Val Asp Ala Lys His Leu Ile Glu Asp Ile Arg Glu Tyr Asp Val
            260                 265                 270

Pro Tyr His Val Arg Val Ser Ile Asp Lys Asp Ile Arg Val Gly Lys
        275                 280                 285

Trp Tyr Lys Val Thr Gln Gln Gly Phe Ile Glu Asp Thr Arg Lys Ile
290                 295                 300

Ala Phe Ala Asp Pro Val Val Met Ala Phe Asp Ile Glu Thr Thr Lys
305                 310                 315                 320

Pro Pro Leu Lys Phe Pro Asp Ser Ala Val Asp Gln Ile Met Met Ile
                325                 330                 335

Ser Tyr Met Ile Asp Gly Glu Gly Phe Leu Ile Thr Asn Arg Glu Ile
            340                 345                 350

Ile Ser Glu Asp Ile Glu Asp Phe Glu Tyr Thr Pro Lys Pro Glu Tyr
        355                 360                 365

Pro Gly Phe Phe Thr Ile Phe Asn Glu Asn Asp Glu Val Ala Leu Leu
370                 375                 380

Gln Arg Phe Phe Glu His Ile Arg Asp Val Arg Pro Thr Val Ile Ser
385                 390                 395                 400

Thr Phe Asn Gly Asp Phe Phe Asp Trp Pro Phe Ile His Asn Arg Ser
                405                 410                 415

Lys Ile His Gly Leu Asp Met Phe Asp Glu Ile Gly Phe Ala Pro Asp
            420                 425                 430

Ala Glu Gly Glu Tyr Lys Ser Ser Tyr Cys Ser His Met Asp Cys Phe
        435                 440                 445

Arg Trp Val Lys Arg Asp Ser Tyr Leu Pro Gln Gly Ser Gln Gly Leu
450                 455                 460

Lys Ala Val Thr Gln Ser Lys Leu Gly Tyr Asn Pro Ile Glu Leu Asp
465                 470                 475                 480

Pro Glu Leu Met Thr Pro Tyr Ala Phe Glu Lys Pro Gln His Leu Ser
```

```
                    485             490                 495
Glu Tyr Ser Val Ser Asp Ala Val Ala Thr Tyr Tyr Leu Tyr Met Lys
                500                 505                 510

Tyr Val His Pro Phe Ile Phe Ser Leu Cys Thr Ile Ile Pro Leu Asn
            515                 520                 525

Pro Asp Glu Thr Leu Arg Lys Gly Thr Gly Thr Leu Cys Glu Met Leu
        530                 535                 540

Leu Met Val Gln Ala Tyr Gln His Asn Ile Leu Leu Pro Asn Lys His
545                 550                 555                 560

Thr Asp Pro Ile Glu Arg Phe Tyr Asp Gly His Leu Leu Glu Ser Glu
                565                 570                 575

Thr Tyr Val Gly Gly His Val Glu Ser Leu Glu Ala Gly Val Phe Arg
                580                 585                 590

Ser Asp Leu Lys Asn Glu Phe Lys Ile Asp Pro Ser Ala Ile Asp Glu
            595                 600                 605

Leu Leu Gln Glu Leu Pro Glu Ala Leu Lys Phe Ser Val Glu Val Glu
        610                 615                 620

Asn Lys Ser Ser Val Asp Lys Val Thr Asn Phe Glu Glu Ile Lys Asn
625                 630                 635                 640

Gln Ile Thr Gln Lys Leu Leu Glu Leu Lys Glu Asn Asn Ile Arg Asn
                645                 650                 655

Glu Leu Pro Leu Ile Tyr His Val Asp Val Ala Ser Met Tyr Pro Asn
                660                 665                 670

Ile Met Thr Thr Asn Arg Leu Gln Pro Asp Ser Ile Lys Ala Glu Arg
            675                 680                 685

Asp Cys Ala Ser Cys Asp Phe Asn Arg Pro Gly Lys Thr Cys Ala Arg
        690                 695                 700

Lys Leu Lys Trp Ala Trp Arg Gly Glu Phe Phe Pro Ser Lys Met Asp
705                 710                 715                 720

Glu Tyr Asn Met Ile Lys Arg Ala Leu Gln Asn Glu Thr Phe Pro Asn
                725                 730                 735

Lys Asn Lys Phe Ser Lys Lys Val Leu Thr Phe Asp Glu Leu Ser
            740                 745                 750

Tyr Ala Asp Gln Val Ile His Ile Lys Lys Arg Leu Thr Glu Tyr Ser
        755                 760                 765

Arg Lys Val Tyr His Arg Val Lys Val Ser Glu Ile Val Glu Arg Glu
        770                 775                 780

Ala Ile Val Cys Gln Arg Glu Asn Pro Phe Tyr Val Asp Thr Val Lys
785                 790                 795                 800

Ser Phe Arg Asp Arg Arg Tyr Glu Phe Lys Gly Leu Ala Lys Thr Trp
                805                 810                 815

Lys Gly Asn Leu Ser Lys Ile Asp Pro Ser Asp Lys His Ala Arg Asp
            820                 825                 830

Glu Ala Lys Lys Met Ile Val Leu Tyr Asp Ser Leu Gln Leu Ala His
        835                 840                 845

Lys Val Ile Leu Asn Ser Phe Tyr Gly Tyr Val Met Arg Lys Gly Ser
        850                 855                 860

Arg Trp Tyr Ser Met Glu Met Ala Gly Ile Thr Cys Leu Thr Gly Ala
865                 870                 875                 880

Thr Ile Ile Gln Met Ala Arg Ala Leu Val Glu Arg Val Gly Arg Pro
                885                 890                 895

Leu Glu Leu Asp Thr Asp Gly Ile Trp Cys Ile Leu Pro Lys Ser Phe
            900                 905                 910
```

```
Pro Glu Thr Tyr Phe Phe Thr Leu Glu Asn Gly Lys Lys Leu Tyr Leu
            915                 920                 925

Ser Tyr Pro Cys Ser Met Leu Asn Tyr Arg Val His Gln Lys Phe Thr
    930                 935                 940

Asn His Gln Tyr Gln Glu Leu Lys Asp Pro Leu Asn Tyr Ile Tyr Glu
945                 950                 955                 960

Thr His Ser Glu Asn Thr Ile Phe Phe Glu Val Asp Gly Pro Tyr Lys
                965                 970                 975

Ala Met Ile Leu Pro Ser Ser Lys Glu Gly Lys Gly Ile Lys Lys
                980                 985                 990

Arg Tyr Ala Val Phe Asn Glu Asp Gly Ser Leu Ala Glu Leu Lys Gly
            995                 1000                1005

Phe Glu Leu Lys Arg Arg Gly Glu Leu Gln Leu Ile Lys Asn Phe
    1010                1015                1020

Gln Ser Asp Ile Phe Lys Val Phe Leu Glu Gly Asp Thr Leu Glu
    1025                1030                1035

Gly Cys Tyr Ser Ala Val Ala Ser Val Cys Asn Arg Trp Leu Asp
    1040                1045                1050

Val Leu Asp Ser His Gly Leu Met Leu Glu Asp Glu Asp Leu Val
    1055                1060                1065

Ser Leu Ile Cys Glu Asn Arg Ser Met Ser Lys Thr Leu Lys Glu
    1070                1075                1080

Tyr Glu Gly Gln Lys Ser Thr Ser Ile Thr Thr Ala Arg Arg Leu
    1085                1090                1095

Gly Asp Phe Leu Gly Glu Asp Met Val Lys Asp Lys Gly Leu Gln
    1100                1105                1110

Cys Lys Tyr Ile Ile Ser Ser Lys Pro Phe Asn Ala Pro Val Thr
    1115                1120                1125

Glu Arg Ala Ile Pro Val Ala Ile Phe Ser Ala Asp Ile Pro Ile
    1130                1135                1140

Lys Arg Ser Phe Leu Arg Arg Trp Thr Leu Asp Pro Ser Leu Glu
    1145                1150                1155

Asp Leu Asp Ile Arg Thr Ile Ile Asp Trp Gly Tyr Tyr Arg Glu
    1160                1165                1170

Arg Leu Gly Ser Ala Ile Gln Lys Ile Ile Thr Ile Pro Ala Ala
    1175                1180                1185

Leu Gln Gly Val Ser Asn Pro Val Pro Arg Val Glu His Pro Asp
    1190                1195                1200

Trp Leu Lys Arg Lys Ile Ala Thr Lys Ser Gly Gly Ser Lys Arg
    1205                1210                1215

Thr Ala Asp Gly Ser Glu Phe Glu Pro Lys Lys Arg Lys Val
    1220                1225                1230
```

RECRUITMENT OF DNA POLYMERASE FOR TEMPLATED EDITING

STATEMENT REGARDING ELECTRONIC FILING OF A SEQUENCE LISTING

A Sequence Listing in ASCII text format, submitted under 37 C.F.R. § 1.821, entitled 1499.14_ST25.txt, 435,307 bytes in size, generated on Jan. 6, 2021 and filed via EFS-Web, is provided in lieu of a paper copy. This Sequence Listing is hereby incorporated herein by reference into the specification for its disclosures.

STATEMENT OF PRIORITY

This application claims the benefit, under 35 U.S.C. § 119 (e), of U.S. Provisional Application No. 62/957,542 filed on Jan. 6, 2019, the entire contents of which is incorporated by reference herein.

FIELD OF THE INVENTION

This invention relates to recombinant nucleic constructs comprising a sequence-specific DNA binding protein, DNA-dependent DNA polymerase and a DNA encoded repair template, optionally a DNA endonuclease or wherein the sequence-specific DNA binding protein comprises DNA endonuclease activity, and methods of use thereof for modifying nucleic acids in cells and organisms.

BACKGROUND OF THE INVENTION

Precise, templated editing typically involves introducing a double strand break (DSB) in the target site and providing a template with the desired edits to be incorporated. The incorporation of the sequence from an edit template to a target site relies on templated repair of DSB through homologous recombination pathway, which is not a dominant pathway for DNA repair in most eukaryotic cells. In addition, the endogenous homologous recombination pathway is a complex process with multiple steps, each of which have inherent bottlenecks and can be difficult to manipulate. Overall, efficiency of homologous recombination mediated templated editing is typically low in human cells, and even lower in plant cells due to the low efficiency of reagent delivery and difficulty in recovering edited plants.

The best templated editing efficiencies in eukaryotes other than yeast have been accomplished in human cell culture where the delivery of a cocktail of reagents (e.g., a DNA endonuclease or nickase, a repair template, NHEJ inhibitors, HDR stimulators) can be readily coordinated and with high efficiency. Specifically, in human cells, precise templated editing has been demonstrated using a complex of three components: 1) a nickase that can be recruited to sequence specific site by a guide RNA; 2) a guide RNA with extended sequence that binds to the 3' of nicked DNA and encodes repair template with desired edits; and 3) a RNA dependent DNA polymerase (reverse transcriptase) fused to the nickase, which uses the 3' end of the nicked DNA and a primer to synthesize DNA (e.g., incorporate the edit). In certain human cell types, up to 50% of precise templated editing has been reported (Anzalone et al. *Nature* 576:149-157(2019)).

Unlike in human cells, in plants, delivery multiple reagents in different compositions can be difficult. It can also be difficult to deliver high doses of repair template, which can improve templated editing efficiency by increasing the availability of the repair template in the cell. To date, the majority of templated editing successes in plants have been achieved by particle bombardment of DNA expression cassettes and repair templates. The best editing efficiencies are in the range of less than 10%, with many studies being less than 1%. The highest efficiencies reported are often only at specific repair loci in the genome with no or a poor understanding of a mechanism that might lead to higher efficiencies of HDR.

SUMMARY OF THE INVENTION

One aspect of the present invention provides a first complex comprising: (a) a first sequence-specific DNA binding protein that is capable of binding to a first site on a target nucleic acid; and (b) a first DNA-dependent DNA polymerase.

A second aspect of the invention provides a first complex comprising: (a) a first sequence-specific DNA binding protein that is capable of binding to a first site on a target nucleic acid and comprises endonuclease activity that is capable of introducing a single stranded nick or a double strand break; (b) a first DNA-dependent DNA polymerase; and (c) a first DNA encoded repair template.

A third aspect of the invention provides a first complex comprising: (a) a first sequence-specific DNA binding protein that is capable of binding to a first site on a target nucleic acid; (b) a first DNA-dependent DNA polymerase; (c) a first DNA endonuclease; and (d) a first DNA encoded repair template.

A fourth aspect of the invention provides a second complex comprising: (a) a second sequence-specific DNA binding protein that is capable of binding to a second site on a target nucleic acid; and (b) a DNA-encoded repair template.

A fifth aspect of the invention provides an engineered (modified) DNA-dependent DNA polymerase fused to an affinity polypeptide that is capable of interacting with a peptide tag or an RNA recruiting motif.

A sixth aspect of the invention provides an RNA molecule comprising (a) a nucleic acid sequence that mediates interaction with a CRISPR-Cas effector protein; (b) a nucleic acid sequence that directs the CRISPR-Cas effector protein to a specific nucleic acid target site through a DNA-RNA interaction, and (c) a nucleic acid sequence that forms a stem loop structure that can interact with the engineered DNA-dependent DNA polymerase of the invention.

A seventh aspect of the invention provides a method of modifying a target nucleic acid, the method comprising contacting the target nucleic acid with: the first complex of the invention, thereby modifying the target nucleic acid.

An eighth aspect of the invention provides a method of modifying a target nucleic acid, the method comprising contacting the target nucleic acid with: (a) a first sequence-specific DNA binding protein that is capable of binding to a first site on a target nucleic acid; (b) a first DNA-dependent DNA polymerase; (c) a first DNA endonuclease; and (d) a first DNA encoded repair template, thereby modifying the target nucleic acid.

A ninth aspect of the invention provides a method of modifying a target nucleic acid, the method comprising contacting the target nucleic acid with: (a) a first sequence-specific DNA binding protein that is capable of binding to a first site on a target nucleic acid and comprises nickase activity and/or endonuclease activity that is capable of introducing a single stranded nick or a double strand break; (b) a first DNA-dependent DNA polymerase; and (c) a first DNA encoded repair template, thereby modifying the target nucleic acid.

A tenth aspect of the invention provides a system for modifying a target nucleic acid comprising the first complex of the invention, a polynucleotide encoding the same, and/or the expression cassette or vector comprising the polynucleotide, wherein (a) the first sequence-specific DNA binding protein comprising DNA endonuclease activity binds to a first site on the target nucleic acid; (b) the first DNA-dependent DNA polymerase is capable of interacting with the first sequence-specific DNA binding protein and is recruited to the first sequence specific DNA binding protein and to the first site on the target nucleic acid, and (c) (i) the first DNA encoded repair template is linked to a first guide nucleic acid that comprises a spacer sequence having substantial complementarity to the first site on the target nucleic acid, thereby guiding the first DNA encoded repair template to the first site on the target nucleic acid, or (c)(ii) the first DNA encoded repair template is capable of interacting with the first sequence-specific DNA binding protein or the first DNA-dependent DNA polymerase and is recruited to the first sequence-specific DNA binding protein or the first DNA-dependent DNA polymerase and to the first site on the target nucleic acid, thereby modifying the target nucleic acid.

An eleventh aspect of the invention provides a system for modifying a target nucleic acid comprising the first complex of the invention, a polynucleotide encoding the same, and/or the expression cassette or vector comprising the polynucleotide, wherein (a) the first sequence-specific DNA binding protein binds to a first site on the target nucleic acid, (b) the first DNA endonuclease is capable of interacting with the first sequence specific DNA binding protein and/or a guide nucleic acid and is recruited to the first sequence specific DNA binding protein and to the first site on the target nucleic acid; (c) the first DNA-dependent DNA polymerase is capable of interacting with the first sequence specific DNA binding protein and/or a guide nucleic acid and is recruited to the first sequence specific DNA binding protein and to the first site on the target nucleic acid; and (d) (i) the first DNA encoded repair template is linked to a guide nucleic acid that comprises a spacer sequence having substantial complementarity to the first site on the target nucleic acid, thereby guiding the first DNA encoded repair template to the first site on the target nucleic acid, or (d)(ii) the first DNA encoded repair template is capable of interacting with the first sequence-specific DNA binding protein or the first DNA-dependent DNA polymerase and is recruited to the sequence-specific DNA binding protein or the first DNA-dependent DNA polymerase and to the first site on the target nucleic acid, thereby modifying the target nucleic acid.

BRIEF DESCRIPTION OF THE SEQUENCES

SEQ ID NOs:1-20 are example Cas12a amino acid sequences useful with this invention.

SEQ ID NO:21-22 are exemplary regulatory sequences encoding a promoter and intron.

SEQ ID NOs:23-25 provide example peptide tags and corresponding affinity polypeptides.

SEQ ID NO:26-36 provide example RNA recruiting motifs and corresponding affinity polypeptides.

SEQ ID NOs:37-39 provide examples of a protospacer adjacent motif position for a Type V CRISPR-Cas12a nuclease.

SEQ ID NOs:40-47 provide example HUH-tags and corresponding recognition sequences.

SEQ ID NOs:48-58 and 88-94 provide example DNA-dependent DNA polymerases from various different organisms.

SEQ ID NOs:59-62 provide example Cas9 sequences.

SEQ ID NOs:63-70 provide example retron reverse transcriptases and retron scaffolds.

SEQ ID NOs:71-74 provide example chimeric guide nucleic acid sequences.

SEQ ID NO:75 provides an example Cas12a ribonucleoprotein (RNP).

SEQ ID NOs:76-87 provides the target sequence and crRNA sequences from Example 11.

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, 1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "enhance," "enhancing," "improve" and "improving" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the reference organism. A "homologous" nucleic acid sequence is a nucleotide sequence naturally associated with a host cell into which it is introduced.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

A "portion" or "fragment" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. As an example, a repeat sequence of guide nucleic acid of this invention may comprise a portion of a wild type CRISPR-Cas repeat sequence (e.g., a wild Type CRISR-Cas repeat; e.g., a repeat from the CRISPR Cas system of a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%8, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, the nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX® version 2.0 for translated nucleotide sequences and BLASTN® version 2.0 for polynucleotide sequences.

Two nucleotide sequences may also be considered substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology—Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

Any polynucleotide, nucleic acid construct, expression cassette and/or vector of this invention may be codon optimized for expression in any species of interest. Codon optimization is well known in the art and involves modification of a nucleotide sequence for codon usage bias using species-specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species-specific codon usage table with the codons present in the native polynucleotide sequences. As is understood in the art, codon optimization of a nucleotide sequence results in a nucleotide sequence having less than 100% identity (e.g., 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function (and in some embodiments, the same structure) as that encoded by the original nucleotide sequence. Thus, in some embodiments, the polynucleotides, nucleic acid constructs, expression cassettes, and/or vectors of the invention (e.g., comprising/encoding a sequence specific DNA binding domain, a DNA-dependent DNA polymerase, a DNA endonuclease, and the like) may be codon optimized for expression in an organism (e.g., a plant (e.g., in a particular plant species), an animal, a bacterium, a fungus, etc.). In some embodiments, the codon optimized nucleic acid constructs, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the polynucleotides, nucleic acid constructs, expression cassettes, and/or vectors of the invention that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a DNA binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid, or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227). In some embodiments, a promoter region may comprise at least one intron (e.g., SEQ ID NOs:21 or 22).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992)*Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as 0-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604, 121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA2-6 promoter from *arabidopsis* (U.S. Pat. No. 7,141, 424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986)*Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/ expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron.

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a nucleic acid construct of the invention (e.g., a sequence specific DNA binding polypeptide or domain, a DNA-dependent DNA polymerase (e.g., engineered DNA-dependent DNA polymerase), a DNA endonuclease polypeptide or domain, a DNA encoded repair template, a guide nucleic acid, a first complex, second complex, third complex, etc.), wherein the nucleic acid construct is operably associated with one or more control sequences (e.g., a promoter, terminator and the like). Thus, some embodiments of the invention provide expression cassettes designed to express, for example, one or more polynucleotides of the invention. When an expression cassette comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, for example, a polynucleotide encoding a sequence specific DNA binding polypeptide or domain, a polynucleotide encoding a DNA endonuclease polypeptide or domain, a polynucleotide encoding a DNA-dependent DNA polymerase polypeptide or domain, a DNA encoded repair template and/or a guide nucleic acid when comprised in an expression cassette may each be operably linked to a separate promoter or they may be operably linked to two or more promoters in any combination. In some embodiments, an expression cassette and/or the polynucleotides comprised therein in may be optimized for expression in a plant.

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to a gene encoding a sequence specific DNA binding polypeptide, a gene encoding a DNA endonuclease polypeptide, a gene encoding a DNA-dependent DNA polymerase, and the like, may be native to a host cell, or may be native to another source (e.g., foreign or heterologous to the promoter, to a gene encoding a sequence specific DNA binding polypeptide, a gene encoding a DNA endonuclease polypeptide, a gene encoding a DNA-dependent DNA polymerase, and the like, to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct comprising the nucleotide sequence(s) to be transferred, delivered, or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid construct or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As a non-limiting example, a target nucleic acid may be contacted with a sequence specific DNA binding domain, a DNA endonuclease, a DNA-dependent DNA polymerase, a DNA encoded repair template, a guide nucleic acid and/or a nucleic acid construct/expression cassette encoding/comprising the same, under conditions whereby the sequence specific DNA binding protein, DNA endonuclease, and the DNA-dependent DNA polymerase are expressed and the sequence specific DNA binding protein binds to the target nucleic acid, and the DNA-dependent DNA polymerase is either fused to the sequence specific DNA binding protein or is recruited to the sequence specific DNA binding protein (e.g., via a peptide tag fused to the sequence specific DNA binding protein and an affinity polypeptide (e.g., a polypeptide capable of binding the peptide tag) fused to the DNA-dependent DNA polymerase), thereby recruiting the DNA-dependent DNA polymerase to the vicinity of the target nucleic acid), thereby modifying the target nucleic acid.

As used herein, "modifying" or "modification" in reference to a target nucleic acid includes editing (e.g., mutating), covalent modification, exchanging/substituting nucleic acids/nucleotide bases, deleting, cleaving, nicking, and/or transcriptional control of a target nucleic acid. In some embodiments, a modification may include an indel of any size and/or a single base change (SNP) of any type.

"Introducing," "introduce," "introduced" (and grammatical variations thereof) in the context of a polynucleotide of interest means presenting a nucleotide sequence of interest (e.g., polynucleotide, a nucleic acid construct, and/or a guide nucleic acid) to a host organism or cell of said organism (e.g., host cell; e.g., a plant cell, animal cell, bacterial cell, fungal cell) in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism may be stably transformed with a polynucleotide/nucleic acid molecule of the invention. In some embodiments, a host cell or host organism may be transiently transformed with a nucleic acid construct of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes encoding, for example, a sequence specific DNA binding polypeptide or domain, a DNA endonuclease polypeptide or domain, a DNA-dependent DNA polymerase polypeptide or domain, etc.) may be transiently introduced into a cell with a guide nucleic acid and as such, no DNA maintained in the cell.

A nucleic acid construct of the invention can be introduced into a cell by any method known to those of skill in the art. In some embodiments of the invention, transformation of a cell comprises nuclear transformation. In other embodiments, transformation of a cell comprises plastid transformation (e.g., chloroplast transformation). In still further embodiments, the recombinant nucleic acid construct of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)).

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, and/or in separate transformation events, or, alternatively, where relevant, a nucleotide sequence can be incorporated into a plant, for example, as part of a breeding protocol.

Endogenous DSB repair through homologous recombination is difficult to manipulate and faces competition from error-prone non-homologous end joining pathways. In this invention, templated editing is improved bypassing steps of DSB that reduce the efficiency of repair. Utilizing novel combinations of polypeptides and nucleic acids and protein-protein fusion and non-covalent recruitments, we deliver high fidelity, processive or distributive DNA polymerases and a repair template, sequence-specifically to the target site, which is cleaved or nicked by either a sequence specific DNA binding domain that comprises DNA endonuclease or nickase activity or by a DNA endonuclease having endonuclease or nickase activity, which is provided in combination with the sequence specific DNA binding protein. Using the DNA encoded repair template and the target DNA having a single stranded nick or a double strand break as primer, the DNA dependent DNA polymerase can initiate DNA synthesis immediately and copy the desired mutation or large insertion fragment into the target site. This invention can be used to generate specific changes of a single or a few bases, deletion of defined genome sequence, or insertion of small or large fragments.

Multiple DNA recruitment strategies may be used as described herein for improving delivery of a repair template to the target including, for example, HUH-tag, DNA aptamer, msDNA of bacterial retron and/or T-DNA recruitment. One specific example for improving template availability is the use of PCV, a type of HUH-tag. PCV domain can be, for example, fused to a CRISPR-Cas effector protein having nickase or endonuclease activity, which creates nick or break in target nucleic acid. A sequence of PCV recognition site is included in the repair template, so the repair template can be recruited to the target site through its ability to interact with the corresponding PCV domain. The recruitment can occur at roughly the same time a nick or break is created in the target nucleic acid by the CRISPR-Cas effector protein.

DNA-dependent DNA polymerase is an important component for carrying out homologous recombination. The 3' end of target nucleic acid comprising a single stranded nick or a double strand break can anneal to a DNA encoded repair template and serve as a primer for DNA-dependent DNA polymerase to initiate strand synthesis, thereby copying genetic information from the repair template to the target site. In some embodiments, a DNA polymerase for use in this process may have high fidelity to prevent errors, and/or may exhibit high processivity to ensure long template being copied before DNA polymerase dissociates. In the context of association of a DNA-dependent DNA polymerase with a CRISPR-Cas effector polypeptide/complex that binds the target nucleic acid, it may be advantageous to have a DNA-dependent DNA polymerase with a distributive functionality to maximize the efficiency of template incorporation into the target. To accelerate this step, a DNA-dependent DNA polymerase with high fidelity plus processive and distributive profiles can be recruited either by protein fusion or non-covalent interaction with, for example, a sequence-specific DNA binding domain and DNA endonuclease (e.g., a CRISPR-Cas effector protein). Direct fusion can be done via optimized linker architecture. Non-covalent recruitment strategies can include recruitment via a guide nucleic acid (e.g., an RNA recruiting motif, e.g., MS2 loop) or recruitment via a sequence specific DNA binding domain (e.g., a CRISPR-Cas effector protein) and/or DNA endonuclease (e.g., via a peptide tag, e.g., antibody/epitope interaction, e.g., SunTag). Of course, the invention is not limited by these specific recruitment techniques and any other known or later developed protein-protein or nucleic acid-protein recruitment techniques now known or later developed may be used to carry out this invention.

The present inventors have developed compositions and methods that provide improved templated editing. Using combinations of protein-protein fusion and non-covalent recruitments, high fidelity, processive or distributive DNA polymerases are delivered sequence-specifically to a target site, which site may be cleaved or nicked by, for example, a CRISPR endonuclease or nickase. The DNA dependent DNA polymerase can initiate DNA synthesis immediately and copy the desired mutation or large insertion fragment into the target site by using the target DNA having a single stranded nick or a double strand break as a primer in combination with a DNA encoded repair template. The invention described herein and variations thereof can be utilized to make specific changes of a single or a few bases, deletion of defined genome sequence, or insertion of small or large fragments.

Thus, in some embodiments, the present invention provides a complex (e.g., a first complex) comprising: (a) a sequence-specific DNA binding protein (e.g., a first sequence-specific DNA binding protein) that is capable of binding to a site (e.g., a first site) on a target nucleic acid; and (b) a DNA-dependent DNA polymerase (e.g., a first DNA-dependent DNA polymerase). In some embodiments, the complex may comprise a DNA encoded repair template (e.g., a first DNA encoded repair template). In some embodiments, the complex may comprise a DNA endonuclease (e.g., a first DNA endonuclease), wherein the DNA endonuclease is capable of introducing a single stranded nick or a double strand break or wherein the sequence-specific DNA binding protein that is capable of binding to the site (e.g., the first site) on a target nucleic acid also comprises endonuclease activity that is capable of introducing a single stranded nick or a double strand break (e.g., a CRISPR-Cas effector protein).

In some embodiments, the present invention provides a complex (e.g., a first complex) comprising: (a) a sequence-specific DNA binding protein (e.g., a first sequence-specific DNA binding protein) that is capable of binding to a site (e.g., a first site) on a target nucleic acid and comprises endonuclease activity that is capable of introducing a single stranded nick or a double strand break; (b) a first DNA-dependent DNA polymerase; and (c) a DNA encoded repair template (e.g., a first DNA encoded repair template).

In some embodiments, the present invention provides a complex (e.g., a first complex) comprising: (a) a sequence-specific DNA binding protein (e.g., a first sequence-specific DNA binding protein) that is capable of binding to a site (e.g., a first site) on a target nucleic acid; (b) a DNA-dependent DNA polymerase (e.g., a first DNA-dependent DNA polymerase); (c) a DNA endonuclease (e.g., a first DNA endonuclease); and (d) a DNA encoded repair template (e.g., a first DNA encoded repair template).

In some embodiments, a sequence-specific DNA binding protein of a complex (e.g., a first complex) of the invention may be from a polynucleotide-guided endonuclease, a CRISPR-Cas effector protein, a protein-guided endonuclease (e.g., a zinc finger nuclease), a transcription activator-like effector nuclease (TALEN) and/or an Argonaute protein. In some embodiments, a sequence-specific DNA binding protein may be from a CRISPR-Cas polypeptide, a zinc finger, a transcription activator-like effector and/or an Argonaute protein.

In some embodiments, a DNA endonuclease or DNA endonuclease activity useful with a complex (e.g., a first complex) of the present invention may be or be from an endonuclease (e.g., Fok1), a polynucleotide-guided endonuclease, a CRISPR-Cas effector protein, a protein-guided endonuclease (e.g., a zinc finger nuclease), and/or a transcription activator-like effector nuclease (TALEN). In some embodiments, a DNA endonuclease may be a nuclease or a nickase or a DNA endonuclease activity may be a nuclease activity or a nickase activity.

In some embodiments, a sequence-specific DNA binding protein may be fused to a DNA-dependent DNA polymerase, optionally via a linker. In some embodiments, a sequence-specific DNA binding protein may be fused at its N-terminus to a DNA-dependent DNA polymerase. In some embodiments, a sequence-specific DNA binding protein may be fused at its C-terminus to a DNA-dependent DNA polymerase.

The present invention further provides an engineered (modified) DNA-dependent DNA polymerase fused to an affinity polypeptide that is capable of interacting with a peptide tag or an RNA recruiting motif. In some embodiments, an engineered DNA-dependent DNA polymerase of the invention may comprise a DNA-dependent DNA polymerase fused to a sequence non-specific DNA binding domain, optionally wherein the sequence non-specific DNA binding domain may be a sequence-nonspecific dsDNA binding protein from Sso7d from *Sulfolobus solfataricus*. An engineered DNA-dependent DNA polymerase of the invention may exhibit increased processivity, increased fidelity, increased affinity, increased sequence specificity, decreased sequence specificity and/or increased cooperativity as compared to the same DNA-dependent DNA polymerase that is not engineered as described herein. In some embodiments, the engineered DNA-dependent DNA polymerase may be modified to reduce or eliminate at least one of 5'→3'-polymerase activity, 3'→5' exonuclease activity, 5'→3' exonuclease activity, and/or 5'→3' RNA-dependent DNA polymerase activity. Thus an engineered DNA-dependent DNA polymerase may not comprise at least one activity of 5'→3'-polymerase activity, 3'→5' exonuclease activity, 5'→3' exonuclease activity, and/or 5'→3' RNA-dependent DNA polymerase activity In some embodiments, a sequence-specific DNA binding protein (e.g., a first sequence-specific DNA binding protein) may be fused to a peptide tag and a DNA-dependent DNA polymerase (e.g., a first DNA-dependent DNA polymerase) may be fused to an affinity polypeptide that is capable of binding the peptide tag, wherein the DNA-dependent DNA polymerase may be recruited to the sequence-specific DNA binding protein that is fused to the peptide tag (and to a target nucleic acid to which the sequence-specific DNA binding protein may be bound). In some embodiments, a DNA-dependent DNA polymerase (e.g., a first sequence-specific DNA binding protein) may be fused to a peptide tag and a sequence-specific DNA binding protein (e.g., a first sequence-specific DNA binding protein) may be fused to an affinity polypeptide that is capable of binding the peptide tag, thereby recruiting the DNA-dependent DNA polymerase to the sequence-specific DNA binding protein that is fused to the affinity polypeptide and to a target nucleic acid to which the sequence-specific DNA binding protein is bound.

A complex of the invention may further comprise a guide nucleic acid (e.g., a CRISPR nucleic acid, crRNA, crDNA). A guide nucleic acid may be used in combination with a CRISPR-Cas effector protein, which, in some embodiments, may comprise endonuclease activity or nickase activity. In some embodiments, endonuclease or nickase activity of a sequence-specific DNA binding protein may be from, for example, a polynucleotide-guided endonuclease, a CRISPR-Cas effector protein, a protein-guided endonuclease (e.g., a zinc finger nuclease), and/or a transcription activator-like effector nuclease (TALEN).

In some embodiments, a guide nucleic acid may be linked to a RNA-recruiting motif and a DNA-dependent DNA polymerase may be fused to an affinity polypeptide that is capable of binding the RNA recruiting motif. In some embodiments, an RNA recruiting motif may be linked to the 5' end or to the 3' end of the CRISPR nucleic acid (e.g., a recruiting crRNA, a recruiting crDNA).

In some embodiments, a DNA encoded repair template may be recruited to a target nucleic acid by linking the DNA encoded repair template to a guide nucleic acid that comprises a spacer having complementarity to the target nucleic acid.

The present invention may provide a further complex (e.g., a second complex), the complex comprising: (a) a sequence-specific DNA binding protein (e.g., a second sequence-specific DNA binding protein) that is capable of binding to a second site on a target nucleic acid; and (b) a DNA-encoded repair template (e.g., a first or a second DNA-encoded repair template). In some embodiments, the sequence-specific DNA binding protein may be from a polynucleotide-guided endonuclease, a CRISPR-Cas effector protein, a protein-guided endonuclease (e.g., a zinc finger nuclease), a transcription activator-like effector nuclease (TALEN) and/or an Argonaute protein. In some embodiments, the complex (e.g., second complex) may further comprise a DNA endonuclease (e.g., a second DNA endonuclease), wherein the DNA endonuclease is capable of introducing a single stranded nick or a double strand break into a target nucleic acid. In some embodiments, the DNA endonuclease may be from polynucleotide-guided endonuclease, a CRISPR-Cas effector protein, a protein-guided endonuclease (e.g., a zinc finger nuclease), a transcription activator-like effector nuclease (TALEN). In some embodiments, a sequence-specific DNA binding protein of the second complex that is capable of binding to a second site on a target nucleic acid may further comprise endonuclease activity that is capable of introducing a single stranded nick or a double strand break in a target nucleic acid. In some embodiments, the sequence-specific DNA binding protein (e.g., the second sequence-specific DNA binding protein) that further comprises endonuclease activity may be a polynucleotide-guided endonuclease, a CRISPR-Cas effector protein, a protein-guided endonuclease (e.g., a zinc finger nuclease), or a transcription activator-like effector nuclease (TALEN)).

In some embodiments, a DNA-encoded repair template may be linked to a DNA recruiting motif and the sequence-specific DNA binding protein may be fused to an affinity polypeptide that is capable of interacting with the DNA recruiting motif, optionally wherein the DNA recruiting motif/affinity polypeptide comprises a HUH-tag, DNA aptamer, msDNA of bacterial retron or antibody/epitope pair (e.g., T-DNA recruitment). In some embodiments, a sequence-specific DNA binding protein may be fused to a Porcine Circovirus 2 (PCV) Rep protein and the DNA template comprises a PCV recognition site. In some embodiments, a sequence-specific DNA binding protein may be fused at its N-terminus to the PCV Rep protein. In some embodiments, a sequence-specific DNA binding protein may be fused at its C-terminus to the PCV Rep protein. Non-limiting examples of HUH-Tags and their corresponding recognitions sequences that may be useful with this invention are provided in Table 1.

TABLE 1

HUH-Tags and recognitions sequences

| HUH-tag | recognition sequence |
|---|---|
| porcine circovirus 2 Rep protein | AAGTATTACCAGAAA SEQ ID NO: 40 |

TABLE 1-continued

HUH-Tags and recognitions sequences

| HUH-tag | recognition sequence |
|---|---|
| duck circovirus Rep protein | AAGTATTACCAGAAA SEQ ID NO: 41 |
| fava bean necrosis yellow virus Rep protein | AAGTATTACCAGAAA SEQ ID NO: 42 |
| RepB *Streptococcus agalactiae* | TGCTTCCGTACTACGACCCCCCA SEQ ID NO: 43 |
| RepB *Fructobacillus tropaeoli* | TGCTTCCGTACTACGACCCCCCA SEQ ID NO: 44 |
| conjugation protein TraI *Escherichia coli* | TTTGCGTGGGGTGTGGTGCTTT SEQ ID NO: 45 |
| mobilization protein A *Escherichia coli* | CCAGTTTCTCGAAGAGAAACCGGTAAGTGCACCCTCCC SEQ ID NO: 46 |
| nicking enzyme *Staphylococcus aureus* | ACGCGAACGGAACGTTCGCATAAGTGCGCCCTTACGGGATTTAAC SEQ ID NO: 47 |

In some embodiments, a DNA encoded repair template may be recruited to a target nucleic acid by integrating the DNA encoded repair template into a T-DNA sequence that interacts with an *Agrobacterium* effector protein (e.g., an *Agrobacterium* virulence polypeptide, optionally, virD2 and/or virE2), wherein the sequence specific DNA binding protein, for example, may be recruited to the *Agrobacterium* effector protein, thereby recruiting the DNA encoded repair template to the sequence specific DNA binding protein and to the target nucleic acid that the sequence specific DNA binding protein binds. As an example, one or more epitope tags may be fused to the sequence specific DNA binding protein and an antibody that recognizes the epitope tag(s) may be fused to the *Agrobacterium* effector protein, thereby enabling the sequence specific DNA binding protein and the *Agrobacterium* effector protein to interact in the plant cell. Any T-DNA sequence associated with the *Agrobacterium* effector protein would be recruited to the target nucleic acid by the action of the sequence specific DNA binding protein.

In some embodiments, a DNA encoded repair template may be recruited to a target nucleic acid by attachment of a DNA aptamer to the DNA encoded repair template. A DNA aptamer is a sequence of DNA that can bind to a specific target with high affinity due to its unique secondary structure. DNA aptamer guided gene targeting has been demonstrated for endonuclease I-SceI mediated gene targeting in human and yeast system. A pool of candidate DNA aptamers may be screened by capillary electrophoresis for affinity with specific CRIPSR protein (Cas9, Cpf1, etc). DNA aptamers with the highest affinity to the selected CRISPR nuclease protein will be attached to single strand DNA template to guide the DNA template to the CRISPR protein target locus.

In some embodiments, the repair template can be expressed as msDNA from a bacterial retron scaffold attached to guide RNA. Bacterial retrons are bacterial elements that encode a reverse transcriptase which recognize a specific part of transcribed retron genome and use it as template to produce multiple copies of single strand DNA (msDNA). The msDNA remains tethered to the RNA template. A retron RNA scaffold sequence can be added to CRISPR guide RNA scaffold as an extension with part of retron genome replaced with desired repair template for gene editing. Expression of the template as an msDNA tethered to the guide RNA scaffold extension enables delivery of multiple copies of repair template to break sites at the same time the break been made. This system has been demonstrated in yeast, but not in mammalian or plant systems. Exemplary bacterial retrons useful with this invention are provided in Table 2.

TABLE 2

Examples of bacterial retrons

| Retron | Retron Reverse Transcriptase | Retron scaffold |
|---|---|---|
| ec67 | atgacaaaaacatctaaacttgacgcacttagggctgctacttcacgtgaagacttgg ctaaaattttagatattaagttggtatttttaactaacgttctatatagaatcggctcgg ataatcaatacactcaatttacaataccgaagaaaggaaaagggtaaggactatttctg cacctacagaccggttgaaggacatccaacgaagaatatgtgacttactttctgattgt agagatgagatctttgctataaggaaaattagtaacaactattcctttggttttgagagg ggaaaatcaataatcctaaatgcttataagcatagaggcaaacaaataatattaaatat agatcttaaggattttttttgaaagctttaattttggacgagttagaggatattttctttc caatcaggattttttattaaatcctgtggtggcaacgacacttgcaaaagctgcatgcta taatggaaccctccccaaggaagtccatgttctcctattatctcaaatctaatttgcaa tattatggatatgagattagctaagctggctaaaaaatatggatgtacttatagcagata tgctgatgatataacaatttctacaaataaaaatacatttccgttagaaatggctactgt gcaacctgaaggggttgttttgggaaaagttttggtaaaagaaatagaaaactctggatt | cacgcatgtaggcagatttgttg gttgtgaatcgcaaccagtggc cttaatggcaggaggaatcgcc tccctaaaatccttgattcagag ctatacggcaggtgtgctgtgcg aaggagtgcctgcatgcgt SEQ ID NO: 64 |

TABLE 2-continued

Examples of bacterial retrons

| Retron | Retron Reverse Transcriptase | Retron scaffold |
|---|---|---|
| | cgaaataaatgattcaaagactaggcttacgtataagacatcaaggcaagaagtaacg<br>ggacttacagttaacagaatcgttaatattgatagatgttattataaaaaaactcgggc<br>gttggcacatgctttgtatcgtacaggtgaatataaagtgccagatgaaatggtgtttt<br>agtttcaggaggtctggataaacttgaggggatgtttggttttattgatcaagttgataa<br>gtttaacaatataaagaaaaaactgaacaagcaacctgatagatatgtattgactaatg<br>cgactttgcatggttttaaattaaagttgaatgcgcgagaaaaagcatatagtaaattta<br>tttactataaattttttcatggcaacacctgtcctacgataattacagaagggaagactg<br>atcggatatatttgaaggctgctttgcattctttggagacatcatatcctgagttgttta<br>gagaaaaaacagatagtaaaaagaaagaaataaatcttaatatatttaaatctaatgaaa<br>agaccaaatatttttagatctttctgggggaactgcagatctgaaaaaatttgtagagc<br>gttataaaaataattatgcttcttattatggttctgttccaaaacagccagtgattatgg<br>ttcttgataatgatacaggtccaagcgatttacttaattttctgcgcaataaagttaaaa<br>gctgcccagacgatgtaactgaaatgagaaagatgaaatatattcatgttttctataatt<br>tatatatagttctcacaccattgagtccttccggcgaacaaacttcaatggaggatcttt<br>tccctaaagatatttagatatcaagattgatggtaagaaattcaacaaaaataatgatg<br>gagactcaaaaacggaatatgggaagcatatttttttccatgagggttgttagagataaaa<br>agcggaaaatagatttaaggcattttgttgtatttttgatgctataaaagatataaagg<br>aacattataaattaatgttaaatagctaa SEQ ID NO: 63 | |
| ec86 | atgaaatcgcatgatcgattgaggatcgtctttgctcagatccgccagaactggcgg<br>cttttgctcatgttatgcatgtgcatgaaaaccactgcataa SEQ ID NO: 65 | Atgcgcacccttagcgagagg<br>tttatcattaaggtcaacctctg<br>gatgttgtttcggcatcctgcat<br>tgaatctgagttactgtctgttt<br>tccttgttggaacggagagcatc<br>gcctgatgctctccgagccaacc<br>aggaaacccgttttttctgacgt<br>aagggtgcgca SEQ ID<br>NO: 66 |
| ec107 | Atggatgctacccggacaaccccttctggcgctcgatttgttcggctcgccgggctg<br>gagcgccgataaagaaatacagcgactgcatgcgctcagtaatcatgccggacgc<br>cattaccgacgcattattctttctaaacgccacggtggtcagcggctggtgttagccc<br>ctgattacttgctcaaaaccgtacagcgcaacattcttaagaacgtcctttcacaatttc<br>cgctttccccttttgctacagcctaccgaccaggttgcccaatcgtcagcaacgcgca<br>gccacactgccaacagccgcagatcctgaaactcgatatcgaaaacttttttcgatag<br>cattagctggttacaggtctggcgtgtgtttcgccaggcccagttgccacgtaatgtg<br>gtaaccatgctgacctggatttgttgttataacgacgcgttaccgcaggggggcacca<br>acttcgccagccatttccaatcttgtgatgcgccgtttttgtgaacgcataggggaatg<br>gtgtcaggctcggggaattacctacacccgctactgcgatgacatgaccttttcaggt<br>cacttcaatgcccgccaggttaaaaataaagtgtgcggattgttagcggagctgggc<br>ctgagcctcaataaacgcaaaggctgcctgatagctgcctgtaagcgccagcaagt<br>aaccggattgttgttaatcacaagccacagcttgcccgtgaagcgcgccgggcgc<br>tgcgtcaggaggtgcatttgtgccaaaaatatggcgttatttcgcatcttagtcatcgt<br>gtgaacttgatccttctggcgatctccacgcacaggcaacggcgtatctttatgctttg<br>cagggaagaataaaactggttattgcaaatcaaccctgaggatgaggcctttcaacag<br>gcgagagagagtgtaaagcgaatgctggttgcatggtaa SEQ ID NO: 67 | Cgccagcagtggcaatagcgt<br>ttccggccttttgtgccgggagg<br>gtcggcgagtcgctgacttaac<br>gccagtagtatgtccatatccc<br>aaagtcgcttcattgtacctgag<br>tacgcttcgcgtacgtcgcgctg<br>acgcgctcagtacagttacgcg<br>ccttcgggatggtttaatg<br>SEQ ID NO: 68 |
| mx162 | atgaccgccaggctggacccgttcgtccccgcagcttcgccgcaggccgtgccca<br>cgcccgagctcaccgctccgtcgtcagacgcggccgcgaagcgtgaagcccgcc<br>ggctcgcgcacgaagcgttgctcgtccgcgcgaaggccatcgacgaagcgggcg<br>gcgccgacgactgggtgcaggcgcagctcgtctccaagggcctgcgcggtggagg<br>acctggacttctccagcgcctccgagaaggacaagaaggcctggaaggagaaga<br>agaaggccgaggcaccgagcgccgcgcgctgaagcgtcaggcgcacgaggc<br>gtggaaggccacgcacgtgggccacctgggcgcgggcgtgcactgggcggagg<br>accgcctggccgacgcgttgacgtgccccaccgcgaggagcgcgccgggcc<br>aacggcctgacggagctggactcggcggaggcgctggccaaggcgctgggct<br>gagcgtgtccaagctgcgctggttcgcgttccaccgcgaggtggacacggccacg<br>cactacgtgagctggacgattccgaagcgggacggcagcaagcgcacgattacgt<br>ccccaagcctgagctgaaggcagcgcagcgctgggtgctgtccaacgtcgtgga<br>gcggctgccggtgcacggcgcggcgcacggcttcgtggcgggacgctccatcct<br>caccaacgcgctggccaccagggcgcggacgtggtggtgaaggtggacctcaa<br>ggacttcttcccctccgtcacctggcgccgggtgaagggcctgttgcgcaagggcg<br>gcctgcgggagggcacgtccacgctgctgtcgctgctctccacggaagcgcccgcg<br>ggaggcggtgcagttccggggcaagctgctgcacgtggccaagggcccgcgcg<br>cgctgccccagggcgcgcccacgtcgccgggcatcaccaacgcgctgtgcctga<br>agctggacaagcggctgtccgcgctcgcgaagcggctgggcttcacgtacacgcg<br>ctacgcggacgacctgaccttctcgtggacgaaggcgaagcagcccaagccgcg<br>gcggacgcagcgtccccggtggcggtgctgctgtctcgcgtgcaggaagtggtg<br>gaggcggagggcttccgcgtgcacccggacaagacgcgcgtggcgcgcaaggg<br>cacgcggcagcgggtgacggggctggtcgtgaatgcggcggcaaggacgcgc<br>cggcgccgagtcccgccgacgtggtgccagctccgcgccgccatccaca<br>accggaagaagggcaagccgggccgcgagggcgagtcgctggacgcagctcaa<br>gggcatggccgccttcatccacatgacggacccggccaagggccgcgccttcctg<br>gctcagctcacggagctggagtccacggcgagcgcggctccgcaggcggagtga<br>SEQ ID NO: 69 | agaggtccggagtgcatcagc<br>ctgagcgcctcgagcggcgga<br>gcggcgttgcgccgctccggtt<br>ggaatgcaggacactctccgca<br>aggtagcctgttcttggctctct<br>ccctcctaggcactacggccagg<br>gtgggtagcggagccaacgac<br>gcgaccgccgtttacccaccc<br>ggccgtagtgcctaggaggg<br>agagccggtgaggctaccgtg<br>ccccaggtaagatg SEQ<br>ID NO: 70 |

Examples of Chimeric guide nucleic acid sequence (guide DNA) designed to introduce templated editing in a human genome target FANCF01 include, but are not limited to: Repair template (bold) in embed in ec67 retron scaffold followed by single guide nucleic acid (sg nucleic acid) (italic lower case):

SEQ ID NO: 71
CACGCATGTAGGCAGATTTGTTGGTTGTGAATCGCAACCAGTGGCCTTA

ATGGCAGGAGGAATCGCCTCCAGAGTCGCCGTCTCCAAGGTGAAAGCGG

AAGTAGGGCCTTCGCGCACCTCATGGAATCCCTTCTGCAGCACCTAGAT

CGCTTTTCTGAACTCCTAGCAGTATCTAGCACTACCTACGTCAGCACCT

GGGACCCCGCGGTGTGCTGTGCGAAGGAGTGCCTGCATGCGTggaatcc cttctgcagcaccgttttagagctagaaatagcaagttaaaataaggct agtccgttatcaacttgaaaaagtggcaccgagtcggtgc Repair template (bold) in embed in ec86 retron scaffold followed by single guide nucleic acid (sg nucleic acid) (italic lower case):

SEQ ID NO: 72
ATGCGCACCCTTAGCGAGAGGTTTATCATTAAGGTCAACCTCTGGATGT

TGTTTCGGCATCCTGCATTGAATCTGAGTTACTGTCTGTTTTCCTAGAG

TCGCCGTCTCCAAGGTGAAAGCGGAAGTAGGGCCTTCGCGCACCTCATG

GAATCCCTTCTGCAGCACCTAGATCGCTTTTCTGAACTCCTAGCAGTAT

CTAGCACTACCTACGTCAGCACCTGGGACCCCGCCAGGAAACCCGTTTT

TTCTGACGTAAGGGTGCGCAggaatcccttctgcagcaccgttttagag ctagaaatagcaagttaaaataaggctagtccgttatcaacttgaaaaa gtggcaccgagtcggtgc Repair template (bold) in embed in ec107 retron scaffold followed by single guide nucleic acid (sg nucleic acid) (italic lower case):

SEQ ID NO: 73
GCCAGCAGTGGCAATAGCGTTTCCGGCCTTTTGTGCCGGGAGGGTCGGC

GAGTCGCTGACTTAACGCCAGTAGTATGTCCATATACCCAAGAGTCGCC

GTCTCCAAGGTGAAAGCGGAAGTAGGGCCTTCGCGCACCTCATGGAATC

CCTTCTGCAGCACCTAGATCGCTTTTCTGAACTCCTAGCAGTATCTAGC

ACTACCTACGTCAGCACCTGGGACCCCGCGGGATGGTTTAATGGTATTG

CCGCggaatcccttctgcagcaccgttttagagctagaaatagcaagtt aaaataaggctagtccgttatcaacttgaaaaagtggcaccgagtcggt gc Repair template (bold) in embed in mx162 retron scaffold followed by single guide nucleic acid (sg nucleic acid) (italic lower case):

SEQ ID NO: 74
AGAGGTCCGGAGTGCATCAGCCTGAGCGCCTCGAGCGGCGGAGCGGCGT

TGCGCCGCTCCGGTTGGAATGCAGGACACTCTCCGCAAGGTAGAGTCGC

-continued
CGTCTCCAAGGTGAAAGCGGAAGTAGGGCCTTCGCGCACCTCATGGAAT

CCCTTCTGCAGCACCTAGATCGCTTTTCTGAACTCCTAGCAGTATCTAG

CACTACCTACGTCAGCACCTGGGACCCCGCTGAGGCTACCGTGCCCCAG

GTAAGATGGTGGTGCTTTCCCGGggaatcccttctgcagcaccgtttta gagctagaaatagcaagttaaaataaggctagtccgttatcaacttgaa aaagtggcaccgagtcggtgc In some embodiments, a complex (e.g., a second complex) may further comprise a DNA-dependent DNA polymerase (e.g., a second DNA-dependent DNA polymerase).

In some embodiments, a complex (e.g., a second complex) may further comprise a guide nucleic acid, optionally wherein the guide nucleic acid may be linked to the DNA-encoded repair template (e.g., a first or a second DNA-encoded repair template).

In some embodiments, a third complex may be provided, the third complex comprising a sequence-specific DNA binding protein (e.g., a third sequence-specific DNA binding protein) that is cable of binding to a site (e.g., a third site) on a target nucleic acid that is on a different strand from the first site and second and a DNA endonuclease (e.g., a third DNA endonuclease) (e.g., a nickase that can generate a single strand break). In some embodiments, contacting the target nucleic acid with the third complex may boost the efficiency of repair by improving mismatch repair.

In some embodiments, the invention provides an RNA molecule, the RNA molecule comprising (a) a nucleic acid sequence that mediates interaction with a CRISPR-Cas effector protein; (b) a nucleic acid sequence that directs the CRISPR-Cas effector protein to a specific nucleic acid target site through a DNA-RNA interaction, and (c) a nucleic acid sequence that forms a stem loop structure (e.g., an RNA recruiting motif) that can interact with the engineered DNA-dependent DNA polymerase of the present invention. In some aspects, the invention provides an engineered DNA-dependent DNA polymerase of the invention complexed with the RNA molecule comprising (a) a nucleic acid sequence that mediates interaction with a CRISPR-Cas effector protein; (b) a nucleic acid sequence that directs the CRISPR-Cas effector protein to a specific nucleic acid target site through a DNA-RNA interaction, and (c) a nucleic acid sequence that forms a stem loop structure.

The present invention further provides polynucleotides encoding the complexes of the invention (e.g., first complex, second complex, and/or third complex) and/or encoding one or more of the sequence-specific DNA binding proteins (e.g., the first sequence-specific DNA binding protein, second sequence-specific DNA binding protein, and/or third sequence-specific DNA binding protein), DNA-dependent DNA polymerases (e.g., the first DNA-dependent DNA polymerase and/or second DNA-dependent DNA polymerase), DNA endonucleases (e.g., the first DNA endonuclease, second DNA endonuclease, and/or third DNA endonuclease) or comprising one or more of the DNA encoded repair templates (e.g., the first DNA encoded repair template and/or second DNA encoded repair template) or one or more guide nucleic acids (e.g., a first guide nucleic acid, second guide nucleic acid, and/or third guide nucleic acid, and the like). In some embodiments, a polynucleotide encoding an engineered DNA-dependent DNA polymerase of the invention is provided. Further provided herein are one or more expression cassettes and/or vectors comprising one or more of the polynucleotides of the invention.

In some embodiments of the invention, polynucleotides encoding sequence specific DNA binding domains, sequence non-specific DNA binding proteins, DNA endonucleases, DNA-dependent DNA polymerases, and/or expression cassettes and/or vectors comprising the same may be codon optimized for expression in a cell or an organism (e.g., an organism and/or a cell of, for example, an animal (e.g., a mammal, an insect, a fish, and the like), a plant (e.g., a dicot plant, a monocot plant), a bacterium, an archaeon, and the like). In some embodiments, an expression cassette comprising the polynucleotides of the invention/encoding the complexes/polypeptides of the invention may be codon optimized for expression in a dicot plant or for expression in a monocot plant.

The present invention further provides methods of using the compositions of the invention for modifying target nucleic acids. Accordingly, the invention provides methods for modifying a target nucleic, the methods comprising contacting a target nucleic acid or a cell comprising the target nucleic acid with a complex or system of the invention, polynucleotides encoding/comprising the same, or one or more of the components of a complex or system of the invention, and/or expression cassettes and/or vectors comprising the same. The methods may be carried out in an in vivo system (e.g., in a cell or in an organism) or in an in vitro system (e.g., cell free). The polypeptides and complexes of the invention, and polynucleotides/expression cassettes/vectors encoding the same may be used in a method for modifying a target nucleic acid, for example, in a plant or plant cell, the method comprising introducing one or more expression cassettes of the invention into a plant or plant cell, thereby modifying the target nucleic acid in the plant or plant cell to produce a plant or plant cell comprising the modified target nucleic acid. In some embodiments, the method may further comprise regenerating the plant cell comprising the modified target nucleic acid to produce a plant comprising the modified target nucleic acid.

In some embodiments, a method of modifying a target nucleic acid is provided, the method comprising: contacting the target nucleic acid with a complex of the invention (e.g., a first complex), thereby modifying the target nucleic acid. In some embodiments, the method may further comprise contacting the target nucleic acid with a second complex of the invention, thereby modifying the target nucleic acid. In some embodiments, the target nucleic acid may be further contacted with a third complex of the invention, thereby improving the repair efficiency of the modifying of the target nucleic acid.

In some embodiments, a method of modifying a target nucleic acid is provided, the method comprising contacting the target nucleic acid with: (a) a first sequence-specific DNA binding protein that is capable of binding to a first site on a target nucleic acid; (b) a first DNA-dependent DNA polymerase; (c) a first DNA endonuclease; and (d) a first DNA encoded repair template, thereby modifying the target nucleic acid. In some embodiments, the first sequence-specific DNA binding protein, the first DNA-dependent DNA polymerase, the first DNA endonuclease, and the first DNA encoded repair template may form a complex, wherein the complex may interact with the target nucleic acid.

In some embodiments, a method of modifying a target nucleic acid is provided, the method comprising contacting the target nucleic acid with: (a) a first sequence-specific DNA binding protein that is capable of binding to a first site on a target nucleic acid, wherein the first sequence-specific DNA binding protein comprises nickase activity or endonuclease activity that can introduce a single stranded nick or a double strand break; (b) a first DNA-dependent DNA polymerase; and (c) a first DNA encoded repair template, thereby modifying the target nucleic acid. In some embodiments, the first sequence-specific DNA binding protein comprising endonuclease activity, the first DNA-dependent DNA polymerase, and the first DNA encoded repair template may form a complex that is capable of interacting with the target nucleic acid. The endonuclease activity and/or nickase activity of the first sequence-specific DNA binding protein may be from, for example, a polynucleotide-guided endonuclease, a CRISPR-Cas effector protein, a protein-guided endonuclease (e.g., a zinc finger nuclease), and/or a transcription activator-like effector nuclease (TALEN). In some embodiments, the first sequence-specific DNA binding protein comprising endonuclease activity may be a polynucleotide-guided endonuclease, a CRISPR-Cas effector protein, a protein-guided endonuclease (e.g., a zinc finger nuclease), and/or a transcription activator-like effector nuclease (TALEN). A first sequence-specific DNA binding protein may be, for example, from a polynucleotide-guided endonuclease, a CRISPR-Cas effector protein, a protein-guided endonuclease (e.g., a zinc finger nuclease), a transcription activator-like effector nuclease (TALEN) and/or an Argonaute protein.

In some embodiments, a first sequence-specific DNA binding protein may be fused to a first DNA-dependent DNA polymerase, optionally via a linker. In some embodiments, a first sequence-specific DNA binding protein may be fused at its N-terminus to a first DNA-dependent DNA polymerase. In some embodiments, a first sequence-specific DNA binding protein may be fused at its C-terminus to a first DNA-dependent DNA polymerase. In some embodiments, a first sequence-specific DNA binding protein may be fused to a peptide tag and a first DNA-dependent DNA polymerase may be fused to an affinity polypeptide that is capable of binding the peptide tag, thereby recruiting the first DNA-dependent DNA polymerase to the first sequence-specific DNA binding protein that is fused to the peptide tag and to a target nucleic acid to which the sequence-specific DNA binding protein is bound and/or is capable of binding. In some embodiments, a first DNA-dependent DNA polymerase may be fused to a peptide tag and a first sequence-specific DNA binding protein may be fused to an affinity polypeptide that is capable of binding the peptide tag, thereby recruiting the first DNA-dependent DNA polymerase to the first sequence-specific DNA binding protein fused to the affinity polypeptide and to a target nucleic acid to which the sequence-specific DNA binding protein is bound and/or is capable of binding.

In some embodiments of the invention, a first sequence-specific DNA binding domain and/or a first DNA endonuclease may be or may be from a CRISPR-Cas effector protein, wherein the target nucleic acid may be contacted with a guide nucleic acid (e.g., a CRISPR nucleic acid, crRNA, crDNA) (e.g., a first guide nucleic acid) that directs the CRISPR-Cas effector protein to a specific nucleic acid target site through a DNA-RNA interaction. In some embodiments, a DNA encoded repair template (e.g., a first DNA encoded repair template) may be linked to the guide nucleic acid, thereby guiding the DNA encoded repair template to the target nucleic acid. In some embodiments, a guide nucleic acid may be linked to a RNA-recruiting motif and a DNA-dependent DNA polymerase (e.g., a first DNA-dependent DNA polymerase) may be fused to an affinity polypeptide that is capable of binding the RNA recruiting motif, thereby guiding the DNA-dependent DNA polymerase to the target nucleic acid. An RNA recruiting motif may be linked to the 5' end or to the 3' end of the guide nucleic acid (e.g., a recruiting crRNA, a recruiting crDNA).

In some embodiments, the target nucleic acid contacted with the first complex of the invention may be contacted with a second complex of the invention, the second complex comprising: (a) a second sequence-specific DNA binding protein that is capable of binding to a second site on the target nucleic acid; and (b) a DNA-encoded repair template (e.g., a first DNA-encoded repair template or a second DNA-encoded repair template). In some embodiments, wherein the target nucleic acid is further contacted with a second DNA endonuclease or the second complex further comprises a second DNA endonuclease, wherein the second DNA endonuclease is capable of introducing into the target nucleic acid a single stranded nick or a double strand break. Alternatively, or in addition, the second sequence-specific DNA binding protein of the second complex may comprise endonuclease activity itself that may introduce a single stranded nick or a double strand break into the target nucleic acid. In some embodiments, the second sequence-specific DNA binding protein that is capable of binding to a second site on the target nucleic acid, the second DNA-encoded repair template, and optionally the DNA endonuclease may form a complex that interacts with the second site on the target nucleic acid.

In some embodiments, a second sequence-specific DNA binding protein may be fused to a peptide tag and a second DNA endonuclease may be fused to an affinity polypeptide that is capable of binding the peptide tag, thereby recruiting the second DNA endonuclease to the second sequence-specific DNA binding protein that is fused to the peptide tag and to the second site on the target nucleic acid to which the second sequence-specific DNA binding protein binds and/or is capable of binding. In some embodiments, a second DNA endonuclease may be fused to a peptide tag and a second sequence-specific DNA binding protein may be fused to an affinity polypeptide that is capable of binding the peptide tag, thereby recruiting second DNA endonuclease to the second sequence-specific DNA binding protein that is fused to the affinity polypeptide and to the second site on the target nucleic acid to which the second sequence-specific DNA binding protein binds and/or is capable of binding.

In some embodiments, a DNA-encoded repair template of a second complex (e.g., a first DNA-encoded repair template or a second DNA-encoded repair template) may be linked to a DNA recruiting motif and a second sequence-specific DNA binding protein may be fused to an affinity polypeptide that is capable of interacting with the DNA recruiting motif, optionally wherein the DNA recruiting motif/affinity polypeptide comprises a HUH-tag (see, e.g., Table 1), DNA aptamer, msDNA of bacterial retron or a T-DNA recruitment, thereby recruiting the second DNA-encoded repair template to the sequence-specific DNA binding protein and the target nucleic acid to which the sequence-specific DNA binding protein can bind. In some embodiments, a second sequence-specific DNA binding protein may be fused, for example, to a Porcine Circovirus 2 (PCV) Rep protein and the DNA encoded repair template may comprise a PCV recognition site.

In some embodiments, a second sequence-specific DNA binding protein may be from and/or may be a polynucleotide-guided endonuclease, a CRISPR-Cas effector protein, a protein-guided endonuclease (e.g., a zinc finger nuclease), a transcription activator-like effector nuclease (TALEN) and/or an Argonaute protein. In some embodiments, a second DNA binding domain and/or second DNA endonuclease may be from and/or may be a CRISPR-Cas effector protein, wherein the target nucleic acid may be contacted with a guide nucleic acid (e.g., a CRISPR nucleic acid, crRNA, crDNA) (e.g., a second guide nucleic acid) that directs the CRISPR-Cas effector protein to a specific nucleic acid target site through a DNA-RNA interaction. In some embodiments, a DNA encoded repair template (e.g., a second DNA encoded repair template) may be linked to the guide nucleic acid, thereby guiding the DNA encoded repair template to the target nucleic acid. In some embodiments, the second guide nucleic acid may be linked to an RNA-recruiting motif and a second DNA endonuclease may be fused to an affinity polypeptide that is capable of binding the RNA recruiting motif, thereby the guide nucleic acid guides the second DNA endonuclease to the target nucleic acid. An RNA recruiting motif may be linked to the 5' end or to the 3' end of the guide nucleic acid (e.g., a recruiting crRNA, a recruiting crDNA).

In some embodiments, a target nucleic acid contacted with the second complex may be further contacted with a DNA-dependent DNA polymerase (e.g., a second DNA-dependent DNA polymerase). In some embodiments, the DNA-dependent DNA polymerase may be comprised in the second complex.

The methods of the invention may further comprise contacting the target nucleic acid with a third complex, the third complex comprising a third sequence-specific DNA binding protein that is cable of binding to a third site on the target nucleic acid that is on a different strand from the first site and the second site, wherein the third sequence-specific DNA binding protein comprises nuclease or nickase activity, thereby improving the repair efficiency of the modifying of the target nucleic acid.

In some embodiments, the present invention provides a system for modifying a target nucleic acid comprising the first complex of the invention, a polynucleotide encoding the same, and/or the expression cassette or vector comprising the polynucleotide, wherein (a) the first sequence-specific DNA binding protein comprising DNA endonuclease activity binds to a first site on the target nucleic acid; (b) the first DNA-dependent DNA polymerase is capable of interacting with the first sequence-specific DNA binding protein and is recruited to the first sequence specific DNA binding protein and to the first site on the target nucleic acid, and (c) (i) the first DNA encoded repair template is linked to a first guide nucleic acid that comprises a spacer sequence having substantial complementarity to the first site on the target nucleic acid, thereby guiding the first DNA encoded repair template to the first site on the target nucleic acid, or (c)(ii) the first DNA encoded repair template is capable of interacting with the first sequence-specific DNA binding protein or the first DNA-dependent DNA polymerase and is recruited to the first sequence-specific DNA binding protein or the first DNA-dependent DNA polymerase and to the first site on the target nucleic acid, thereby modifying the target nucleic acid.

In some embodiments, a system for modifying a target nucleic acid is provided, the system comprising the first complex of the invention, a polynucleotide encoding the same, and/or the expression cassette or vector comprising the polynucleotide, wherein (a) the first sequence-specific DNA binding protein binds to a first site on the target nucleic acid, (b) the first DNA endonuclease is capable of interacting with the first sequence specific DNA binding protein and/or a guide nucleic acid and is recruited to the first sequence specific DNA binding protein and to the first site on the target nucleic acid; (c) the first DNA-dependent DNA polymerase is capable of interacting with the first sequence specific DNA binding protein and/or a guide nucleic acid and is recruited to the first sequence specific DNA binding protein and to the first site on the target nucleic acid; and (d) (i) the first DNA encoded repair template is linked to a guide nucleic acid that comprises a spacer sequence having substantial complementarity to the first site on the target nucleic acid, thereby guiding the first DNA encoded repair template to the first site on the target nucleic acid, or (d)(ii) the first DNA encoded repair template is capable of interacting with the first sequence-specific DNA binding protein or the first DNA-dependent DNA polymerase and is recruited to the sequence-specific DNA binding protein or the first DNA-dependent DNA polymerase and to the first site on the target nucleic acid, thereby modifying the target nucleic acid.

In some embodiments, the system of the invention for modifying a target nucleic acid may further comprise the second complex of the invention, a polynucleotide encoding the same, and/or an expression cassette and/or vector comprising the polynucleotide, wherein the second sequence-specific DNA binding domain binds to a second site proximal to the first site on the target nucleic acid and the second DNA-encoded repair template is recruited to the second sequence-specific DNA binding protein (via covalent or non-covalent interactions), thereby modifying the target nucleic acid.

A DNA-dependent DNA polymerase useful with this invention (e.g., a first and/or a second DNA-dependent DNA polymerase) may be any DNA dependent DNA polymerase. DNA-dependent DNA polymerases are well known in the art, a non-limiting list of which may be found at the Polbase website (polbase.neb.com). In some embodiments, a DNA-dependent DNA polymerase useful with this invention may comprise 3'-5' exonuclease activity, 5'-3' exonuclease activity and/or 5'-3' RNA-dependent DNA polymerase activity. In some embodiments, a DNA-dependent DNA polymerase may be modified or engineered to remove one or more of 3'-5' exonuclease activity, 5'-3' exonuclease activity and 5'-3' RNA-dependent DNA polymerase activity.

In some embodiments, a DNA-dependent DNA polymerase (e.g., a first and/or a second DNA-dependent DNA polymerase) with improve delivery and/or activity may be provided, the DNA-dependent DNA polymerase comprising a Klenow fragment or sub-fragment thereof. As an example, the *E. coli* Klenow fragment may be used, which is about 68 kDa in size or 62% the molecular weight of full length (109 kDa) DNA polymerase I.

A DNA-dependent DNA polymerase may be improved for temperature-sensitivity, processivity, and template affinity via fusion to a DNA binding domain. Thus, for example, a DNA-dependent DNA polymerase (e.g., a first and/or the second DNA-dependent DNA polymerase) may be fused to a sequence non-specific DNA binding protein to provide a DNA-dependent DNA polymerase having improved temperature-sensitivity, processivity, and/or template affinity. In some embodiments, a sequence non-specific DNA binding protein may be a sequence-nonspecific dsDNA binding protein that may include, but is not limited to, Sso7d from *Sulfolobus solfataricus*.

A DNA-dependent DNA polymerase (e.g., a first DNA-dependent DNA polymerase and/or the second DNA-dependent DNA polymerase) may be from a human, a yeast, a bacterium, or a plant. In some embodiments, a DNA-dependent DNA polymerase useful with the invention can include but is not limited to a DNA polymerase ε (e.g., human and yeast), DNA polymerase δ, *E. coli* polymerase I, Phusion® DNA polymerase, Vent® DNA polymerase, Vent (exo−)® DNA polymerase, Deep Vent® DNA polymerase, Deep Vent (exo−)® DNA polymerase, 9° Nm™ DNA polymerase, Q5® DNA polymerase, Q5U® DNA polymerase, Pfu DNA polymerase, and/or Phire™ DNA polymerase. In some embodiments, a DNA-dependent DNA polymerase may be a human DNA-dependent DNA polymerase ε, plant DNA-dependent DNA polymerase ε and/or yeast DNA-dependent DNA polymerase ε (see, e.g., SEQ ID NOS:48-58).

In some embodiments, a DNA-dependent DNA polymerase useful with this invention may exhibit high fidelity and/or high processivity. Processivity relates to the number of nucleotides incorporated in a single binding event of the polymerase to the template. In some cases, DNA-dependent DNA polymerases can have a processivity of more than 100 kb (e.g., about 100, 110, 120, 130, 140, 150, 160, 170, 180, 190, 200 kb or more, and any range or value therein). In some embodiments, a DNA-dependent DNA polymerase may exhibit a high distributive profile. Thus, a DNA-dependent DNA polymerase may be a high-fidelity DNA-dependent DNA polymerase and/or a high processivity DNA-dependent DNA polymerase. In some embodiments, a DNA-dependent DNA polymerase may be a distributive polymerase (e.g., a low processivity polymerase) or may be a DNA-dependent DNA polymerase having a high distributive profile.

A DNA-dependent DNA polymerase useful with the invention (e.g., the first DNA-dependent DNA polymerase and/or the second DNA-dependent DNA polymerase) may be the engineered DNA-dependent DNA polymerase of the present invention.

In some embodiments, a sequence-specific DNA binding protein (e.g., a first sequence-specific DNA binding protein, second sequence-specific DNA binding protein and/or third sequence-specific DNA binding protein) may be from a polynucleotide-guided endonuclease, a CRISPR-Cas effector protein, a protein-guided endonuclease (e.g., a zinc finger nuclease), a transcription activator-like effector nuclease (TALEN) and/or an Argonaute protein. In some embodiments, a sequence-specific DNA binding protein may comprise endonuclease or nickase activity and may be a polynucleotide-guided endonuclease, a CRISPR-Cas effector protein, a protein-guided endonuclease (e.g., a zinc finger nuclease), and/or a transcription activator-like effector nuclease (TALEN).

A DNA endonuclease (e.g., a first DNA endonuclease, second DNA endonuclease, and/or third DNA endonuclease) may be a nuclease and/or a nickase (capable of generating a double strand break or a single strand break in a nucleic acid, respectively). In some embodiments, a DNA endonuclease (e.g., a first DNA endonuclease, second DNA endonuclease, and/or third DNA endonuclease) may be an endonuclease (e.g., Fok1, or other similar endonuclease domain), a polynucleotide-guided endonuclease, a CRISPR-Cas effector protein, a protein-guided endonuclease (e.g., a zinc finger nuclease), and/or a transcription activator-like effector nuclease (TALEN).

In some embodiments, a sequence-specific DNA binding domain (e.g., a first sequence-specific DNA binding protein, second sequence-specific DNA binding protein and/or third sequence-specific DNA binding protein) and/or DNA endonuclease (e.g., a first DNA endonuclease, second DNA endonuclease and/or third DNA endonuclease) may be a CRISPR-Cas effector protein, optionally wherein the CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

Nonlimiting examples of a CRISPR-Cas effector protein can include a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site may have impaired activity or reduced activity as compared to the same CRISPR-Cas effector protein without the mutation. In some embodiments, a mutation in the nuclease active cite results in a CRISPR-Cas effector protein having nickase activity (e.g., Cas9n)

A CRISPR Cas9 effector protein or CRISPR Cas9 effector domain useful with this invention may be any known or later identified Cas9 polypeptide. In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. (See, e.g., SEQ ID NOs:59-62).

Cas12a is a Type V Clustered Regularly Interspaced Short Palindromic Repeats (CRISPR)-Cas nuclease. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity.

In some embodiments, a peptide tag (e.g., an epitope, a peptide repeat unit) useful with this invention for recruiting polypeptides to selected locations (e.g., target nucleic acid, site on a target nucleic acid) may comprise 1 or 2 or more copies of a peptide tag (epitope, multimerized epitope) (e.g., 1, 2, 3, 4, 5, 6, 7, 8, 9, 10, 11, 12, 13, 14, 15, 16, 17, 18, 19, 20, 21, 22, 23, 24, 25 or more copies (repeat units). In some embodiments, a peptide tag useful with this invention can include, but is not limited to, a GCN4 peptide tag (e.g., Sun-Tag) (see, e.g., SEQ ID NOs:23-24), a c-Myc affinity tag, an HA affinity tag, a His affinity tag, an S affinity tag, a methionine-His affinity tag, an RGD-His affinity tag, a FLAG octapeptide, a strep tag or strep tag 11, a V5 tag, and/or a VSV-G epitope. In some embodiments, the peptide tag may be a GCN4 peptide tag. In some embodiments, a peptide tag may comprise two or more copies of the peptide tag (a peptide repeat; e.g., two or more tandem copies; e.g., tandem copies of GCN4).

In some embodiments, an affinity polypeptide capable of binding a peptide tag can include, but is not limited to, an antibody, optionally a scFv antibody that is capable of binding a peptide tag (e.g., a GCN4 peptide tag (see, e.g., SEQ ID NO:25), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope), an affibody, an anticalin, a monobody, and/or a DARPin, each of which are capable of binding a peptide tag (e.g., a GCN4 peptide tag, a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope).

In some embodiments of the invention, a guide nucleic acid (CRISPR nucleic acid, crRNA, crDNA) may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs, whereby the guide nucleic acid linked to one or more RNA recruiting motifs may be used to recruit one or more polypeptides that are fused to an affinity polypeptide that is capable of interacting with/binding an RNA recruiting motif linked to the guide.

In some embodiments, an RNA recruiting motif and affinity polypeptide capable of interacting with the RNA recruiting motif (e.g., a corresponding affinity polypeptide) may include, but is not limited to, a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein and/or a synthetic RNA-aptamer and the aptamer ligand as the corresponding affinity polypeptide (see, e.g., SEQ ID NOs:26-36). In some embodiments, an RNA recruiting motif and its corresponding affinity polypeptide useful with the invention may be an MS2 phage operator stem-loop and the affinity polypeptide MS2 Coat Protein (MCP), and/or a PUF binding site (PBS) and the affinity polypeptide Pumilio/fem-3 mRNA binding factor (PUF).

As described herein, polypeptides of the invention may be fusion proteins comprising one or more polypeptides linked to one another. In some embodiments, the fusion is via a linker. In some embodiments, a linker may be an amino acid or peptide linker. In some embodiments, a peptide linker may be about 2 to about 100 amino acids (residues) in length. In some embodiments, a peptide linker may be a GS linker.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof, a repeat of a Type II Cas9 CRISPR-Cas system, or fragment thereof, a repeat of a Type V C2c1 CRISPR Cas system, or a fragment thereof, a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer. In some embodiments, as described herein, a guide RNA may include a template for editing and a primer binding site. In some embodiments, a guide RNA may include a region or sequence on its 5' end or 3' end that is complementary to an editing template (a reverse transcriptase template), thereby recruiting the editing template to the target nucleic acid.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas nuclease encoded by the nucleic acid constructs of the invention that encode a base editor. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35(Web Server issue):W52-7). In some embodiments, a repeat sequence or portion thereof is linked at its 3' end to the 5' end of a spacer sequence, thereby forming a repeat-spacer sequence (e.g., guide RNA, crRNA).

In some embodiments, a repeat sequence comprises, consists essentially of, or consists of at least 10 nucleotides depending on the particular repeat and whether the guide RNA comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein; e.g., about). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g., protospacer). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 23 nucleotides in length.

In some embodiments, the 5' region of a spacer sequence of a guide RNA may be identical to a target DNA, while the 3' region of the spacer may be substantially complementary to the target DNA (e.g., Type V CRISPR-Cas), or the 3' region of a spacer sequence of a guide RNA may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of an organism's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide RNA of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome, an animal genome, a bacterial genome, a fungal genome, and the like). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide RNAs, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
5'-NNNNNNNNNNNNNNNNNNNN-3' RNA Spacer (SEQ ID NO: 37)
   ||||||||||||||||||||
3'AAANNNNNNNNNNNNNNNNNNNN-5' Target strand (SEQ ID NO: 38)
   ||||
5'TTTNNNNNNNNNNNNNNNNNNNN-3' Non-target strand (SEQ ID NO: 39
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST® searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors encoding the same but which have not been codon optimized for expression in a plant.

In some embodiments, the invention provides cells comprising one or more polynucleotides, guide nucleic acids, nucleic acid constructs, expression cassettes or vectors of the invention.

When used in combination with guide nucleic acids, the nucleic acid constructs of the invention of the invention may be used to modify a target nucleic acid. A target nucleic acid may be contacted with a nucleic acid construct of the invention prior to, concurrently with or after contacting the target nucleic acid with the guide nucleic acid. In some embodiments, the nucleic acid constructs of the invention and a guide nucleic acid may be comprised in the same expression cassette or vector and therefore, a target nucleic acid may be contacted concurrently with the nucleic acid constructs of the invention and guide nucleic acid. In some embodiments, the nucleic acid constructs of the invention and a guide nucleic acid may be in different expression cassettes or vectors and thus, a target nucleic acid may be contacted with the nucleic acid constructs of the invention prior to, concurrently with, or after contact with a guide nucleic acid.

A target nucleic acid of any organism or cell thereof may be modified (e.g., mutated, e.g., base edited, cleaved, nicked, etc.) using the nucleic acid constructs of the invention (e.g., the polypeptides and complexes (e.g., sequence specific DNA binding proteins, DNA-dependent DNA polymerases (e.g., engineered DNA-dependent DNA polymerases), DNA endonucleases, DNA encoded repair templates, guide nucleic acids, and the like) and polynucleotides, expression cassettes, and/or vectors encoding the same).

In some embodiments, a target nucleic acid of any plant or plant part may be modified (e.g., mutated, e.g., base edited, cleaved, nicked, etc.) using the nucleic acid constructs of the invention (e.g., the polypeptides and complexes (e.g., sequence specific DNA binding proteins, DNA-dependent DNA polymerases (e.g., engineered DNA-dependent DNA polymerases), DNA endonucleases, DNA encoded repair templates, guide nucleic acids, and the like) and polynucleotides, expression cassettes, and/or vectors encoding the same). Any plant (or groupings of plants, for example, into a genus or higher order classification) may be modified using the nucleic acid constructs of this invention including an angiosperm, a gymnosperm, a monocot, a dicot, a C3, C4, CAM plant, a bryophyte, a fern and/or fern ally, a microalgae, and/or a macroalgae. A plant and/or plant part useful with this invention may be a plant and/or plant part of any plant species/variety/cultivar. The term "plant part," as used herein, includes but is not limited to, embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell can be in the form of an isolated single cell or can be a cultured cell or can be a part of a higher-organized unit such as, for example, a plant tissue or a plant organ.

Non-limiting examples of plants useful with the present invention include turf grasses (e.g., bluegrass, bentgrass, ryegrass, fescue), feather reed grass, tufted hair grass, *miscanthus, arundo*, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, *papaya*, and lychee, a field crop plant such as clover, alfalfa, timothy, evening primrose, meadow foam, corn/maize (field, sweet, popcorn), hops, jojoba, buckwheat, safflower, *quinoa*, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis* indica, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, *eucalyptus*, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, sunflower, raspberry, blackberry, black raspberry and/or cherry. In some embodiments, the nucleic acid constructs of the invention and/or expression cassettes and/or vectors encoding the same may be used to modify a *Rubus* spp. (e.g., blackberry, black raspberry, boysenberry, loganberry, raspberry, e.g., caneberry), a *Vaccinium* spp. (e.g., cranberry), a *Ribes* spp. (e.g., gooseberry, currants (e.g., red currant, black currant)), or a Fragaria spp. (e.g., strawberry).

The present invention further comprises a kit or kits to carry out the methods of this invention. A kit of this invention can comprise reagents, buffers, and apparatus for mixing, measuring, sorting, labeling, etc, as well as instructions and the like as would be appropriate for modifying a target nucleic acid.

In some embodiments, the invention provides a kit comprising one or more nucleic acid constructs of the invention and/or expression cassettes and/or vectors comprising the same (e.g., comprising or encoding the polypeptides/complexes of the invention), with optional instructions for the use thereof. In some embodiments, a kit may further comprise a CRISPR-Cas guide nucleic acid (corresponding to the CRISPR-Cas nuclease encoded by the polynucleotide of the invention) and/or expression cassette and/or vector comprising the same. In some embodiments, the guide nucleic acid may be provided on the same expression cassette and/or vector as a nucleic acid construct of the invention. In some embodiments, the guide nucleic acid may be provided on a separate expression cassette or vector from that comprising the nucleic acid construct of the invention.

In some embodiments, the kit may further comprise a nucleic acid construct encoding a guide nucleic acid, wherein the construct comprises a cloning site for cloning of a nucleic acid sequence identical or complementary to a target nucleic acid sequence into backbone of the guide nucleic acid.

In some embodiments, a nucleic acid construct of the invention and/or an expression cassette and/or vector comprising the same, may further encode one or more selectable markers useful for identifying transformants (e.g., a nucleic acid encoding an antibiotic resistance gene, herbicide resistance gene, and the like).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. In Vivo Precision Templated Editing

Precision templated editing via fusion of DNA-dependent DNA polymerase to CRISPR protein in human cells can be demonstrated by co-transfecting a mix of components into the human cell line HEK293T. The mix of components includes a recipient plasmid, which contains a copy of mutant EGFP gene driven by CMV promoter; a single stranded DNA repair template containing the correcting sequence for the mutant EGFP flanked by 100-200 nt of homologous sequence to facilitate binding of template to the target site; a second plasmid that expresses fusion protein of a CRISPR protein (e.g., eCas9, nCas9 (D10A), or nCas9 (H840A)) and a DNA-dependent DNA polymerase of interest (e.g., Pol I from E. coli), where the fusion of DNA-dependent DNA polymerase to the N- or C-terminus CRISPR protein is via a linker; a third plasmid that expresses a guide RNA that targets the mutant EGFP sequence. As a control, the second plasmid will be replaced with a plasmid that expresses only the relative CRISPR protein. Desired templated editing events will be identified with flow cytometry, as the mutant EGFP is corrected to a functional copy of EGFP resulting in a green fluorescent phenotype.

Alternatively, the DNA repair template and the third plasmid that expresses guide RNA (or guide DNA) can be replaced by a plasmid that expresses a retron reverse transcriptase and chimeric guide RNA (or chimeric guide DNA) with retron scaffold containing the repair template.

Example 2. Precision Templated Editing Via CRISPR Protein and DNA-Dependent DNA Polymerase In Vitro Precision templated editing via CRISPR protein and DNA-dependent DNA polymerase in vitro. Commercially available DNA-dependent DNA polymerases are evaluated in vitro for their potential to conduct templated replacement of target DNA sequence from a nick introduced by CRISPR nickase nCas9 (H840A). Non-limiting examples of DNA-dependent DNA polymerases for evaluation include Q5 High-Fidelity DNA polymerase, Phusion® High-Fidelity DNA polymerase, Hemo Klen Taq DNA polymerase, Bst 2.0 DNA polymerase, Bsu DNA polymerase, Phi29 DNA polymerase, T7 DNA polymerase, Terminator™ DNA polymerase, Klenow Fragment (3'→5' exo−), Vent (exo−).

A 2 kb DNA fragment that contains a Cas9 binding site in the center of the fragment is used as the recipient, a single stranded DNA repair template of ~100nt is used to introduce mismatches to the recipient adjacent to the Cas9 target site. A mixture of recipient DNA, repair template, nCas9 (H840A) protein and guide RNA, and a DNA-dependent DNA polymerase is incubated at 37° C. or 25° C. Desired repair products containing mismatches can be digested by T7 endonuclease I, separated from other products and quantitated by gel electrophoresis.

Example 3. Precision Templated Editing Via MS2 RNA Loop Recruitment of DNA-Dependent DNA Polymerase to Target Site Precision templated editing via MS2 RNA loop recruitment of DNA-dependent DNA polymerase to target site can be demonstrated by co-transfecting a mix of components into the human cell line HEK293T. The mix of components includes a recipient plasmid that contains a copy of mutant EGFP gene driven by CMV promoter; a single stranded DNA repair template containing the correcting sequence for the mutant EGFP flanked by 100-200 nt of homologous sequence to facilitate binding of template to the target site; a second plasmid that expresses a DNA-dependent DNA polymerase of interest (e.g., Pol I from E. coli) with a MCP domain fused to its N-terminus via a linker; a third plasmid that expresses a guide RNA that targets the mutant EGFP sequence, where the guide nucleic acid scaffold is modified to contain MS2 stem loop that interacts with the MCP domain; and a fourth plasmid that expresses the CRISPR protein (e.g., eCas9, nCas9 (D10A), or nCas9 (H840A)). As a control, the second plasmid is omitted from the transfection mix. Desired templated editing events are identified with flow cytometry, as the mutant EGFP is corrected to a functional copy of EGFP. Alternatively, the DNA repair template and the third plasmid that expresses MS2 guide RNA can be replaced by a plasmid that expresses a retron reverse transcriptase and chimeric MS2 guide RNA with retron scaffold containing the repair template.

Example 4. Precision Templated Editing Via PUF-Binding Site (PBS) RNA Aptamer Recruitment of DNA-Dependent DNA Polymerase to Target Site Precision templated editing via PUF-binding site (PBS) RNA aptamer recruitment of DNA-dependent DNA polymerase to target site can be demonstrated by co-transfecting a mix of components into the human cell line HEK293T. The mix of components includes a recipient plasmid that contains a copy of mutant EGFP gene driven by CMV promoter; a single stranded DNA repair template containing the correcting sequence for the mutant EGFP flanked by 100-200 nt of homologous sequence to facilitate binding of template to the target site; a second plasmid that expresses a DNA-dependent DNA polymerase of interest (eg. Pol I from *E. coli*) with a PUF domain fused to its N-terminus via a linker; a third plasmid that expresses a guide RNA that targets the mutant EGFP sequence, where the guide RNA scaffold is modified to contain PUF-binding site that interacts with the PUF domain; and a fourth plasmid that expresses the CRISPR protein (eg. eCas9, nCas9 (D10A), or nCas9 (H840A)). As a control, the second plasmid is omitted from the transfection mix. Desired templated editing events are identified with flow cytometry, as the mutant EGFP is corrected to a functional copy of EGFP. Alternatively, the DNA repair template and the third plasmid that expresses guide RNA with PBS can be replaced by a plasmid that expresses a retron reverse transcriptase and chimeric guide RNA with PBS and retron scaffold containing the repair template.

Example 5. Precision Templated Editing Via PUF-Binding Site (PBS) RNA Aptamer Recruitment of DNA-Dependent DNA Polymerase to Target Site Precision templated editing via antibody/epitope recruitment of DNA-dependent DNA polymerase to target site can be demonstrated by co-transfecting a mix of components into the human cell line HEK293T. The mix of components includes: a recipient plasmid that contains a copy of mutant EGFP gene driven by CMV promoter; a single stranded DNA repair template containing the correcting sequence for the mutant EGFP flanked by 100-200 nt of homologous sequence to facilitate binding of template to the target site; a second plasmid that expresses a DNA-dependent DNA polymerase of interest (e.g., Pol I from *E. coli*) with a scFV domain fused to its N-terminus via a linker; a third plasmid that expresses a guide RNA that targets the mutant EGFP sequence; and a fourth plasmid that expresses the CRISPR protein (eg. eCas9, nCas9 (D10A), or nCas9 (H840A)), with 8 copies of GCN4 tags fused to its C-terminus. As a control, the second plasmid is omitted from the transfection mix. Desired templated editing events are identified with flow cytometry, as the mutant EGFP is corrected to a functional copy of EGFP. Alternatively, the DNA repair template and the third plasmid that expresses guide RNA can be replaced by a plasmid that expresses a retron reverse transcriptase and chimeric guide RNA with retron scaffold containing the repair template.

Example 6. Precision Templated Editing Via PUF-Binding Site (PBS) RNA Aptamer Recruitment of DNA-Dependent DNA Polymerase to Target Site Precision templated editing and site directed integration of long fragment via recruitment of DNA-dependent DNA polymerase in plants can be demonstrated by inserting an EGFP gene (~700 bp) in frame into an exon of a highly expressed gene (e.g., actin). In this experiment design, two T-DNAs will be co transformed into plant tissue. The first T-DNA contains a tool cassette that expressed CRISPR protein and DNA-dependent DNA polymerase in the correct architecture for efficient recruitment of the DNA-dependent DNA polymerase to target site, and a guide cassette that expresses guide RNA targeting the last exon of actin in the necessary configuration for protein recruitment. The second T-DNA contains repair template that encodes full length of EGFP and in-frame deletion of the stop codon in the targeted exon. This repair template is flanked by target sites recognized by the guide RNA expressed in the first T-DNA. Desired site directed integration of the EGFP results in expression of EGFP driving by the promoter of actin gene, while random integration does not yield EGFP express due to lack of promoter. Frequency of site directed integration can be quantitated by microscopy. Alternatively, the first T-DNA will only express the tool cassette, the second T-DNA will contain a retron reverse transcriptase cassette and a chimeric guide RNA cassette that encodes repair template in a retron scaffold attached to the guide RNA scaffold.

Example 7. Recruitment and Optimization of DNA-Dependent DNA Polymerase

As described in the above examples and more generally herein, many different methods may be used to recruit a DNA-dependent DNA polymerase to an editing site. For example, DNA-dependent DNA polymerase can be fused to the C- or N-terminus of CRISPR protein via a flexible linker, such as in the architecture of base editors. Alternatively, DNA-dependent DNA polymerase can be recruited to the target broken or nicked DNA via interaction with guide RNA (eg. MS2 loop) or CRISPR protein (eg. SunTag).

The function of a DNA-dependent DNA polymerase may be improved/optimized in any number of ways including, but not limited to, by removing 3'-5' exonuclease, 5'-3' exonuclease and/or 5'-3' RNA-dependent DNA polymerase activities. A DNA dependent DNA polymerase may further comprise the Klenow fragment or other sub-fragment of the protein. Klenow fragments or other active fragments may be useful for delivery or activity purposes. As an example, the *E. coli* Klenow fragment is 68 kDa or 62% the molecular weight of the full (109 kDa) DNA polymerase I.

Protein domain fusions to the DNA-dependent DNA polymerase enzyme can have significant effects on the temperature-sensitivity and processivity of the editing system. The DNA-dependent DNA polymerase enzyme can be improved for temperature-sensitivity, processivity, and template affinity through fusions to DNA binding domains (DBDs). These DBDs may have sequence specificity, non-specificity or sequence preferences. A range of affinity distributions may be beneficial to editing in different cellular and in vitro environments. Adding one or more DBD to the DNA-dependent DNA polymerase enzyme can result in increased affinity, increased or decreased sequence specificity, and/or promote cooperativity. One particular DBD known to increase processivity of DNA-dependent DNA polymerases is sequence-nonspecific dsDNA binding protein Sso7d, from *Sulfolobus solfataricus* (Wang, 2004). The dsDNA binding protein may be fused to either the C-terminus, N-terminus or flexible loop of the polymerase. Increased processivity can be demonstrated by inserting a larger reporter gene such as tdTomato (~1500 bp) in frame into an exon of a highly expressed gene (eg. actin). For example, two T-DNAs may be co transformed into plant tissue. The first T-DNA contains a tool cassette that expressed CRISPR protein and DNA-dependent DNA polymerase::ssDBD in the correct architecture for efficient recruitment of the DNA-dependent DNA polymerase:: ssDBD to target site, and a guide cassette that expresses guide RNA targeting the last exon of actin in the necessary configuration for protein recruitment. The second T-DNA contains repair template that encodes full length of tdTomato (or other reporter) and in-frame deletion of the stop codon in the targeted exon. This repair template is flanked by target sites recognized by the guide RNA expressed in the first T-DNA. Desired site directed integration of the tdTomato (or other reporter) results in expression of tdTomato driving by the promoter of actin gene, while random integration does not yield tdTomato express due to lack of promoter. Frequency of site directed integration can be quantitated by microscopy.

Example 8. CRISPR Polypeptides

This invention takes advantage of high processivity DNA-dependent DNA polymerase to rapidly initiate DNA synthesis primed by the 3' end of broken or nicked target DNA annealed to a provided repair template. Cas9 nuclease and nickase, and Cas12a nuclease and nickase and other CRISPR-Cas effector polypeptides can be used to produce 3'DNA target ends. Successful incorporation of repair templates, particularly templates having a large size, can depend on the ability of DNA-dependent DNA polymerase to move along the DNA templates away from the broken or nick site. It is possible that fusion directly to Cas9 protein, which may remain bound to cleaved or nicked DNA, may hinder the movement of DNA-dependent DNA polymerase. For that reason, a Cas9 with reduced binding affinity to DNA such as eCas9 (three amino acid mutations (K848A, K1003A, R1060A)[4]) nuclease or nickase may be used. Alternatively, non-covalent recruitment of the polymerase to the CRISPR complex may be used to maximize the opportunity for the polymerase to function without steric inhibition or mobility constraints. Several covalent and non-covalent recruitment strategies are described herein. For example, Cpf1/Cas12a has a longer seed sequence for stable binding (17-bp vs. 9-10-bp for Cas9) this indicates a lower affinity for target DNA (Jeon et. al, 2018), consistent with the lower off-target rate of editing found with Cpf1. The lower affinity, of Cpf1 relative to Cas9, for target DNA may be an advantage for polymerase fusions requiring mobility of the editing tool.

Example 9. Repair Template Recruitment

In human cell experiments, a repair template may be recruited through a number of different strategies, including, but not limited to: 1) interaction between PCV domain that is fused to CRISPR protein, and the PCV recognition sites embedded in the repair template; and 2) msDNA encoding repair template produced from chimeric retron-guide RNA scaffold and tethered to the guide RNA scaffold.

Example 10. Genome Editing in Plants

In editing of plants, various methods of repair template delivery can be used and these can vary depending on transformation method. For example, for *Agrobacterium*-mediated plant transformation, VirD2 or VirE2 mediated T-DNA recruitment may be used or msDNA, and for particle bombardment, a HUH tagging system and msDNA may be used.

Example 11. Editing in Human Cells

Eukaryotic HEK293T (ATCC CRL-3216) cells were cultured in Dulbecco's Modified Eagle's Medium plus Gluta-Max (ThermoFisher) supplemented with 10% (v/v) FBS (FBS), at 37° C. with 5% CO2. HEK293T cells were seeded on 48-well collagen-coated BioCoat plates (Corning). Cells were transfected at about 70% confluency. DNA was transfected using 1.5 µl of Lipofectamine 3000 (ThermoFisher Scientific) per well according to the manufacturer's protocol. RNP was transfected using 1.5 µl of RNAiMAX (ThermoFisher Scientific) per well according to the manufacturer's protocol. Genomic DNA from transfected cells were obtained after 3 days and precise editing was detected and quantified using high-throughput Illumina amplicon sequencing.

To test DNA polymerase-mediated elongation of DNA template, the following was done. HEK293T cells were first transfected with 1 ug of DNA encoding various DNA-dependent DNA polymerases including Klentaq, Therminator, Pfu-Ssod7, Klenow, *E. coli* polI, HU pol E (N-term), yeast pol E under constitutive CMV promoter (see, e.g., SEQ ID NOs:48-58, 88-94). All DNA-dependent DNA polymerases were augmented with at least one SV40 nuclear localization sequence to ensure importation into the nucleus. After 4 h, the cells were placed under a fresh media. Then Cas12a RNP complexes (see, e.g., SEQ ID NO:75) containing various synthetic crRNA extensions (see, e.g., SEQ ID NOs:78, 79, 82, 83, 86, 87) were transfected into the cells. DNA extension encoding a homology arm downstream of Cas12a cut site and a template sequence encoding a desired edit was conjugated to the crRNA via chemical synthesis (Integrated DNA Technologies). Two different homology lengths were tested (PBS; 24 bp and 36 bp) and the length of the template containing the desired edit (RTT) was 36 base pairs (Table 2). Three different spacers were used to test the system (PWsp137 (SEQ ID NO:76), PWsp453 (SEQ ID NO:80), PWsp454 (SEQ ID NO:84) (Table 2). For all the constructs, the template contained precise dinucleotide changes at position −2 and −3 of the spacer into adenines (TT to AA), with the PAM sequence (TTTV) corresponding to position −4, −3, −2, and −1.

```
PWsp137 Target Sequence:
                                                        SEQ ID NO: 76
CCUCACUCCUGCUCGGUGAAUUU PWsp137 crRNA-No extension:
                                                        SEQ ID NO: 77
AAUUUCUACUAAGUGUAGAUCCUCACUCCUGCUCGGUGAAUUU PWsp137 crRNA-PBS 24 bp; RTT 36 bp:
                                                        SEQ ID NO: 78
AAUUUCUACUAAGUGUAGAUCCUCACUCCUGCUCGGUGAAUUU
CTGGGGCCGTAACCCTCACTCCTGCTCGGTGAATTTGGCTCAGCAGGCACCTGCCTCAGC
```

-continued

PWsp137 crRNA-PBS 36 bp; RTT 36 bp:
SEQ ID NO: 79
AAUUUCUACUAAGUGUAGAUCCUCACUCCUGCUCGGUGAAUUU
CTGGGGCCGTAACCCTCACTCCTGCTCGGTGAATTTGGCTCAGCAGGCACCTGCCTCAGCTGCT
CACTTGAG

PWsp453 Target Sequence:
SEQ ID NO: 80
UAUGAGUUACAACGAACACCUCA

PWsp453 crRNA-No extension:
SEQ ID NO: 81
AAUUUCUACUAAGUGUAGAUUAUGAGUUACAACGAACACCUCA PWsp453 crRNA-PBS 24 bp; RTT 36 bp:
SEQ ID NO: 82
AAUUUCUACUAAGUGUAGAUUAUGAGUUACAACGAACACCUCA
GGAACTCAGTAAATATGAGTTACAACGAACACCTCAGGTAATGACTAAGATGACTGCCAA PWsp453 crRNA-PBS 36 bp; RTT 36 bp:
SEQ ID NO: 83
AAUUUCUACUAAGUGUAGAUUAUGAGUUACAACGAACACCUCA
GGAACTCAGTAAATATGAGTTACAACGAACACCTCAGGTAATGACTAAGATGACTGCCAAGGGG
CATATGAG PWsp454 Target Sequence:
SEQ ID NO: 84
CACGUCUCAUAUGCCCCUUGGCA PWsp454 crRNA-No extension:
SEQ ID NO: 85
AAUUUCUACUAAGUGUAGAUCACGUCUCAUAUGCCCCUUGGCA PWsp454 crRNA-PBS 24 bp; RTT 36 bp:
SEQ ID NO: 86
AAUUUCUACUAAGUGUAGAUCACGUCUCAUAUGCCCCUUGGCA
GTATCCCAGTAAACACGTCTCATATGCCCCTTGGCAGTCATCTTAGTCATTACCTGAGGT PWsp454 crRNA-PBS 36 bp; RTT 36 bp:
SEQ ID NO: 87
AAUUUCUACUAAGUGUAGAUCACGUCUCAUAUGCCCCUUGGCA
GTATCCCAGTAAACACGTCTCATATGCCCCTTGGCAGTCATCTTAGTCATTACCTGAGGTGTTCG
TTGTAAC We detected precise editing without any side products using DNA polymerases in 50 conjunction with Cas12a RNP that contains DNA extensions on crRNA (Table 2). Precise editing was detected in all 3 spacers tested (Table 2). As indel rates are expected to be efficient from a LbCas12a RNPs (5-50% editing efficiency in 293T—see, e.g., Liu et al. *Nucleic Acids Res.* 47(8):4169-4180 (2019)), our low (~1%) indel rates (Table 3) suggest that the two rounds of transfection in our experiment significantly decreased efficiency of the delivery system. 55 Given that precise editing rates in our experiment were similar to the indel rates (Table 3 and Table 4) suggests that precise editing via DNA-dependent DNA polymerase is potentially quite efficient for precise editing. When background levels of precise editing are subtracted and precise edits are normalized to the rate of indel edits (to normalize for transfection and viability rates), it is apparent that addition of the DNA polymerases and template lead to substantial increases in precise edits relative to the No DNA polymerase control at most spacer sites and PBS lengths (Table 4).

TABLE 2

Precise editing detected in NGS amplicon sequencing from treated samples expressed as % of total reads.

| | % indels | | | % Precise Editing (TT to AA at position −2 and −3) | | | | | |
|---|---|---|---|---|---|---|---|---|---|
| | No Extension | | | PBS 24bp; RTT 36bp | | | PBS 36bp; RTT 36bp | | |
| Polymerase Used | PWsp 137 | PWsp 453 | PWsp 454 | PWsp 137 | PWsp 453 | PWsp 454 | PWsp 137 | PWsp 453 | PWsp 454 |
| No DNA Polymerase | 0.247 | 0 | 0 | 0.191 | 0.105 | N/D* | 0.154 | 0.062 | 0 |
| Klentaq | 0 | 0. | 0 | 0 | 0.058 | 0 | 0.172 | 0.049 | N/D |
| Therminator | 0 | N/D | 0 | 0 | 0 | 0.04 | 0 | 0.018 | 0 |
| Pfu-Ssod7 | 0 | 0 | 0 | 0.352 | N/D | 0 | No Data | 0.041 | 0 |
| Klenow | 0 | 0 | 0 | 0.364 | N/D | 0 | N/D | 0.07 | 0.057 |
| E. Coli polI | N/D | 0 | 0 | 0.074 | 0.012 | 0 | N/D | 0.038 | 0.047 |
| HU pol E (N-term) | 0 | N/D | 0 | 0.152 | 0 | 0.043 | N/D | 0.022 | N/D |
| yeast pol E | 0 | N/D | 0 | 0.258 | 0.029 | 0.083 | N/D | 0.076 | N/D |

*N/D is no data

TABLE 3

Percent indels per total reads NGS amplicon sequencing from treated samples. N/D is no data

| | % indels | | | | | | | | |
|---|---|---|---|---|---|---|---|---|---|
| | No Extension | | | PBS 24bp; RTT 36bp | | | PBS 36bp; RTT 36bp | | |
| Polymerase Used | PWsp 137 | PWsp 453 | PWsp 454 | PWsp 137 | PWsp 453 | PWsp 454 | PWsp 137 | PWsp 453 | PWsp 454 |
| No DNA Polymerase | 0.64 | 0.48 | 0.34 | 0.01 | 0.25 | No Data | 0.31 | 0.04 | 0.11 |
| Klentaq | 0.78 | 0.37 | 0.56 | 0.19 | 0.08 | 0.11 | 0.03 | 0.1 | N/D* |
| Therminator | 1.30 | N/D | 0.30 | 0.51 | 0. | 0 | 0.15 | 0.09 | 0 |
| Pfu-Ssod7 | 0.21 | 0.56 | 0 | 0.09 | N/D | 0 | N/D | 0.04 | 0.02 |
| Klenow | 1.32 | 0.46 | 0 | 0.55 | N/D | 0 | N/D | 0.21 | 0.11 |
| *E. Coli* poll | N/D | 0.49 | 0.28 | 0.25 | 0 | 0.15 | N/D | 0.1 | 0.12 |
| HU pol E (N-term) | 0.460 | N/D | 0 | 0.04 | 0 | 0.02 | N/D | 0.08 | N/D |
| yeast pol E | 1.100 | N/D | 0.12 | 0.11 | 0.05 | 0.08 | N/D | 0.10 | N/D |

*N/D is no data

TABLE 4

Precise edit reads normalized to the indel editing rate of each sample after subtracting background rates of precise editing without a template extension (expressed as a fold change relative to the indel rate). N/D is no data

| | Normalized Precise Editing (TT to AA at position −2 and −3) (precise/indels) | | | | | |
|---|---|---|---|---|---|---|
| | PBS 24bp; RTT 36bp | | | PBS 36bp; RTT 36bp | | |
| Polymerase Used | PWsp 137 | PWsp 453 | PWsp 454 | PWsp 137 | PWsp 453 | PWsp 454 |
| No DNA Polymerase | 0 | 0.42 | N/D* | 0 | 1.561 | 0 |
| Klentaq | 0 | 0.722 | 0 | 5.749 | 0.488 | N/D |
| Therminator | 0 | — | — | 0 | 0.2 | — |
| Pfu-Ssod7 | 3.916 | N/D | — | N/D | 1.025 | 0 |
| Klenow | 0.662 | N/D | — | N/D | 0.332 | 0.517 |
| *E. Coli* poll | 0.297 | — | 0 | N/D | 0.384 | 0.389 |
| HU pol E (N-term) | 3.8 | — | 2.142 | N/D | 0.276 | N/D |
| yeast pol E | 2.348 | 0.577 | 1.04 | N/D | 0.764 | N/D |

*N/D is no data

The foregoing is illustrative of the present invention and is not to be construed as limiting thereof. The invention is defined by the following claims, with equivalents of the claims to be included therein.

That which is claimed is:

1. A method of modifying a target nucleic acid, the method comprising
contacting the target nucleic acid with:
(a) a sequence-specific DNA binding protein that binds to a site on a target nucleic acid, wherein the sequence-specific DNA binding protein is from a CRISPR-Cas effector protein;
(b) a DNA endonuclease having nickase or nuclease activity that introduces a single strand nick or a double strand break in the target nucleic acid;
(c) an RNA:DNA hybrid guide comprising an RNA guide nucleic acid and a DNA encoded repair template, wherein the DNA encoded repair template is linked to the RNA guide nucleic acid, thereby guiding the DNA encoded repair template to the target nucleic acid; and
(d) a DNA-dependent DNA polymerase that initiates strand synthesis copying genetic information from the DNA encoded repair template to the target nucleic acid, wherein the DNA-dependent DNA polymerase is fused to the sequence-specific DNA binding protein, thereby modifying the target nucleic acid.

2. The method of claim 1, wherein the sequence-specific DNA binding protein, the DNA-dependent DNA polymerase, the DNA endonuclease, and the DNA encoded repair template form a complex.

3. The method of claim 1, wherein the DNA endonuclease is from a CRISPR-Cas effector protein or is a Fok1 endonuclease.

4. The method of claim 1, wherein the RNA guide nucleic acid is linked to a RNA-recruiting motif and the DNA-dependent DNA polymerase is fused to an affinity polypeptide that binds to the RNA recruiting motif, thereby guiding the DNA-dependent DNA polymerase to the target nucleic acid.

5. The method of claim 4, wherein the RNA recruiting motif is linked to the 5' end or to the 3' end of the RNA guide nucleic acid.

6. The method of claim 4, wherein the RNA recruiting motif and a corresponding affinity polypeptide are a telomerase Ku binding motif and the affinity polypeptide of Ku; a telomerase Sm7 binding motif and the affinity polypeptide of Sm7; an MS2 phage operator stem-loop and the affinity polypeptide MS2 Coat Protein (MCP), a PP7 phage operator stem-loop and the affinity polypeptide PP7 Coat Protein (PCP); an SfMu phage Com stem-loop and the affinity polypeptide Com RNA binding protein; a PUF binding site (PBS) and the affinity polypeptide Pumilio/fem-3 mRNA binding factor (PUF); and/or a synthetic RNA-aptamer and the corresponding aptamer ligand.

7. The method of claim 4, wherein the RNA recruiting motif and corresponding affinity polypeptide are an MS2 phage operator stem-loop and the affinity polypeptide MS2 Coat Protein (MCP), and/or a PUF binding site (PBS) and the affinity polypeptide Pumilio/fem-3 mRNA binding factor (PUF).

8. The method of claim 1, wherein the CRISPR-Cas effector protein is from a Type II CRISPR-Cas system or a Type V CRISPR-Cas system.

9. The method of claim 1, wherein the CRISPR-Cas effector protein is a Cas9 effector protein or a Cas12 effector protein.

10. The method of claim 1, further comprising contacting the target nucleic acid with a complex comprising:
    (a) a second sequence-specific DNA binding protein that binds to a second site on the target nucleic acid; and
    (b) a DNA-encoded repair template.

11. The method of claim 10, wherein the target nucleic acid is further contacted with a second DNA endonuclease, wherein the second DNA endonuclease introduces a single stranded nick or a double strand break into the target nucleic acid or wherein the second sequence-specific DNA binding protein comprises DNA endonuclease activity that introduces a single stranded nick or a double strand break into the target nucleic acid.

12. The method of claim 10, further comprising contacting the target nucleic acid with a second DNA-dependent DNA polymerase that initiates strand synthesis.

13. The method of claim 10, comprising contacting the target nucleic acid with a third complex, the third complex comprising a third sequence-specific DNA binding protein that binds to a third site on the target nucleic acid that is on a different strand from the site and the second site, wherein the third sequence-specific DNA binding protein comprises nuclease or nickase activity and introduces a single stranded nick into the third site on the target nucleic acid, thereby improving the repair efficiency of the modifying of the target nucleic acid.

14. The method of claim 1, wherein the DNA-dependent DNA polymerase is a high fidelity DNA polymerase.

15. The method of claim 1, wherein the DNA endonuclease is a CRISPR-Cas effector protein, optionally wherein the CRISPR-Cas effector protein is the CRISPR-Cas effector protein of (a) or is a different CRISPR-Cas effector protein.

16. The method of claim 1, wherein the DNA-dependent DNA polymerase is fused to the sequence-specific DNA binding protein via a linker.

* * * * *

UNITED STATES PATENT AND TRADEMARK OFFICE
CERTIFICATE OF CORRECTION

PATENT NO. : 12,173,335 B2  
APPLICATION NO. : 17/142570  
DATED : December 24, 2024  
INVENTOR(S) : Nie et al.

Page 1 of 2

It is certified that error appears in the above-identified patent and that said Letters Patent is hereby corrected as shown below:

In the Specification

Column 5, Line 1: Please correct "1%," to read --±1%,--

Column 8, Line 21: Please correct "86%8, 87%," to read --86%, 87%,--

Column 13, Line 54: Please correct "PLA2-6" to read --PLA$_2$-δ--

Column 27, Lines 9-19: Please delete SEQ ID NO: 71 and replace with the following:
CACGCATGTAGGCAGATTTGTTGGTTGTGAATCGCAACCAGTGGCCTTAATGGCAGGAGG
AATCGCCTCC**AGAGTCGCCGTCTCCAAGGTGAAAGCGGAAGTAGGGCCTTCGCGCAC
CTCATGGAATCCCTTCTGCAGCACCTAGATCGCTTTTCTGAACTCCTAGCAGTATCT
AGCACTACCTACGTCAGCACCTGGGACCCCGC**GGTGTGCTGTGCGAAGGAGTGCCTGC
ATGCGT*ggaatcccttctgcagcaccgtttagagctagaaatagcaagttaaaataaggctagtccgttatcaacttgaaaaagtggcac
cgagtcggtgc* SEQ ID NO:71

Column 27, Lines 26-38: Please delete SEQ ID NO: 72 and replace with the following:
ATGCGCACCCTTAGCGAGAGGTTTATCATTAAGGTCAACCTCTGGATGTTGTTTCGGCAT
CCTGCATTGAATCTGAGTTACTGTCTGTTTTCCT**AGAGTCGCCGTCTCCAAGGTGAAAG
CGGAAGTAGGGCCTTCGCGCACCTCATGGAATCCCTTCTGCAGCACCTAGATCGCTT
TTCTGAACTCCTAGCAGTATCTAGCACTACCTACGTCAGCACCTGGGACCCCGC**CAG
GAAACCCGTTTTTTCTGACGTAAGGGTGCGCA*ggaatcccttctgcagcaccgtttagagctagaaatagcaagtt
aaaataaggctagtccgttatcaacttgaaaaagtggcaccgagtcggtgc* SEQ ID NO:72

Column 27, Lines 44-56: Please delete SEQ ID NO: 73 and replace with the following:
GCCAGCAGTGGCAATAGCGTTTCCGGCCTTTTGTGCCGGGAGGGTCGGCGAGTCGCTGAC
TTAACGCCAGTAGTATGTCCATATACCC**AGAGTCGCCGTCTCCAAGGTGAAAGCGGA
AGTAGGGCCTTCGCGCACCTCATGGAATCCCTTCTGCAGCACCTAGATCGCTTTTCT
GAACTCCTAGCAGTATCTAGCACTACCTACGTCAGCACCTGGGACCCCGC**GGGATGG Signed and Sealed this  
Fifteenth Day of July, 2025

Coke Morgan Stewart  
*Acting Director of the United States Patent and Trademark Office*

CERTIFICATE OF CORRECTION (continued)
U.S. Pat. No. 12,173,335 B2

TTTAATGGTATTGCCGC*ggaatcccttctgcagcaccgttttagagctagaaatagcaagttaaaataaggctagtccgttatcaa cttgaaaaagtggcaccgagtcggtgc* SEQ ID NO:73

Column 27, Lines 62-65 – Column 28, Lines 1-10: Please delete SEQ ID NO: 74 and replace with the following:
AGAGGTCCGGAGTGCATCAGCCTGAGCGCCTCGAGCGGCGGAGCGGCGTTGCGCCGCTC CGGTTGGAATGCAGGACACTCTCCGCAAGGTAGAGTCGCCGTCTCCAAGGTGAAAGCG GAAGTAGGGCCTTCGCGCACCTCATGGAATCCCTTCTGCAGCACCTAGATCGCTTTT CTGAACTCCTAGCAGTATCTAGCACTACCTACGTCAGCACCTGGGACCCCGCTGAGG CTACCGTGCCCCAGGTAAGATGGTGGTGCTTTCCCGG*ggaatcccttctgcagcaccgttttagagctagaaat agcaagttaaaataaggctagtccgttatcaacttgaaaaagtggcaccgagtcggtgc* SEQ ID NO:74

Column 36, Line 27: Please correct "tag 11," to read --tag II,--

Column 48, Line 32: Please correct "poll" to read --polI--

Column 48, Lines 65-67: Please delete SEQ ID NO: 78 and replace with the following:
AAUUUCUACUAAGUGUAGAUCCUCACUCCUGCUCGGUGAAUUU
CTGGGGCCGTAACCCTCACTCCTGCTCGGTGAATTTGGCTCAGCAGGCACCTGCCT CAGC SEQ ID NO:78

Column 49, Line 47: Please correct "system. 55 Given" to read --system. Given--